United States Patent
Ishihara et al.

(10) Patent No.: US 7,601,868 B2
(45) Date of Patent: Oct. 13, 2009

(54) AMINE DERIVATIVE

(75) Inventors: Yuji Ishihara, Osaka (JP); Makoto Kamata, Osaka (JP); Shiro Takekawa, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 397 days.

(21) Appl. No.: 10/545,120

(22) PCT Filed: Feb. 12, 2004

(86) PCT No.: PCT/JP2004/001467

§ 371 (c)(1),
(2), (4) Date: Aug. 10, 2005

(87) PCT Pub. No.: WO2004/072018

PCT Pub. Date: Aug. 26, 2004

(65) Prior Publication Data

US 2006/0128690 A1    Jun. 15, 2006

(30) Foreign Application Priority Data

Feb. 12, 2003   (JP) ............................... 2003-034010

(51) Int. Cl.
C07C 233/65 (2006.01)
C07D 207/06 (2006.01)
A61K 31/165 (2006.01)
A61K 31/40 (2006.01)

(52) U.S. Cl. ...................... 564/184; 548/567; 514/408; 514/617

(58) Field of Classification Search ................. 564/184; 514/617, 408; 548/567
See application file for complete search history.

(56) References Cited

U.S. PATENT DOCUMENTS

| | | | |
|---|---|---|---|
| 4,562,201 A * | 12/1985 | Stout et al. .................. 514/422 |
| 6,586,475 B1 | 7/2003 | Kato et al. | |
| 6,930,185 B2 | 8/2005 | Ishihara et al. | |
| 7,183,415 B2 | 2/2007 | Ishihara et al. | |
| 2004/0242572 A1 | 12/2004 | Stenkamp et al. | |

FOREIGN PATENT DOCUMENTS

| | | |
|---|---|---|
| CA | 2 496 563 | 3/2004 |
| DE | 4438028 | 5/1996 |
| EP | 0 023 569 | 2/1981 |
| EP | 1 132 376 A1 | 9/2001 |
| JP | 51-141829 | 12/1976 |
| JP | 51-141831 | 12/1976 |
| JP | 53-059675 | 5/1978 |
| JP | 2001-072660 | 3/2001 |
| WO | WO 95/00493 | 1/1995 |
| WO | WO 00/31021 | 6/2000 |
| WO | WO 01/21577 A2 | 3/2001 |
| WO | WO 01/82925 A1 | 11/2001 |
| WO | WO 02/06245 A1 | 1/2002 |
| WO | WO 02/051809 A1 | 7/2002 |
| WO | WO 03/035624 A1 | 5/2003 |
| WO | WO 2004/024702 A1 | 3/2004 |

OTHER PUBLICATIONS

R.L. Melo, et al., "Synthesis and Hydrolysis by Cathepsin B of Fluorogenic Substrates with the General Structure Benzoyl-X-ARG-MCA Containing Non-natural basic amino acids at position X", Biochimica et Biphysica Acta, (2001), pp. 82-94, vol. 1547.
European Search Report for Application No. 04710515.0 dated Feb. 3, 2009.

* cited by examiner

*Primary Examiner*—Shailendra Kumar
(74) *Attorney, Agent, or Firm*—Finnegan, Henderson, Farabow, Garrett & Dunner, LLP

(57) ABSTRACT

The present invention provides a compound represented by the formula $$Ar^1-\overset{O}{\underset{}{C}}-\underset{R}{N}-\underset{Ra^2}{\overset{Ra^1}{C}}-\underset{Ra^4}{\overset{Ra^3}{C}}-Ar-Y-N\overset{R^1}{\underset{R^2}{\diagdown}} \quad (I)$$

or salts thereof, wherein, $Ar^1$, Ar, R, $R^1$, $R^2$, $Ra^1$, $Ra^2$, $Ra^3$, $Ra^4$ and Y have meanings described in the specification, having a melanin-concentrating hormone antagonistic, action and useful as an agent for the prophylaxis or treatment of obesity and the like.

21 Claims, No Drawings

AMINE DERIVATIVE

This application is the National Phase filing of International Patent Application No. PCT/JP2004/001467, filed Feb. 12, 2004.

TECHNICAL FIELD

The present invention relates to an amine derivative having a melanin-concentrating hormone (hereinafter sometimes to be abbreviated as MCH) antagonistic action and useful as an agent for the prophylaxis or treatment of obesity and the like.

BACKGROUND ART

Feeding behavior is an indispensable action for many organisms including humans. An abnormality in feeding behavior causes deviation from normal life support activities, which in most cases results in diseases. Along with the recent changes in feeding environments, obesity is becoming a social problem. It is widely known that obesity is not only a serious risk factor of life-style related diseases, such as diabetes, hypertension, arteriosclerosis and the like, but also causes arthritis and pain resulting from an excessive burden on knee joints etc. due to increased body weight. In addition, the dieting boom and the like have increased the potential population that desires weight loss. There are many reports on eating disorders, such as hyperphagia and the like, due to neuropathy and the like, which are genetic or caused by stress.

Consequently, the development and investigation of agents for the prophylaxis or treatment of obesity or feeding deterrents started some time ago, and mazindol has been on the market as a centrally acting anorectic agent.

Along therewith, a number of appetite-regulating factors represented by leptin have been found in recent years, and new anti-obesity agents and anorectic agents that suppress the activity of such appetite-regulating factors have been developed. Among others, a melanin-concentrating hormone is a hormone derived from hypothalamus and known to have an appetite stimulating action. Furthermore, MCH knockout mouse has been reported to show significantly decreased food intake and be lean, as compared to normal mouse, though normal in daily behavior [see *Nature*, vol. 396, p. 670, 1998]. From the foregoing, an MCH antagonist, once completed, is expected to be a superior anorectic agent or anti-obesity agent.

On the other hand, the following compounds are known as amine derivatives.

1) As β amyloid protein production and secretion inhibitor, a compound represented by the formula:

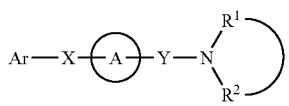

wherein
Ar is an aromatic group optionally having substituent(s);
X and Y are the same or different and each is a divalent group selected from —O—, —S—, —CO—, —SO—, —SO$_2$—, —NR$^8$—, —CONR$^8$—, —SO$_2$NR$^8$— and —COO— (R$^8$ is a hydrogen atom, a hydrocarbon group optionally having substituent(s) or an acyl) or a divalent C$_{1-6}$ aliphatic hydrocarbon group optionally having one or two groups from these divalent groups;

R$^1$ and R$^2$ are a hydrogen atom or a C$_{1-6}$ alkyl optionally having substituent(s), or R$^1$ and R$^2$ may form a nitrogen-containing heterocycle optionally having substituent(s) together with the adjacent nitrogen atom; and
ring A is a monocyclic aromatic ring optionally further having substituent(s),
or a salt thereof, has been reported (see WO00/31021).

2) As MCH antagonist, a compound represented by the formula:

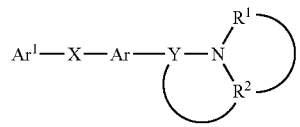

wherein Ar$^1$ is a cyclic group optionally having substituent(s);
X is a spacer having 1 to 6 atoms in a main chain;
Y is bond or a spacer having 1 to 6 atoms in a main chain;
Ar is a monocyclic aromatic ring optionally fused with a 4- to 8-membered non-aromatic ring, which optionally further has substituent(s); and
R$^1$ and R$^2$ are the same or different and each is a hydrogen atom or a hydrocarbon group optionally having substituent(s), or R$^1$ and R$^2$ may form a nitrogen-containing heterocycle optionally having substituent(s) together with the adjacent nitrogen atom, R$^2$ may form a spiro ring together with Ar, or R$^2$ may form a nitrogen-containing heterocycle optionally having substituent(s) together with the adjacent nitrogen atom and Y,
or a salt thereof, has been reported (see WO01/21577).

3) As MCH antagonist, a compound represented by the formula:

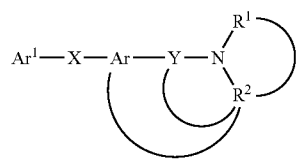

wherein
Ar$^1$ is a cyclic group optionally having substituent(s);
X and Y are the same or different and each is a spacer having 1 to 6 atoms in a main chain;
Ar is a fused polycyclic aromatic ring optionally having substituent(s); and
R$^1$ and R$^2$ are the same or different and each is a hydrogen atom or a hydrocarbon group optionally having substituent(s), or R$^1$ and R$^2$ may form a nitrogen-containing heterocycle optionally having substituent(s) together with the adjacent nitrogen atom, R$^2$ may form a nitrogen-containing heterocycle optionally having substituent(s) together with the adjacent nitrogen atom and Y, or R$^2$ may form a fused ring together with the adjacent nitrogen atom, Y and Ar,
or a salt thereof, has been reported (see WO01/82925).

4) As cathepsin B substrate, a compound represented by the formula: Bz-X-Arg-MCA (Bz is a benzoyl group, MCA is a 7-methylcoumarinamido and X is a 4-aminomethyl-phenylalanine, a 4-guanidine-phenylalanine, a 4-aminomethyl-N- isopropylphenylalanine or the like), has been described (see *Biochimica et Biophysica Acta*, vol. 1547, pages 82-94, 2001).

5) It has been reported that an aminoalcohol derivative having a hypotensive, analgesic, antiinflammatory or psychotropic action is produced by the reaction shown in the scheme:

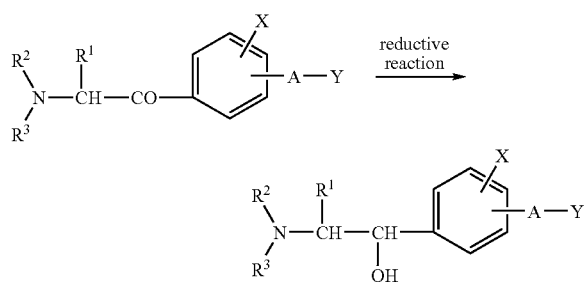

wherein
A is a straight chain or branched alkylene having 2 to 5 carbon atoms;
Y is $-N(R^4)(R^5)$ [$R^4$, $R^5$ are the same or different and each is a hydrogen, a lower alkyl or an acyl] or $-OR^6$ [$R^6$ is a hydrogen, a lower alkyl, an aryl or an acyl];
$R^1$ is a hydrogen or a lower alkyl;
$R^2$ and $R^3$ are the same or different and each is a hydrogen, a lower alkyl or an aralkyl, or a group forming a heterocycle together with the adjacent nitrogen atom; and
X is a hydrogen, a halogen or a lower alkyl (see JP51-141829A).

6) As an aminoalcohol derivative having a hypotensive, analgesic or psychotropic action, a compound represented by the formula:

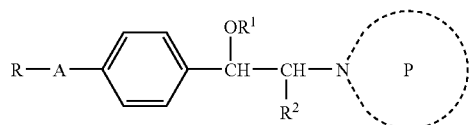

wherein
R is an amino, a hydroxyl group, a lower alkoxy, an acyloxy, an aroyloxy, an acylamino or an aroylamino;
A is a lower alkylene;
$R^1$ is a hydrogen or an acyl;
$R^2$ is a hydrogen or a lower alkyl; and
ring P is a group forming, together with the nitrogen atom, a piperidine, a 4-substituted piperidine or a 4-substituted piperazine,
or an acid addition salt thereof, has been reported (see JP61-2663A).

7) As an aminoketone derivative having a hypotensive, analgesic, antiinflammatory or psychotropic action, a compound represented by the formula:

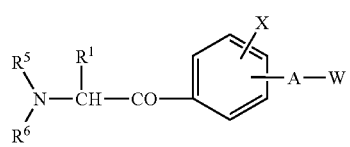

wherein
A is a straight chain or branched alkylene having 2 to 5 carbon atoms;
W is $-N(R^2)(R^8)$ [$R^2$ is a hydrogen or a lower alkyl; and $R^8$ is a hydrogen or an acyl] or $-OR^4$ [$R^4$ is a hydrogen, a lower alkyl, an aryl or an acyl];
$R^1$ is a hydrogen or a lower alkyl;
$R^5$ and $R^6$ are the same or different and each is a hydrogen, a lower alkyl or an aralkyl, or form, together with the adjacent nitrogen atom, a 1-pyrrolidinyl, a piperidino, a 4-carbamoyl-4-piperidinopiperidino, a 4-hydroxy-4-(p-tolyl)piperidino, a morpholino or a 4-substituted-1-piperazinyl; and
X is a hydrogen, a halogen or a lower alkyl,
or a salt thereof, has been disclosed (see JP51-141831A).

8) As a TNF-α-production suppressor and/or IL-10 production promoter, a compound represented by the formula:

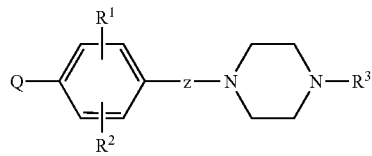

wherein
Q is a group: X—Y [X is an amino optionally having substituent(s) or the like; and Y is an alkylene], or a heterocycle;
Z is an alkylene or the like;
$R^1$ and $R^2$ are a hydrogen, a halogen, an alkyl, an amino, a nitro or a hydroxyl group; and
$R^3$ is a lower alkyl, an aryl, an aralkyl, a heteroaryl or a heteroaralkyl,
or a salt thereof, has been reported (see JP2001-72660A).

9) A compound useful for the treatment of inflammation, allergy and the like, which is represented by the formula:

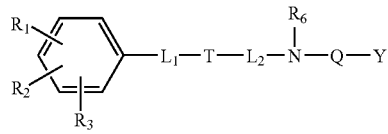

wherein
$R_1$ is a hydrogen, a halo, a cyano, a cyanoalkyl, an alkyl, an alkoxy, a phenoxy, a phenyl, an alkoxycarbonyl, $-NR_{13}R_{14}$, $-N(R_{15})SO_2R_{16}$, a halogenated alkoxy, a halogenated alkyl, an arylalkoxy, a hydroxyl group, a phenylalkyl, an alkoxycarbonylvinyl, $-S(O)nR_7$, an alkoxycarbonylalkyl, a carboxyalkyl, $-CONR_{11}R_{12}$, a carbamoylvinyl, $-OSO_2R_{21}$, a 4,5-dihydrothiazol-2-yl, a 4,4-dimethyl-2-oxazolin-2-yl or $-NR_{60}R_{61}$; or $R_1$ is $-(O)z-L_3G$ [z is 0 or 1; $L_3$ is a $C_{1-4}$ alkylene chain; and G is $-NR_{22}R_{23}$, $-S(O)mR_{26}$, $-CONR_{27}R_{28}$ or $-OR_{29}$];
$R_2$ and $R_3$ are independently a hydrogen, a halo, an alkyl, an alkoxy, $-NR_{13}R_{14}$, a halogenated alkoxy, a halogenated alkyl, a hydroxyl group, $-S(O)nR_7$ or $-NR_{60}R_{61}$;
$L_1$ is bond, an alkylene, a cycloalkylene or a cycloalkylidene;
T is bond, O, S, $SO_2$, a carbonyl group or a 1,3-dioxolan-2-ylidene;
$L_2$ is a alkylene, a cycloalkylene or a cycloalkylidene;

R₆ is a hydrogen or an alkyl (optionally substituted by an alkoxycarbonyl or a hydroxyl group);
Q is a $C_{1-9}$ alkylene chain (optionally substituted by an alkyl or a hydroxyl group); and
Y is an optionally substituted imidazole ring,
or a salt thereof, has been reported (see WO95/00493).

DISCLOSURE OF THE INVENTION

The present invention aims at providing a compound having a melanin-concentrating hormone antagonistic action, which is useful as an agent for the prophylaxis or treatment of obesity and the like.

As a result of the intensive studies of compounds having an MCH antagonistic action, the present inventors have found that a compound represented by the formula:

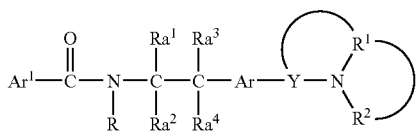

(I)

wherein
$Ar^1$ is a cyclic group optionally having substituent(s);
R is a hydrogen atom, an optionally halogenated $C_{1-6}$ alkyl, a phenyl optionally having substituent(s) or a pyridyl optionally having substituent(s);
$Ra^1$, $Ra^2$, $Ra^3$ and $Ra^4$ are the same or different and each is a hydrogen atom, an optionally halogenated $C_{1-6}$ alkyl, a phenyl optionally having substituent(s), a halogen atom, a pyridyl optionally having substituent(s), a cyano, an optionally halogenated $C_{1-6}$ alkoxy, an optionally halogenated $C_{1-6}$ alkylthio, an amino, a mono- or di-$C_{1-6}$ alkylamino, a formyl, an optionally halogenated $C_{1-6}$ alkylcarbonyl or an optionally halogenated $C_{1-6}$ alkylsulfonyl;
Ar is a monocyclic aromatic ring optionally having substituent(s);
Y is an optionally halogenated alkylene group; and
$R^1$ and $R^2$ are (1) the same or different and each is a hydrogen atom or a $C_{1-6}$ alkyl, (2) $R^1$ and $R^2$ form a nitrogen-containing heterocycle optionally having substituent(s) together with the adjacent nitrogen atom, or (3) $R^1$ and Y form a nitrogen-containing heterocycle optionally having substituent(s) together with the adjacent nitrogen atom, and $R^2$ is a hydrogen atom or a $C_{1-6}$ alkyl;
provided that when the nitrogen-containing heterocycle formed by $R^1$ and $R^2$ together with the adjacent nitrogen atom is a piperazine, or when R is a $C_{1-4}$ alkyl, $Ar^1$ is a cyclic group having substituent(s),
or a salt thereof [hereinafter sometimes to be abbreviated as compound (I)], which is constituted by introducing a group represented by the formula:

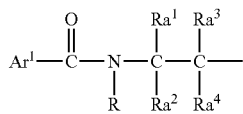

wherein the symbols in the formula are as defined above, into a compound represented by the formula:

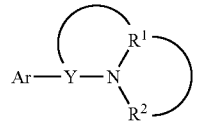

wherein the symbols in the formula are as defined above, has a superior MCH antagonistic action, which resulted in the completion of the present invention.

Accordingly, the present invention relates to
1) compound (I);
2) compound (I) wherein $R^1$ and $R^2$ are the same or different and each is a hydrogen atom or a $C_{1-6}$ alkyl, or $R^1$ and $R^2$ form a nitrogen-containing heterocycle optionally having substituent(s) together with the adjacent nitrogen atom;
3) compound (I) wherein $Ar^1$ is a group represented by the formula: $Ar^3$—$Ar^2$— (wherein $Ar^2$ is a cyclic group optionally having substituent(s) and $Ar^3$ is an aromatic group optionally having substituent(s));
4) compound (I) wherein R is a hydrogen atom;
5) compound (I) wherein $Ra^1$, $Ra^2$, $Ra^3$ and $Ra^4$ are each a hydrogen atom;
6) compound (I) wherein Ar is a benzene ring;
7) compound (I) wherein Y is a $C_{1-6}$ alkylene group;
8) compound (I) wherein $R^1$ and $R^2$ form a nitrogen-containing heterocycle optionally having substituent(s) together with the adjacent nitrogen atom;
9) compound (I) of the aforementioned 8), wherein the nitrogen-containing heterocycle is a piperidine, a pyrrolidine, a hexamethylenimine, a morpholine or a thiomorpholine;
10) compound (I) which is 4'-chloro-N-{2-[4-(1-pyrrolidinylmethyl)phenyl]ethyl}[1,1'-biphenyl]-4-carboxamide;
4'-chloro-3-fluoro-N-{2-[4-(1-pyrrolidinylmethyl)phenyl]ethyl}[1,1'-biphenyl]-4-carboxamide;
4'-chloro-N-(2-{4-[1-(1-pyrrolidinyl)propyl]phenyl}ethyl)[1,1'-biphenyl]-4-carboxamide;
4-(cyclopropylmethoxy)-N-(2-{4-[1-(1-pyrrolidinyl)ethyl]phenyl}ethyl)benzamide;
4'-methoxy-N-{2-[4-(1-pyrrolidinylmethyl)phenyl]ethyl}[1,1'-biphenyl]-4-carboxamide;
N-{2-[4-(1-azepanylmethyl)phenyl]ethyl}-4-(cyclopropylmethoxy)benzamide;
N-{2-[4-(1-azepanylmethyl)phenyl]ethyl}-4-(2-cyclopropylethoxy)benzamide;
4'-chloro-N-{2-[4-(1-methyl-2-pyrrolidinyl)phenyl]ethyl}[1,1'-biphenyl]-4-carboxamide; or
4-(2-cyclopropylethoxy)-N-(2-{4-[1-(1)-pyrrolidinyl)ethyl]phenyl}ethyl)benzamide;
11) a pharmaceutical agent which comprises compound (I) or a prodrug thereof;
12) the pharmaceutical agent of the aforementioned 11), which is a melanin-concentrating hormone antagonist;
13) the pharmaceutical agent of the aforementioned 11), which is an agent for the prophylaxis or treatment of a disease caused by a melanin-concentrating hormone;
14) the pharmaceutical agent of the aforementioned 11), which is an agent for the prophylaxis or treatment of obesity;
15) the pharmaceutical agent of the aforementioned 11), which is a feeding deterrent;
16) the pharmaceutical agent of the aforementioned 11), which is an agent for the prophylaxis or treatment of depression;

17) the pharmaceutical agent of the aforementioned 11), which is an agent for the prophylaxis or treatment of anxiety;
18) use of compound (I) or a prodrug thereof for the production of a melanin-concentrating hormone antagonist;
19) a method for antagonizing a melanin-concentrating hormone receptor in a mammal, which comprises administering an effective amount of compound (I) or a prodrug thereof to said mammal;
20) use of compound (I) or a prodrug thereof for the production of an agent for the prophylaxis or treatment of a disease caused by a melanin-concentrating hormone;
21) a method for preventing or treating a disease caused by a melanin-concentrating hormone in a mammal, which comprises administering an effective amount of compound (I) or a prodrug thereof to said mammal;
22) use of compound (I) or a prodrug thereof for the production of an agent for the prophylaxis or treatment of obesity;
23) a method for preventing or treating obesity in a mammal, which comprises administering an effective amount of compound (I) or a prodrug thereof to said mammal;
24) use of compound (I) or a prodrug thereof for the production of a feeding deterrent;
25) a method for suppressing food intake by a mammal, which comprises administering an effective amount of compound (I) or a prodrug thereof to said mammal;
26) use of compound (I) or a prodrug thereof for the production of an agent for the prophylaxis or treatment of depression;
27) a method for preventing or treating depression in a mammal, which comprises administering an effective amount of compound (I) or a prodrug thereof to said mammal;
28) use of compound (I) or a prodrug thereof for the production of an agent for the prophylaxis or treatment of anxiety;
29) a method for preventing or treating anxiety in a mammal, which comprises administering an effective amount of compound (I) or a prodrug thereof to said mammal;
and the like.

The definition of each substituent of compound (I) is described in detail in the following.

As the "cyclic group" of the "cyclic group optionally having substituent(s)" for $Ar^1$, an aromatic group, a non-aromatic cyclic hydrocarbon group, a non-aromatic heterocyclic group and the like can be mentioned.

Here, as the "aromatic group", a monocyclic aromatic group and a fused polycyclic aromatic group can be mentioned.

As the monocyclic aromatic group, for example, phenyl and a 5- or 6-membered aromatic heterocyclic group can be mentioned.

As the "5- or 6-membered aromatic heterocyclic group", for example, a 5- or 6-membered aromatic heterocyclic group containing, besides carbon atoms, one or more (e.g., 1 to 3) hetero atoms selected from a nitrogen atom, a sulfur atom and an oxygen atom, and the like can be mentioned. To be specific, thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, oxadiazolyl, thiadiazolyl, furazanyl and the like can be mentioned.

As specific examples of the "monocyclic aromatic group", phenyl, 2- or 3-thienyl, 2-, 3- or 4-pyridyl, 2- or 3-furyl, 2-, 4- or 5-thiazolyl, 2-, 4- or 5-oxazolyl, 1-, 3- or 4-pyrazolyl, 2-pyrazinyl, 2-, 4- or 5-pyrimidinyl, 1-, 2- or 3-pyrrolyl, 1-, 2- or 4-imidazolyl, 3- or 4-pyridazinyl, 3-, 4- or 5-isothiazolyl, 3-, 4- or 5-isoxazolyl, 1,2,4-oxadiazol-5-yl, 1,2,4-oxadiazol-3-yl, 1,3,4-oxadiazol-2-yl and the like can be mentioned.

The "fused polycyclic aromatic group" is preferably a bicyclic to tetracyclic, more preferably bicyclic or tricyclic aromatic group. As the "fused polycyclic aromatic group", for example, a fused polycyclic aromatic hydrocarbon group, a fused polycyclic aromatic heterocyclic group and the like can be mentioned.

As the "fused polycyclic aromatic hydrocarbon group", for example, a fused polycyclic (bicyclic or tricyclic) aromatic hydrocarbon group having 9 to 14 carbon atoms (e.g., naphthalenyl, indenyl, fluorenyl, anthracenyl and the like) and the like can be mentioned.

As the "fused polycyclic aromatic heterocyclic group", for example, a 9- to 14-membered, preferably 9- or 10-membered fused polycyclic (preferably bicyclic or tricyclic) aromatic heterocyclic group containing, besides carbon atoms, one or more (e.g., 1 to 4) hetero atoms selected from a nitrogen atom, a sulfur atom and an oxygen atom, and the like can be mentioned. The "fused polycyclic aromatic heterocyclic group" is more preferably a 10-membered fused polycyclic aromatic heterocyclic group.

As specific examples of the "fused polycyclic aromatic heterocyclic group", benzothienyl, benzofuranyl, benzimidazolyl, benzoxazolyl, benzothiazolyl, benzisothiazolyl, naphtho[2,3-b]thiophenyl, isoquinolyl, quinolyl, indolyl, quinoxalinyl, phenanthridinyl, phenothiazinyl, phenoxazinyl, phthalazinyl, naphthyridinyl, quinazolinyl, cinnolinyl, carbazolyl, β-carbolinyl, acridinyl, phenazinyl, phthalimido, thioxanthenyl and the like can be mentioned.

As specific examples of the "fused polycyclic aromatic group", 1- or 2-naphthyl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzothienyl; 2-, 3-, 4-, 5- or 6-benzofuranyl; 2-, 4-, 5- or 6-benzothiazolyl; 1-, 2-, 4-, 5- or 6-benzimidazolyl and the like can be mentioned.

As the "non-aromatic cyclic hydrocarbon group", for example, a $C_{3-8}$ cycloalkyl, a $C_{3-8}$ cycloalkenyl and the like can be mentioned.

Here, as specific examples of the $C_{3-8}$ cycloalkyl, cyclopropyl, cyclobutyl, cyclopentyl, cyclohexyl, cycloheptyl, cyclooctyl and the like can be mentioned.

As specific examples of the $C_{3-8}$ cycloalkenyl, cyclopropenyl, cyclobutenyl, cyclopentenyl, cyclohexenyl, cycloheptenyl, cyclooctenyl and the like can be mentioned.

As the "non-aromatic heterocyclic group", for example, a monocyclic non-aromatic heterocyclic group, a fused polycyclic non-aromatic heterocyclic group and the like can be mentioned.

As the "monocyclic non-aromatic heterocyclic group", for example, a 5- to 8-membered monocyclic non-aromatic heterocyclic group containing, besides carbon atoms, one or more (e.g., 1 to 3) hetero atoms selected from a nitrogen atom, a sulfur atom and an oxygen atom, and the like can be mentioned. To be specific, tetrahydrothiophenyl, tetrahydrofuranyl, pyrrolidinyl, imidazolinyl, imidazolidinyl, pyrazolinyl, pyrazolidinyl, tetrahydrothiazolyl, tetrahydroisothiazolyl, tetrahydrooxazolyl, tetrahydroisoxazolyl, piperidinyl, tetrahydropyridyl, dihydropyridyl, piperazinyl, morpholinyl, thiomorpholinyl, tetrahydropyrimidinyl, tetrahydropyridazinyl, hexamethyleniminyl, dioxanyl and the like can be mentioned.

The "fused polycyclic non-aromatic heterocyclic group" is preferably a bicyclic to tetracyclic, more preferably bicyclic or tricyclic non-aromatic heterocyclic group. As the "fused polycyclic non-aromatic heterocyclic group", for example, a 9- to 14-membered, preferably 9- or 10-membered fused polycyclic (preferably bicyclic or tricyclic) non-aromatic heterocyclic group containing, besides carbon atoms, one or more (e.g., 1 to 4) hetero atoms selected from a nitrogen atom, a sulfur atom and an oxygen atom, and the like can be mentioned. To be specific, dihydrobenzofuranyl, dihydrobenzimidazolyl, dihydrobenzoxazolyl, dihydrobenzothiazolyl, dihydrobenzisothiazolyl, dihydronaphtho[2,3-b]thiophenyl, tetrahydroisoquinolyl, tetrahydroquinolyl, indolinyl, isoindolinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanthenyl, dihydrobenzopyranyl, tetrahydrobenzoxepinyl and the like can be mentioned.

The "cyclic group" for $Ar^1$ is preferably phenyl, a 5- or 6-membered aromatic heterocyclic group, a 5- to 8-membered monocyclic non-aromatic heterocyclic group and the like, more preferably phenyl, pyridyl, piperidinyl and the like.

As the "substituent" of the "cyclic group optionally having substituent(s)" for $Ar^1$, for example, a halogen atom (e.g., fluorine, chlorine, bromine, iodine and the like), a $C_{1-3}$ alkylenedioxy (e.g., methylenedioxy, ethylenedioxy and the like), a nitro, a cyano, an optionally halogenated $C_{1-10}$ alkyl, a hydroxy-$C_{1-10}$ alkyl (e.g., hydroxymethyl, hydroxyethyl), a $C_{6-14}$ aryloxy-$C_{1-6}$ alkyl (e.g., phenoxymethyl and the like), a $C_{1-6}$ alkyl-$C_{6-14}$ aryl-$C_{2-6}$ alkenyl (e.g., methylphenylethenyl and the like), an optionally halogenated $C_{1-10}$ alkoxy, an optionally halogenated $C_{1-10}$ alkylthio, a $C_{7-19}$ aralkyl optionally having substituent(s), a hydroxy, a $C_{6-14}$ aryloxy optionally having substituent(s), a $C_{7-19}$ aralkyloxy optionally having substituent(s), an amino, an amino-$C_{1-10}$ alkyl (e.g., aminomethyl, aminoethyl, aminopropyl, aminobutyl and the like), a mono- or di-$C_{1-10}$ alkylamino (e.g., methylamino, ethylamino, propylamino, isopropylamino, butylamino, dimethylamino, diethylamino, dipropylamino, dibutylamino, ethylmethylamino and the like), a mono- or di-$C_{1-10}$ alkylamino-$C_{1-6}$ alkyl (e.g., methylaminomethyl, ethylaminomethyl, propylaminomethyl, isopropylaminoethyl, butylaminoethyl, dimethylaminomethyl, diethylaminomethyl, dipropylaminomethyl, diisopropylaminoethyl, dibutylaminoethyl and the like), an aromatic group optionally having substituent(s), a non-aromatic group optionally having substituent(s), a $C_{3-6}$ cycloalkyl-$C_{1-6}$ alkyl optionally having substituent(s), a $C_{3-6}$ cycloalkyl-$C_{1-6}$ alkoxy optionally having substituent(s), a $C_{1-6}$ alkoxy-$C_{1-6}$ alkoxy, an acyl, an acylamino, an acyloxy, an acyl-$C_{1-6}$ alkyl, an acylamino-$C_{1-6}$ alkyl, an acyloxy-$C_{1-6}$ alkyl and the like can be mentioned.

The "cyclic group" for $Ar^1$ optionally has 1 to 5, preferably 1 to 3, substituents mentioned above at substitutable positions on the cyclic group. When the number of the substituents is not less than 2, respective substituents may be the same or different.

As the aforementioned "optionally halogenated $C_{1-10}$ alkyl", for example, a $C_{1-10}$ alkyl (e.g., methyl, ethyl, propyl, isopropyl, butyl, isobutyl, sec-butyl, tert-butyl, pentyl, hexyl, heptyl, octyl, nonyl, decyl and the like) optionally having 1 to 5, preferably 1 to 3, halogen atoms (e.g., fluorine, chlorine, bromine, iodine and the like) can be mentioned. As specific examples, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, heptyl, octyl, nonyl, decyl and the like can be mentioned.

As the aforementioned "optionally halogenated $C_{1-10}$ alkoxy", for example, a $C_{1-10}$ alkoxy (e.g., methoxy, ethoxy, propoxy, butoxy, pentyloxy, hexyloxy, heptyloxy, octyloxy, nonyloxy, decyloxy and the like) optionally having 1 to 5, preferably 1 to 3, halogen atoms (e.g., fluorine, chlorine, bromine, iodine and the like) and the like can be mentioned. As specific examples, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, isopentyloxy, hexyloxy, heptyloxy, octyloxy, nonyloxy, decyloxy and the like can be mentioned.

As the aforementioned "optionally halogenated $C_{1-10}$ alkylthio", for example, a $C_{1-10}$ alkylthio (e.g., methylthio, ethylthio, propylthio, isopropylthio, butylthio, sec-butylthio, tert-butylthio, pentylthio, hexylthio, heptylthio, octylthio, nonylthio, decylthio and the like) optionally having 1 to 5, preferably 1 to 3, halogen atoms (e.g., fluorine, chlorine, bromine, iodine and the like) and the like can be mentioned. As specific examples, for example, methylthio, difluoromethylthio, trifluoromethylthio, ethylthio, propylthio, isopropylthio, butylthio, 4,4,4-trifluorobutylthio, pentylthio, hexylthio, heptylthio, octylthio, nonylthio, decylthio and the like can be mentioned.

As the "$C_{7-19}$ aralkyl" of the aforementioned "$C_{7-19}$ aralkyl optionally having substituent(s)", for example, benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl and the like can be mentioned.

As the "$C_{6-14}$ aryloxy" of the aforementioned "$C_{6-14}$ aryloxy optionally having substituent(s)", for example, phenyloxy, 1-naphthyloxy, 2-naphthyloxy and the like can be mentioned.

As the "$C_{7-19}$ aralkyloxy" of the aforementioned "$C_{7-19}$ aralkyloxy optionally having substituent(s)", for example, benzyloxy, phenethyloxy, diphenylmethyloxy, triphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy and the like can be mentioned.

As the "aromatic group" of the aforementioned "aromatic group optionally having substituent(s)", the "aromatic group" exemplified for the aforementioned $Ar^1$ can be mentioned. The "aromatic group" is preferably phenyl, naphthyl, a 5- or 6-membered aromatic heterocyclic group, a 9- or 10-membered fused polycyclic aromatic heterocyclic group and the like, more preferably phenyl, a 5- or 6-membered aromatic heterocyclic group and the like. Of these, phenyl, pyridyl and the like are preferable.

As the "non-aromatic group" of the aforementioned "non-aromatic group optionally having substituent(s)", the "non-aromatic cyclic hydrocarbon group" and the "non-aromatic heterocyclic group" exemplified for the aforementioned $Ar^1$ can be mentioned. The "non-aromatic group" is preferably a $C_{3-8}$ cycloalkyl, a 5- to 8-membered monocyclic non-aromatic heterocyclic group and the like, more preferably cyclohexyl and the like.

As the "$C_{3-6}$ cycloalkyl-$C_{1-6}$ alkyl" of the aforementioned "$C_{3-6}$ cycloalkyl-$C_{1-6}$ alkyl optionally having substituent(s)", for example, cyclopropylmethyl, cyclopropylethyl, cyclobutylmethyl, cyclobutylethyl, cyclopentylmethyl, cyclopentylethyl, cyclohexylmethyl, cyclohexylethyl, cyclohexylpropyl and the like can be mentioned.

As the "$C_{3-6}$ cycloalkyl-$C_{1-6}$ alkoxy" of the aforementioned "$C_{3-6}$ cycloalkyl-$C_{1-6}$ alkoxy optionally having substituent(s)", for example, cyclopropylmethoxy, cyclopropylethoxy, cyclobutylmethoxy, cyclobutylethoxy, cyclopentylmethoxy, cyclopentylethoxy, cyclohexylmethoxy, cyclohexylethoxy, cyclohexylpropoxy and the like can be mentioned.

As the aforementioned "$C_{1-6}$ alkoxy-$C_{1-6}$ alkoxy", for example, methoxymethoxy, methoxyethoxy, ethoxymethoxy, ethoxyethoxy and the like can be mentioned.

As the "substituent" of the aforementioned "$C_{7-19}$ aralkyl optionally having substituent(s)", "$C_{6-14}$ aryloxy optionally having substituent(s)", "$C_{7-19}$ aralkyloxy optionally having substituent(s)", "aromatic group optionally having substituent(s)", "non-aromatic group optionally having substituent(s)", "$C_{3-6}$ cycloalkyl-$C_{1-6}$ alkyl optionally having substituent(s)" and "$C_{3-6}$ cycloalkyl-$C_{1-6}$ alkoxy optionally having substituent(s)", for example, a halogen atom (e.g., fluorine, chlorine, bromine, iodine and the like), a $C_{1-3}$ alkylenedioxy (e.g., methylenedioxy, ethylenedioxy and the like), a nitro, a cyano, an optionally halogenated $C_{1-10}$ alkyl, a hydroxy-$C_{1-10}$ alkyl (e.g., hydroxymethyl, hydroxyethyl), an optionally halogenated $C_{3-6}$ cycloalkyl, an optionally halogenated $C_{1-10}$ alkoxy, an optionally halogenated $C_{1-10}$ alkylthio, a hydroxy, an amino, a mono- or di-$C_{1-10}$ alkylamino (e.g., methylamino, ethylamino, propylamino, isopropylamino, butylamino, dimethylamino, diethylamino, dipropylamino, dibutylamino, ethylmethylamino and the like), an amino-$C_{1-10}$ alkyl (e.g., aminomethyl, aminoethyl, aminopropyl, aminobutyl and the like), a mono- or di-$C_{1-10}$ alkylamino-$C_{1-6}$ alkyl (e.g., methylaminomethyl, ethylaminomethyl, propylaminomethyl, isopropylaminoethyl, butylaminoethyl, dimethylaminomethyl, diethylaminomethyl, dipropylaminomethyl, diisopropylaminoethyl, dibutylaminoethyl and the like), a formyl, a carboxy, a carbamoyl, a thiocarbamoyl, an optionally halogenated $C_{1-6}$ alkyl-carbonyl, a $C_{1-6}$ alkoxy-carbonyl (e.g., methoxycarbonyl, ethoxycarbonyl, propoxycarbonyl, tert-butoxycarbonyl and the like), a 5- or 6-membered heterocyclylcarbonyl, a mono- or di-$C_{1-6}$ alkyl-carbamoyl (e.g., methylcarbamoyl, ethylcarbamoyl, dimethylcarbamoyl, diethylcarbamoyl, ethylmethylcarbamoyl and the like), a 5- or 6-membered heterocyclylcarbamoyl, a carbamoyl-$C_{1-6}$ alkyl (e.g., carbamoylmethyl, carbamoylethyl, carbamoylpropyl and the like), a mono- or di-$C_{1-6}$ alkyl-carbamoyl-$C_{1-6}$ alkyl (e.g., methylcarbamoylmethyl, methylcarbamoylethyl, methylcarbamoylpropyl, dimethylcarbamoylmethyl, dimethylcarbamoylethyl, dimethylcarbamoylpropyl, ethylcarbamoylmethyl, ethylcarbamoylethyl, ethylcarbamoylpropyl, diethylcarbamoylmethyl, diethylcarbamoylethyl, diethylcarbamoylpropyl and the like), a 5- or 6-membered heterocyclylcarbonyl-$C_{1-6}$ alkyl, a 5- or 6-membered heterocyclylcarbamoyl-$C_{1-6}$ alkyl, an optionally halogenated $C_{1-6}$ alkylsulfonyl, a formylamino, an optionally halogenated $C_{1-6}$ alkyl-carboxamido, a $C_{1-6}$ alkoxy-carboxamido (e.g., methoxycarboxamido, ethoxycarboxamido, propoxycarboxamido, butoxycarboxamido and the like), a $C_{1-6}$ alkylsulfonylamino (e.g., methylsulfonylamino, ethylsulfonylamino and the like), a $C_{1-6}$ alkyl-carbonyloxy (e.g., acetoxy, propanoyloxy and the like), a $C_{1-6}$ alkoxy-carbonyloxy (e.g., methoxycarbonyloxy, ethoxycarbonyloxy, propoxycarbonyloxy, butoxycarbonyloxy and the like), a mono- or di-$C_{1-6}$ alkyl-carbamoyloxy (e.g., methylcarbamoyloxy, ethylcarbamoyloxy, dimethylcarbamoyloxy, diethylcarbamoyloxy and the like), a mono- or di-$C_{1-6}$ alkyl-carbamoyl-$C_{1-6}$ alkoxy (e.g., methylcarbamoylmethoxy, ethylcarbamoylmethoxy, dimethylcarbamoylmethoxy, diethylcarbamoylmethoxy and the like), a 5- or 6-membered non-aromatic heterocyclic group (e.g., pyrrolidinyl, piperidinyl and the like) and the like can be mentioned. The number of the substituents is, for example, 1 to 5, preferably 1 to 3. When the number of the substituents is not less than 2, respective substituents may be the same or different.

Here, as the "optionally halogenated $C_{1-10}$ alkyl", "optionally halogenated $C_{1-10}$ alkoxy" and "optionally halogenated $C_{1-10}$ alkylthio", those exemplified as the "substituent" of the "cyclic group optionally having substituent(s)" for the aforementioned $Ar^1$ can be used respectively.

As the aforementioned "optionally halogenated $C_{3-6}$ cycloalkyl", for example, a $C_{3-6}$ cycloalkyl (e.g., cyclopropyl, cyclobutyl, cyclopentyl, cyclohexyl and the like) optionally having 1 to 5, preferably 1 to 3, halogen atoms (e.g., fluorine, chlorine, bromine, iodine and the like) and the like can be mentioned. As specific examples, cyclopropyl, cyclobutyl, cyclopentyl, cyclohexyl, 4,4-dichlorocyclohexyl, 2,2,3,3-tetrafluorocyclopentyl, 4-chlorocyclohexyl and the like can be mentioned.

As the aforementioned "optionally halogenated $C_{1-6}$ alkyl-carbonyl", for example, a $C_{1-6}$ alkyl-carbonyl (e.g., acetyl, propanoyl, 2-methylpropanoyl, butanoyl, 3-methylbutanoyl, pentanoyl, hexanoyl and the like) optionally having 1 to 5, preferably 1 to 3, halogen atoms (e.g., fluorine, chlorine, bromine, iodine and the like) and the like can be mentioned. As specific examples, for example, acetyl, monochloroacetyl, trifluoroacetyl, trichloroacetyl, propanoyl, 2-methylpropanoyl, butanoyl, 3-methylbutanoyl, pentanoyl, hexanoyl and the like can be mentioned.

As the "5- or 6-membered heterocyclylcarbonyl" of the aforementioned "5- or 6-membered heterocyclylcarbonyl" and "5- or 6-membered heterocyclylcarbonyl-$C_{1-6}$ alkyl", for example, nicotinoyl, isonicotinoyl, 2-thenoyl, 3-thenoyl, 2-furoyl, 3-furoyl, morpholinocarbonyl, piperidinocarbonyl, 1-pyrrolidinylcarbonyl and the like can be mentioned.

As the "5- or 6-membered heterocyclylcarbonyl-$C_{1-6}$ alkyl", for example, morpholinocarbonylmethyl, morpholinocarbonylethyl, morpholinocarbonylpropyl, piperidinocarbonylmethyl, piperidinocarbonylethyl, piperidinocarbonylpropyl, 1-pyrrolidinylcarbonylmethyl, 1-pyrrolidinylcarbonylethyl, 1-pyrrolidinylcarbonylpropyl and the like can be mentioned.

As the "5- or 6-membered heterocyclylcarbamoyl" of the aforementioned "5- or 6-membered heterocyclylcarbamoyl" and "5- or 6-membered heterocyclylcarbamoyl-$C_{1-6}$ alkyl", for example, morpholinocarbamoyl, piperidinocarbamoyl, 1-pyrrolidinylcarbamoyl, 2-pyridylcarbamoyl, 3-pyridylcarbamoyl, 4-pyridylcarbamoyl, 2-thienylcarbamoyl, 3-thienylcarbamoyl and the like can be mentioned.

As the "5- or 6-membered heterocyclylcarbamoyl-$C_{1-6}$ alkyl", for example, morpholinocarbamoylmethyl, morpholinocarbamoylethyl, morpholinocarbamoylpropyl, piperidinocarbamoylmethyl, piperidinocarbamoylethyl, piperidinocarbamoylpropyl, 1-pyrrolidinylcarbamoylmethyl, 1-pyrrolidinylcarbamoylethyl, 1-pyrrolidinylcarbamoylpropyl and the like can be mentioned.

As the aforementioned "optionally halogenated $C_{1-6}$ alkylsulfonyl", for example, a $C_{1-6}$ alkylsulfonyl (e.g., methylsulfonyl, ethylsulfonyl, propylsulfonyl, isopropylsulfonyl, butylsulfonyl, sec-butylsulfonyl, tert-butylsulfonyl and the like) optionally having 1 to 5, preferably 1 to 3, halogen atoms (e.g., fluorine, chlorine, bromine, iodine and the like) and the like can be mentioned. As specific examples, for example, methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, hexylsulfonyl and the like can be mentioned.

As the aforementioned "optionally halogenated $C_{1-6}$ alkyl-carboxamido", for example, a $C_{1-6}$ alkyl-carboxamido (e.g., acetamido, propaneamido, butaneamido and the like) optionally having 1 to 5, preferably 1 to 3, halogen atoms (e.g., fluorine, chlorine, bromine, iodine and the like) and the like can be mentioned. As specific examples, for example, acetamido, trifluoroacetamido, propaneamido, butaneamido and the like can be mentioned.

As the "acyl" exemplified as the "substituent" for the aforementioned $Ar^1$, for example, a group represented by the formula: —CO—$R^3$, —CO—$OR^3$, —CO—$NR^3R^4$, —CS—$NR^3R^4$, —$SO_2$—$R^3$, —SO—$R^3$, —PO(—$OR^3$)—$OR^4$ or —$PO_2$—$R^3$ (wherein $R^3$ is (i) a hydrogen atom, (ii) a hydrocarbon group optionally having substituent(s) or (iii) a heterocyclic group optionally having substituent(s); $R^4$ is a hydrogen atom or a $C_{1-6}$ alkyl; or $R^3$ and $R^4$ optionally form a nitrogen-containing heterocycle optionally having substituent(s) together with the adjacent nitrogen atom), and the like can be mentioned.

As the "hydrocarbon group" of the "hydrocarbon group optionally having substituent(s)" for $R^3$, for example, a chain or cyclic hydrocarbon group (e.g., an alkyl, an alkenyl, an alkynyl, a cycloalkyl, an aryl, an aralkyl, a cycloalkyl-alkyl and the like) and the like can be mentioned. Of these, a chain or cyclic hydrocarbon group having 1 to 19 carbon atoms and the like as shown below are preferable. The cycloalkyl of the above-mentioned cycloalkyl and cycloalkyl-alkyl is optionally fused with a benzene ring.
a) a $C_{1-6}$ alkyl (e.g., methyl, ethyl, propyl, isopropyl, butyl, isobutyl, sec-butyl, tert-butyl, pentyl, hexyl and the like);
b) a $C_{2-6}$ alkenyl (e.g., vinyl, allyl, isopropenyl, 2-butenyl and the like);
c) a $C_{2-6}$ alkynyl (e.g., ethynyl, propargyl, 2-butynyl and the like);
d) a $C_{3-6}$ cycloalkyl (e.g., cyclopropyl, cyclobutyl, cyclopentyl, cyclohexyl and the like) optionally fused with a benzene ring;
e) a $C_{6-14}$ aryl (e.g., phenyl, 1-naphthyl, 2-naphthyl, 2-indenyl, 2-anthryl and the like);
f) a $C_{7-19}$ aralkyl (e.g., benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl and the like); and
g) a $C_{3-6}$ cycloalkyl-$C_{1-6}$ alkyl (e.g., cyclopropylmethyl, cyclopropylethyl, cyclobutylmethyl, cyclopentylmethyl, cyclopentylethyl, cyclohexylpropyl and the like) optionally fused with a benzene ring.

The "hydrocarbon group" is preferably a $C_{1-6}$ alkyl, a $C_{6-14}$ aryl, a $C_{7-19}$ aralkyl, a $C_{3-6}$ cycloalkyl optionally fused with a benzene ring, a $C_{3-6}$ cycloalkyl-$C_{1-6}$ alkyl optionally fused with a benzene ring and the like.

As the "substituent" of the aforementioned "hydrocarbon group optionally having substituent(s)", for example, a halogen atom (e.g., fluorine, chlorine, bromine, iodine and the like), a $C_{1-3}$ alkylenedioxy (e.g., methylenedioxy, ethylenedioxy and the like), a nitro, a cyano, an optionally halogenated $C_{1-10}$ alkoxy, an optionally halogenated $C_{1-10}$ alkylthio, a hydroxy, an amino, a mono- or di-$C_{1-10}$ alkylamino (e.g., methylamino, ethylamino, propylamino, isopropylamino, butylamino, dimethylamino, diethylamino, dipropylamino, dibutylamino, ethylmethylamino and the like), a formyl, a carboxy, carbamoyl, thiocarbamoyl, an optionally halogenated $C_{1-6}$ alkyl-carbonyl, a $C_{1-6}$ alkoxy-carbonyl (e.g., methoxycarbonyl, ethoxycarbonyl, propoxycarbonyl, tert-butoxycarbonyl and the like), a 5- to 10-membered aromatic heterocyclic group optionally having substituent(s), a $C_{6-14}$ aryl-carbonyl optionally having substituent(s), a $C_{6-14}$ aryloxy-carbonyl optionally having substituent(s), a $C_{7-19}$ aralkyloxy-carbonyl optionally having substituent(s), a 5- or 6-membered heterocyclylcarbonyl optionally having substituent(s), a mono- or di-$C_{1-6}$ alkyl-carbamoyl (e.g., methylcarbamoyl, ethylcarbamoyl, dimethylcarbamoyl, diethylcarbamoyl, ethylmethylcarbamoyl and the like), a $C_{6-14}$ arylcarbamoyl optionally having substituent(s), a 5- or 6-membered heterocyclylcarbamoyl optionally having substituent(s), an optionally halogenated $C_{1-6}$ alkylsulfonyl, a $C_{6-14}$ arylsulfonyl optionally having substituent(s), a formylamino, a $C_{1-6}$ alkyl-carbonyloxy (e.g., acetoxy, propanoyloxy and the like), a $C_{6-14}$ aryl-carbonyloxy optionally having substituent(s), a $C_{1-6}$ alkoxy-carbonyloxy (e.g., methoxycarbonyloxy, ethoxycarbonyloxy, propoxycarbonyloxy, butoxycarbonyloxy and the like), a mono- or di-$C_{1-6}$ alkyl-carbamoyloxy (e.g., methylcarbamoyloxy, ethylcarbamoyloxy, dimethylcarbamoyloxy, diethylcarbamoyloxy and the like), a $C_{6-14}$ aryl-carbamoyloxy optionally having substituent(s), a 5- or 6-membered heterocyclylcarbonyloxy optionally having substituent(s) and the like can be mentioned. The number of the substituents is, for example, 1 to 5, preferably 1 to 3. When the number of the substituents is not less than 2, respective substituents may be the same or different.

Here, as the "optionally halogenated $C_{1-10}$ alkoxy" and "optionally halogenated $C_{1-10}$ alkylthio", those exemplified as the "substituent" of the "cyclic group optionally having substituent(s)" for the aforementioned $Ar^1$ can be used respectively.

As the aforementioned "optionally halogenated $C_{1-6}$ alkyl-carbonyl" and "optionally halogenated $C_{1-6}$ alkylsulfonyl", those exemplified as the "substituent" of the aforementioned "$C_{7-19}$ aralkyl optionally having substituent(s)" can be used respectively.

As the "5- to 10-membered aromatic heterocyclic group" of the aforementioned "5- to 10-membered aromatic heterocyclic group optionally having substituent(s)", for example, a 5- to 10-membered monocyclic or bicyclic aromatic heterocyclic group containing, besides carbon atoms, 1 to 4 hetero atoms selected from a nitrogen atom, a sulfur atom and an oxygen atom, can be mentioned. To be specific, for example, 2- or 3-thienyl; 2-, 3- or 4-pyridyl; 2- or 3-furyl; 2-, 4- or 5-thiazolyl; 2-, 4- or 5-oxazolyl; 1-, 3- or 4-pyrazolyl; 2-pyrazinyl; 2-, 4- or 5-pyrimidinyl; 1-, 2- or 3-pyrrolyl; 1-, 2- or 4-imidazolyl; 3- or 4-pyridazinyl; 3-isothiazolyl; 3-isoxazolyl; 1,2,4-oxadiazol-5-yl; 1,2,4-oxadiazol-3-yl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzofuranyl; 2-, 4-, 5- or 6-benzothiazolyl; 1-, 2-, 4-, 5- or 6-benzimidazolyl and the like can be mentioned.

As the "$C_{6-14}$ aryl-carbonyl" of the aforementioned "$C_{6-14}$ aryl-carbonyl optionally having substituent(s)", for example, benzoyl, 1-naphthoyl, 2-naphthoyl and the like can be mentioned.

As the "$C_{6-14}$ aryloxy-carbonyl" of the aforementioned "$C_{6-14}$ aryloxy-carbonyl optionally having substituent(s)", for example, phenyloxycarbonyl, 1-naphthyloxycarbonyl, 2-naphthyloxycarbonyl and the like can be mentioned.

As the "$C_{7-19}$ aralkyloxy-carbonyl" of the aforementioned "$C_{7-19}$ aralkyloxy-carbonyl optionally having substituent(s)", for example, benzyloxycarbonyl, phenethyloxycarbonyl, diphenylmethyloxycarbonyl, triphenylmethyloxycarbonyl, 1-naphthylmethyloxycarbonyl, 2-naphthylmethyloxycarbonyl, 2,2-diphenylethyloxycarbonyl, 3-phenylpropyloxycarbonyl, 4-phenylbutyloxycarbonyl, 5-phenylpentyloxycarbonyl and the like can be mentioned.

As the "5- or 6-membered heterocyclylcarbonyl" of the aforementioned "5- or 6-membered heterocyclylcarbonyl optionally having substituent(s)", those exemplified as the "substituent" of the aforementioned "$C_{7-19}$ aralkyl optionally having substituent(s)" can be used.

As the "$C_{6-14}$ aryl-carbamoyl" of the aforementioned "$C_{6-14}$ aryl-carbamoyl optionally having substituent(s)", for example, phenylcarbamoyl, 1-naphthylcarbamoyl, 2-naphthylcarbamoyl and the like can be mentioned.

As the "5- or 6-membered heterocyclylcarbamoyl" of the aforementioned "5- or 6-membered heterocyclylcarbamoyl optionally having substituent(s)", those exemplified as the "substituent" of the aforementioned "$C_{7-19}$ aralkyl optionally having substituent(s)" can be used.

As the "$C_{6-14}$ arylsulfonyl" of the aforementioned "$C_{6-14}$ arylsulfonyl optionally having substituent(s)", for example, phenylsulfonyl, 1-naphthylsulfonyl, 2-naphthylsulfonyl and the like can be mentioned.

As the "$C_{6-14}$ aryl-carbonyloxy" of the aforementioned "$C_{6-14}$ aryl-carbonyloxy optionally having substituent(s)", for example, benzoyloxy, 1-naphthoyloxy, 2-naphthoyloxy and the like can be mentioned.

As the "$C_{6-14}$ aryl-carbamoyloxy" of the aforementioned "$C_{6-14}$ aryl-carbamoyloxy optionally having substituent(s)", for example, phenylcarbamoyloxy, naphthylcarbamoyloxy and the like can be mentioned.

As the "5- or 6-membered heterocyclylcarbonyloxy" of the aforementioned "5- or 6-membered heterocyclylcarbonyloxy optionally having substituent(s)", for example, nicotinoyloxy, isonicotinoyloxy, 2-thenoyloxy, 3-thenoyloxy, 2-furoyloxy, 3-furoyloxy, morpholinocarbonyloxy, piperidinocarbonyloxy, pyrrolidin-1-ylcarbonyloxy and the like can be mentioned.

As the "substituent" of the aforementioned "5- to 10-membered aromatic heterocyclic group optionally having substituent(s)", "$C_{6-14}$ aryl-carbonyl optionally having substituent(s)", "$C_{6-14}$ aryloxy-carbonyl optionally having substituent(s)", "$C_{7-19}$ aralkyloxy-carbonyl optionally having substituent(s)", "5- or 6-membered heterocyclylcarbonyl optionally having substituent(s)", "$C_{6-14}$ aryl-carbamoyl optionally having substituent(s)", "5- or 6-membered heterocyclylcarbamoyl optionally having substituent(s)", "$C_{6-14}$ arylsulfonyl optionally having substituent(s)", "$C_{6-14}$ aryl-carbonyloxy optionally having substituent(s)", "$C_{6-14}$ aryl-carbamoyloxy optionally having substituent(s)" and "5- or 6-membered heterocyclylcarbonyloxy optionally having substituent(s)", those exemplified as the. "substituent" of the aforementioned "$C_{7-19}$ aralkyl optionally having substituent(s)" can be mentioned. The number of the substituents is, for example, 1 to 5, preferably 1 to 3. When the number of the substituents is not less than 2, respective substituents may be the same or different.

As the "heterocyclic group" of the "heterocyclic group optionally having substituent(s)" for $R^3$, for example, a 5- to 14-membered (monocyclic, bicyclic or tricyclic) heterocyclic group containing, besides carbon atoms, 1 to 4 hetero atoms selected from a nitrogen atom, a sulfur atom and an oxygen atom, can be mentioned, preferably (i) a aromatic heterocyclic group, (ii) a 5- to 10-membered non-aromatic heterocyclic group, (iii) a 7- to 10-membered crosslinked heterocyclic group and the like can be mentioned.

Here, as the "aromatic heterocyclic group", for example, a 5- to 14-membered, preferably 5- to 10-membered aromatic heterocyclic group containing, besides carbon atoms, one or more (e.g., 1 to 4) hetero atoms selected from a nitrogen atom, a sulfur atom and an oxygen atom, and the like can be mentioned. To be specific, an aromatic heterocyclic group such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, oxadiazolyl, thiadiazolyl, furazanyl, benzothienyl, benzofuranyl, benzimidazolyl, benzoxazolyl, benzothiazolyl, benzisothiazolyl, naphtho[2,3-b]thiophenyl, phenoxathiinyl, indolyl, isoindolyl, 1H-indazolyl, purinyl, 4H-quinolizinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl, phthalimido and the like, a group formed by condensing such group with one or more (preferably 1 or 2) aromatic rings (e.g., a benzene ring etc.), and the like can be mentioned.

As the "5- to 10-membered non-aromatic heterocyclic group", for example, pyrrolidinyl, imidazolidinyl, 2- or 4-imidazolinyl, 2-oxazolinyl, oxazolidinyl, 2- or 3-pyrazolinyl, pyrazolidinyl, 2-thiazolinyl, piperidinyl, piperazinyl, hexamethyleniminyl, morpholinyl, thiomorpholinyl and the like can be mentioned.

As the "7- to 10-membered crosslinked heterocyclic group", for example, quinuclidinyl, 7-azabicyclo[2.2.1]heptanyl and the like can be mentioned.

The "heterocyclic group" is preferably a 5- to 10-membered (monocyclic or bicyclic) heterocyclic group containing, besides carbon atoms, 1 to 4 hetero atoms selected from a nitrogen atom, a sulfur atom and an oxygen atom. As specific examples, an aromatic heterocyclic group such as 2- or 3-thienyl; 2-, 3- or 4-pyridyl; 2- or 3-furyl; 2-, 4- or 5-thiazolyl; 2-, 4- or 5-oxazolyl; 1-, 3- or 4-pyrazolyl; 2-pyrazinyl; 2-, 4- or 5-pyrimidinyl; 1-, 2- or 3-pyrrolyl; 1-, 2- or 4-imidazolyl; 3- or 4-pyridazinyl; 3-isothiazolyl; 3-isoxazolyl; 1,2,4-oxadiazol-5-yl; 1,2,4-oxadiazol-3-yl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzofuranyl; 2-, 3-, 4-, 5- or 6-benzothienyl; 2-, 4-, 5- or 6-benzothiazolyl; 1-, 2-, 4-, 5- or 6-benzimidazolyl and the like;

a non-aromatic heterocyclic group such as 1-, 2- or 3-pyrrolidinyl; 1-, 2-, 4- or 5-imidazolidinyl; 2- or 4-imidazolinyl; 2-, 3- or 4-pyrazolidinyl; piperidino; 2-, 3- or 4-piperidinyl; 1- or 2-piperazinyl; morpholino and the like, and the like can be mentioned.

As the "substituent" of the "heterocyclic group optionally having substituent(s)", those exemplified as the "substituent" of the aforementioned "$C_{7-19}$ aralkyl optionally having substituent(s)" can be used. The number of the substituents is, for example, 1 to 5, preferably 1 to 3. When the number of the substituents is not less than 2, respective substituents may be the same or different.

As the "$C_{1-6}$ alkyl" for $R^4$, for example, methyl, ethyl, propyl, isopropyl, butyl, isobutyl, sec-butyl, tert-butyl, pentyl, hexyl and the like can be mentioned.

As the "nitrogen-containing heterocycle" of the "nitrogen-containing heterocycle optionally having substituent(s)" formed by $R^3$ and $R^4$ together with the adjacent nitrogen atom, for example, a 3- to 10-membered (preferably 3- to 8-membered) nitrogen-containing heterocycle containing at least one nitrogen atom and optionally further containing, besides carbon atoms, 1 to 3 hetero atoms selected from a nitrogen atom, a sulfur atom and an oxygen atom, and optionally fused with a benzene ring, can be mentioned. As specific examples, aziridine, azetidine, morpholine, thiomorpholine, piperidine, piperazine, pyrrolidine, hexamethylenimine (azepane), heptamethylenimine, hexahydropyrimidine, 1,4-diazepane, thiazolidine, imidazolidine, heptahydroindole, decahydroquinoline, decahydroisoquinoline, and an unsaturated cyclic amine thereof (e.g., 1,2,5,6-tetrahydropyridine, 1H-imidazole, 4,5-dihydro-1H-imidazole, 2,3-dihydroindole, 1,2,3,4-tetrahydroquinoline, 1,2,3,4-tetrahydroisoquinoline and the like) and the like can be mentioned. Of these, piperidine, piperazine, pyrrolidine, hexamethylenimine (azepane), morpholine, thiomorpholine and the like are preferable.

As the "substituent" of the "nitrogen-containing heterocycle optionally having substituent(s)", those exemplified as the "substituent" of the aforementioned "$C_{7-19}$ aralkyl optionally having substituent(s)" can be used. The number of the substituents is, for example, 1 to 5, preferably 1 to 3. When the number of the substituents is not less than 2, respective substituents may be the same or different. The substituent is preferably an optionally halogenated $C_{1-10}$ alkyl, an optionally halogenated $C_{1-6}$ alkylsulfonyl and the like.

The "acyl" is preferably a formyl, a carboxy, a carbamoyl, an optionally halogenated $C_{1-6}$ alkyl-carbonyl (e.g., acetyl, propanoyl, 2-methylpropanoyl, butanoyl, 3-methylbutanoyl, pentanoyl, hexanoyl and the like), a $C_{1-6}$ alkoxy-carbonyl (e.g., methoxycarbonyl, ethoxycarbonyl, propoxycarbonyl, tert-butoxycarbonyl and the like), a $C_{6-14}$ aryl-carbonyl (e.g., benzoyl, 1-naphthoyl, 2-naphthoyl and the like) optionally having substituent(s), a $C_{6-14}$ aryloxy-carbonyl (e.g., phenyloxycarbonyl, 1-naphthyloxycarbonyl, 2-naphthyloxycarbonyl and the like) optionally having substituent(s), a $C_{7-19}$ aralkyloxy-carbonyl (e.g., benzyloxycarbonyl, phenethyloxycarbonyl and the like) optionally having substituent(s), a 5- or 6-membered heterocyclylcarbonyl (e.g., nicotinoyl, tetrahydrofuroyl and the like) optionally having substituent(s), a mono- or di-$C_{1-6}$ alkyl-carbamoyl (e.g., methylcarbamoyl, ethylcarbamoyl, dimethylcarbamoyl, diethylcarbamoyl, ethylmethylcarbamoyl and the like), a $C_{6-14}$ aryl-carbamoyl optionally having substituent(s) (e.g., phenylcarbamoyl, 4-methoxyphenylcarbamoyl, 3,4-dimethoxyphenylcarbamoyl and the like), a 5- or 6-membered heterocyclylcarbamoyl (e.g., pyridylcarbamoyl and the like) optionally having substituent(s), an optionally halogenated $C_{1-6}$ alkylsulfonyl (e.g., methylsulfonyl, propylsulfonyl, butylsulfonyl and the like), a $C_{6-14}$ arylsulfonyl (e.g., phenylsulfonyl and the like) optionally having substituent(s), a $C_{3-6}$ cycloalkyl-carbonyl (e.g., cyclopropylcarbonyl, cyclohexylcarbonyl and the like) optionally having substituent(s), a $C_{3-6}$ cycloalkyl-$C_{1-6}$ alkyl-carbonyl (e.g., cyclopropylmethylcarbonyl, cyclopropylethylcarbonyl, cyclopentylmethylcarbonyl, cyclohexylmethylcarbonyl and the like) optionally having substituent(s) and the like.

Here, as the "optionally halogenated $C_{1-6}$ alkyl-carbonyl" and "optionally halogenated $C_{1-6}$ alkylsulfonyl", those exemplified as the "substituent" of the aforementioned "$C_{7-19}$ aralkyl optionally having substituent(s)" can be used respectively.

As the "$C_{6-14}$ aryl-carbonyl optionally having substituent(s)", "$C_{6-14}$ aryloxy-carbonyl optionally having substituent(s)", "$C_{7-19}$ aralkyloxy-carbonyl optionally having substituent(s)", "5- or 6-membered heterocyclylcarbonyl optionally having substituent(s)", "$C_{6-14}$ aryl-carbamoyl optionally having substituent(s)", "5- or 6-membered heterocyclylcarbamoyl optionally having substituent(s)" and "$C_{6-14}$ arylsulfonyl optionally having substituent(s)", those exemplified as the "substituent" of the "hydrocarbon group optionally having substituent(s)" for the aforementioned $R^4$ can be used respectively.

As the substituent of the "$C_{3-6}$ cycloalkyl-carbonyl optionally having substituent(s)" and "$C_{3-6}$ cycloalkyl-$C_{1-6}$ alkyl-carbonyl optionally having substituent(s)", those exemplified as the "substituent" of the aforementioned "$C_{7-19}$ aralkyl optionally having substituent(s)" can be used. The number of the substituents is, for example, 1 to 3. When the number of the substituents is not less than 2, respective substituents may be the same or different.

As the "acylamino" exemplified as the "substituent" for the aforementioned $Ar^1$, for example, an amino mono- or di-substituted by the aforementioned "acyl" can be mentioned, preferably an acylamino represented by formula: —$NR^5$—$COR^6$, —$NR^5$—$COOR^6$, —$NR^5$—$SO_2R^6$, —$NR^5$—$CONR^6R^7$, —$NR^5$—PO(—$OR^6$)—$OR^7$ or —$NR^5$—$PO_2$—$R^6$ [wherein $R^5$ is a hydrogen atom or a $C_{1-6}$ alkyl; $R^6$ is as defined for the aforementioned $R^3$; and $R^7$ is as defined for $R^4$], and the like can be mentioned.

As the "$C_{1-6}$ alkyl" for $R^5$, those exemplified for the aforementioned $R^4$ can be mentioned.

The "acylamino" is preferably a formylamino, an optionally halogenated $C_{1-6}$ alkyl-carboxamido (e.g., methylcarboxamido, trifluoromethylcarboxamido, propylcarboxamido, isopropylcarboxamido, butylcarboxamido and the like), a $C_{6-14}$ aryl-carboxamido optionally having substituent(s) (e.g., phenylcarboxamido, 2-methoxyphenylcarboxamido, 4-methoxyphenylcarboxamido, propanoylmethylphenylcarboxamido and the like), a N—($C_{6-14}$ aryl-carbonyl optionally having substituent(s)) —N—$C_{1-6}$ alkylamino (e.g., N-4-methoxybenzoyl-N-methylamino and the like), a $C_{7-19}$ aralkyl-carboxamido (e.g., benzylcarboxamido and the like) optionally having substituent(s), an aromatic heterocyclyl-carboxamido (e.g., benzothiophen-2-yl-carboxamido and the like) optionally having substituent(s), an optionally halogenated $C_{1-6}$ alkoxy-carboxamido (e.g., methoxycarboxamido, ethoxycarboxamido, propoxycarboxamido, butoxycarboxamido and the like), a $C_{6-14}$ arylamino-carbonylamino (e.g., phenylaminocarbonylamino and the like) optionally having substituent(s), an optionally halogenated $C_{1-6}$ alkylsulfonylamino (e.g., methylsulfonylamino, trifluoromethylsulfonylamino, ethylsulfonylamino and the like), a $C_{6-14}$ arylsulfonylamino optionally having substituent(s) (e.g., 4-methoxyphenylsulfonylamino and the like) and the like.

Here, as the "substituent" of the "$C_{6-14}$ aryl-carboxamido optionally having substituent(s)", "N—($C_{6-14}$ aryl-carbonyl optionally having substituent(s)) —N—$C_{1-6}$ alkylamino", "$C_{7-19}$ aralkyl-carboxamido optionally having substituent(s)", "aromatic heterocyclyl-carboxamido optionally having substituent(s)", "$C_{6-14}$ arylamino-carbonylamino optionally having substituent(s)" and "$C_{6-14}$ arylsulfonylamino optionally having substituent(s)", those exemplified as the "substituent" of the aforementioned "$C_{7-19}$ aralkyl optionally having substituent(s)" can be used. The number of the substituents is, for example, 1 to 5, preferably 1 to 3. When the number of the substituents is not less than 2, respective substituents may be the same or different.

As the "acyloxy" exemplified as the "substituent" for the aforementioned $Ar^1$, for example, an oxy mono-substituted by the aforementioned "acyl" can be mentioned, preferably an acyloxy represented by the formula: —O—$COR^8$, —O—$COOR^8$, —O—$CONHR^8$, —O—PO(OH)—$OR^8$ or —O—$PO_2$—$R^8$ [wherein $R^8$ is as defined for the aforementioned $R^3$], and the like can be mentioned.

The "acyloxy" is preferably an optionally halogenated $C_{1-6}$ alkyl-carbonyloxy (e.g., acetoxy, propanoyloxy, butanoyloxy and the like), a $C_{6-14}$ aryl-carbonyloxy optionally having substituent(s) (e.g., benzoyloxy, 4-methoxybenzoyloxy and the like), an optionally halogenated $C_{1-6}$ alkoxy-carbonyloxy (e.g., methoxycarbonyloxy, trifluoromethoxycarbonyloxy, ethoxycarbonyloxy, propoxycarbonyloxy, butoxycarbonyloxy and the like), a mono- or di-$C_{1-6}$ alkyl-carbamoyloxy (e.g., methylcarbamoyloxy, ethylcarbamoyloxy, dimethylcarbamoyloxy, diethylcarbamoyloxy and the like), a $C_{6-14}$ aryl-carbamoyloxy (e.g., phenylcarbamoyloxy, naphthylcarbamoyloxy and the like) optionally having substituent(s), nicotinoyloxy and the like.

As the "substituent" of the "$C_{6-14}$ aryl-carbonyloxy optionally having substituent(s)" and "$C_{6-14}$ aryl-carbamoyloxy optionally having substituent(s)", those exemplified as the "substituent" of the aforementioned "$C_{7-19}$ aralkyl optionally having substituent(s)" can be used. The number of the substituents is, for example, 1 to 5, preferably 1 to 3. When the number of the substituents is not less than 2, respective substituents may be the same or different.

As the "acyl-$C_{1-6}$ alkyl", "acylamino-$C_{1-6}$ alkyl" and "acyloxy-$C_{1-6}$ alkyl" exemplified as the "substituent" for the aforementioned $Ar^1$, a $C_{1-6}$ alkyl (e.g., methyl, ethyl, propyl, isopropyl, butyl, isobutyl, sec-butyl, tert-butyl, pentyl, hexyl and the like) substituted by the aforementioned "acyl", "acylamino" and "acyloxy" can be mentioned respectively.

The "substituent" of the "cyclic group optionally having substituent(s)" for $Ar^1$ is preferably a halogen atom (e.g., fluorine, chlorine, bromine, iodine and the like), a $C_{1-3}$ alkylenedioxy (e.g., methylenedioxy, ethylenedioxy and the like), a nitro, a cyano, an optionally halogenated $C_{1-10}$ alkyl, an aromatic group optionally having substituent(s), a non-aromatic group optionally having substituent(s), an optionally halogenated $C_{1-10}$ alkoxy, a $C_{6-14}$ aryloxy optionally having substituent(s), a $C_{7-19}$ aralkyloxy optionally having substituent(s), a $C_{3-6}$ cycloalkyl-$C_{1-6}$ alkyl optionally having substituent(s), a $C_{3-6}$ cycloalkyl-$C_{1-6}$ alkoxy optionally having substituent(s), an acyl, an acyl-$C_{1-6}$ alkyl, a hydroxy, a $C_{1-6}$ alkoxy-$C_{1-6}$ alkoxy, an optionally halogenated $C_{1-10}$ alkylthio, an acylamino, an acyloxy, an acyl-$C_{1-6}$ alkyl and the like.

$Ar^1$ is preferably a group represented by the formula: $Ar^3$—$Ar^2$— (wherein $Ar^2$ is a cyclic group optionally having substituent(s) and $Ar^3$ is an aromatic group optionally having substituent(s)).

Here, as the "cyclic group" of the "cyclic group optionally having substituent(s)" for $Ar^2$, the "aromatic group", "non-aromatic cyclic hydrocarbon group" and "non-aromatic heterocyclic group" exemplified for the aforementioned $Ar^1$ can be mentioned. The "cyclic group" is preferably phenyl, a 5- or 6-membered aromatic heterocyclic group, a 5- to 8-membered monocyclic non-aromatic heterocyclic group and the like, more preferably phenyl, pyridyl, piperidinyl and the like.

As the "substituent" of the "cyclic group optionally having substituent(s)" for $Ar^2$, those exemplified as the substituent for the aforementioned $Ar^1$ can be used. The number of the substituents is, for example, 1 to 4, preferably 1 to 3. When the number of the substituents is not less than 2, respective substituents may be the same or different. The substituent is preferably a halogen atom (preferably fluorine, chlorine and the like), an optionally halogenated $C_{1-6}$ alkyl (preferably methyl, trifluoromethyl, ethyl and the like) and the like.

As the "aromatic group optionally having substituent(s)" for $Ar^3$, those exemplified as the "substituent" of the "cyclic group optionally having substituent(s)" for the aforementioned $Ar^1$ can be mentioned. The "aromatic group" is preferably phenyl, naphthyl, a 5- or 6-membered aromatic heterocyclic group, a 9- to 10-membered fused polycyclic aromatic heterocyclic group and the like, more preferably phenyl, a 5- or 6-membered aromatic heterocyclic group and the like. Of these, phenyl, pyridyl and the like are preferable.

The "aromatic group" optionally has, for example, 1 to 4, preferably 1 to 3, substituents at substitutable positions. As such substituents, those exemplified as the "substituent" of the aforementioned "$C_{7-19}$ aralkyl optionally having substituent(s)" can be mentioned. Of these, a halogen atom (preferably fluorine, chlorine and the like), an optionally halogenated $C_{1-6}$ alkyl (preferably methyl, trifluoromethyl, ethyl and the like), an optionally halogenated $C_{1-6}$ alkoxy (preferably methoxy, trifluoromethoxy and the like), an optionally halogenated $C_{1-6}$ alkylthio (preferably methylthio and the like), a $C_{1-3}$ alkylenedioxy (preferably methylenedioxy, ethylenedioxy and the like), an optionally halogenated $C_{1-6}$ alkyl-carbonyl (preferably acetyl and the like), an optionally halogenated $C_{1-6}$ alkyl-carboxamido (preferably isopropylcarboxamido and the like) and the like are preferable.

As specific examples of the aforementioned group represented by the formula: $Ar^3$—$Ar^2$— (the symbols in the formula are as defined above), 2-, 3- or 4-biphenylyl; 3-(1-naphthyl)-1,2,4-oxadiazol-5-yl; 3-(2-naphthyl)-1,2,4-oxadiazol-5-yl; 3-(2-benzofuranyl)-1,2,4-oxadiazol-5-yl; 3-phenyl-1,2,4-oxadiazol-5-yl; 3-(2-benzoxazolyl)-1,2,4-oxadiazol-5-yl; 3-(3-indolyl)-1,2,4-oxadiazol-5-yl; 3-(2-indolyl)-1,2,4-oxadiazol-5-yl; 4-phenylthiazol-2-yl; 4-(2-benzofuranyl)thiazol-2-yl; 4-phenyl-1,3-oxazol-5-yl; 5-phenylisothiazol-4-yl; 5-phenyloxazol-2-yl; 4-(2-thienyl)phenyl; 4-(3-thienyl)phenyl; 3-(3-pyridyl)phenyl; 4-(3-pyridyl)phenyl; 6-phenyl-3-pyridyl; 5-phenyl-1,3,4-oxadiazol-2-yl; 4-(2-naphthyl)phenyl; 4-(2-benzofuranyl)phenyl; 4,4'-terphenyl; 5-phenyl-2-pyridyl; 2-phenyl-5-pyrimidinyl; 4-(4-pyridyl)phenyl; 2-phenyl-1,3-oxazol-5-yl; 2,4-diphenyl-1,3-oxazol-5-yl; 3-phenyl-isoxazol-5-yl; 5-phenyl-2-furyl; 4-(2-furyl)phenyl; 4-(3-furyl)phenyl; 4-(2-benzothienyl)phenyl; 4-phenyl-1-pyrrolidinyl; 4-phenyl-1-piperidinyl and the like, each of which optionally has 1 to 3 substituents, can be mentioned. Of these, 2-, 3- or 4-biphenylyl; 4-(2-thienyl)phenyl; 4-(3-thienyl)phenyl; 4-(2-furyl)phenyl; 4-(3-furyl)phenyl; 6-phenyl-3-pyridyl; 5-phenyl-2-pyridyl; 4-(2-naphthyl)phenyl; 4-(2-benzofuranyl)phenyl; 4-(2-benzothienyl) phenyl; 4-phenyl-1-piperidinyl and the like are preferable.

Here, as preferable examples of the substituent, a halogen atom (preferably fluorine, chlorine and the like), an optionally halogenated $C_{1-6}$ alkyl (preferably methyl, trifluoromethyl, ethyl and the like), an optionally halogenated $C_{1-6}$ alkoxy (preferably methoxy, trifluoromethoxy and the like), an optionally halogenated $C_{1-6}$ alkylthio (preferably methylthio and the like), a $C_{1-3}$ alkylenedioxy (preferably methylenedioxy, ethylenedioxy and the like), an optionally halogenated $C_{1-6}$ alkyl-carbonyl (preferably acetyl and the like), an optionally halogenated $C_{1-6}$ alkyl-carboxamido (preferably isopropylcarboxamido and the like) and the like can be mentioned.

As preferable examples of $Ar^1$, phenyl, a 5- or 6-membered aromatic heterocyclic group or a 5- to 8-membered monocyclic non-aromatic heterocyclic group (preferably phenyl, pyridyl, piperidinyl), each optionally having 1 to 3 substituents selected from a halogen atom (e.g., fluorine, chlorine, bromine, iodine and the like), a $C_{1-3}$ alkylenedioxy (e.g., methylenedioxy, ethylenedioxy and the like), a nitro, a cyano, an optionally halogenated $C_{1-10}$ alkyl (e.g., methyl, ethyl, propyl, butyl, pentyl), an optionally halogenated $C_{1-10}$ alkoxy (e.g., methoxy, ethoxy, propoxy, butoxy, isobutoxy, pentyloxy, isopentyloxy and the like), a $C_{6-14}$ aryloxy (preferably phenoxy) optionally having substituent(s) (preferably a halogen atom, an optionally halogenated $C_{1-10}$ alkyl, an optionally halogenated $C_{1-10}$ alkoxy and the like), a $C_{7-19}$ aralkyloxy (preferably benzyloxy) optionally having substituent(s) (preferably a halogen atom, an optionally halogenated $C_{1-10}$ alkyl, an optionally halogenated $C_{1-10}$ alkoxy and the like), a $C_{3-6}$ cycloalkyl-$C_{1-6}$ alkyl (preferably cyclopropylmethyl) optionally having substituent(s) (preferably a halogen atom, an optionally halogenated $C_{1-10}$ alkyl, an optionally halogenated $C_{1-10}$ alkoxy and the like), a $C_{3-6}$ cycloalkyl-$C_{1-6}$ alkoxy (preferably cyclopropylmethoxy, cyclopropylethoxy) optionally having substituent(s) (preferably a halogen atom, an optionally halogenated $C_{1-10}$ alkyl, an optionally halogenated $C_{1-10}$ alkoxy and the like), an acyl [preferably an optionally halogenated $C_{1-6}$ alkyl-carbonyl (e.g., pentanoyl, hexanoyl and the like), an optionally halogenated $C_{1-6}$ alkylsulfonyl (e.g., butylsulfonyl and the like) and the like], an acyl-$C_{1-6}$ alkyl [preferably an optionally halogenated $C_{1-6}$ alkyl-carbonyl-$C_{1-6}$ alkyl (e.g., propanoylmethyl, propanoylethyl, 2-methylpropanoylmethyl, butanoylmethyl, 3-methylbutanoylmethyl, pentanoylmethyl and the like), an optionally halogenated $C_{1-6}$ alkylsulfonyl-$C_{1-6}$ alkyl (e.g., propylsulfonylmethyl, butylsulfonylmethyl and the like), a $C_{6-14}$ aryl-carbonyl-$C_{1-6}$ alkyl (e.g., benzoylmethyl and the like), a $C_{3-6}$ cycloalkyl-carbonyl-$C_{1-6}$ alkyl (e.g., cyclopropylcarbonylmethyl, cyclobutylcarbonylmethyl and the like), a 5- or 6-membered heterocyclylcarbonyl-$C_{1-6}$ alkyl (e.g., tetrahydrofuroylmethyl and the like) and the like], a hydroxy, a $C_{1-6}$ alkoxy-$C_{1-6}$ alkoxy (preferably methoxymethoxy, ethoxyethoxy), an optionally halogenated $C_{1-10}$ alkylthio (preferably methylthio, butylthio and the like), an acylamino [preferably an optionally halogenated $C_{1-6}$ alkyl-carboxamido (e.g., propylcarboxamido, isopropylcarboxamido, butylcarboxamido and the like), a $C_{6-14}$ aryl-carboxamido optionally having substituent(s) (preferably a $C_{1-6}$ alkyl-carbonyl-$C_{1-6}$ alkyl) (preferably phenylcarboxamido, propanoylmethylphenylcarboxamido and the like) and the like], an acyloxy [preferably a $C_{1-6}$ alkyl-carbonyloxy (e.g., propanoyloxy, butanoyloxy and the like)] and the like, can be also mentioned.

Of the above-mentioned substituents, a halogen atom, a $C_{1-3}$ alkylenedioxy, a nitro, a cyano, an optionally halogenated $C_{1-10}$ alkyl, an optionally halogenated $C_{1-10}$ alkoxy, a $C_{6-14}$ aryloxy optionally having substituent(s), a $C_{7-19}$ aralkyloxy optionally having substituent(s), a $C_{3-6}$ cycloalkyl-$C_{1-6}$ alkoxy optionally having substituent(s), an acyl, an acyl-$C_{1-6}$ alkyl and the like are preferable.

As the "alkylene group" of the "optionally halogenated alkylene group" for Y, for example, a $C_{1-6}$ alkylene group [for example, —$CH_2$—, —$(CH_2)_2$—, —$(CH_2)_3$—, —$(CH_2)_4$—, —$(CH_2)_5$—, —$(CH_2)_6$—, —$CH(CH_3)$—, —$CH(C_2H_5)$—, —$CH(CH(CH_3)_2)$—, —$C(CH_3)_2$—, —$(CH(CH_3))_2$—, —$(CH_2)_2C(CH_3)_2$— and —$(CH_2)_3C(CH_3)_2$—] and the like can be mentioned.

The alkylene group is optionally substituted by 1 to 5, preferably 1 to 3, halogen atoms (e.g., fluorine, chlorine, bromine, iodine). The halogen atom is preferably fluorine. When the alkylene group is substituted by two or more halogen atoms, the kinds of the halogen atoms may be the same or different.

Y is preferably a $C_{1-6}$ alkylene group, more preferably —$CH_2$—, —$CH(CH_3)$—, —$CH(C_2H_5)$—, —$CH(CH(CH_3)_2)$— and the like.

As the "optionally halogenated $C_{1-6}$ alkyl" for R, of the "optionally halogenated $C_{1-10}$ alkyl" exemplified as the "substituent" of the "cyclic group optionally having substituent(s)" for the aforementioned $Ar^1$, those having 1 to 6 carbon atoms can be used. The "optionally halogenated $C_{1-6}$ alkyl" is preferably a $C_{1-6}$ alkyl, particularly, methyl, ethyl, propyl, isopropyl and the like are preferable.

As the "substituent" of the "phenyl optionally having substituent(s)" and "pyridyl optionally having substituent(s)" for R, for example, a halogen atom (e.g., fluorine, chlorine, bromine, iodine and the like), a $C_{1-3}$ alkylenedioxy (e.g., methylenedioxy, ethylenedioxy and the like), a nitro, a cyano, an optionally halogenated $C_{1-10}$ alkyl, an optionally halogenated $C_{3-6}$ cycloalkyl, an optionally halogenated $C_{1-10}$ alkoxy, an optionally halogenated $C_{1-10}$ alkylthio, a hydroxy, an amino, a mono- or di-$C_{1-10}$ alkylamino (e.g., methylamino, ethylamino, propylamino, isopropylamino, butylamino, dimethylamino, diethylamino, dipropylamino, dibutylamino, ethylmethylamino and the like), a formyl, a carboxy, a carbamoyl, a thiocarbamoyl, an optionally halogenated $C_{1-6}$ alkyl-carbonyl, a $C_{1-6}$ alkoxy-carbonyl (e.g., methoxycarbonyl, ethoxycarbonyl, propoxycarbonyl, tert-butoxycarbonyl and the like), a mono- or di-$C_{1-6}$ alkyl-carbamoyl (e.g., methylcarbamoyl, ethylcarbamoyl, dimethylcarbamoyl, diethylcarbamoyl, ethylmethylcarbamoyl and the like), an optionally halogenated $C_{1-6}$ alkylsulfonyl, a formylamino, an optionally halogenated $C_{1-6}$ alkyl-carboxamido, a $C_{1-6}$ alkoxy-carboxamido (e.g., methoxycarboxamido, ethoxycarboxamido, propoxycarboxamido, butoxycarboxamido and the like), a $C_{1-6}$ alkylsulfonylamino (e.g., methylsulfonylamino, ethylsulfonylamino and the like), a $C_{1-6}$ alkyl-carbonyloxy (e.g., acetoxy, propanoyloxy and the like), a $C_{1-6}$ alkoxy-carbonyloxy (e.g., methoxycarbonyloxy, ethoxycarbonyloxy, propoxycarbonyloxy, butoxycarbonyloxy and the like), a mono- or di-$C_{1-6}$ alkyl-carbamoyloxy (e.g., methylcarbamoyloxy, ethylcarbamoyloxy, dimethylcarbamoyloxy, diethylcarbamoyloxy and the like), an aromatic group optionally having substituent(s) and the like can be mentioned. The number of the substituents is, for example, 1 to 5, preferably 1 to 3. When the number of the substituents is not less than 2, respective substituents may be the same or different.

Here, as the "optionally halogenated $C_{1-10}$ alkyl", "optionally halogenated $C_{1-10}$ alkoxy" and "optionally halogenated $C_{1-10}$ alkylthio", those exemplified as the "substituent" of the "cyclic group optionally having substituent(s)" for the aforementioned $Ar^1$ can be used.

As the "optionally halogenated $C_{1-6}$ alkyl-carbonyl", "optionally halogenated $C_{1-6}$ alkylsulfonyl" and "optionally halogenated $C_{1-6}$ alkyl-carboxamido", those exemplified as the "substituent" of the aforementioned "$C_{7-19}$ aralkyl optionally having substituent(s)" can be used.

As the "aromatic group optionally having substituent(s)", those exemplified as the substituent of the "cyclic group optionally having substituent(s)" for the aforementioned $Ar^1$ can be used.

R is preferably a hydrogen atom.

As the "optionally halogenated $C_{1-6}$ alkyl", "optionally halogenated $C_{1-6}$ alkoxy" and "optionally halogenated $C_{1-6}$ alkylthio" for $Ra^1$, $Ra^2$, $Ra^3$ or $Ra^4$, of the "optionally halogenated $C_{1-10}$ alkyl", "optionally halogenated $C_{1-10}$ alkoxy" and "optionally halogenated $C_{1-10}$ alkylthio" exemplified as the "substituent" of the "cyclic group optionally having substituent(s)" for the aforementioned $Ar^1$, those having 1 to 6 carbon atoms can be used respectively.

As the "optionally halogenated $C_{1-6}$ alkyl-carbonyl" and "optionally halogenated $C_{1-6}$ alkylsulfonyl" for $Ra^1$, $Ra^2$, $Ra^3$ or $Ra^4$, those exemplified as the "substituent" of the aforementioned "$C_{7-19}$ aralkyl optionally having substituent(s)" can be used respectively.

As the "substituent" of the "phenyl optionally having substituent(s)" and "pyridyl optionally having substituent(s)" for $Ra^1$, $Ra^2$, $Ra^3$ or $Ra^4$, those exemplified for the aforementioned R can be used.

As the "halogen atom" for $Ra^1$, $Ra^2$, $Ra^3$ or $Ra^4$, for example, fluorine, chlorine, bromine and iodine can be mentioned respectively.

As the "mono- or di-$C_{1-6}$ alkylamino" for $Ra^1$, $Ra^2$, $Ra^3$ or $Ra^4$, for example, an amino mono- or di-substituted by $C_{1-6}$ alkyl (e.g., methyl, ethyl, propyl, isopropyl, butyl) can be mentioned. To be specific, methylamino, ethylamino, propylamino, isopropylamino, butylamino, dimethylamino, diethylamino, dipropylamino, dibutylamino, ethylmethylamino and the like can be mentioned.

$Ra^1$, $Ra^2$, $Ra^3$ and $Ra^4$ are the same or different and each is preferably a hydrogen atom or an optionally halogenated $C_{1-6}$ alkyl. $Ra^1$, $Ra^2$, $Ra^3$ and $Ra^4$ are each more preferably a hydrogen atom.

As the "monocyclic aromatic ring" of the "monocyclic aromatic ring optionally having substituent(s)" for Ar, benzene and a 5- or 6-membered aromatic heterocycle can be mentioned.

As the "5- or 6-membered aromatic heterocycle", for example, a 5- or 6-membered aromatic heterocycle containing, besides carbon atoms, one or more (e.g., 1 to 3) hetero atoms selected from a nitrogen atom, a sulfur atom and an oxygen atom, can be mentioned. To be specific, thiophene, furan, pyrrole, imidazole, pyrazole, thiazole, isothiazole, oxazole, isoxazole, pyridine, pyrazine, pyrimidine, pyridazine, oxadiazole, thiadiazole, furazan and the like can be mentioned.

The "monocyclic aromatic ring" is preferably a benzene ring, a pyridine ring, a furan ring or a thiophene ring, more preferably a benzene ring.

When the "monocyclic aromatic ring" for Ar is a benzene ring, a pyridine ring, a furan ring or a thiophene ring, substitutable positions of a group represented by the formula

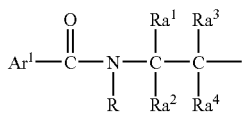

wherein the symbols in the formula are as defined above, and a group represented by the formula

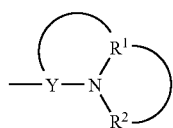

wherein the symbols in the formula are as defined above, are preferably 1,4-positions on benzene ring; 2,5-positions on pyridine ring; 2,5-positions or 2,4-positions on furan ring; or 2,5-positions or 2,4-positions on thiophene ring, represented by the formula

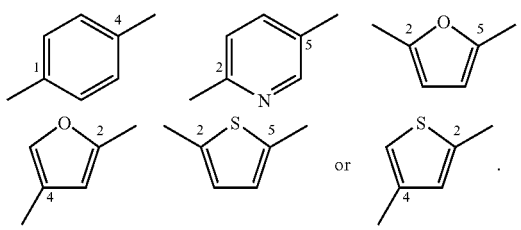

The "monocyclic aromatic ring" for Ar optionally further has substituent(s), besides a group represented by the formula

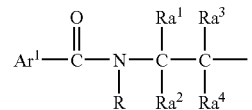

wherein the symbols in the formula are as defined above, and a group represented by the formula

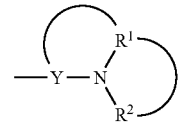

wherein the symbols in the formula are as defined above. As such "substituent", those similar to the "substituent" of the aforementioned "$C_{7-19}$ aralkyl optionally having substituent(s)" can be used.

The number of the substituents is 1 to 4, preferably 1 or 2. When the number of the substituents is not less than 2, respective substituents may be the same or different.

The substituent is preferably a halogen atom (preferably fluorine, chlorine, bromine and the like), an optionally halogenated $C_{1-10}$ alkyl (preferably methyl, ethyl, propyl, trifluoromethyl and the like), an optionally halogenated $C_{1-10}$ alkoxy (preferably methoxy, ethoxy and the like), an optionally halogenated $C_{1-10}$ alkylthio (preferably methylthio and the like), a hydroxy, an amino, a mono- or di-$C_{1-10}$ alkylamino (preferably methylamino, dimethylamino and the like), a formyl, a carboxy, a $C_{1-6}$ alkoxy-carbonyl (preferably methoxycarbonyl, ethoxycarbonyl and the like), an optionally halogenated $C_{1-6}$ alkyl-carboxamido (preferably methylcarboxamido, trifluoromethylcarboxamido and the like), a 5- or 6-membered non-aromatic heterocyclic group (preferably pyrrolidinyl and the like) and the like, more preferably a halogen atom (preferably fluorine, chlorine, bromine and the like), an optionally halogenated $C_{1-6}$ alkyl (preferably methyl, ethyl, propyl, trifluoromethyl and the like), an optionally halogenated $C_{1-6}$ alkoxy (preferably methoxy, ethoxy and the like) and the like.

Ar is preferably an unsubstituted benzene ring.

As the "$C_{1-6}$ alkyl" for $R^1$ or $R^2$, those exemplified for the aforementioned $R^5$ can be used. Of those, methyl, ethyl, propyl and isopropyl are preferable.

As the "nitrogen-containing heterocycle" of the "nitrogen-containing heterocycle optionally having substituent(s)" formed by $R^1$ and $R^2$ together with the adjacent nitrogen atom, those exemplified as the "nitrogen-containing heterocycle" of the "nitrogen-containing heterocycle optionally having substituent(s)" formed by the aforementioned $R^3$ and $R^4$ together with the adjacent nitrogen atom can be used. Of those, azetidine, morpholine, thiomorpholine, piperidine, piperazine, pyrrolidine, hexamethylenimine (azepane), 1,3-thiazolidine, 1H-imidazole, 4,5-dihydro-1H-imidazole, 2,3-dihydroindole, 1,2,3,4-tetrahydroquinoline, 1,2,3,4-tetrahydroisoquinoline and the like are preferable, and piperidine, piperazine, pyrrolidine, hexamethylenimine (azepane), morpholine, thiomorpholine and the like are more preferable. Particularly, piperidine, pyrrolidine, hexamethylenimine, morpholine and thiomorpholine are preferable.

As the "substituent" of the "nitrogen-containing heterocycle optionally having substituent(s)", for example, "$C_{7-19}$ aralkyl optionally having substituent(s)" and "aromatic group optionally having substituent(s)" exemplified as the "substituent" of the "cyclic group optionally having substituent(s)" for $Ar^1$ can be used in addition to the "substituent" exemplified for the aforementioned "$C_{7-19}$ aralkyl optionally having substituent(s)". The number of the substituents is, for example, 1 to 5, preferably 1 to 3. When the number of the substituents is not less than 2, the respective substituents may be the same or different.

The substituent is preferably an optionally halogenated $C_{1-10}$ alkyl (preferably methyl, ethyl, propyl, butyl, isobutyl and the like); an optionally halogenated $C_{3-6}$ cycloalkyl (preferably cyclohexyl and the like); a carbamoyl; a mono- or di-$C_{1-6}$ alkyl-carbamoyl (preferably methylcarbamoyl, ethylcarbamoyl, dimethylcarbamoyl, diethylcarbamoyl and the like); a 5- or 6-membered heterocyclylcarbonyl (preferably morpholinocarbonyl, piperidinocarbonyl, 1-pyrrolidinylcarbonyl and the like); an optionally halogenated $C_{1-6}$ alkylsulfonyl (preferably methylsulfonyl and the like); an optionally halogenated $C_{1-6}$ alkyl-carboxamido (preferably acetamido and the like); a hydroxy-$C_{1-6}$ alkyl (preferably hydroxymethyl, hydroxyethyl and the like); a carbamoyl-$C_{1-6}$ alkyl (preferably carbamoylmethyl, carbamoylethyl, carbamoylpropyl and the like); a mono- or di-$C_{1-6}$ alkyl-carbamoyl-$C_{1-6}$ alkyl (preferably methylcarbamoylmethyl, methylcarbamoylethyl, methylcarbamoylpropyl, dimethylcarbamoylmethyl, dimethylcarbamoylethyl, dimethylcarbamoylpropyl, ethylcarbamoylmethyl, ethylcarbamoylethyl, ethylcarbamoylpropyl, diethylcarbamoylmethyl, diethylcarbamoylethyl, diethylcarbamoylpropyl and the like); a 5- or 6-membered heterocyclylcarbonyl-$C_{1-6}$ alkyl (preferably morpholinocarbonylmethyl, morpholinocarbonylethyl, morpholinocarbonylpropyl, piperidinocarbonylmethyl, piperidinocarbonylethyl, piperidinocarbonylpropyl, 1-pyrrolidinylcarbonylmethyl, 1-pyrrolidinylcarbonylethyl, 1-pyrrolidinylcarbonylpropyl and the like); a mono- or di-$C_{1-6}$ alkyl-carbamoyl-$C_{1-6}$ alkoxy (preferably ethylcarbamoylmethoxy and the like); a $C_{7-19}$ aralkyl (preferably benzyl and the like) optionally having substituent(s); an aromatic group (preferably phenyl and the like) optionally having substituent(s) and the like.

As the substituent of the "$C_{7-19}$ aralkyl optionally having substituent(s)" and "aromatic group optionally having substituent(s)", a halogen atom (preferably fluorine, chlorine and the like), an optionally halogenated $C_{1-6}$ alkyl (preferably methyl and the like), an optionally halogenated $C_{1-6}$ alkoxy (preferably methoxy and the like) and the like are preferable. The number of the substituents is, for example, 1 to 3, preferably 1 or 2. When the number of the substituents is not less than 2, the respective substituents may be the same or different.

In addition, the above-mentioned "5- or 6-membered heterocyclylcarbonyl" and "5- or 6-membered heterocyclylcarbonyl-$C_{1-6}$ alkyl" optionally have 1 to 3 substituents selected from a halogen atom (preferably fluorine, chlorine and the like), an optionally halogenated $C_{1-6}$ alkyl (preferably methyl and the like), an optionally halogenated $C_{1-6}$ alkoxy (preferably methoxy and the like) and the like.

The "substituent" of the "nitrogen-containing heterocycle optionally having substituent(s)" is more preferably an optionally halogenated $C_{1-10}$ alkyl, an optionally halogenated $C_{1-6}$ alkylsulfonyl and the like.

As the "nitrogen-containing heterocycle optionally having substituent(s)" formed by $R^1$ and Y together with the adjacent nitrogen atom, those exemplified as the "nitrogen-containing heterocycle optionally having substituent(s)" formed by the aforementioned $R^1$ and $R^2$ together with the adjacent nitrogen atom can be used.

Of compound (I), a compound wherein $R^1$ and $R^2$ are the same or different and each is a hydrogen atom or a $C_{1-6}$ alkyl, or $R^1$ and $R^2$ form a nitrogen-containing heterocycle optionally having substituent(s) together with the adjacent nitrogen atom is preferable, a compound wherein $R^1$ and $R^2$ form a nitrogen-containing heterocycle optionally having substituent(s) together with the adjacent nitrogen atom is more preferable.

In compound (I), when the nitrogen-containing heterocycle formed by $R^1$ and $R^2$ together with the adjacent nitrogen atom is piperazine, or when R is a $C_{1-4}$ alkyl, then $Ar^1$ is a cyclic group having substituent(s).

As preferable examples of compound (I), the following compounds can be mentioned.

1) A compound wherein
$Ar^1$ is a group represented by the formula: $Ar^3—Ar^2—$, wherein
  $Ar^2$ is a phenyl, a 5- or 6-membered aromatic heterocyclic group or a 5- to 8-membered monocyclic non-aromatic heterocyclic group (preferably phenyl, pyridyl, piperidinyl), each optionally having 1 to 3 substituents selected from a halogen atom (preferably fluorine, chlorine and the like) and an optionally halogenated $C_{1-6}$ alkyl (preferably methyl, trifluoromethyl, ethyl and the like), and
  $Ar^3$ is a phenyl or a 5- or 6-membered aromatic heterocyclic group (preferably phenyl, pyridyl and the like), each optionally having 1 to 3 substituents selected from a halogen atom (preferably fluorine, chlorine and the like), an optionally halogenated $C_{1-6}$ alkyl (preferably methyl, trifluoromethyl, ethyl and the like), an optionally halogenated $C_{1-6}$ alkoxy (preferably methoxy, trifluoromethoxy and the like), an optionally halogenated $C_{1-6}$ alkylthio (preferably methylthio and the like), a $C_{1-3}$ alkylenedioxy (preferably methylenedioxy, ethylenedioxy and the like), an optionally halogenated $C_{1-6}$ alkyl-carbonyl (preferably acetyl and the like) and an optionally halogenated $C_{1-6}$ alkyl-carboxamido (preferably isopropylcarboxamido and the like);
$Ra^1$, $Ra^2$, $Ra^3$ and $Ra^4$ are the same or different and each is a hydrogen atom or an optionally halogenated $C_{1-6}$ alkyl;
$R^1$ and $R^2$ are the same or different and each is a hydrogen atom or a $C_{1-6}$ alkyl (preferably methyl, ethyl, propyl, isopropyl);
Y is a $C_{1-6}$ alkylene group (preferably —$CH_2$—, —CH($CH_3$)—, —CH($C_2H_5$)—, —CH(CH($CH_3$)$_2$)—);
R is a hydrogen atom; and
Ar is a monocyclic aromatic ring (preferably a benzene ring, a pyridine ring) optionally further having 1 to 3 substituents selected from a halogen atom (preferably fluorine, chlorine, bromine and the like), an optionally halogenated $C_{1-6}$ alkyl (preferably methyl, ethyl, propyl, trifluoromethyl and the like) and an optionally halogenated $C_{1-6}$ alkoxy (preferably methoxy, ethoxy and the like).

2) A compound wherein
$Ar^1$ is a group represented by the formula: $Ar^3—Ar^2—$, wherein
  $Ar^2$ is a phenyl, a 5- or 6-membered aromatic heterocyclic group or a 5- to 8-membered monocyclic non-aromatic heterocyclic group (preferably phenyl, pyridyl, piperidinyl), each optionally having 1 to 3 substituents selected from a halogen atom (preferably fluorine, chlorine and the like) and an optionally halogenated $C_{1-6}$ alkyl (preferably methyl, trifluoromethyl, ethyl and the like), or Ar³ is a phenyl or a 5- or 6-membered aromatic heterocyclic group (preferably phenyl, pyridyl and the like), each optionally having 1 to 3 substituents selected from a halogen atom (preferably fluorine, chlorine and the like), an optionally halogenated $C_{1-6}$ alkyl (preferably methyl, trifluoromethyl, ethyl and the like), an optionally halogenated $C_{1-6}$ alkoxy (preferably methoxy, trifluoromethoxy and the like), an optionally halogenated $C_{1-6}$ alkylthio (preferably methylthio and the like), a $C_{1-3}$ alkylenedioxy (preferably methylenedioxy, ethylenedioxy and the like), an optionally halogenated $C_{1-6}$ alkyl-carbonyl (preferably acetyl and the like) and an optionally halogenated $C_{1-6}$ alkyl-carboxamido (preferably isopropylcarboxamido and the like);

Ra¹, Ra², Ra³ and Ra⁴ are the same or different and each is a hydrogen atom or an optionally halogenated $C_{1-6}$ alkyl;

R¹ and R² form, together with the adjacent nitrogen atom, a 3- to 8-membered nitrogen-containing heterocycle (preferably piperidine, piperazine, pyrrolidine, hexamethylenimine (azepane), morpholine, thiomorpholine), each optionally having 1 to 3 substituents selected from an optionally halogenated $C_{1-10}$ alkyl (preferably methyl, ethyl, propyl, butyl, isobutyl and the like) and an optionally halogenated $C_{1-6}$ alkylsulfonyl (preferably methylsulfonyl and the like);

Y is a $C_{1-6}$ alkylene group (preferably —CH₂—, —CH(CH₃)—, —CH(C₂H₅)—, —CH(CH(CH₃)₂)—);

R is a hydrogen atom; and

Ar is a monocyclic aromatic ring (preferably a benzene ring, a pyridine ring) optionally further having 1 to 3 substituents selected from a halogen atom (preferably fluorine, chlorine, bromine and the like), an optionally halogenated $C_{1-6}$ alkyl (preferably methyl, ethyl, propyl, trifluoromethyl and the like) and an optionally halogenated $C_{1-6}$ alkoxy (preferably methoxy, ethoxy and the like).

3) A compound wherein

Ar¹ is a phenyl, a 5- or 6-membered aromatic heterocyclic group or a 5- to 8-membered monocyclic non-aromatic heterocyclic group (preferably phenyl, pyridyl, piperidinyl), each optionally having 1 to 3 substituents selected from a halogen atom (e.g., fluorine, chlorine, bromine, iodine and the like), a $C_{1-3}$ alkylenedioxy (e.g., methylenedioxy, ethylenedioxy and the like), a nitro, a cyano, an optionally halogenated $C_{1-10}$ alkyl, an optionally halogenated $C_{1-10}$ alkoxy, a $C_{6-14}$ aryloxy (preferably phenoxy) optionally having substituent(s) (preferably a halogen atom, an optionally halogenated $C_{1-10}$ alkyl, an optionally halogenated $C_{1-10}$ alkoxy and the like), a $C_{7-19}$ aralkyloxy (preferably benzyloxy) optionally having substituent(s) (preferably a halogen atom, an optionally halogenated $C_{1-10}$ alkyl, an optionally halogenated $C_{1-10}$ alkoxy and the like), a $C_{3-6}$ cycloalkyl-$C_{1-6}$ alkoxy (preferably cyclopropylmethoxy, cyclopropylethoxy and the like) optionally having substituent(s) (preferably a halogen atom, an optionally halogenated $C_{1-10}$ alkyl, an optionally halogenated $C_{1-10}$ alkoxy and the like), an acyl [preferably an optionally halogenated $C_{1-6}$ alkyl-carbonyl (e.g., pentanoyl, hexanoyl and the like), an optionally halogenated $C_{1-6}$ alkylsulfonyl (e.g., butylsulfonyl and the like) and the like], an acyl-$C_{1-6}$ alkyl [preferably an optionally halogenated $C_{1-6}$ alkyl-carbonyl-$C_{1-6}$ alkyl (e.g., propanoylmethyl, propanoylethyl, 2-methylpropanoylmethyl, butanoylmethyl, 3-methylbutanoylmethyl, pentanoylmethyl and the like), an optionally halogenated $C_{1-6}$ alkylsulfonyl-$C_{1-6}$ alkyl (e.g., propylsulfonylmethyl, butylsulfonylmethyl and the like), a $C_{6-14}$ aryl-carbonyl-$C_{1-6}$ alkyl (e.g., benzoylmethyl and the like), a $C_{3-6}$ cycloalkyl-carbonyl-$C_{1-6}$ alkyl (e.g., cyclopropylcarbonylmethyl, cyclobutylcarbonylmethyl and the like), a 5- or 6-membered heterocyclylcarbonyl-$C_{1-6}$ alkyl (e.g., tetrahydrofuroylmethyl and the like) and the like] and the like;

Ra¹, Ra², Ra³ and Ra⁴ are the same or different and each is a hydrogen atom or an optionally halogenated $C_{1-6}$ alkyl;

R¹ and R² form, together with the adjacent nitrogen atom, a 3- to 8-membered nitrogen-containing heterocycle (preferably piperidine, piperazine, pyrrolidine, hexamethylenimine (azepane), morpholine, thiomorpholine), each optionally having 1 to 3 substituents selected from an optionally halogenated $C_{1-10}$ alkyl (preferably methyl, ethyl, propyl, butyl, isobutyl and the like) and an optionally halogenated $C_{1-6}$ alkylsulfonyl (preferably methylsulfonyl and the like);

Y is a $C_{1-6}$ alkylene group (preferably —CH₂—, —CH(CH₃)—, —CH(C₂H₅)—, —CH(CH(CH₃)₂)—);

R is a hydrogen atom; and

Ar is a monocyclic aromatic ring (preferably a benzene ring, a pyridine ring) optionally further having 1 to 3 substituents selected from a halogen atom (preferably fluorine, chlorine, bromine and the like), an optionally halogenated $C_{1-6}$ alkyl (preferably methyl, ethyl, propyl, trifluoromethyl and the like) and an optionally halogenated $C_{1-6}$ alkoxy (preferably methoxy, ethoxy and the like).

4)

4'-chloro-N-{2-[4-(1-pyrrolidinylmethyl)phenyl]ethyl}[1,1'-biphenyl]-4-carboxamide (Example 2);

4'-chloro-3-fluoro-N-{2-[4-(1-pyrrolidinylmethyl)phenyl]ethyl}[1,1'-biphenyl]-4-carboxamide (Example 7);

4'-chloro-N-(2-{4-[1-(1-pyrrolidinyl)propyl]phenyl}ethyl)[1,1'-biphenyl]-4-carboxamide (Example 33);

4-(cyclopropylmethoxy)-N-(2-{4-[1-(1-pyrrolidinyl)ethyl]phenyl}ethyl)benzamide (Example 40);

4'-methoxy-N-{2-[4-(1-pyrrolidinylmethyl)phenyl]ethyl}[1,1'-biphenyl]-4-carboxamide (Example 97);

N-{2-[4-(1-azepanylmethyl)phenyl]ethyl}-4-(cyclopropylmethoxy)benzamide (Example 127);

N-{2-[4-(1-azepanylmethyl)phenyl]ethyl}-4-(2-cyclopropylethoxy)benzamide (Example 128);

4'-chloro-N-{2-[4-(1-methyl-2-pyrrolidinyl)phenyl]ethyl}[1,1'-biphenyl]-4-carboxamide (Example 137); or 4-(2-cyclopropylethoxy)-N-(2-{4-[1-(1-pyrrolidinyl)ethyl]phenyl}ethyl)benzamide (Example 148).

When the compound (I) is in the form of a salt, concrete examples thereof include salts with inorganic bases, ammonium salts, salts with organic bases, salts with inorganic acids, salts with organic acids, salts with basic or acidic amino acids and the like.

Preferable examples of the salts with inorganic bases include alkali metal salts such as sodium salt, potassium salt, and the like; alkaline earth metal salts such as calcium salts, magnesium salts, barium salts, and the like; aluminum salts, and the like.

Preferable examples of the salts with organic bases include salts with trimethylamine, triethylamine, pyridine, picoline, ethanolamine, diethanolamine, triethanolamine, dicyclohexylamine, N,N-dibenzylethylenediamine, and the like.

Preferable examples of the salts with inorganic acids include salts with hydrochloric acid, hydrobromic acid, nitric acid, sulfuric acid, phosphoric acid, and the like.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

Preferable examples of the salts with basic amino acids include salts with arginine, lysine, ornithine, and the like.

Preferable examples of the salts with acidic amino acids include salts with aspartic acid, glutamic acid, and the like.

Of these, pharmaceutically acceptable salts are preferable. Preferable examples when compound (I) has an acidic functional group include inorganic salts such as alkali metal salts (e.g., sodium salt, potassium salt, etc.), alkaline earth metal salts (e.g., calcium salt, magnesium salt, barium salt, etc.) and the like, ammonium salts, etc.; and when compound (I) has a basic functional group, inorganic salts such as hydrochloride, sulfate, phosphate and hydrobromide; or organic salts such as acetate, maleate, fumarate, succinate, methanesulfonate, p-toluenesulfonate, citrate and tartrate.

The compound (I) may be an anhydrate or a hydrate. When it is a hydrate, it may contain 0.5 to 3 water molecules.

Furthermore, compound (I) may be labeled with an isotope (e.g., $^3H$, $^{14}C$, $^{35}S$, etc.).

Where compound (I) includes optical isomers, stereo isomers, regio isomers and rotational isomers, these are within the scope of compound (I), and can be isolated as their single compound through synthesis or separation known per se. For example, where optical isomers of compound (I) exist, those resolved from their mixtures through optical resolution are within the scope of compound (I).

Said optical isomers can be produced by methods known per se. Concretely, optically active synthetic intermediates may be used, or mixtures of racemate of the final product are subjected to ordinary optical resolution to give the corresponding optical isomers.

As the optical resolution method, methods known per se such as fractional recrystallization method, chiral column method, diastereomer method which are described in detail below and the like are employed.

1) Fractional Recrystallization Method

The method which comprises allowing a racemate to react with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) to give a salt, which is then isolated through fractional recrystallization method, followed by, when desired, subjecting the isolated compound to neutralization to obtain free optical isomers.

2) Chiral Column Method

The method of separating a racemate or a salt thereof, which comprises utilizing a column for fractionating optical isomers (chiral column). In the case of liquid chromatography, for example, a mixture of optical isomers is applied to a chiral column, such as ENANTIO-OVM (manufactured by Tosoh Corp.), CHIRAL SERIES (manufactured by Daicel Co.), and the like, which is then eluted with water, various buffers (e.g., phosphate buffer) and organic solvents (e.g., ethanol, methanol, isopropanol, acetonitrile, trifluoroacetic acid, diethylamine, etc.), singly or as a suitable mixture of them, to isolate the individual optical isomers. In the case of gas chromatography, for example, a chiral column such as CP-Chirasil-DeX CB (manufactured by GL Science Co.), and the like is used for isolation.

3) Diastereomer Method

A racemic mixture is chemically reacted with an optically-active reagent to give a mixture of diastereomer, which is subjected to ordinary separation means (e.g., fractional recrystallization, chromatography, etc.) to give single compounds. The thus-isolated single compounds are then chemically processed, for example, through hydrolysis to thereby remove the optically-active reagent site from the compounds to obtain optical isomers. For example, where compound (I) has a hydroxy group or a primary or secondary amino group in the molecule, it is condensed with an optically-active organic acid (e.g., MTPA [α-methoxy-α-(trifluoromethyl) phenyl-acetic acid], (−)-menthoxyacetic acid, etc.) or the like to give the corresponding ester-type or amide-type diastereomer. On the other hand, where compound (I) has a carboxylic acid group, it is condensed with an optically active amine or alcohol reagent to give the corresponding amide-type or ester-type diastereomer, respectively. The thus-isolated diastereomer is then subjected to acidic or basic hydrolysis, through which it is converted into the optical isomer of the original compound.

The prodrug of the compound (I) means a compound capable of being converted to the compound (I) in vivo by the action of an enzyme or gastric juice and the like under physiological conditions, namely a compound capable of being converted to the compound (I) upon enzymatic oxidation, reduction or hydrolysis and the like, or a compound capable of being converted to the compound (I) upon hydrolysis and the like by gastric juice and the like. As the prodrug of the compound (I), compounds derived by acylation, alkylation or phosphorylation of the amino group of the compound (I) (e.g., compounds derived by eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation of the amino group of the compound (I) etc.); compounds derived by acylation, alkylation, phosphorylation or boration of the hydroxy group of the compound (I) (e.g., compounds derived by acetylation, palmitoylation, propanoylation, pivaloylation, succinylation, fumarylation, alanylation or dimethylaminomethylcarbonylation of the hydroxy group of the compound (I), etc.); and compounds derived by esterification or amidation of the carboxyl group of the compound (I) (e.g., compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methylamidation of the carboxyl group of the compound (I) etc.), and the like can be mentioned. These compounds can be produced from the compound (I) by methods known per se.

The prodrug of the compound (I) may be one capable of being converted to the compound (I) under physiological conditions, as described in "*Iyakuhin no Kaihatsu (Development of Drugs)*", vol. 7, Molecular Designing, published by Hirokawa Shoten, 1990, pages 163-198.

For example, the compound (I) can be produced according to [Production Method 1] to [Production Method 3], which are described in detail below, or an analogous method thereto.

In the following [Production Method 1] to [Production Method 3], the compounds for the starting material compound may be used in the form of a salt, respectively. As such salt, those exemplified as the salt of the aforementioned compound (I) can be used.

In the following production methods, when alkylation reaction, hydrolysis reaction, amination reaction, esterification reaction, amidation reaction, esterification reaction, etherification reaction, oxidation reaction, reduction reaction etc. are to be conducted, these reactions are carried out according to methods known per se, for example, those described in *Organic Functional Group Preparations,* 2nd Ed., Academic Press Inc., 1989; *Comprehensive Organic Transformations*, VCH Publishers Inc., 1989; and the like.

[Production Method 1]

The compound (I) is produced by, for example, the following amidation reaction.

(Amidation Reaction)

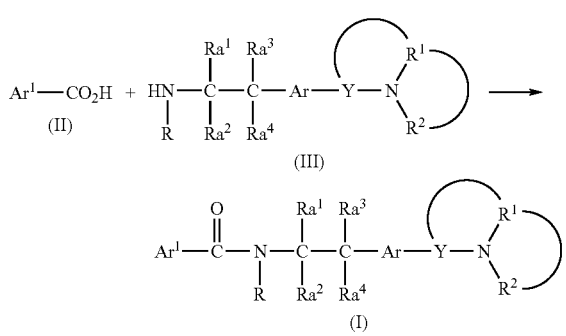

wherein the symbols in the formula are as defined above.

The "amidation reaction" includes "a method using a dehydration condensing agent" and "a method using a reactive derivative of carboxy" described below.

i) Method Using a Dehydration Condensing Agent

The compound (III), 1 to 5 equivalents of compound (II) and 1 to 2 equivalents of dehydration condensing agent are reacted in an inert solvent. Where necessary, the reaction may be carried out in the co-presence of 1 to 1.5 equivalents of 1-hydroxybenzotriazole (HOBT) and/or catalytic amount to 5 equivalents of a base.

As the "dehydration condensing agent", for example, dicyclohexylcarbodiimide (DCC), 1-ethyl-3-(3-dimethylaminopropyl)carbodiimide hydrochloride (WSC) and the like can be mentioned. Of these, WSC is preferable.

As the "inert solvent", for example, nitrile solvents (preferably acetonitrile), amide solvents (preferably DMF), halogenated hydrocarbon solvents (preferably dichloromethane), ether solvents (preferably THF) and the like can be mentioned. Two or more kinds of these can be mixed in an appropriate ratio and used.

As the "base", for example;
1) strong bases such as alkali metal or alkaline earth metal hydrides (e.g., lithium hydride, sodium hydride, potassium hydride, calcium hydride, etc.), alkali metal or alkaline earth metal amides (e.g., lithium amide, sodium amide, lithium diisopropylamide, lithium dicyclohexylamide, lithium hexamethyldisilazide, sodium hexamethyldisilazide, potassium hexamethyldisilazide, etc.), alkali metal or alkaline earth metal lower-alkoxides (e.g., sodium methoxide, sodium ethoxide, potassium tert-butoxide, etc.), and the like;
2) inorganic bases such as alkali metal or alkaline earth metal hydroxides (e.g., sodium hydroxide, potassium hydroxide, lithium hydroxide, barium hydroxide, etc), alkali metal or alkaline earth metal carbonates (e.g., sodium carbonate, potassium carbonate, cesium carbonate, etc), alkali metal or alkaline earth metal hydrogencarbonates (e.g., sodium hydrogencarbonate, potassium hydrogencarbonate, etc.) and the like; and
3) organic bases such as amines (e.g., triethylamine, diisopropylethylamine, N-methylmorpholine, dimethylaminopyridine, DBU (1,8-diazabicyclo[5.4.0]undec-7-ene), DBN (1,5-diazabicyclo[4.3.0]non-5-ene) and the like); basic heterocyclic compound (e.g., pyridine, imidazole, 2,6-lutidine and the like) and the like, and the like can be mentioned.

Of the above-mentioned base, triethylamine, 4-dimethylaminopyridine and the like are preferable.

The reaction temperature is generally room temperature (1 to 30° C., hereinafter the same). The reaction time is, for example, 10 hrs to 24 hrs.

ii) Method Using a Reactive Derivative of Carboxy

The reactive derivative of the compound (II) and 1 to 5 equivalents (preferably 1 to 3 equivalents) of the compound (III) are reacted in an inert solvent. Where necessary, the reaction may be carried out in the co-presence of 1 to 10 equivalents, preferably 1 to 3 equivalents, of a base.

As the "reactive derivative" of the compound (II), for example, acid halide (e.g., acid chloride, acid bromide, etc.), mixed acid anhydride (e.g., acid anhydride with $C_{1-6}$ alkyl-carboxylic acid, $C_{6-10}$ aryl-carboxylic acid or $C_{1-6}$ alkyl-carbonic acid, etc.), activated ester (e.g., ester with phenol optionally having substituent(s), 1-hydroxybenzotriazole or N-hydroxysuccinimide, etc.) and the like can be mentioned.

As the "substituent(s)" of the "phenol optionally having substituent(s)", for example, halogen atom (e.g., fluorine, chlorine, bromine, iodine, etc.), nitro, optionally halogenated $C_{1-6}$ alkyl and optionally halogenated $C_{1-6}$ alkoxy can be mentioned. The number of the substituents is, for example, 1 to 5.

As the "optionally halogenated $C_{1-6}$ alkyl" and "optionally halogenated $C_{1-6}$ alkoxy", those exemplified for the aforementioned $Ra^1$ can be used respectively.

As specific examples of the "phenol optionally having substituent(s)", phenol, pentachlorophenol, pentafluorophenol, p-nitrophenol and the like can be mentioned. The reactive derivative is preferably acid halide.

As the "inert solvent", for example, ether solvents, halogenated hydrocarbon solvents, aromatic solvents, nitrile solvents, amide solvents, ketone solvents, sulfoxide solvents, water and the like can be mentioned. These may be used on mixing two or more kinds at a suitable proportion. Of these, preferred are acetonitrile, THF, dichloromethane, chloroform, and the like.

As the "base", those similar to the aforementioned can be used. The base is preferably sodium hydride, potassium carbonate, sodium carbonate, sodium hydroxide, potassium hydroxide, sodium hydrogen carbonate, potassium hydrogen carbonate, triethylamine, pyridine and the like.

The reaction temperature is generally −20° C. to 50° C., preferably room temperature. The reaction time is generally 5 min to 40 hrs., preferably 1 to 18 hrs.

The aforementioned compound (III) can be produced by a method known per se, such as the method described in WO01/82925 or a method analogous thereto.

The aforementioned compound (II) can be produced by methods known per se.

[Production Method 2]

The compound (Ia) wherein $Ar^1$ is a non-aromatic cyclyl amino group optionally having substituent(s) can be also produced by, for example, the following ureation reaction.

(Ureation Reaction)

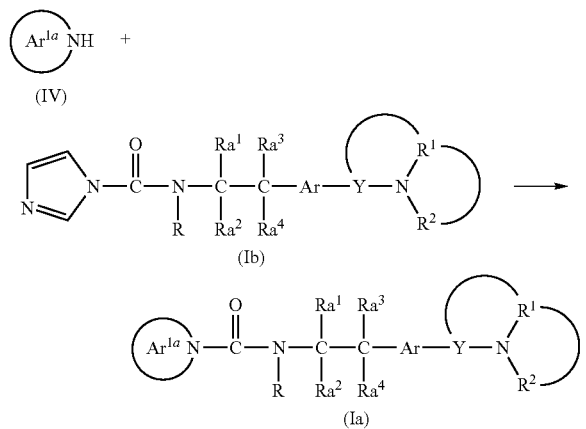

(Aryl-coupling Reaction)

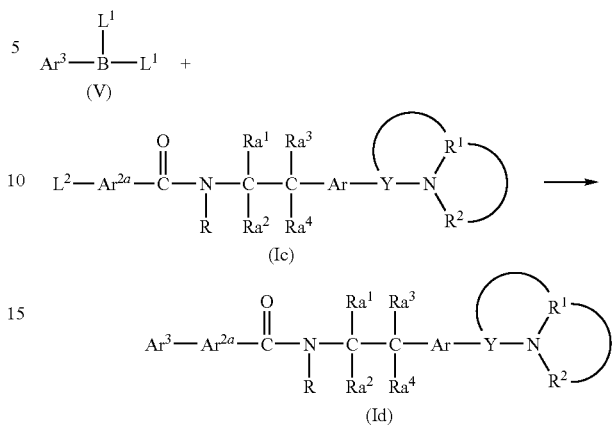

wherein $Ar^{1a}$ is a non-aromatic cyclyl amino group optionally having substituent(s) and other symbols are as defined above.

As the "non-aromatic cyclyl amino group optionally having substituent(s)" for $Ar^{1a}$, of the "cyclic group optionally having substituent(s)" exemplified for the aforementioned $Ar^1$, those wherein a cyclic group is a non-aromatic cyclyl amino group, can be used. Here, as specific examples of the non-aromatic cyclyl amino group, pyrrolidinyl, piperidinyl, piperazinyl, morpholinyl, thiomorpholinyl and the like can be mentioned.

This reaction is carried out by reacting compound (Ib) with 1 to 5 equivalents (preferably 1 to 1.5 equivalents) of compound (IV) in the co-presence of a base in an inert solvent.

As the "base", those exemplified in the aforementioned "method using a dehydration condensing agent" can be used. The base is preferably potassium carbonate, sodium carbonate, sodium hydroxide, potassium hydroxide, sodium hydrogen carbonate, potassium hydrogen carbonate, triethylamine, pyridine and the like. The amount of the base to be used is, for example, 1 to 10 equivalents, preferably 1 to 3 equivalents, relative to compound (Ib).

As the "inert solvent", for example, alcohol solvents, ether solvents, halogenated hydrocarbon solvents, aromatic solvents, nitrile solvents, amide solvents, ketone solvents, sulfoxide solvents, water and the like can be mentioned. Two or more kinds of these can be mixed in an appropriate ratio and used of these, acetonitrile, DMF, acetone, ethanol, pyridine and the like are preferable.

The reaction temperature is generally about −20° C. to 100° C., preferably room temperature to 80° C. The reaction time is, for example, about 0.5 hr to 1 day.

The aforementioned compound (IV) can be produced by a method known per se.

In addition, compound (Ib) can be produced by, for example, according to the aforementioned [Production Method 1].

[Production Method 3]

The compound (Id) wherein, in the formula (I), $Ar^1$ is a group represented by the formula: $Ar^3-Ar^{2a}-$ (wherein $Ar^{2a}$ is an aromatic group optionally having substituent(s) and $Ar^3$ is as defined above) can be also produced by, for example, the following aryl-coupling reaction.

wherein $L^1$ is hydroxy or $C_{1-6}$ alkoxy; $L^2$ is a halogen atom or trifluoromethanesulfonyloxy; and other symbols are as defined above.

As the $C_{1-6}$ alkoxy for $L^1$, for example, methoxy, ethoxy, propoxy, butoxy, pentyloxy, hexyloxy and the like can be mentioned.

As the halogen atom for $L^2$, for example, fluorine, chlorine, bromine, iodine and the like can be mentioned. Of these, chlorine and bromine are preferable.

As the "aromatic group optionally having substituent(s)" for $Ar^{2a}$, of the "cyclic group optionally having substituent(s)" for the aforementioned $Ar^2$, those wherein the cyclic group is an aromatic group, can be mentioned.

In compound (Id), a compound wherein $Ar^3$ and $Ar^{2a}$ are each a phenyl optionally having substituent(s) and $Ar^3-Ar^{2a}-$ is a biphenylyl optionally having substituent(s), is particularly preferable.

The aryl-coupling reaction can be carried out according to a method known per se, for example, the method described in *Acta. Chemica Scandinavia*, pp. 221-230 (1993) and the like, or a method analogous thereto.

This reaction is carried out by, for example, reacting compound (Ic) with 1 to 3 equivalents (preferably 1 to 1.5 equivalents) of compound (V) in the presence of a base and a transition metal catalyst in an inert solvent.

As the "base", those exemplified in the aforementioned "method using a dehydration condensing agent" can be used. As the base, sodium carbonate, sodium hydrogen carbonate and the like are preferable.

The amount of the "base" to be used is, for example, generally about 1 to 10 equivalents relative to compound (Ic)

As the "transition metal catalyst", for example, palladium catalyst, nickel catalyst and the like can be mentioned. As the "palladium catalyst", for example, tetrakis(triphenylphosphine)palladium(0), palladium acetate, bis(triphenylphosphine)palladium(II) chloride, palladium-carbon and the like can be mentioned. As the "nickel catalyst", for example, tetrakis(triphenylphosphine)nickel (0) and the like can be mentioned.

The amount of the "transition metal catalyst" to be used is generally about 0.01 to 1 equivalent, preferably about 0.01 to 0.5 equivalent, relative to compound (Ic).

The reaction temperature is generally from room temperature to 150° C., preferably about 80° C. to 150° C. The reaction time is, for example, about 1 to 48 hrs.

As the "inert solvent", for example, water, alcohol solvents, aromatic solvents and the like can be mentioned. Two or more kinds of these can be mixed in an appropriate ratio for use. Of these, a single solvent of water, ethanol, toluene and the like or a mixed solvent of two or more of these is preferable.

The aforementioned compound (V) can be produced by a method known per se.

In addition, compound (Ic) can be produced according to, for example, the aforementioned [Production Method 1].

As the aforementioned "alcohol solvent", for example, methanol, ethanol, isopropanol, tert-butanol and the like can be used.

As the aforementioned "ether solvent", for example, diethyl ether, tetrahydrofuran (THF), 1,4-dioxane, 1,2-dimethoxyethane and the like can be used.

As the aforementioned "halogenated hydrocarbon solvent", for example, dichloromethane, chloroform, 1,2-dichloroethane, carbon tetrachloride and the like can be used.

As the aforementioned "aromatic solvent", for example, benzene, toluene, xylene, pyridine and the like can be used.

As the aforementioned "hydrocarbon solvent", for example, hexane, pentane, cyclohexane and the like can be used.

As the aforementioned "amide solvent", for example, N,N-dimethylformamide (DMF), N,N-dimethylacetamide, N-methylpyrrolidone and the like can be used.

As the aforementioned "ketone solvent", for example, acetone, methyl ethyl ketone and the like can be used.

As the aforementioned "sulfoxide solvent", for example, dimethyl sulfoxide (DMSO) and the like can be used.

As the aforementioned "nitrile solvent", for example, acetonitrile, propionitrile and the like can be used.

In the compound (I) thus obtained, the functional group in a molecule can be also converted to the object functional group by combining chemical reactions known per se. As the examples of such chemical reaction, oxidation reaction, reduction reaction, alkylation reaction, hydrolysis reaction, amination reaction, esterification reaction, aryl-coupling reaction, deprotection reaction and the like can be mentioned.

In each of the aforementioned reactions, when the starting material compound has an amino group, carboxy group, hydroxy group or carbonyl group as a substituent, a protecting group generally used in peptide chemistry and the like may be introduced and an object compound can be obtained by removing the protecting group after the reaction where necessary.

Examples of the protecting group for amino group include formyl, $C_{1-6}$ alkyl-carbonyl (e.g., acetyl, propionyl and the like), $C_{1-6}$ alkoxy-carbonyl (e.g., methoxycarbonyl, ethoxycarbonyl, tert-butoxycarbonyl and the like), benzoyl, $C_{7-10}$ aralkyl-carbonyl (e.g., benzylcarbonyl and the like), $C_{7-14}$ aralkyloxy-carbonyl (e.g., benzyloxycarbonyl, 9-fluorenylmethoxycarbonyl and the like), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like. These groups may be substituted by 1 to 3 halogen atoms (e.g., fluorine, chlorine, bromine, iodine, etc.), $C_{1-6}$ alkoxy (e.g., methoxy, ethoxy, propoxy, etc.) or nitro etc.

Examples of the protecting group for carboxy group include $C_{1-6}$ alkyl (e.g., methyl, ethyl, propyl, isopropyl, butyl, tert-butyl, etc.), $C_{7-11}$ aralkyl (e.g., benzyl, etc.), phenyl, trityl, silyl (e.g., trimethylsilyl, triethylsilyl, dimethylphenylsilyl, tert-butyldimethylsilyl, tert-butyldiethylsilyl, etc.), $C_{2-6}$ alkenyl (e.g., 1-allyl, etc.) and the like. These groups may be substituted by 1 to 3 halogen atoms (e.g., fluorine, chlorine, bromine, iodine, etc.), $C_{1-6}$ alkoxy (e.g., methoxy, ethoxy, propoxy, etc.) or nitro etc.

Examples of the protecting group for hydroxy group include $C_{1-6}$ alkyl (e.g., methyl, ethyl, propyl, isopropyl, butyl, tert-butyl, etc.), phenyl, trityl, $C_{7-10}$ aralkyl (e.g., benzyl, etc.), formyl, $C_{1-6}$ alkyl-carbonyl (e.g., acetyl, propionyl, etc.), benzoyl, $C_{7-10}$ aralkyl-carbonyl (e.g., benzylcarbonyl, etc.), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl, etc.), $C_{2-6}$ alkenyl (e.g., 1-allyl, etc.) and the like. These groups may be substituted by 1 to 3 of halogen atoms (e.g., fluorine, chlorine, bromine, iodine, etc.), $C_{1-6}$ alkyl (e.g., methyl, ethyl, n-propyl, etc.), $C_{1-6}$ alkoxy (e.g., methoxy, ethoxy, propoxy, etc.) or nitro etc.

Examples of the protecting group for carbonyl group include cyclic acetal (e.g., 1,3-dioxane, etc.), and acyclic acetal (e.g., di-$C_{1-6}$ alkylacetal, etc.) and the like.

Removal of the above protecting groups can be carried out in accordance with methods known per se such as those described in *Protective Groups in Organic Synthesis*, published by John Wiley and Sons (1980) and the like. For instance, the methods using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide, etc.) and the like, a reduction method and the like can be used.

The compound (I) can be isolated and purified by methods known per se such as solvent extraction, changing of liquid properties, transdissolution, crystallization, recrystallization, chromatography, and the like. It is also possible to isolate and purify the starting material compounds of a compound (I), or their salts using the same known methods as above, but they can be also used as starting materials in the next process as a reaction mixture without being isolated.

Inasmuch as the compound (I) and a prodrug thereof (hereinafter abbreviated as the compound of the present invention) has a superior MCH receptor antagonistic action, it is useful as an agent for the prophylaxis or treatment of diseases caused by MCH. In addition, the compound of the present invention shows low toxicity (e.g., acute toxicity, chronic toxicity, genetic toxicity, reproductive toxicity, cardiac toxicity, drug interaction, carcinogenicity), and superior oral absorption performance and transfer into the brain.

Accordingly, the compound of the present invention is safely administered as an agent for the prophylaxis or treatment of diseases caused by MCH to mammals (e.g., rat, mouse, guinea pig, rabbit, sheep, horse, pig, cow, monkey, human, etc.).

The diseases caused by MCH include, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity and the like], hyperphagia, emotional disorder, sexual dysfunction, depression, anxiety and the like.

The compound of the present invention is also useful as an agent for the prophylaxis or treatment of life-style related diseases such as diabetes, diabetic complications (e.g., diabetic retinopathy, diabetic neuropathy, diabetic nephropathy, etc.), arteriosclerosis, gonarthritis and the like.

Furthermore, the compound of the present invention is also useful as a feeding deterrent.

The compound of the present invention can be also concurrently used with diet therapy (e.g., diet therapy for diabetes, etc.), or an exercise therapy.

The compound of the present invention can be used for the prophylaxis or treatment of pigmentation disorder based on abnormality of melanin or melanocyte. Here, as the pigmentation disorder, pigment proliferation, pigment decrease and the like can be mentioned. As the pigment proliferation, drug pigmentation caused by antitumor agent and the like; chromatosis and incompetence of pigment associated with diseases such as endocrine metabolism disorder (e.g., Addison's disease), genetic diseases, chronic hepatopathy, kidney failure, acanthosis nigricans, systemic scleroderma and the like; and the like can be mentioned. As the pigment decrease, phenylketonuria, systemic or localized albinism, foliaceous leukoderma or leukoderma vulgaris associated with tuberous sclerosis; depigmentation associated with systemic scleroderma and the like can be mentioned.

The compound of the present invention can be used for the prophylaxis or treatment of depigmentation due to chloasma, ephelides, sunburn and the like; and further, hyperpigmentation or hypopigmentation for cosmetic purposes.

The pharmaceutical agent of the present invention can be produced by formulating the compound of the present invention as it is or along with a pharmacologically acceptable carrier according to a method known per se.

As the pharmacologically acceptable carrier, various organic or inorganic carrier substance conventionally used as a material for preparation, such as excipient, lubricant, binder, disintegrant for solid preparation; solvent, dissolution aids, suspending agent, isotonicity agent, buffer, soothing agent and the like for liquid preparation are mentioned. In formulating a preparation, additives such as preservative, antioxidant, coloring agent, sweetening agent, absorbent, moistening agent and the like can be also added as necessary.

Examples of the excipient include lactose, saccharose, D-mannitol, starch, cornstarch, crystalline cellulose, light silicic anhydride and the like.

Examples of the lubricant include magnesium stearate, calcium stearate, talc, colloidal silica and the like.

Examples of the binder include crystalline cellulose, saccharose, D-mannitol, dextrin, hydroxypropyl cellulose, hydroxypropylmethyl cellulose, polyvinylpyrrolidone, starch, sucrose, gelatin, methyl cellulose, carboxymethyl cellulose sodium and the like.

Examples of the disintegrant include starch, carboxymethyl cellulose, carboxymethyl cellulose calcium, crosscarmellose sodium, carboxymethyl starch sodium, low substituted hydroxypropyl cellulose (L-HPC) and the like.

Examples of the solvent include water for injection, alcohol, propylene glycol, macrogol, sesame oil, corn oil and the like.

Examples of the dissolution aids include polyethylene glycol, propylene glycol, D-mannitol, benzyl benzoate, ethanol, tris-aminomethane, cholesterol, triethanolamine, sodium carbonate, sodium citrate and the like.

Examples of the suspending agent include surfactant such as stearyl triethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose and the like, and the like.

Examples of the isotonicity agent include glucose, D-sorbitol, sodium chloride, glycerine, D-mannitol and the like.

Examples of the buffer include buffers such as phosphate, acetate, carbonate, citrate and the like and the like.

Examples of the soothing agent include benzyl alcohol and the like.

Examples of the preservative include p-oxybenzoate, chlorobutanol, benzyl alcohol, phenethyl alcohol, dehydroacetic acid, sorbic acid and the like.

Examples of the antioxidant include sulfite, ascorbic acid and the like.

Examples of the dosage form of a pharmaceutical agent of the present invention include oral preparations such as tablet (inclusive of sugar-coated tablet, film coated tablet, sublingual tablet and orally disintegrable tablet), powder, granule, capsule (inclusive of soft capsule), liquid and the like; parenteral preparations such as injection (e.g., subcutaneous injection, intravenous injection, intramuscular injection, intraperitoneal injection, etc.), external preparation (e.g., transnasal administration preparation, percutaneous preparation, ointment, etc.), suppository (e.g., rectal suppository, pessary, etc.), sustained-release preparation (e.g., sustained-release microcapsule, etc.), pellet, drops, transpulmonary agent (inhalant), eye drops and the like; and the like, and can be safely administered orally or parenterally (e.g., topical, rectal, intravenous administration, etc.).

The content of the compound of the present invention in the pharmaceutical agent of the present invention is, for example, about 0.1 to 100 wt % of the whole amount of pharmaceutical agent.

The dose of the compound of the present invention is appropriately determined according to the administration subject, administration route, disease and the like.

For example, when the compound of the present invention is orally administered to adult patients (body weight about 60 kg) with obesity, the daily dose is about 0.1 to about 500 mg, preferably about 1 to about 100 mg, more preferably about 5 to about 100 mg, which dose is administered once or divided in several times a day.

With the aim of, for example, "enhancement of treatment effect of the compound of the present invention against obesity", "enhancement of treatment effect of the compound of the present invention against depression or anxiety", "reduction of the amount of the compound of the present invention to be used" and the like, the compound of the present invention may be used in combination with a combination drug, which does not exert an adverse influence on the compound of the present invention. As such combination drug, for example, "antidiabetic agent", "agent for treating diabetic complication", "anti-obesity agent other than MCH antagonist", "agent for treating hypertension", "agent for treating hyperlipidemia (agent for treating arteriosclerosis), "agent for treating arthritis", "anti-anxiety agent", "antidepressant" and the like are mentioned. These combination drugs may be used in a combination of two or more thereof in an appropriate proportion.

As the above-mentioned "antidiabetic agent", for example, insulin sensitizer, insulin secretagogue, biguanide agent, insulin, α-glucosidase inhibitor, β3 adrenergic receptor agonist and the like are mentioned.

As the insulin sensitizer, for example, pioglitazone or a salt thereof (preferably hydrochloride), troglitazone, rosiglitazone or a salt thereof (preferably maleate), Reglixane (JTT-501), GI-262570, Netoglitazone (MCC-555), YM-440, DRF-2593, BM-13-1258, KRP-297, R-119702, CS-011, FK-614, compounds described in WO99/58510 (e.g., (E)-4-[4-(5-methyl-2-phenyl-4-oxazolylmethoxy)benzyloxyimino]-4-phenylbutyric acid), Tesaglitazar (AZ-242), Ragaglitazar (NN- 622), BMS-298585, ONO-5816, BM-13-1258, LM-4156, MBX-102, LY-519818, MX-6054, LY-510929 and the like are mentioned.

As the insulin secretagogue, for example, sulfonylurea agent is mentioned. Specific examples of the sulfonylurea agent include tolbutamide, chlorpropamide, tolazamide, acetohexamide, glyclopyramide and ammonium salt thereof, glibenclamide, gliclazide, glimepiride and the like.

In addition to the above, insulin secretagogue includes, for example, repaglinide, nateglinide, mitiglinide (KAD-1229), JTT-608 and the like.

As the biguanide agent, for example, metformin, buformin, phenformin, a salt thereof (e.g., hydrochloride, fumarate, succinate) and the like are mentioned.

As the insulin, for example, animal insulin extracted from pancreas of cow and swine; semi-synthetic human insulin enzymatically synthesized from insulin extracted from pancreas of swine; human insulin genetically synthesized using *Escherichia coli* or yeast; and the like are mentioned. As insulin, insulin zinc containing 0.45 to 0.9 (w/w) % of zinc; protamine insulin zinc produced from zinc chloride, protamine sulfate and insulin, and the like can be also used. Moreover, insulin can be a fragment or derivative thereof (e.g., INS-1, etc.).

While insulin includes various types such as very rapid acting type, short-acting type, biphasic type, intermediate-acting type, extended type and the like, which can be determined depending on the disease state of patients.

As the α-glucosidase inhibitor, for example, acarbose, voglibose, miglitol, emiglitate and the like are mentioned.

As the β3 adrenergic receptor agonist, for example, AJ-9677, BMS-196085, SB-226552, AZ40140, CP-331684 and the like are mentioned.

In addition to the above, the "antidiabetic agent" includes, for example, ergoset, pramlintide, leptin, BAY-27-9955 and the like.

As the above-mentioned "agent for treating diabetic complication", for example, aldose reductase inhibitor, glycation inhibitor, protein kinase C inhibitor and the like are mentioned.

As the aldose reductase inhibitor, for example, tolrestat; epalrestat; imirestat; zenarestat; fidarestat (SNK-860); zopolrestat; ARI-509; AS-3201 and the like are mentioned.

As the glycation inhibitor, for example, pimagedine and the like are mentioned.

As the protein kinase C inhibitor, for example, NGF, LY-333531 and the like are mentioned.

In addition to the above, the "agent for treating diabetic complication" includes, for example, alprostadil, tiapride hydrochloride, cilostazol, mexiletine hydrochloride, ethyl icosapentate, memantine, pimagedline (ALT-711), neurotrophic factor and enhancer thereof (e.g., NGF, NT-3, BDNF, neurotrophin production/secretion promoters (e.g., 4-(4-chlorophenyl)-2-(2-methyl-1-imidazolyl)-5-[3-(2-methylphenoxy)propyl]oxazole, etc.) described in WO01/14372 and the like), neuranagenesis accelerating drug (e.g., Y-128, etc.) and the like.

As the above-mentioned "anti-obesity agent other than MCH antagonist", for example, lipase inhibitor, anorectic agent, β3 adrenergic receptor agonist and the like are mentioned.

As the lipase inhibitor, for example, orlistat, ATL-962 and the like are mentioned.

As the anorectic agent, for example, mazindol, dexfenfluramine, fluoxetine, sibutramine, biamine and the like are mentioned.

As the β3 adrenergic receptor agonist, "β3 adrenergic receptor agonist" exemplified for the above-mentioned "antidiabetic agent" can be mentioned.

In addition to the above, the "anti-obesity agent other than MCH antagonist" includes, for example, lipstatin and the like.

As the above-mentioned "agent for treating hypertension", for example, angiotensin converting enzyme inhibitor, calcium antagonist, potassium channel opener, angiotensin II antagonist and the like are mentioned.

As the angiotensin converting enzyme inhibitor, for example, captoril, enalapril, alacepril, delapril (hydrochrolide), lisinopril, imidapril, benazepril, cilazapril, temocapril, trandolapril, manidipine (hydrochrolide) and the like are mentioned.

As the calcium antagonist, for example, nifedipine, amlodipine, efonidipine, nicardipine and the like are mentioned.

As the potassium channel opener, for example, levcromakalim, L-27152, AL 0671, NIP-121 and the like are mentioned.

As the angiotensin II antagonist, for example, losartan, candesartan cilexetil, valsartan, irbesartan, CS-866, E4177 and the like are mentioned.

As the above-mentioned "agent for treating hyperlipidemia (agent for treating arteriosclerosis)", for example, HMG-CoA reductase inhibitor, fibrate compound and the like are mentioned.

As the HMG-CoA reductase inhibitor, for example, pravastatin, simvastatin, lovastatin, atorvastatin, fluvastatin, lipantil, cerivastatin, itavastatin, rosuvastatin (ZD-4522) or a salt thereof (e.g., sodium salt, calcium salt and the like) and the like are mentioned.

As the fibrate compound, for example, bezafibrate, clinofibrate, clofibrate, simfibrate and the like are mentioned.

As the above-mentioned "agent for treating arthritis", for example, ibuprofen and the like are mentioned.

As the above-mentioned "anti-anxiety agent", for example, chlordiazepoxide, diazepam, oxazolam, medazepam, cloxazolam, bromazepam, lorazepam, alprazolam, fludiazepam and the like are mentioned.

As the above-mentioned "antidepressant", for example, fluoxetine, fluvoxamine, imipramine, paroxetine, sertraline and the like are mentioned.

The time of administration of the aforementioned combination drug is not limited. The compound of the present invention and a combination drug may be simultaneously administered to an administration subject or administered in a staggered manner. The dose of the combination drug can be determined according to the dose clinically employed, and can be determined as appropriate depending on the administration subject, administration route, disease, combination and the like.

The mode of administration of the combination drug is not particularly limited, and may be any as long as the compound of the present invention and combination drug are combined on administration. Such administration mode is exemplified by 1) administration of a single preparation obtained by simultaneously formulating the compound of the present invention and combination drug, 2) simultaneous administration by the same administration route of two kinds of preparations obtained by separately formulating the compound of the present invention and combination drug, 3) staggered administration by the same administration route of two kinds of preparations obtained by separately formulating the compound of the present invention and combination drug, 4) simultaneous administration by different administration routes of two kinds of preparations obtained by separately formulating the compound of the present invention and combination drug, 5) staggered administration by different administration routes of two kinds of preparations obtained by separately formulating the compound of the present invention and combination drug (e.g., administration of compound of the present invention and combination drug in this order, and administration in the reversed order) and the like.

The admixing ratio of the compound of the present invention and combination drug can be appropriately determined depending on the administration subject, administration route, disease and the like.

Of compounds (I), since a compound wherein a group represented by the partial structural formula: —CO—N(R)—C($Ra^1$)($Ra^2$)—C($Ra^3$)($Ra^4$)— [wherein the symbols in the formula are as defined above] is —CH$_2$—NH—CO—CH$_2$—, —NH—CO—CH$_2$—CH$_2$—, —NH—CO—CH=CH—, —CH$_2$—CH$_2$—NH—CO—, —NH—CO—CH$_2$—O—, —NH—CO—C(Ph)=CH—, —NH—CO—CH=C(4-Cl-Ph)—, —CH$_2$—CH$_2$—CO—NH—, —CH=CH—CO—NH—, —CH$_2$—CO—NH—CH$_2$—, —NH—CO—CH(CH$_3$)—O—, —SO$_2$—NH—CH$_2$—CH$_2$—, —SO$_2$—CH$_2$—CH$_2$—CH$_2$—, —CH$_2$—CH$_2$—C≡C—, —CH$_2$—CH$_2$—CO—CH$_2$—, —CO—CH$_2$—CH$_2$—CO—, —CO—CH$_2$—CH$_2$—CH(OH)—, —CO—CH$_2$—CH=CH—, —CO—CH$_2$—CH$_2$—CH$_2$— or —CH$_2$—CH$_2$—CH$_2$—CO— [wherein Ph is a phenyl group and 4-Cl-Ph is a 4-chlorophenyl group], a salt thereof and a prodrug thereof (hereinafter sometimes to be abbreviated as compound group A) have an MCH receptor antagonistic action, they can be used as agents for the prophylaxis or treatment of diseases caused by MCH in mammals in the same manner as the compound of the present invention.

Here, as the salt and a prodrug thereof, those exemplified as the salt of compound (I) and prodrug of compound (I) can be used. As specific examples of compound group A, the compounds of the below-mentioned Reference Examples 38-75, 90-114 and the like can be mentioned.

The compound group A can be produced in the same manner as in compound (I).

The compound group A can be formulated into preparations in the same manner as in compound (I), and can be also used in combination with a combination drug.

The present invention is described in detail by way of the following Reference Examples, Examples, Formulation Example and Experimental Example. These are not intended to restrict the present invention, and may be modified within the range not deviating from the scope of this invention.

The "room temperature" in the following Reference Examples and Examples means a temperature of 0° C. to 30° C. For drying an organic layer, anhydrous magnesium sulfate or anhydrous sodium sulfate was employed. Unless otherwise specifically indicated, "%" means percent by weight.

The infrared spectrum was measured using Fourier transform infrared spectrophotometer by Diffuse Reflectance method. FABMS(pos) is mass spectrum measured by the (+) method in the Fast Atom Bombardment Mass Spectrometry.

The abbreviations used in the present specification mean the following.
s: singlet
d: doublet
t: triplet
q: quartet
m: multiplet
br: broad
J: coupling constant
Hz: Hertz
CDCl$_3$: deuterated chloroform
DMSO-d$_6$: deuterated dimethyl sulfoxide
THF: tetrahydrofuran
DMF: N,N-dimethylformamide
DMSO: dimethylsulfoxide
WSCD: 1-ethyl-3-(3-dimethylaminopropyl)carbodiimide
WSC: 1-ethyl-3-(3-dimethylaminopropyl)carbodiimide hydrochloride
$^1$H-NMR: proton nuclear magnetic resonance (free compound is generally used for measurement in CDCl$_3$)
IR: infrared spectrum
Me: methyl
Et: ethyl
HOBt: 1-hydroxy-1H-benzotriazole
IPE: diisopropyl ether
DMAP: 4-dimethylaminopyridine

REFERENCE EXAMPLE 1

3-[4-(methoxycarbonyl)phenyl]propionic acid

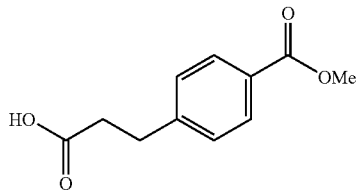

To a solution of methyl 4-(3-methoxy-3-oxopropyl)benzoate (5.05 g, 22.7 mmol) in methanol (120 ml) was added 1N aqueous sodium hydroxide solution (22.7 ml) at 0° C., and the mixture was stirred at room temperature for 16 hrs. After the reaction mixture was concentrated, the residue was dissolved in water, and the solution was washed with diethyl ether. To the aqueous layer was added 6N hydrochloric acid, and the mixture was extracted with ethyl acetate. The extract was washed with saturated brine and dried over anhydrous sodium sulfate. The solvent was concentrated under reduced pressure, and the obtained residue was dissolved in chloroform, and insoluble materials were filtered off. The solvent was evaporated under reduced pressure, and the obtained residue was powderized with hexane to give the title compound (3.61 g) as a powder.
$^1$H-NMR (CDCl$_3$) δ: 2.71 (2H, d, J=8.0 Hz), 3.01 (2H, d, J=8.0 Hz), 3.90 (3H, s), 7.28 (2H, d, J=8.0 Hz), 7.97 (2H, t, J=8.0 Hz).

REFERENCE EXAMPLE 2 methyl 4-{2-[(tert-butoxycarbonyl)amino]ethyl}benzoate

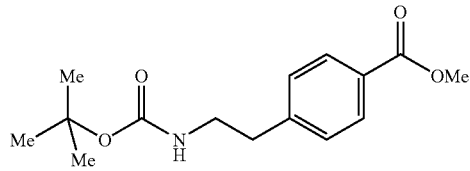

A solution (120 ml) of 3-[4-(methoxycarbonyl)phenyl]propionic acid (5.00 g, 24.0 mmol) obtained in Reference Example 1, triethylamine (4.34 ml, 31.2 mmol) and DPPA (6.21 ml, 28.8 mmol) in tert-butanol was stirred at 90° C. for 5 hrs, and the solvent was evaporated. Ethyl acetate was added to the residue and the mixture was washed with 10% aqueous citric acid solution, saturated aqueous potassium carbonate solution and saturated brine, and dried over anhydrous sodium sulfate. The solvent was evaporated under reduced pressure, and the obtained residue was purified by silica gel column chromatography (developing solvent; ethyl acetate:hexane=1:1), and powderized with hexane to give the title compound (2.46 g).

$^1$H-NMR (DMSO-d$_6$) δ: 1.35 (9H, s), 2.76 (2H, d, J=7.2 Hz), 3.17 (2H, m), 3.83 (3H, s), 6.90 (1H, d, J=5.4 Hz), 7.34 (2H, d, J=8.4 Hz), 7.87 (2H, d, J=8.4 Hz).

REFERENCE EXAMPLE 3 tert-butyl 2-[4-(1-pyrrolidinylmethyl)phenyl]ethylcarbamate

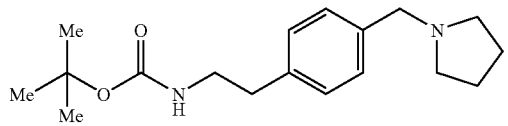

To a solution (10 ml) of methyl 4-{2-[(tert-butoxycarbonyl)amino]ethyl}benzoate (550 mg, 1.97 mmol) obtained in Reference Example 2 in tetrahydrofuran was added lithium aluminum hydride at 0° C., and the mixture was stirred at room temperature for 1 hr. To the reaction mixture was added ethyl acetate and the mixture was washed with 0.5N hydrochloric acid and saturated brine, and dried over anhydrous sodium sulfate. The solvent was evaporated under reduced pressure, and the obtained residue was purified by alumina column chromatography (developing solvent; ethyl acetate) to give a colorless oil. To a solution (10 ml) of the obtained oil (495 mg, 1.97 mmol) and triethylamine (274 ml, 1.97 mmol) in dimethylformamide was added methanesulfonyl chloride (152 ml, 1.97 mmol) at 0° C., and the mixture was stirred for 1 hr. Pyrrolidine (329 ml, 3.94 mmol) and potassium carbonate (816 mg, 5.91 mmol) were added and the mixture was stirred at 60° C. for 16 hrs. To the reaction mixture was added 0.5N hydrochloric acid, and the mixture was washed with diethyl ether. The aqueous layer was basified with potassium carbonate and extracted with ethyl acetate. The extract was washed with saturated brine, and dried over anhydrous sodium sulfate. The solvent was evaporated under reduced pressure, and the obtained residue was purified by alumina column chromatography (developing solvent; ethyl acetate) to give the title compound (527 mg).

$^1$H-NMR (CDCl$_3$) δ: 1.43 (9H, s), 1.78 (4H, m), 2.55 (4H, m), 2.77 (2H, t, J=7.0Hz), 3.36 (2H, m), 3.58 (2H, s), 4.55 (1H, s), 7.12 (2H, d, J=7.8 Hz), 7.25 (2H, d, J=7.8 Hz).

REFERENCE EXAMPLE 4

2-[4-(1-pyrrolidinylmethyl)phenyl]ethylamine

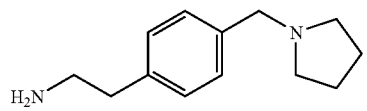

To tert-butyl 2-[4-(1-pyrrolidinylmethyl)phenyl]ethylcarbamate (526 mg, 1.73 mmol) obtained in Reference Example 3 was added trifluoroacetic acid (9 ml), and the mixture was stirred for 2 hrs. The mixture was concentrated under reduced pressure, and ethyl acetate was added to the residue. The mixture was washed with saturated aqueous potassium carbonate solution and saturated brine, and dried over anhydrous sodium sulfate. The solvent was evaporated under reduced pressure to give the title compound (239 mg).

$^1$H-NMR (CDCl$_3$) δ: 1.80 (4H, m), 2.50 (4H, m), 2.74 (2H, m), 2.96 (2H, m), 3.59 (2H, s), 7.14 (2H, d, J=8.0 Hz), 7.26 (2H, d, J=8.0 Hz).

REFERENCE EXAMPLE 5

N-[4-(2-aminoethyl)benzyl]-N,N-dimethylamine trifluoroacetate

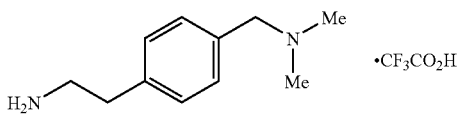

The title compound was obtained by similar operations as in Reference Example 3 and Reference Example 4 and using methyl 4-{2-[(tert-butoxycarbonyl)amino]ethyl}benzoate obtained in Reference Example 2.

$^1$H-NMR (CDCl$_3$) δ: 2.24 (6H, s), 2.79 (2H, t, J=7.2Hz), 2.99 (2H, t, J=7.2Hz), 3.42 (2H, s), 4.75 (3H, br), 7.12 (2H, m), 7.19 (2H, m).

REFERENCE EXAMPLE 6

2-[4-(1-piperidinylmethyl)phenyl]ethylamine dihydrochloride

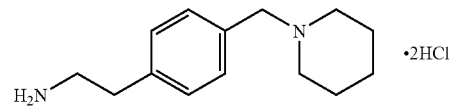

The title compound was obtained by similar operations as in Reference Example 3 and Reference Example 4 and using methyl 4-{2-[(tert-butoxycarbonyl)amino]ethyl}benzoate obtained in Reference Example 2.

$^1$H-NMR (DMSO-d$_6$) δ: 1.60-1.80 (6H, m), 2.80-3.30 (8H, m) 4.20 (2H, d, J=4.4 Hz), 7.33 (2H, d, J=8.1 Hz), 7.59 (2H, d, J=8.1 Hz), 8.18 (2H, br).

REFERENCE EXAMPLE 7

2-{4-[(4-methyl-1-piperazinyl)methyl]phenyl}ethylamine trihydrochloride

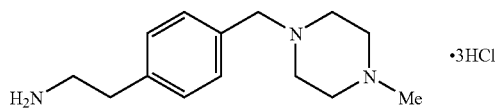

The title compound was obtained by similar operations as in Reference Example 3 and Reference Example 4 and using methyl 4-{2-[(tert-butoxycarbonyl)amino]ethyl}benzoate obtained in Reference Example 2.

$^1$H-NMR (DMSO-d$_6$) δ: 2.79 (3H, s), 2.80-3.20 (4H, m), 3.20-3.80 (8H, m), 4.27 (2H, br), 7.34 (2H, d, J=7.8 Hz), 7.58 (2H, d, J=7.8 Hz), 8.10 (2H, br).

REFERENCE EXAMPLE 8

2-(4-{[(2R,6S)-2,6-dimethyl-1-piperidinyl]methyl}phenyl)ethylamine dihydrochloride

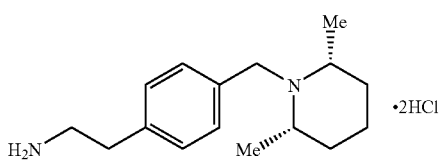

The title compound was obtained by similar operations as in Reference Example 3 and Reference Example 4 and using methyl 4-{2-[(tert-butoxycarbonyl)amino]ethyl}benzoate obtained in Reference Example 2.

$^1$H-NMR (DMSO-d$_6$) δ: 1.55 (6H, d, J=6.2 Hz), 1.74 (6H, m), 2.96 (4H, m), 3.43 (2H, m), 4.42 (2H, d, J=1.9 Hz), 7.36 (2H, d, J=8.1 Hz), 7.52 (2H, d, J=8.1 Hz), 8.25 (3H, br), 10.85 (1H, s).

REFERENCE EXAMPLE 9

2-[4-(1-azepanylmethyl)phenyl]ethylamine dihydrochloride

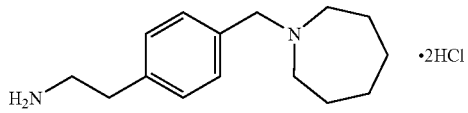

The title compound was obtained by similar operations as in Reference Example 3 and Reference Example 4 and using methyl 4-{2-[(tert-butoxycarbonyl)amino]ethyl}benzoate obtained in Reference Example 2.

$^1$H-NMR (DMSO-d$_6$) δ: 1.60 (4H, m), 1.84 (4H, m), 2.98 (6H, m), 3.26 (2H, m), 4.27 (2H, d, J=5.5 Hz), 7.33 (2H, d, J=8.1 Hz), 7.65 (2H, d, J=8.1 Hz), 8.31 (3H, br), 11.20 (1H, s).

REFERENCE EXAMPLE 10 tert-butyl 2-{4-[(2-methyl-1-pyrrolidinyl)methyl]phenyl}ethylcarbamate

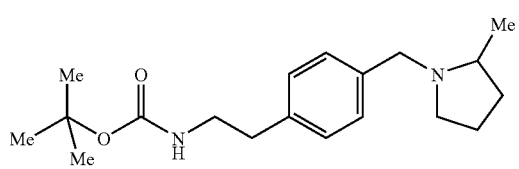

To a solution of tert-butyl 2-(4-formylphenyl)ethylcarbamate (3.0 g, 12.0 mmol), 2-methylpyrrolidine (1.44 ml, 14.4 mmol) and acetic acid (1.4 ml, 24.0 mmol) in THF (100 ml) was added sodium triacetoxyborohydride (5.1 g, 24.0 mmol), and the mixture was stirred at room temperature for 16 hrs. 10% Sodium hydrogencarbonate solution (100 ml) was added to the reaction solution, and the mixture was extracted with ethyl acetate (200 ml). The extract was washed with saturated brine, and dried over magnesium sulfate, and solvent was evaporated under reduced pressure. The residue was purified by alumina column chromatography (developing solvent; hexane:ethyl acetate=4:1) to give the title compound (3.10 g).

$^1$H-NMR (CDCl$_3$) δ: 1.17 (3H, d, J=6.0 Hz), 1.39-1.51 (2H, m), 1.44 (9H, s), 1.59-1.75 (2H, m), 1.88-1.99 (1H, m), 2.34-2.41 (1H, m), 2.77 (2H, t, J=6.9 Hz), 2.87-2.94 (1H, m), 3.10 (1H, d, J=12.8 Hz), 3.35-3.37 (2H, q like), 3.99 (1H, d, J=12.8 Hz), 4.53 (1H, br), 7.13 (2H, d, J=8.1 Hz), 7.25 (2H, d, J=8.1 Hz).

REFERENCE EXAMPLE 11

2-{4-[(2-methyl-1-pyrrolidinyl)methyl]phenyl}ethylamine dihydrochloride

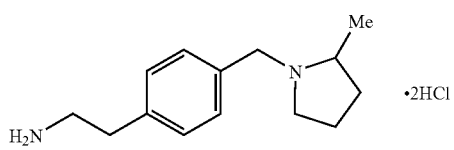

To a solution of tert-butyl 2-{4-[(2-methyl-1-pyrrolidinyl)methyl]phenyl}ethylcarbamate (3.10 g, 9.70 mmol) obtained in Reference Example 10 in methanol (50 ml) was added 4N hydrogen chloride-ethyl acetate (60 ml), and the mixture was stirred for 16 hrs, and concentrated under reduced pressure to give the title compound (2.8 g).

$^1$H-NMR (DMSO-d$_6$) δ: 1.37 (3H, d, J=6.6 Hz), 1.63-1.96 (3H, m), 2.15-2.24 (1H, m), 2.80-3.22 (6H, m), 3.24-3.46 (1H, m), 4.10 (1H, m), 4.49 (1H, m), 7.33 (2H, d, J=8.1 Hz), 7.60 (2H, d, J=8.1 Hz), 8.23 (2H, br).

REFERENCE EXAMPLE 12 ethyl 4-(3-ethoxy-1-methyl-3-oxopropyl)benzoate

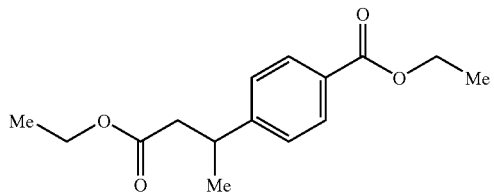

Ethyl 4-acetylbenzate (5.00 g, 26.0 mmol) was added to a solution (130 ml) of ethyl diethylphosphonoacetate (6.71 ml, 33.8 mmol) and tert-butoxy potassium (4.38 g, 39.0 mmol) in tetrahydrofuran at 0° C., and the mixture was stirred at room temperature for 16 hrs. Ethyl acetate was added to the reaction mixture, and the mixture was washed with saturated brine and dried over anhydrous sodium sulfate. The solvent was evaporated under reduced pressure, and the obtained residue was purified by NH-silica gel column chromatography (developing solvent; ethyl acetate). The mixture of the obtained oil and 10% palladium carbon (1 g) in ethanol (150 ml) was stirred under a hydrogen atmosphere for 2 hrs, and filtered through celite. The solvent was evaporated under reduced pressure, and the obtained residue was purified by NH-silica gel column chromatography (developing solvent; ethyl acetate) to give the title compound (5.67 g).

$^1$H-NMR (CDCl$_3$) δ: 1.17 (3H, t, J=7.2 Hz), 1.31 (3H, d, J=6.6 Hz), 1.38 (3H, d, J=7.2 Hz), 2.59 (2H, m), 3.32 (1H, m), 4.05 (2H, q, J=7.2 Hz), 4.34 (2H, q, J=7.2 Hz), 7.28 (2H, d, J=6.6 Hz), 7.96 (2H, d, J=6.6 Hz).

REFERENCE EXAMPLE 13 tert-butyl 2-[4-(1-pyrrolidinylmethyl)phenyl]propylcarbamate

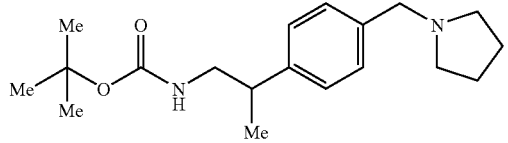

The title compound was obtained by similar operations as in Reference Example 1, Reference Example 2 and Reference Example 3 and using ethyl 4-(3-ethoxy-1-methyl-3-oxopropyl)benzoate obtained in Reference Example 12.

$^1$H-NMR (CDCl$_3$) δ: 1.24 (3H, d, J=7.2 Hz), 1.41 (9H, s), 1.79 (4H, m), 2.50 (4H, m), 2.93 (1H, m), 3.16, (1H, m), 3.40 (1H, m), 3.58 (2H, s), 4.42 (1H, m), 7.13 (2H, d, J=7.8 Hz), 7.26 (2H, d, J=7.8 Hz).

REFERENCE EXAMPLE 14

2-{4-[1-(1-pyrrolidinyl)ethyl]phenyl}ethylamine

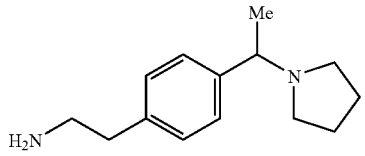

The title compound was obtained by similar operations as in Reference Example 3 and Reference Example 4 and using tert-butyl 2-(4-acetylphenyl)ethylcarbamate.

$^1$H-NMR (CDCl$_3$) δ: 1.38 (3H, d, J=6.6 Hz), 1.75 (4H, m) 2.34 (2H, m), 2.53 (2H, m), 2.72 (2H, t, J=6.9 Hz), 2.93 (2H, t, J=6.6 Hz), 3.15 (1H, q, J=6.3 Hz), 7.12 (2H, d, J=8.1 Hz), 7.26 (2H, d, J=8.1 Hz).

REFERENCE EXAMPLE 15

2-{4-[1-(1-piperidinyl)ethyl]phenyl}ethylamine

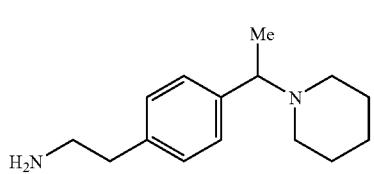

The title compound was obtained by similar operations as in Reference Example 3 and Reference Example 4 and using tert-butyl 2-(4-acetylphenyl)ethylcarbamate.

$^1$H-NMR (CDCl$_3$) δ: 1.34 (2H, m), 1.37 (3H, d, J=6.6 Hz), 1.54 (4H, m), 1.86 (2H, m), 2.35 (4H, m), 2.72 (2H, t, J=6.9 Hz), 2.94 (2H, t, J=6.6 Hz), 3.36 (1H, q, J=6.3 Hz), 7.12 (2H, d, J=8.1 Hz), 7.21 (2H, d, J=8.1 Hz).

REFERENCE EXAMPLE 16

2-{4-[1-(2-methyl-1-pyrrolidinyl)ethyl]phenyl}ethylamine

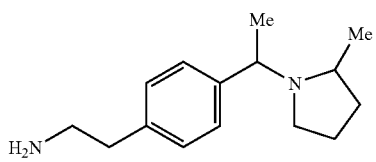

The title compound was obtained by similar operations as in Reference Example 3 and Reference Example 4 and using tert-butyl 2-(4-acetylphenyl)ethylcarbamate.

ESIMS(pos) 233 [M+H]$^+$

REFERENCE EXAMPLE 17

2-{4-[1-(1-azepanyl)ethyl]phenyl}ethylamine

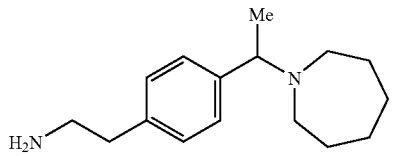

The title compound was obtained by similar operations as in Reference Example 3 and Reference Example 4 and using tert-butyl 2-(4-acetylphenyl)ethylcarbamate.

$^1$H-NMR (CDCl$_3$) δ: 1.16 (2H, m), 1.33 (3H, d, J=6.6 Hz), 1.57 (8H, m), 2.61 (4H, m), 2.72 (2H, t, J=6.9 Hz), 2.96 (2H, t, J=6.6 Hz), 3.74 (1H, q, J=6.6 Hz), 7.12 (2H, d, J=8.1 Hz), 7.27 (2H, d, J=8.1 Hz).

REFERENCE EXAMPLE 18

2-{4-[1-(4-methyl-1-piperazinyl)ethyl]phenyl}ethylamine

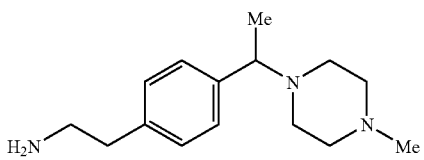

The title compound was obtained by similar operations as in Reference Example 3 and Reference Example 4 and using tert-butyl 2-(4-acetylphenyl)ethylcarbamate.

¹H-NMR (CDCl₃) δ: 1.22 (2H, m), 1.35 (3H, d, J=6.9 Hz), 2.52 (3H, s), 2.41 (8H, m), 2.72 (2H, t, J=6.6 Hz), 2.95 (2H, t, J=6.6 Hz), 3.34 (1H, q, J=6.9 Hz), 7.12 (2H, d, J=8.1 Hz), 7.24 (2H, d, J=8.1 Hz).

REFERENCE EXAMPLE 19

N-[2-(4-acetylphenyl)ethyl]-4-bromobenzamide

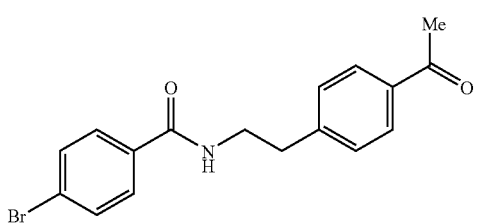

To a solution of 4-bromo-N-(2-phenylethyl)benzamide (10.0 g, 32.9 mmol) and acetyl chloride (3.04 ml, 42.7 mmol) in dichloromethane (80 ml) was added aluminum chloride (11.0 g, 82.2 mmol), and the mixture was stirred at room temperature for one day. The reaction mixture was poured into ice, and the mixture was extracted with ethyl acetate. The extract was washed with saturated brine and dried over anhydrous sodium sulfate. The solvent was concentrated under reduced pressure, and the obtained residue was powderized with isopropyl ether to give the title compound (9.79 g).

¹H-NMR (DMSO-d₆) δ: 2.55 (3H, s), 2.92 (2H, d, J=6.9 Hz), 3.51 (2H, m), 7.39 (2H, d, J=8.7 Hz), 7.67 (2H, d, J=8.7 Hz), 7.75 (2H, d, J=8.7 Hz), 7.89 (2H, d, J=8.7 Hz), 8.67 (1H, d, J=5.4 Hz).

REFERENCE EXAMPLE 20

4-bromo-N-{2-[4-(1-hydroxyethyl)phenyl]ethyl}benzamide

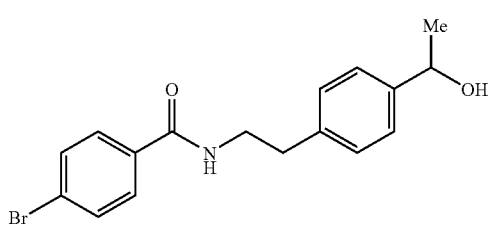

To a solution of N-[2-(4-acetylphenyl)ethyl]-4-bromobenzamide (9.79 g, 28.3 mmol) obtained in Reference Example 19 in a mixed solvent of methanol (140 ml) and tetrahydrofuran (30 ml) was added sodium borohydride (2.14 g, 56.6 mmol), and the mixture was stirred at room temperature for 3 hrs. The reaction mixture was concentrated under reduced pressure, and water was added to the residue. The mixture was extracted with ethyl acetate, and the extract was washed with saturated brine and dried over anhydrous sodium sulfate. The solvent was concentrated under reduced pressure, and the obtained residue was purified by alumina column chromatography (developing solvent; ethyl acetate), and powderized with isopropyl ether to give the title compound (8.76 g).

¹H-NMR (DMSO-d₆) δ: 1.29 (3H, d, J=6.6 Hz), 2.81 (2H, m), 3.45 (2H, m), 4.67 (1H, m), 5.07 (1H, m), 7.17 (2H, d, J=8.4 Hz), 7.26 (2H, d, J=8.4 Hz), 7.68 (2H, d, J=8.7 Hz), 7.77 (2H, d, J=8.7 Hz), 8.66 (1H, d, J=5.4 Hz).

REFERENCE EXAMPLE 21

4-bromo-N-{2-[4-(1-chloroethyl)phenyl]ethyl}benzamide

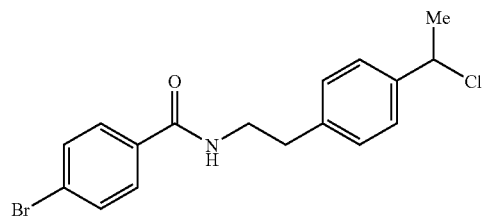

A solution of 4-bromo-N-{2-[4-(1-hydroxyethyl)phenyl]ethyl}benzamide (1.65 g, 4.74 mmol) obtained in Reference Example 20 in thionyl chloride (24 ml) was stirred at room temperature for 1 hr, and the reaction mixture was concentrated under reduced pressure. Ethyl acetate was added to the residue, and the mixture was washed with aqueous potassium hydrogencarbonate solution and saturated brine, and dried over anhydrous sodium sulfate. The solvent was concentrated under reduced pressure, and the obtained residue was purified by alumina column chromatography (developing solvent; ethyl acetate), and powderized with isopropyl ether to give the title compound (1.52 g).

¹H-NMR (DMSO-d₆) δ: 1.77 (3H, d, J=6.9 Hz), 2.84 (2H, m), 3.47 (2H, m), 5.32 (1H, m), 7.24 (2H, d, J=8.1 Hz), 7.40 (2H, d, J=8.1 Hz), 7.68 (2H, d, J=8.7 Hz), 7.77 (2H, d, J=8.7 Hz), 8.68 (1H, d, J=5.4 Hz).

REFERENCE EXAMPLE 22

4'-chloro-N-[2-(4-methoxyphenyl)ethyl][1,1'-biphenyl]-4-carboxamide

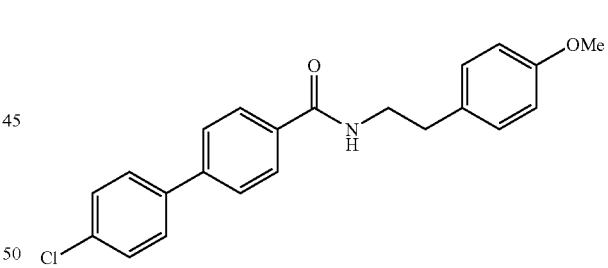

To a solution of 2-(4-methoxyphenyl)ethaneamine (500 mg, 3.31 mmol), 4'-chloro[1,1'-biphenyl]-4-carboxylic acid (846 mg, 3.64 mmol) and 1-hydroxybenzotriazole (760 mg, 4.96 mmol) in dimethylformamide (10 ml) was added ethyldimethylaminopropylcarbodiimide hydrochloride (951 mg, 4.96 mmol) at 0° C., and the mixture was was stirred at room temperature for 16 hrs. Ethyl acetate was added to the reaction mixture, and the mixture was washed with 1N aqueous sodium hydroxide solution and brine, and dried over anhydrous sodium sulfate. The solvent was concentrated under reduced pressure to give the title compound (1.03 g).

¹H-NMR (CDCl₃) δ: 2.89 (2H, t, J=6.8 Hz), 3.71 (2H, m), 3.80 (3H, s), 6.13 (1H, t, J=5.3 Hz), 6.87 (2H, d, J=9.1 Hz), 7.16 (2H, d, J=9.1 Hz), 7.41 (2H, d, J=8.9 Hz), 7.51 (2H, d, J=8.9 Hz), 7.58 (2H, d, J=8.6 Hz), 7.75 (2H, d, J=8.6 Hz).

REFERENCE EXAMPLE 23

4-bromo-N-{2-[4-(4-chlorobutanoyl)phenyl]ethyl}benzamide

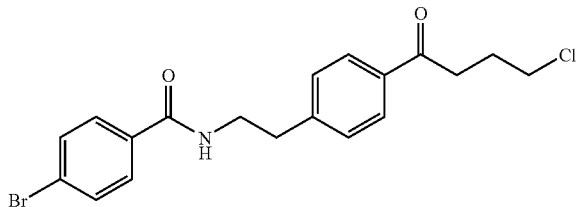

The title compound was obtained by a similar operation as in Reference Example 19 and using 4-bromo-N-(2-phenylethyl)benzamide and 4-chlorobutyryl chloride.

$^1$H NMR (DMSO-$d_6$) δ2.06 (2H, m), 2.92 (2H, m), 3.15 (2H, m), 3.52 (2H, m), 3.71 (2H, m), 7.39 (2H, d, J=8.4 Hz), 7.67 (2H, d, J=8.8 Hz), 7.76 (2H, d, J=8.8 Hz), 7.90 (2H, d, J=8.4 Hz), 8.66 (1H, m).

REFERENCE EXAMPLE 24

4-bromo-N-{2-[4-(cyclopropylcarbonyl)phenyl]ethyl}benzamide

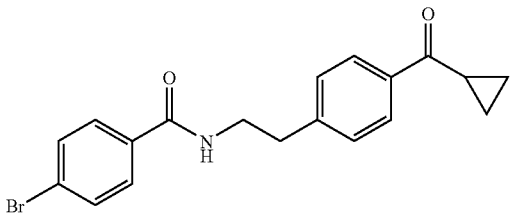

A solution of 4-bromo-N-{2-[4-(4-chlorobutanoyl)phenyl]ethyl}benzamide (4.10 g, 10.0 mmol) obtained in Reference Example 23 and 85% potassium hydroxide (993 mg, 15.0 mmol) in tetrahydrofuran (60 ml)-methanol(60 ml) was stirred at room temperature for 1 hr. Water was added to the reaction mixture, and the mixture was extracted with ethyl acetate. The extract was washed with saturated brine, and dried over anhydrous sodium sulfate. The solvent was concentrated under reduced pressure, and the obtained residue was purified by alumina column chromatography (developing solvent; ethyl acetate), and powderized with ethyl acetate-isopropyl ether (1:5) to give the title compound (3.38 g).

$^1$H NMR (DMSO-$d_6$) δ1.01 (4H, m), 2.85-2.96 (3H, m), 3.52 (2H, m), 7.39 (2H, d, J=8.1 Hz), 7.66 (2H, d, J=8.4 Hz), 7.74 (2H, d, J=8.4 Hz), 7.97 (2H, d, J=8.1 Hz), 8.65 (1H, t, J=6.0 Hz).

REFERENCE EXAMPLE 25

2-[4-(1-methyl-2-pyrrolidinyl)phenyl]ethylamine

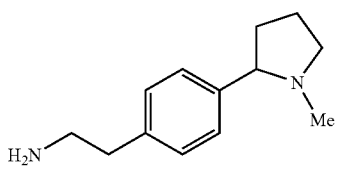

A solution of 4-bromo-N-{2-[4-(1-methyl-2-pyrrolidinyl)phenyl]ethyl}benzamide (1.12 g, 2.89 mmol) obtained in Example 136 in concentrated hydrochloric acid (14 ml) was stirred at 100° C. for one day. Water was added to the reaction mixture, and the mixture was washed with diethyl ether and basified with potassium carbonate. This was extracted with ethyl acetate, and the extract was washed with saturated brine, and dried over anhydrous sodium sulfate. The solvent was concentrated under reduced pressure, and the obtained residue was purified by alumina column chromatography (developing solvent; ethyl acetate:methanol=1:1) to give the title compound (305 mg).

$^1$H NMR (CDCl$_3$) δ1.75-1.83 (2H, m), 1.93-2.05 (1H, m) 2.11-2.31 (5H, m), 2.74 (2H, m), 2.95-3.03 (3H, m), 3.24 (1H, m), 7.15 (2H, d, J=8.1 Hz), 7.27 (2H, d, J=8.1 Hz).

REFERENCE EXAMPLE 26

N-methyl-2-{4-[1-(1-pyrrolidinyl)ethyl]phenyl}ethylamine

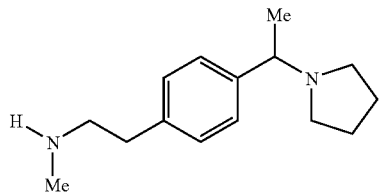

To a solution of 2-{4-[1-(1-pyrrolidinyl)ethyl]phenyl}ethylamine (9.26 g, 31.8 mmol) obtained in Reference Example 14 and triethylamine (15.5 ml, 111 mmol) in tetrahydrofuran (200 ml) was added dropwise methyl chlorocarbonate (2.46 ml, 31.8. mmol) at 0° C., and the mixture was stirred at room temperature for 3 hrs. Water was added to the reaction mixture, and the mixture was extracted with ethyl acetate. The extract was washed with saturated brine, and dried over anhydrous sodium sulfate. The solvent was concentrated under reduced pressure, and the obtained pale-yellow solid was dissolved in tetrahydrofuran (200 ml). Lithium aluminum hydride (1.21 g, 32.0 mmol) was added at 0° C., and the mixture was heated under reflux for 3 hrs. The reaction mixture was cooled to 0° C. and water was added. The mixture was extracted with ethyl acetate, and the extract was washed with saturated brine, and dried over anhydrous sodium sulfate. The solvent was concentrated under reduced pressure, and the obtained residue was purified by NH-silica gel column chromatography (developing solvent; ethyl acetate) to give the title compound (4.05 g).

$^1$H NMR (CDCl$_3$) δ1.38 (3H, d, J=6.6 Hz), 1.75 (4H, m) 2.34 (2H, m), 2.44 (3H, s), 2.55 (2H, m), 2.77 (4H, m), 3.15 (1H, q, J=6.6 Hz), 7.13 (2H, d, J=8.0 Hz), 7.25 (2H, d, J=8.0 Hz).

REFERENCE EXAMPLE 27

(E)-N-(4-bromophenyl)-3-(4-formylphenyl)-2-propenamide

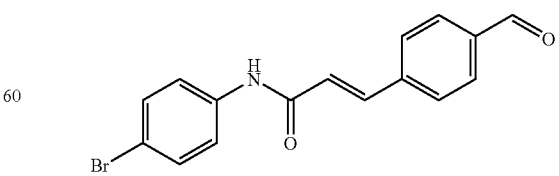

The title compound was obtained by a similar operation as in Example 2 and using (E)-3-(4-formylphenyl)-2-propenoic acid.

$^1$H-NMR (DMSO-d$_6$) δ: 6.95 (1H, d, J=15.9 Hz), 7.53 (2H, d, J=9.0 Hz), 7.66 (3H, m), 7.84 (2H, d, J=8.4 Hz), 7.97 (2H, d, J=8.4 Hz), 10.02 (1H, s), 10.45 (1H, s).

REFERENCE EXAMPLE 28

4-(1-pyrrolidinylmethyl)benzoic acid hydrochloride

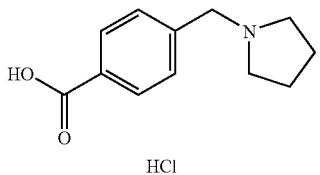

A solution of methyl 4-(1-pyrrolidinylmethyl)benzoate hydrochloride (3.18 g, 12.4 mmol) in 6N hydrochloric acid (30 ml) was stirred at 100° C. for 16 hrs. The solvent was evaporated under reduced pressure, and the residue was powderized with tetrahydrofuran to give the title compound (1.74 g).
$^1$H-NMR (CD$_3$OD) δ: 2.11 (4H, m), 3.40 (4H, m), 4.47 (2H, s), 7.65 (2H, d, J=8.8 Hz), 8.12 (2H, d, J=8.8 Hz).

REFERENCE EXAMPLE 29

N-(4-bromophenyl)-2-[4-(hydroxymethyl)phenoxy]acetamide

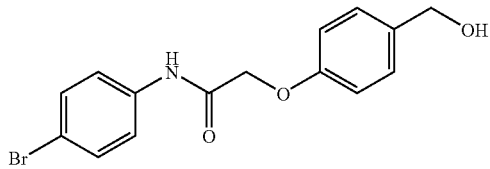

The title compound was obtained by a similar operation as in Example 2 and using 4-bromoaniline and [4-(hydroxymethyl)phenoxy]acetic acid.
$^1$H-NMR (DMSO-d$_6$) δ: 4.41 (2H, d, J=5.7 Hz), 4.67 (2H, s), 5.06 (1H, t, J=5.7 Hz), 6.94 (2H, d, J=8.7 Hz), 7.24 (2H, d, J=8.7 Hz), 7.49 (2H, d, J=8.7 Hz), 7.62 (2H, d, J=8.7 Hz), 10.19 (1H, s).

REFERENCE EXAMPLE 30

4-(1-pyrrolidinylmethyl)benzaldehyde

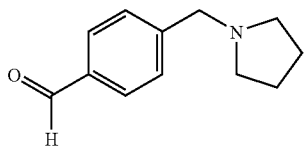

To a solution of 4-(dimethoxymethyl)benzaldehyde (25.0 g, 120 mmol), pyrrolidine (10.0 ml, 120 mmol), acetic acid (6.87 ml, 120 mmol) and anhydrous sodium sulfate (34.1 g, 240 mmol) in dichloromethane (300 ml) was added sodium triacetoxyborohydride (38.2 g, 180 mmol), and the mixture was stirred for 3 days. Potassium carbonate was added to the reaction mixture, and the solvent was evaporated under reduced pressure. Ethyl acetate was added to the residue, and the mixture was washed with saturated brine and dried over anhydrous sodium sulfate. The solvent was evaporated under reduced pressure, and the obtained residue was purified by alumina column chromatography (developing solvent; ethyl acetate). 1N Hydrochloric acid (300 ml) was added to the obtained oil, and the mixture was washed with diethyl ether after 2 hrs. The aqueous layer was basified with potassium carbonate, and extracted with ethyl acetate. The extract was washed with saturated brine and dried over anhydrous sodium sulfate. The solvent was evaporated under reduced pressure, and the obtained residue was purified by alumina column chromatography (developing solvent; ethyl acetate) to give the title compound (22.7 g).
$^1$H-NMR (CDCl$_3$) δ: 1.80 (4H, m), 2.52 (4H, m), 3.68. (2H, s), 7.50 (2H, d, J=8.1 Hz), 7.82 (2H, d, J=8.1 Hz), 9.98 (1H, s).

REFERENCE EXAMPLE 31

(E)-2-phenyl-3-[4-(1-pyrrolidinylmethyl)phenyl]-2-propenoic acid hydrochloride

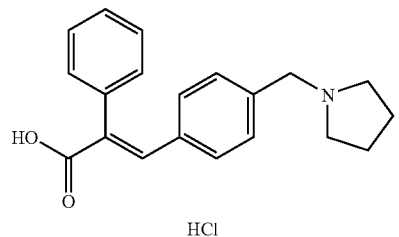

Triethyl phosphite (8.58 ml, 50 mmol) was added to ethyl bromo(phenyl)acetate (9.73 g, 40.0 mmol), and the mixture was stirred at 160° C. for 1 hr. Triethyl phosphate (8.58 ml, 50 mmol) was further added, and the mixture was stirred for 1 hr. Excess triethyl phosphite was evaporated under reduced pressure, and the residue was dissolved in tetrahydrofuran (100 ml). This solution was added dropwise to a solution of 60% sodium hydride (1.60 g, 40.0 mmol) in tetrahydrofuran (50 ml) at 0° C. After stirring for 10 min., a solution of 4-(1-pyrrolidinylmethyl)benzaldehyde (7.58 g, 40.0 mmol) obtained in Reference Example 30 in tetrahydrofuran (50 ml) was added dropwise, and the mixture was stirred at room temperature for 1 hr. The solvent was evaporated under reduced pressure, and isopropyl ether was added to the residue. The mixture was washed with saturated brine, and extracted with 1N hydrochloric acid. The aqueous layer was washed with isopropyl ether, and the aqueous layer was basified with potassium carbonate, and extracted with ethyl acetate. The extract was washed with saturated brine, and dried over anhydrous sodium sulfate. The solvent was evaporated under reduced pressure, and the obtained residue was purified by alumina column chromatography (developing solvent; ethyl acetate) to give an oil (10.3 g). A solution of the obtained oil (1.00 g, 2.98 mmol) in concentrated hydrochloric acid (15 ml) was stirred at 100° C. for one day and concentrated under reduced pressure. The obtained residue was washed with acetonitrile and tetrahydrofuran to give the title compound (150 mg).

$^1$H-NMR (DMSO-$d_6$) δ: 1.85 (2H, m), 1.97 (2H, m), 2.98 (2H, m), 3.33 (2H, m), 4.23 (2H, s), 7.09 (2H, d, J=8.1 Hz), 7.16 (2H, m), 7.38 (5H, m), 7.76 (1H, s), 10.72 (1H, br).

REFERENCE EXAMPLE 32

(4-chlorophenyl)[4-(1-pyrrolidinylmethyl)phenyl]methanone

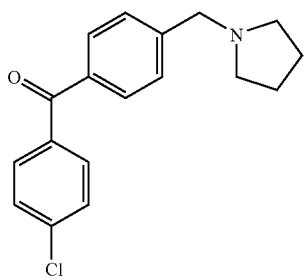

Acetonitrile (55 ml) was added to [4-(bromomethyl)phenyl](4-chlorophenyl)methanone (6.71 g, 21.7 mmol), potassium carbonate (5.99 g, 43.3 mmol) and pyrrolidine (3.62 ml, 43.3 mmol), and the mixture was stirred at 80° C. for 16 hrs. The solvent was concentrated, and diethyl ether was added to the residue. The mixture was extracted with 1N hydrochloric acid. The extract was basified with potassium carbonate, and the mixture was extracted with ethyl acetate. The extract was washed with saturated brine, and the solvent was evaporated under reduced pressure. The obtained residue was purified by alumina column chromatography (developing solvent; ethyl acetate) to give the title compound (4.79 g).

$^1$H-NMR (DMSO-$d_6$) δ: 1.71 (4H, m), 2.46 (4H, m), 3.67 (2H, s), 7.49 (2H, d, J=8.1 Hz), 7.62 (2H, d, J=8.4 Hz), 7.69 (2H, d, J=8.1 Hz), 7.74 (2H, d, J=8.4 Hz).

REFERENCE EXAMPLE 33

(Z)-3-(4-chlorophenyl)-3-[4-(1-pyrrolidinylmethyl)phenyl]-2-propenoic acid hydrochloride

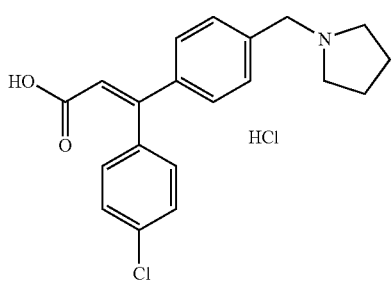

To a solution of (4-chlorophenyl) [4-(1-pyrrolidinylmethyl)phenyl]methanone (1.00 g, 3.34 mmol) obtained in Reference Example 32 and tert-butyl (diethoxyphosphoryl)acetate (1.18 ml, 5.00 mmol) in tetrahydrofuran (17 ml) was added 60% sodium hydride (200 mg, 5.00 mmol) at 0° C., and the mixture was stirred at room temperature for 4 hrs. Ethyl acetate was added to the reaction mixture, and the mixture was washed with aqueous potassium carbonate solution and saturated brine, and dried over anhydrous sodium sulfate. The solvent was evaporated under reduced pressure, and the obtained residue was purified by alumina column chromatography (developing solvent; ethyl acetate) to give an oil (10.3 g). A solution of the obtained oil (1.33 g, 3.34 mmol) in 4N hydrogen chloride-ethyl acetate (17 ml) was stirred at room temperature for one day, and concentrated under reduced pressure. The obtained residue was washed with isopropanol and acetonitrile to give the title compound (425 mg).

$^1$H-NMR (DMSO-$d_6$) δ: 1.88 (2H, m), 1.99 (2H, m), 3.05 (2H, m), 3.34 (2H, m), 4.34 (2H, d, J=5.7 Hz), 6.45 (1H, s), 7.16 (2H, d, J=8.1 Hz), 7.34 (2H, d, J=8.1 Hz), 7.45 (2H, d, J=8.1 Hz), 7.55 (2H, d, J=8.1 Hz), 10.37 (1H, br).

REFERENCE EXAMPLE 34

2-(4-formylphenoxy)propionic acid

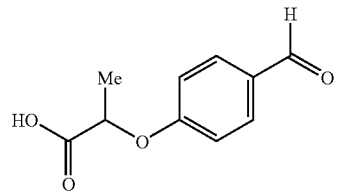

A solution of ethyl 2-bromopropanoate (6.38 ml, 49.1 mmol), 4-hydroxybenzaldehyde (5.00 g, 40.9 mmol) and potassium carbonate (6.79 g, 49.1 mmol) in acetonitrile (25 ml) was stirred at 60° C. for 16 hrs. Ethyl acetate was added to the reaction mixture, and the mixture was washed with saturated brine and dried over anhydrous sodium sulfate. The solvent was evaporated under reduced pressure, and the obtained residue was purified by alumina column chromatography (developing solvent; ethyl acetate) to give an oil. To a solution of the obtained oil (9.10 g, 40.9 mmol) in ethanol (200 ml) was added 1N aqueous sodium hydroxide solution (61.4 ml), and the mixture was stirred at room temperature for 16 hrs, and concentrated under reduced pressure. Ethyl acetate was added to the obtained residue. The mixture was washed with 1N hydrochloric acid and saturated brine and dried over anhydrous sodium sulfate. The solvent was evaporated under reduced pressure, and the obtained redsidue was powderized with isopropyl ether to give the title compound (5.68 g).

$^1$H-NMR (DMSO-$d_6$) δ: 1.71 (3H, d, J=6.6 Hz), 4.91 (1H, q, J=6.6 Hz), 6.99 (2H, d, J=8.4 Hz), 7.83 (2H, d, J=8.4 Hz), 9.87 (1H, s).

REFERENCE EXAMPLE 35

N-(4-bromophenyl)-2-(4-formylphenoxy)propanamide

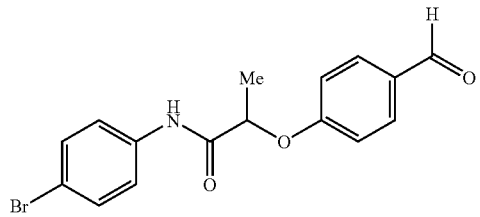

The title compound was obtained by a similar operation as in Example 2 and using 2-(4-formylphenoxy)propanoic acid obtained in Reference Example 34 and 4-bromoaniline.

$^1$H-NMR (DMSO-$d_6$) δ: 1.71 (3H, d, J=6.6 Hz), 4.91 (1H, q, J=6.6 Hz), 7.09 (2H, d, J=8.8 Hz), 7.44 (4H, s-like), 7.89 (2H, d, J=8.8 Hz), 8.03 (1H, s), 9.92 (1H, s).

REFERENCE EXAMPLE 36

N-(4-bromophenyl)-2-[4-(2-oxopropyl)phenoxy]propanamide

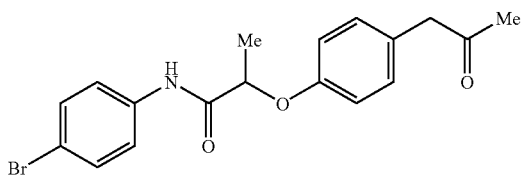

A solution of 2-bromo-N-(4-bromophenyl)propanamide (3.00 g, 10.2 mmol), 1-(4-hydroxyphenyl)acetone (1.54 g, 10.2 mmol) and potassium carbonate (2.83 g, 20.5 mmol) in DMF (20 ml) was stirred at room temperature for 4 hrs. Ethyl acetate was added to the reaction mixture, and the mixture was washed with 1N aqueous sodium hydroxide solution and brine. The solvent was evaporated under reduced pressure, and the obtained crude crystals were recrystallized from isopropyl ether-ethyl acetate to give the title compound (2.75 g).
$^1$H-NMR (CDCl$_3$) δ: 2.17 (3H, s), 3.68 (2H, s), 4.60 (2H, s), 6.95 (2H, m), 7.18 (2H, m), 7.48 (4H, m), 8.24 (1H, s).

REFERENCE EXAMPLE 37

N-(4'-chloro-1,1'-biphenyl-4-yl)-2-[4-(2-oxopropyl)phenoxy]propanamide

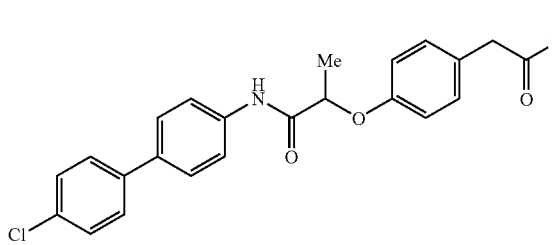

The title compound was obtained by a similar operation as in Example 6 and using N-(4-bromophenyl)-2-[4-(2-oxopropyl)phenoxy]propanamide obtained in Reference Example 36 and 4-chlorophenylboronic acid.
$^1$H-NMR (CDCl$_3$) δ: 2.18 (3H, s), 3.68 (2H, s), 4.63 (2H, s), 6.98 (2H, m), 7.19 (2H, m), 7.40 (2H, m), 7.52 (4H, m), 7.67 (2H, m), 8.32 (1H, s).

REFERENCE EXAMPLE 38

N-(4-bromobenzyl)-2-[4-(1-pyrrolidinylmethyl)phenyl]acetamide

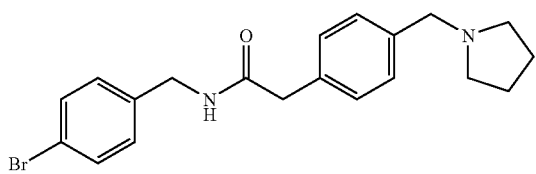

To a solution of 4-bromobenzylamine hydrochloride (971 mg, 4.37 mmol), [4-(bromomethyl)phenyl]acetic acid (1.00 g, 4.37 mmol), 1-hydroxybenzotriazole (590 mg, 4.37 mmol) and triethylamine (668 μl, 4.80 mmol) in dimethylformamide (11 ml) was added ethyldimethylaminopropylcarbodiimide hydrochloride (837 mg, 4.37 mmol) at 0° C., and the mixture was stirred at room temperature 16 hrs. Ethyl acetate was added to the reaction mixture. The mixture was washed with aqueous potassium carbonate solution and saturated brine and dried over anhydrous sodium sulfate. The solvent was concentrated under reduced pressure, and the obtained residue was purified by alumina column chromatography (developing solvent; ethyl acetate), and powderized with ethyl acetate-isopropyl ether (1:5). A solution of the obtained powder (850 mg, 2.24 mmol), pyrrolidine (561 μl, 6.37 mmol) and potassium carbonate (930 mg, 6.37 mmol) in dimethylformamide (10 ml) was stirred at 80° C. for 16 hrs. Ethyl acetate was added to the reaction mixture, and the mixture was washed with saturated brine and dried over anhydrous sodium sulfate. The solvent was concentrated under reduced pressure and the obtained residue was purified by NH-silica gel column chromatography (developing solvent; ethyl acetate), and powderized with isopropyl ether to give the title compound (437 mg).
$^1$H-NMR (DMSO-d$_6$) δ: 1.68 (4H, m), 2.40 (4H, m), 3.44 (2H, s), 3.52 (2H, s), 4.21 (2H, d, J=6.0 Hz), 7.14-7.23 (3H, m), 7.46 (2H, d, J=8.7 Hz), 8.53 (2H, t, J=6.0 Hz). melting point: 107-109° C. (ethyl acetate-isopropyl ether) FABMS (pos) 387 [M+H]+

REFERENCE EXAMPLE 39

N-[(4'-chloro-1,1'-biphenyl-4-yl)methyl]-2-[4-(1-pyrrolidinylmethyl)phenyl]acetamide

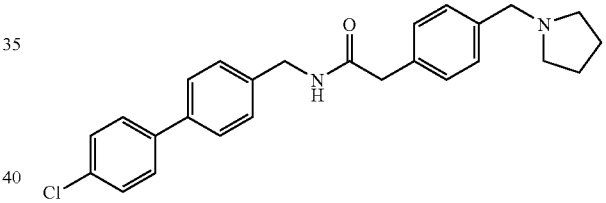

The title compound was obtained by a similar operation as in Example 6 and using N-(4-bromobenzyl)-2-[4-(1-pyrrolidinylmethyl)phenyl]acetamide obtained in Reference Example 38 and 4-chlorophenylboronic acid.
$^1$H-NMR (DMSO-d$_6$) δ: 1.67 (4H, m), 2.40 (4H, m), 3.46 (2H, s), 3.53 (2H, s), 4.29 (2H, d, J=5.7 Hz), 7.21 (4H, s-like), 7.30 (2H, d, J=9.0 Hz), 7.49 (2H, d, J=9.0 Hz), 7.59 (2H, d, J=9.0 Hz), 7.66 (2H, d, J=9.0 Hz), 8.55 (2H, t, J=6.0 Hz). melting point: 151-153° C. (ethyl acetate-isopropyl ether) FABMS (pos) 419 [M+H]+

REFERENCE EXAMPLE 40

N-(4-pentylphenyl)-3-[4-(1-pyrrolidinylmethyl)phenyl]propanamide

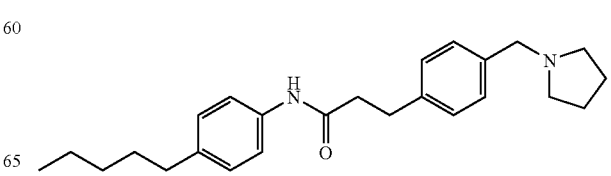

The title compound was obtained by similar operations as in Example 2 and Reference Example 3 and using 3-[4-(methoxycarbonyl)phenyl]propionic acid obtained in Reference Example 1.

¹H-NMR (DMSO-d₆) δ: 0.85 (3H, t, J=6.9 Hz), 1.26 (4H, m), 1.53 (2H, m), 1.66 (4H, m), 2.38 (4H, m), 2.49 (2H, m), 2.57 (2H, t, J=7.5 Hz), 2.87 (2H, t, J=7.5 Hz), 3.50 (2H, s), 7.07 (2H, d, J=8.7 Hz), 7.18 (4H, m), 7.44 (2H, d, J=8.7 Hz), 9.78 (1H, s). melting point: 104-105° C. (ethyl acetate-isopropyl ether) FABMS (pos) 379 [M+H]+

REFERENCE EXAMPLE 41

N-(4-bromophenyl)-3-[4-(1-pyrrolidinylmethyl)phenyl]propanamide

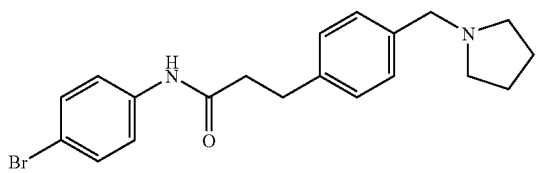

The title compound was obtained by similar operations as in Example 2 and Reference Example 3 and using 3-[4-(methoxycarbonyl)phenyl]propionic acid obtained in Reference Example 1.

¹H-NMR (DMSO-d₆) δ: 1.66 (4H, m), 2.38 (4H, m), 2.60 (2H, t, J=7.5 Hz), 2.88 (2H, t, J=7.5 Hz), 3.50 (2H, s), 7.18 (4H, m), 7.45 (2H, d, J=9.0 Hz), 7.54 (2H, d, J=9.0 Hz), 10.01 (1H, s). melting point: 137-138° C. (ethyl acetate-isopropyl ether) FABMS (pos) 387 [M+H]+

REFERENCE EXAMPLE 42

N-(4'-chloro-1,1'-biphenyl-4-yl)-3-[4-(1-pyrrolidinylmethyl)phenyl]propanamide

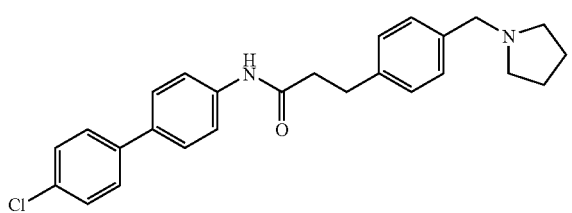

The title compound was obtained by a similar operation as in Example 6 and using N-(4-bromophenyl)-3-[4-(1-pyrrolidinylmethyl)phenyl]propanamide obtained in Reference Example 41.

¹H-NMR (DMSO-d₆) δ: 1.66 (4H, m), 2.38 (4H, m), 2.63 (2H, t, J=7.5 Hz), 2.90 (2H, t, J=7.5 Hz), 3.50 (2H, s), 7.19 (4H, m), 7.47 (2H, d, J=8.4 Hz), 7.59-7.68 (6H, m), 10.00 (1H, s). melting point: 179-181° C. (ethyl acetate-isopropyl ether) FABMS (pos) 419 [M+H]+

REFERENCE EXAMPLE 43

(E)-N-(4-bromophenyl)-3-[4-(1-pyrrolidinylmethyl)phenyl]-2-propenamide

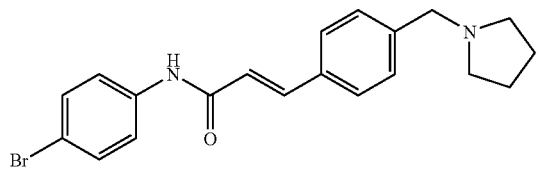

To a solution of (E)-N-(4-bromophenyl)-3-(4-formylphenyl)-2-propenamide (400 mg, 1.21 mmol) obtained in Reference Example 27 and pyrrolidine (303 μl, 3.63 mmol) in acetic acid-methanol-tetrahydrofuran (3 ml×3) was added sodium triacetoxyborohydride (770 mg, 3.63 mmol), and the mixture was stirred at room temperature for 2 days. Ethyl acetate was added to the reaction mixture, and the mixture was washed with saturated aqueous potassium carbonate solution and saturated brine, and dried over anhydrous sodium sulfate. The solvent was evaporated under reduced pressure, and the obtained residue was purified by NH-silica gel column chromatography (developing solvent; ethyl acetate:hexane=1:1), and powderized with hexane to give the title compound (123 mg).

¹H-NMR (DMSO-d₆) δ: 1.70 (4H, m), 2.46 (4H, m), 3.62 (2H, s), 6.78 (1H, d, J=15.6 Hz), 7.37 (2H, d, J=8.1 Hz), 7.49-7.60 (5H, m), 7.67 (2H, d, J=8.7 Hz), 10.31 (1H, s). melting point: 184-186° C. (ethyl acetate-isopropyl ether) FABMS (pos) 385 [M+H]+

REFERENCE EXAMPLE 44

(E)-N-(4'-chloro-1,1'-biphenyl-4-yl)-3-[4-(1-pyrrolidinylmethyl)phenyl]-2-propenamide

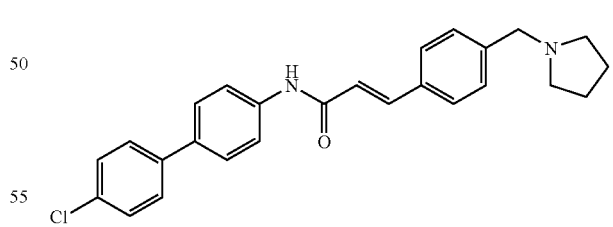

The title compound was obtained by a similar operation as in Example 6 and using (E)-N-(4-bromophenyl)-3-[4-(1-pyrrolidinylmethyl)phenyl]-2-propenamide obtained in Reference Example 43.

¹H-NMR (DMSO-d₆) δ: 1.71 (4H, m), 2.45 (4H, m), 3.61 (2H, s), 6.83 (1H, d, J=15.3 Hz), 7.38 (2H, d, J=8.1 Hz), 7.49 (2H, d, J=8.1 Hz), 7.59 (3H, m), 7.67 (4H, m), 7.80 (2H, d, J=8.7 Hz), 10.32 (1H, s). melting point: 207-209° C. (ethyl acetate-isopropyl ether) FABMS (pos) 417 [M+H]+

REFERENCE EXAMPLE 45

N-[2-(4'-chloro-1,1'-biphenyl-4-yl)ethyl]-4-(1-pyrrolidinylmethyl)benzamide

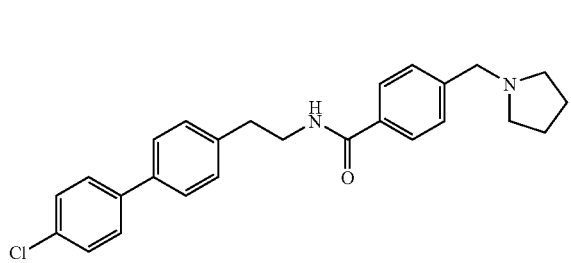

The title compound was obtained by a similar operation as in Example 2 and using 4-(1-pyrrolidinylmethyl)benzoic acid hydrochloride obtained in Reference Example 28.

$^1$H-NMR (DMSO-$d_6$) δ: 1.69 (4H, m), 2.43 (4H, m), 2.89 (2H, t, J=7.0 Hz), 3.50 (2H, m), 3.61 (2H, s), 7.36 (4H, m), 7.50 (2H, d, J=8.8 Hz), 7.61 (2H, d, J=8.4 Hz), 7.68 (2H, d, J=8.4 Hz), 7.78 (2H, d, J=8.0 Hz), 8.57 (1H, t, J=7.8 Hz). melting point: 187-189° C. (ethyl acetate-isopropyl ether) FABMS (pos) 419 [M+H]+

REFERENCE EXAMPLE 46

N-(4-bromophenyl)-2-[4-(1-pyrrolidinylmethyl)phenoxy]acetamide

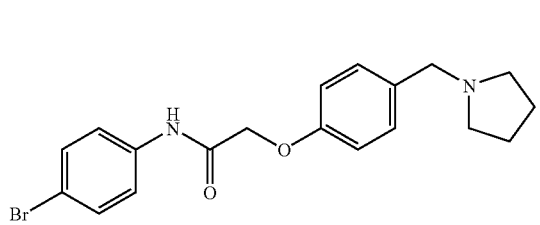

To a solution (15 ml) of N-(4-bromophenyl)-2-[4-(hydroxymethyl)phenoxy]acetamide (1.00 g, 2.97 mmol) obtained in Reference Example 29 and triethylamine (0.496 ml, 3.57 mmol) in dimethylformamide was added methanesulfonyl chloride (0.253 ml, 3.27 mmol) at 0° C., and the mixture was stirred for 1 hr. Pyrrolidine (0.745 ml, 8.92 mmol) and potassium carbonate (1.23 g, 8.92 mmol) were added, and the mixture was stirred at 60° C. for 16 hrs. 1N Hydrochloric acid was added to the reaction mixture and the mixture was washed with diethyl ether. The aqueous layer was basified with potassium carbonate and extracted with ethyl acetate. The extract was washed with saturated brine and dried over anhydrous sodium sulfate. The solvent was evaporated under reduced pressure, and the obtained residue was purified by alumina column chromatography (developing solvent; ethyl acetate), and powderized with diisopropyl ether to give the title compound (484 mg).

$^1$H-NMR (DMSO-$d_6$) δ: 1.67 (4H, m), 2.38 (4H, m), 3.48 (2H, s), 4.67 (2H, s), 6.92 (2H, d, J=8.7 Hz), 7.21 (2H, d, J=8.7 Hz), 7.50 (2H, d, J=8.7 Hz), 7.62 (2H, d, J=8.7 Hz), 10.19 (1H, s). melting point: 143-145° C. (ethyl acetate-isopropyl ether) FABMS (pos) 389 [M+H]+

REFERENCE EXAMPLE 47

N-(4'-chloro-1,1'-biphenyl-4-yl)-2-[4-(1-pyrrolidinylmethyl)phenoxy]acetamide

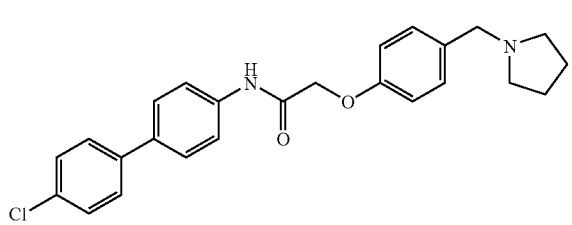

The title compound was obtained by a similar operation as in Example 6 and using N-(4-bromophenyl)-2-[4-(1-pyrrolidinylmethyl)phenoxy]acetamide obtained in Reference Example 46.

$^1$H-NMR (DMSO-$d_6$) δ: 1.67 (4H, m), 2.40 (4H, m), 3.50 (2H, s), 4.69 (2H, s), 6.94 (2H, d, J=8.7 Hz), 7.23 (2H, d, J=8.7 Hz), 7.48 (2H, d, J=8.7 Hz), 7.65 (4H, m), 7.74 (2H, d, J=8.7 Hz), 10.18 (1H, s). melting point: 167-169° C. (ethyl acetate-isopropyl ether) FABMS (pos) 421 [M+H]+

REFERENCE EXAMPLE 48

(E)-N-(4-bromophenyl)-2-phenyl-3-[4-(1-pyrrolidinylmethyl)phenyl]-2-propenamide

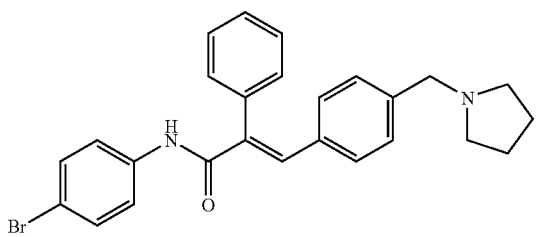

The title compound was obtained by a similar operation as in Example 2 and using (E)-2-phenyl-3-[4-(1-pyrrolidinylmethyl)phenyl]-2-propenoic acid hydrochloride obtained in Reference Example 31.

$^1$H-NMR (DMSO-$d_6$) δ: 1.67 (4H, m), 2.38 (4H, m), 3.50 (2H, s), 7.01 (2H, d, J=8.1 Hz), 7.12 (2H, d, J=8.1 Hz), 7.23 (2H, m), 7.38 (4H, m), 7.49 (2H, d, J=8.7 Hz), 7.66 (2H, d, J=8.7 Hz), 10.07 (1H, s). melting point: 158-160° C. (ethyl acetate-hexane) FABMS (pos) 461 [M+H]+

REFERENCE EXAMPLE 49

(E)-N-(4'-chloro-1,1'-biphenyl-4-yl)-2-phenyl-3-[4-(1-pyrrolidinylmethyl)phenyl]-2-propenamide

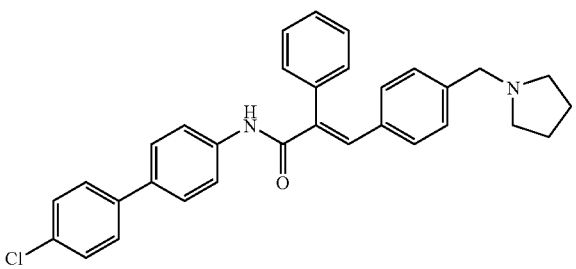

The title compound was obtained by a similar operation as in Example 6 and using (E)-N-(4-bromophenyl)-2-phenyl-3-[4-(1-pyrrolidinylmethyl)phenyl]-2-propenamide obtained in Reference Example 48.

$^1$H-NMR (DMSO-$d_6$) δ: 1.67 (4H, m), 2.39 (4H, m), 3.51 (2H, s), 7.02 (2H, d, J=8.0 Hz), 7.13 (2H, d, J=8.0 Hz), 7.27 (2H, m), 7.39 (4H, m), 7.49 (2H, d, J=8.8 Hz), 7.67 (4H, m), 7.80 (2H, d, J=8.8 Hz), 10.05 (1H, s). melting point: 146-147° C. (ethyl acetate-isopropyl ether) FABMS (pos) 493 [M+H]+

REFERENCE EXAMPLE 50

N-(4-bromo-2-fluorophenyl)-3-[4-(1-pyrrolidinylmethyl)phenyl]propanamide

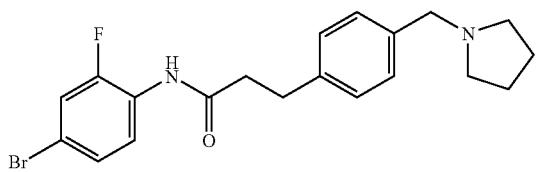

The title compound was obtained by similar operations as in Example 2 and Reference Example 3 and using 3-[4-(methoxycarbonyl)phenyl]propionic acid obtained in Reference Example 1.

$^1$H-NMR (DMSO-$d_6$) δ: 1.67 (4H, m), 2.38 (4H, m), 2.68 (2H, m), 2.87 (2H, m), 3.50 (2H, s), 7.17 (4H, m), 7.35 (1H, m), 7.55 (1H, dd, J=2.1, 10.5 Hz), 7.85 (1H, m), 9.76 (1H, s). melting point: 101-102° C. (ethyl acetate-hexane) FABMS (pos) 405 [M+H]+

REFERENCE EXAMPLE 51

N-(4'-chloro-3-fluoro-1,1'-biphenyl-4-yl)-3-[4-(1-pyrrolidinylmethyl)phenyl]propanamide

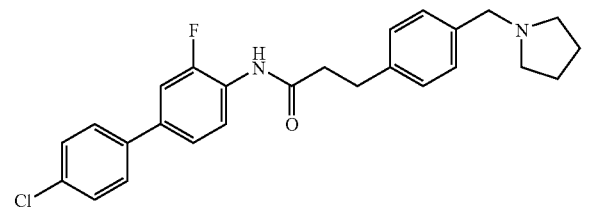

The title compound was obtained by a similar operation as in Example 6 and using N-(4-bromo-2-fluorophenyl)-3-[4-(1-pyrrolidinylmethyl)phenyl]propanamide obtained in Reference Example 50.

$^1$H-NMR (DMSO-$d_6$) δ: 1.67 (4H, m), 2.40 (4H, m), 2.71 (2H, m), 2.90 (2H, m), 3.52 (2H, s), 7.20 (4H, m), 7.52 (3H, m), 7.57-7.63 (1H, m), 7.72 (2H, d, J=8.8 Hz), 8.00 (1H, m), 9.78 (1H, s). melting point: 141-143° C. (ethyl acetate-isopropyl ether) FABMS (pos) 437 [M+H]+

REFERENCE EXAMPLE 52

N-(4-bromo-2-fluorophenyl)-2-[4-(1-pyrrolidinylmethyl)phenoxy]acetamide

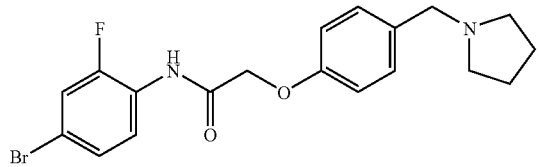

The title compound was obtained by similar operations as in Example 2 and Reference Example 46 and using 4-(hydroxymethyl)phenoxyacetic acid.

$^1$H-NMR (DMSO-$d_6$) δ: 1.67 (4H, m), 2.40 (4H, m), 3.49 (2H, s), 4.73 (2H, s), 6.91 (2H, d, J=8.7 Hz), 7.22 (2H, d, J=8.7 Hz), 7.39 (1H, m), 7.62 (1H, dd, J=2.4, 10.5 Hz), 7.79 (1H, m), 9.93 (1H, s). melting point: 102-103° C. (ethyl acetate-hexane) FABMS (pos) 407 [M+H]+

REFERENCE EXAMPLE 53

N-(4'-chloro-3-fluoro-1,1'-biphenyl-4-yl)-2-[4-(1-pyrrolidinylmethyl)phenoxy]acetamide

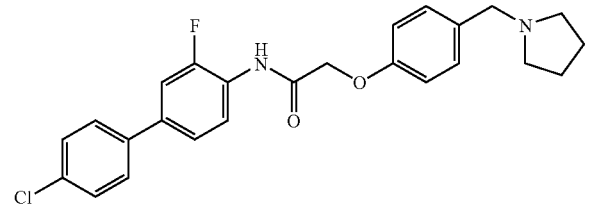

The title compound was obtained by a similar operation as in Example 6 and using N-(4-bromo-2-fluorophenyl)-2-[4-(1-pyrrolidinylmethyl)phenoxy]acetamide obtained in Reference Example 52.

$^1$H-NMR (DMSO-$d_6$) δ: 1.68 (4H, m), 2.41 (4H, m), 3.51 (2H, s), 4.77 (2H, s), 6.94 (2H, d, J=8.4 Hz), 7.24 (2H, d, J=8.4 Hz), 7.52 (3H, m), 7.65 (1H, m), 7.74 (2H, d, J=8.8 Hz), 7.95 (1H, m), 9.94 (1H, s). melting point: 121-123° C. (ethyl acetate-isopropyl ether) FABMS (pos) 439 [M+H]+

REFERENCE EXAMPLE 54

(Z)-N-(4-bromophenyl)-3-(4-chlorophenyl)-3-[4-(1-pyrrolidinylmethyl)phenyl]-2-propenamide

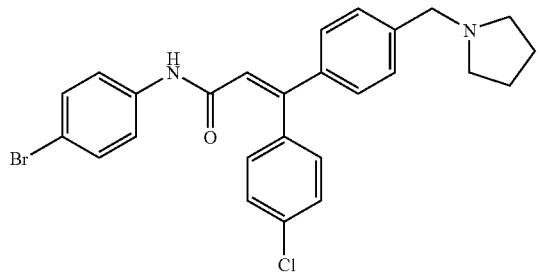

The title compound was obtained by a similar operation as in Example 2 and using (Z)-3-(4-chlorophenyl)-3-[4-(1-pyrrolidinylmethyl)phenyl]-2-propenoic acid hydrochloride obtained in Reference Example 33.

¹H-NMR (DMSO-d₆) δ: 1.69 (4H, m), 2.43 (4H, m), 3.59 (2H, s), 6.64 (1H, s), 7.17 (2H, d, J=8.4 Hz), 7.21 (2H, d, J=8.4 Hz), 7.32 (2H, d, J=8.4 Hz), 7.41 (2H, d, J=8.4 Hz), 7.43 (2H, d, J=8.4 Hz), 7.50 (2H, d, J=8.4 Hz), 10.26 (1H, s). melting point: 144-146° C. (ethyl acetate-isopropyl ether) FABMS (pos) 495 [M+H]+

REFERENCE EXAMPLE 55

(Z)-N-(4'-chloro-1,1'-biphenyl-4-yl)-3-(4-chlorophenyl)-3-[4-(1-pyrrolidinylmethyl)phenyl]-2-propenamide

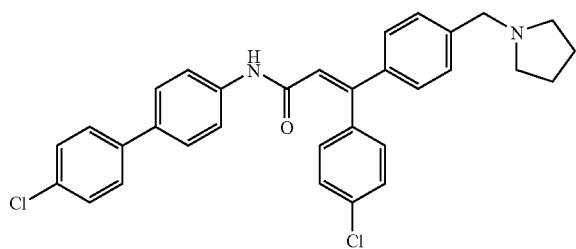

The title compound was obtained by a similar operation as in Example 6 and using (Z)-N-(4-bromophenyl)-3-(4-chlorophenyl)-3-[4-(1-pyrrolidinylmethyl)phenyl]-2-propenamide obtained in Reference Example 54.

¹H-NMR (DMSO-d₆) δ: 1.69 (4H, m), 2.43 (4H, m), 3.58 (2H, s), 6.68 (1H, s), 7.21 (4H, m), 7.33 (2H, d, J=8.1 Hz), 7.42 (2H, d, J=8.4 Hz), 7.47 (2H, d, J=8.4 Hz), 7.62 (6H, m), 10.25 (1H, s). melting point: 178-180° C. (ethyl acetate-isopropyl ether) FABMS (pos) 527 [M+H]+

REFERENCE EXAMPLE 56

3-(4-bromophenyl)-N-[4-(1-pyrrolidinylmethyl)phenyl]propanamide

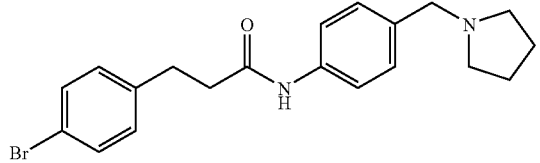

The title compound was obtained by a similar operation as in Example 2 and using 3-(4-bromophenyl)propanoic acid and 4-(1-pyrrolidinylmethyl)aniline.

¹H-NMR (DMSO-d₆) δ: 1.67 (4H, m), 2.38 (4H, m), 2.59 (2H, d, J=7.8 Hz), 2.87 (2H, d, J=7.8 Hz), 3.48 (2H, s), 7.19 (4H, m), 7.45 (2H, d, J=8.1 Hz), 7.48 (2H, d, J=8.7 Hz), 9.84 (1H, s). melting point: 132-134° C. (ethyl acetate-isopropyl ether) FABMS (pos) 387 [M+H]+

REFERENCE EXAMPLE 57

3-(4'-chloro-1,1'-biphenyl-4-yl)-N-[4-(1-pyrrolidinylmethyl)phenyl]propanamide

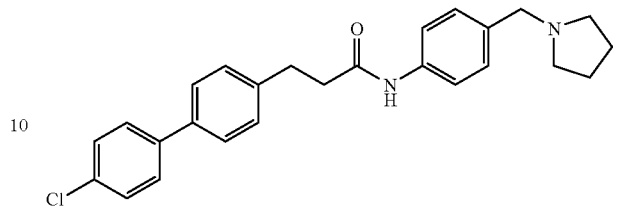

The title compound was obtained by a similar operation as in Example 6 and using 3-(4-bromophenyl)-N-[4-(1-pyrrolidinylmethyl)phenyl]propanamide obtained in Reference Example 56.

¹H-NMR (DMSO-d₆) δ: 1.67 (4H, m), 2.39 (4H, m), 2.65 (2H, m), 2.95 (2H, m), 3.49 (2H, s), 7.20 (1H, d, J=8.4 Hz), 7.35 (2H, d, J=8.4 Hz), 7.49 (2H, d, J=8.4 Hz), 7.51 (2H, d, J=8.4 Hz), 7.60 (2H, d, J=8.4 Hz), 7.67 (2H, d, J=8.4 Hz), 9.89 (1H, s). melting point: 173-175° C. (ethyl acetate-isopropyl ether) FABMS (pos) 419 [M+H]+

REFERENCE EXAMPLE 58

(E)-3-(4-bromophenyl)-N-[4-(1-pyrrolidinylmethyl)phenyl]-2-propenamide

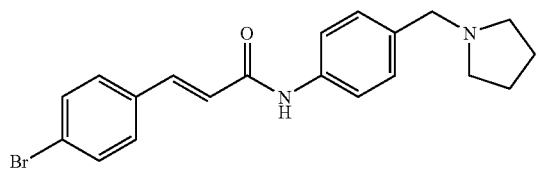

The title compound was obtained by a similar operation as in Example 2 and using (E)-3-(4-bromophenyl)-2-propenoic acid and 4-(1-pyrrolidinylmethyl)aniline.

¹H-NMR (DMSO-d₆) δ: 1.68 (4H, m), 2.40 (4H, m), 3.51 (2H, s), 6.83 (1H, d, J=15.9 Hz), 7.24 (2H, d, J=8.4 Hz), 7.53 (1H, d, J=15.9 Hz), 7.55-7.65 (6H, m), 10.17 (1H, s). melting point: 183-185° C. (ethyl acetate-isopropyl ether) FABMS (pos) 385 [M+H]+

REFERENCE EXAMPLE 59

(E)-3-(4'-chloro-1,1'-biphenyl-4-yl)-N-[4-(1-pyrrolidinylmethyl)phenyl]-2-propenamide

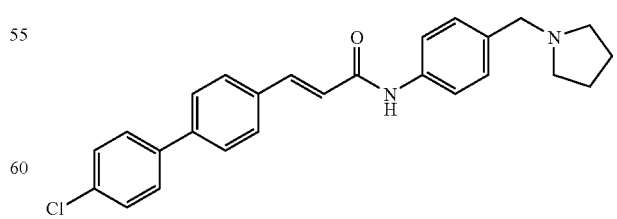

The title compound was obtained by a similar operation as in Example 6 and using (E)-3-(4-bromophenyl)-N-[4-(1-pyrrolidinylmethyl)phenyl]-2-propenamide obtained in Reference Example 58.

¹H-NMR (DMSO-d₆) δ: 1.69 (4H, m), 2.42 (4H, m), 3.53 (2H, s), 6.88 (1H, d, J=15.6 Hz), 7.25 (2H, d, J=8.4 Hz), 7.53 (2H, d, J=8.4 Hz), 7.61 (1H, d, J=15.6 Hz), 7.64 (2H, d, J=8.4 Hz), 7.69-7.78 (8H, m), 10.17 (1H, s). melting point: 204-207° C. (ethyl acetate-isopropyl ether) FABMS (pos) 417 [M+H]+

REFERENCE EXAMPLE 60

2-(4-bromophenyl)-N-[4-(1-pyrrolidinylmethyl)benzyl]acetamide

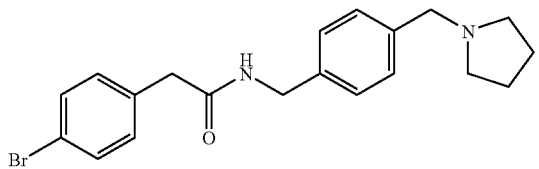

The title compound was obtained by a similar operation as in Example 2 and using 4-(1-pyrrolidinylmethyl)benzylamine and (4-bromophenyl)acetic acid.

¹H-NMR (DMSO-d₆) δ: 1.67 (4H, m), 2.39 (4H, m), 3.45 (2H, s), 3.52 (2H, s), 4.23 (2H, d, J=6.0 Hz), 7.14 (2H, d, J=8.4 Hz), 7.22 (4H, m), 7.48 (2H, d, J=8.4 Hz), 8.51 (1H, t, J=6.0 Hz). melting point: 150-152° C. (ethyl acetate-isopropyl ether) FABMS (pos) 387 [M+H]+

REFERENCE EXAMPLE 61

2-(4'-chloro-1,1'-biphenyl-4-yl)-N-[4-(1-pyrrolidinylmethyl)benzyl]acetamide

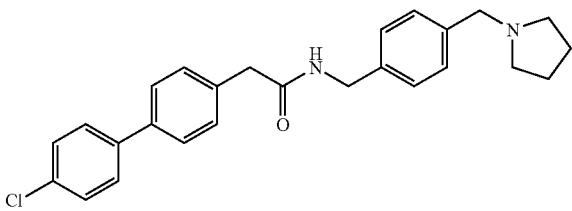

The title compound was obtained by a similar operation as in Example 6 and using 2-(4-bromophenyl)-N-[4-(1-pyrrolidinylmethyl)benzyl]acetamide obtained in Reference Example 60.

¹H-NMR (DMSO-d₆) δ: 1.67 (4H, m), 2.39 (4H, m), 3.52 (4H, m), 4.25 (2H, d, J=6.0 Hz), 7.20 (4H, m), 7.37 (2H, d, J=8.4 Hz), 7.51 (2H, d, J=8.4 Hz), 7.61 (2H, d, J=8.4 Hz), 7.68 (2H, d, J=8.4 Hz), 8.55 (1H, t, J=6.0 Hz). melting point: 174-176° C. (ethyl acetate-isopropyl ether) FABMS (pos) 419 [M+H]+

REFERENCE EXAMPLE 62

N-(4-bromophenyl)-2-[4-(1-pyrrolidinylmethyl)phenoxy]propanamide

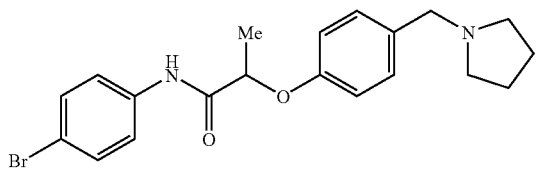

The title compound was obtained by a similar operation as in Reference Example 43 and using N-(4-bromophenyl)-2-(4-formylphenoxy)propanamide in obtained Reference Example 35 and pyrrolidine.

¹H-NMR (DMSO-d₆) δ: 1.53 (3H, d, J=6.6 Hz), 1.66 (4H, m), 2.37 (4H, m), 3.46 (2H, s), 4.82 (1H, q, J=6.6 Hz), 6.88 (2H, d, J=8.7 Hz), 7.19 (2H, d, J=8.7 Hz), 7.47 (2H, d, J=8.7 Hz), 7.59 (2H, d, J=8.7 Hz), 10.21 (1H, s). melting point: 116-118° C. (ethyl acetate-isopropyl ether) FABMS (pos) 403 [M+H]+

REFERENCE EXAMPLE 63

N-(4'-chloro-1,1'-biphenyl-4-yl)-2-[4-(1-pyrrolidinylmethyl)phenoxy]propanamide

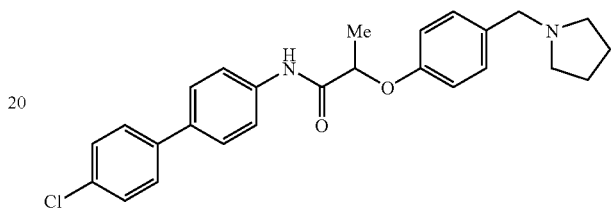

The title compound was obtained by a similar operation as in Example 6 and using N-(4-bromophenyl)-2-[4-(1-pyrrolidinylmethyl)phenoxy]propanamide obtained in Reference Example 62.

¹H-NMR (DMSO-d₆) δ: 1.55 (3H, d, J=6.6 Hz), 1.66 (4H, m), 2.39 (4H, m), 3.48 (2H, s), 4.86 (1H, q, J=6.6 Hz), 6.91 (2H, d, J=8.7 Hz), 7.21 (2H, d, J=8.7 Hz), 7.49 (2H, d, J=8.7 Hz), 7.63 (2H, d, J=8.7 Hz), 7.67 (2H, d, J=8.7 Hz), 7.74 (2H, d, J=8.7 Hz), 10.23 (1H, s). melting point: 123-125° C. (ethyl acetate-isopropyl ether) FABMS (pos) 435 [M+H]+

REFERENCE EXAMPLE 64

4-bromo-N-{2-[4-(1-piperidinylmethyl)phenyl]ethyl}benzenesulfonamide

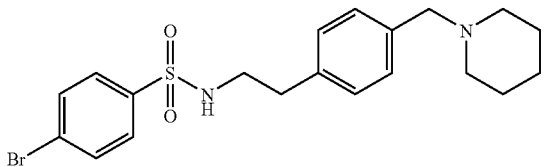

To a solution of 2-[4-(1-piperidinylmethyl)phenyl]ethylamine dihydrochloride (300 mg, 1.03 mmol) obtained in Reference Example 6 and triethylamine (0.473 ml, 3.40 mmol) in tetrahydrofuran (5 ml) was added 4-bromobenzenesulfonyl chloride (290 mg, 1.13 mmol), and the mixture was stirred at room temperature for 4 hrs. Ethyl acetate was added to the reaction mixture. The mixture was washed with aqueous potassium carbonate solution and saturated brine, and dried over anhydrous sodium sulfate. The solvent was evaporated under reduced pressure, and the obtained residue was purified by NH silica gel column chromatography (developing solvent; ethyl acetate), and powderized with hexane to give the title compound (404 mg).

¹H-NMR (DMSO-d₆) δ: 1.38 (2H, m), 1.47 (4H, m), 2.28 (4H, m), 2.65 (2H, m), 2.97 (2H, m), 3.36 (2H, s), 7.08 (2H, d, J=8.1 Hz), 7.16 (2H, d, J=8.1 Hz), 7.68 (2H, d, J=8.4 Hz), 7.79 (2H, d, J=8.4 Hz), 7.83 (1H, m). melting point: 109-110° C. (ethyl acetate-hexane)

REFERENCE EXAMPLE 65

4'-chloro-N-{2-[4-(1-piperidinylmethyl)phenyl]ethyl}[1,1'-biphenyl]-4-sulfonamide

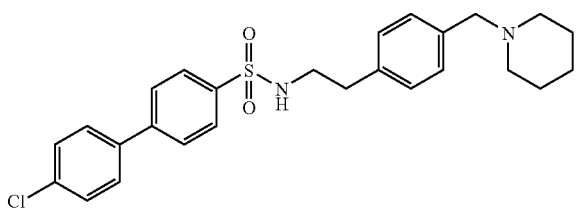

The title compound was obtained by a similar operation as in Example 6 and using 4-bromo-N-{2-[4-(1-piperidinylmethyl)phenyl]ethyl}benzenesulfonamide obtained in Reference Example 64.

$^1$H-NMR (DMSO-d$_6$) δ: 1.37 (2H, m), 1.45 (4H, m), 2.27 (4H, m), 2.67 (2H, m), 2.97 (2H, m), 3.33 (2H, s), 7.08 (2H, d, J=8.1 Hz), 7.15 (2H, d, J=8.1 Hz), 7.56 (2H, d, J=8.7 Hz), 7.74-7.88 (7H, m). melting point: 136-138° C. (ethyl acetate-isopropyl ether)

REFERENCE EXAMPLE 66

N-(4'-chloro-1,1'-biphenyl-4-yl)-2-{4-[2-(1-pyrrolidinyl)propyl]phenoxy}acetamide

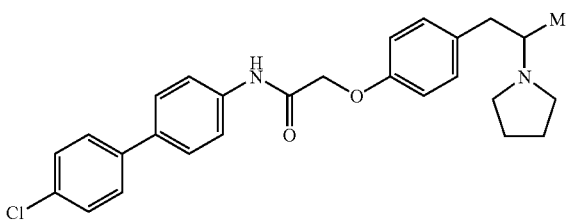

The title compound was obtained by a similar operation as in Reference Example 43 and using N-(4'-chloro-1,1'-biphenyl-4-yl)-2-[4-(2-oxopropyl)phenoxy]acetamide and pyrrolidine.

$^1$H-NMR (CDCl$_3$) δ: 0.98 (3H, d, J=6.1Hz), 1.81 (4H, m) 2.47 (2H, m), 2.67 (4H, m), 3.08 (1H, dd, J=12.5, 3.2 Hz), 4.61 (2H, s), 6.92 (2H, m), 7.15 (2H, m), 7.39 (2H, m), 7.51 (4H, m), 7.66 (2H, m), 8.33 (1H, s), melting point: 176-177° C. (ethyl acetate-isopropyl ether)

REFERENCE EXAMPLE 67

N-(4'-chloro-1,1'-biphenyl-4-yl)-2-[2-methoxy-4-(1-pyrrolidinylmethyl)phenoxy]acetamide

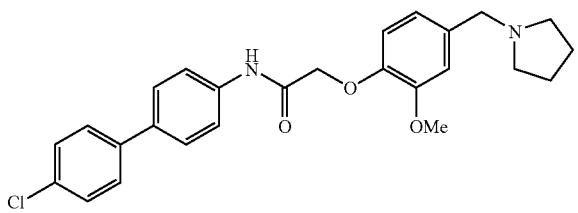

To 4-hydroxy-3-methoxybenzaldehyde (2.02 g, 13.3 mmol), 2-bromo-N-(4-bromophenyl)acetamide (3.00 g, 10.2 mmol) and potassium carbonate (2.12 g, 15.4 mmol) was added propionitrile (10 ml), and the mixture was stirred at 80° C. for one day. The reaction mixture was diluted with ethyl acetate, washed with saturated brine, and dried over anhydrous sodium sulfate. The solvent was evaporated under reduced pressure, and the obtained residue was purified by alumina column chromatography (developing solvent; ethyl acetate), and powderized with ethyl acetate-diisopropyl ether (1:5) to give a phenoxyacetamide derivative (2.93 g). The title compound was obtained by similar operations as in Reference Example 43 and Example 6 and using this compound.

$^1$H-NMR (DMSO-d$_6$) δ: 1.68 (4H, m), 2.41 (4H, m), 3.49 (2H, s), 3.81 (3H, s), 4.67 (2H, s), 6.79 (1H, dd, J=7.8, 2.1 Hz), 6.91 (1H, d, J=7.8 Hz), 6.94 (1H, d, J=2.1 Hz), 7.50 (2H, d, J=8.7 Hz), 7.64-7.76 (6H, m), 10.16 (1H, s). melting point: 89-91° C. (ethyl acetate-isopropyl ether)

REFERENCE EXAMPLE 68

N-(4'-chloro-1,1'-biphenyl-4-yl)-2-[2-chloro-4-(1-pyrrolidinylmethyl)phenoxy]acetamide

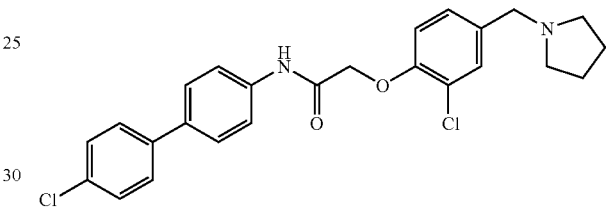

The title compound was obtained by a similar operation as in Reference Example 67 and using 3-chloro-4-hydroxybenzaldehyde.

$^1$H-NMR (DMSO-d$_6$) δ: 1.68 (4H, m), 2.41 (4H, m), 3.51 (2H, s), 4.83 (2H, s), 7.02 (1H, s, J=8.4 Hz), 7.20 (1H, dd, J=8.4, 1.8 Hz), 7.36 (1H, d, J=1.8 Hz), 7.49 (2H, d, J=8.4 Hz), 7.68 (6H, m), 10.25 (1H, s). melting point: 121-123° C. (ethyl acetate-isopropyl ether)

REFERENCE EXAMPLE 69

N-(4'-chloro-1,1'-biphenyl-4-yl)-2-[3-chloro-4-(1-pyrrolidinylmethyl)phenoxy]acetamide

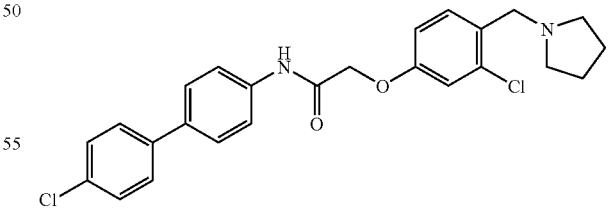

The title compound was obtained by a similar operation as in Reference Example 67 and using 2-chloro-4-hydroxybenzaldehyde.

$^1$H-NMR (DMSO-d$_6$) δ: 1.69 (4H, m), 2.46 (4H, m), 3.60 (2H, s), 3.76 (2H, s), 6.98 (1H, dd, J=8.7, 2.4 Hz), 7.10 (1H, d, J=2.4 Hz), 7.40 (1H, d, J=8.7 Hz), 7.50 (2H, d, J=8.7 Hz), 7.65-7.76 (6H, m), 10.21 (1H, s). melting point: 136-138° C. (ethyl acetate-isopropyl ether)

REFERENCE EXAMPLE 70

N-(4'-chloro-1,1'-biphenyl-4-yl)-2-[2-fluoro-4-(1-pyrrolidinylmethyl)phenoxy]acetamide

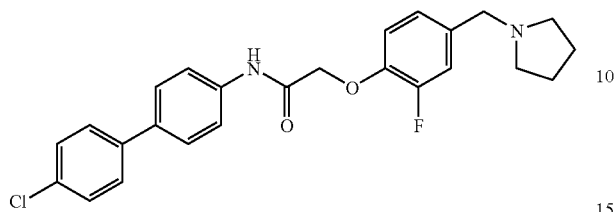

The title compound was obtained by a similar operation as in Reference Example 67 and using 3-fluoro-4-hydroxybenzaldehyde.

¹H-NMR (DMSO-d$_6$) δ: 1.68 (4H, m), 2.40 (4H, m), 3.50 (2H, s), 4.80 (2H, s), 7.05 (2H, m), 7.16 (1H, d, J=11.4 Hz), 7.49 (1H, d, J=8.7 Hz), 7.64-7.74 (6H, m), 10.28 (1H, s). melting point: 158-160° C. (ethyl acetate-isopropyl ether)

REFERENCE EXAMPLE 71

N-(4'-chloro-1,1'-biphenyl-4-yl)-2-[3-methoxy-4-(1-pyrrolidinylmethyl)phenoxy]acetamide

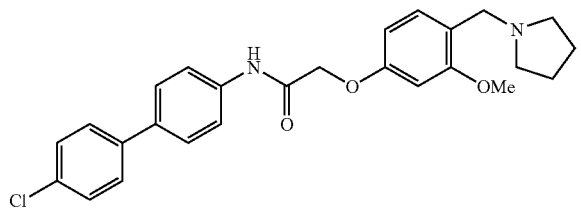

The title compound was obtained by a similar operation as in Reference Example 67 and using 4-hydroxy-2-methoxybenzaldehyde.

¹H-NMR (DMSO-d$_6$) δ: 1.66 (4H, m), 2.41 (4H, m), 3.49 (2H, s), 3.77 (3H, s), 4.71 (2H, s), 6.53 (1H, dd, J=8.1, 2.4 Hz), 6.66 (1H, d, J=2.4 Hz), 7.19 (1H, d, J=8.1 Hz), 7.50 (2H, d, J=8.7 Hz), 7.65-7.70 (4H, m), 7.77 (2H, d, J=8.7 Hz), 10.19 (1H, s). melting point: 133-135° C. (ethyl acetate-isopropyl ether)

REFERENCE EXAMPLE 72

N-(4'-chloro-1,1'-biphenyl-4-yl)-2-[2-methyl-4-(1-pyrrolidinylmethyl)phenoxy]acetamide

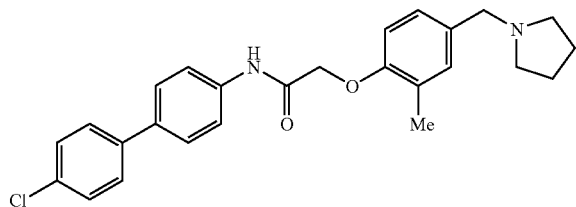

The title compound was obtained by a similar operation as in Reference Example 67 and using 4-hydroxy-3-methylbenzaldehyde.

¹H-NMR (DMSO-d$_6$) δ: 1.67 (4H, m), 2.24 (3H, s), 2.38 (4H, m), 3.46 (2H, s), 4.71 (2H, s), 6.81 (1H, d, J=8.7 Hz), 7.05 (1H, d, J=8.7 Hz), 7.10 (1H, s), 7.49 (2H, d, J=8.7 Hz), 7.64-7.70 (4H, m), 7.74 (2H, d, J=8.7 Hz), 10.17 (1H, s). melting point: 142-144° C. (ethyl acetate-isopropyl ether)

REFERENCE EXAMPLE 73

N-(4'-chloro-1,1'-biphenyl-4-yl)-2-{4-[1-(1-pyrrolidinyl)ethyl]phenoxy}acetamide

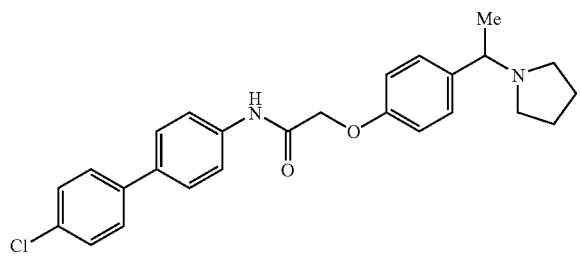

DMF (20 ml) was added to 1-(4-hydroxyphenyl)ethanone (1.81 g, 13.3 mmol), 2-bromo-N-(4-bromophenyl)acetamide (3.00 g, 10.2 mmol), and potassium carbonate (4.25 g, 30.7 mmol), and the mixture was stirred at room temperature for 16 hrs. The reaction mixture was diluted with ethyl acetate, washed with saturated brine, and dried over anhydrous sodium sulfate. The solvent was evaporated under reduced pressure, and the obtained residue was purified by alumina column chromatography (developing solvent; ethyl acetate), and powderized with ethyl acetate-diisopropyl ether (1:5) to give a phenoxyacetamide derivative (3.44 g). The title compound was obtained by similar operations as in Reference Example 20, Reference Example 21, Example 10 and Example 6 and using this compound.

¹H-NMR (DMSO-d$_6$) δ: 1.26 (3H, d, J=6.6 Hz), 1.65 (4H, m), 2.27 (2H, m), 2.43 (2H, m), 3.13 (1H, m), 4.69 (2H, s), 6.93 (2H, d, J=8.7 Hz), 7.23 (1H, d, J=8.7 Hz), 7.48 (2H, d, J=8.7 Hz), 7.63-7.69 (4H, m), 7.74 (2H, d, J=8.7 Hz), 10.18 (1H, s). melting point: 156-158° C. (ethyl acetate-isopropyl ether)

REFERENCE EXAMPLE 74

N-(4'-chloro-1,1'-biphenyl-4-yl)-2-{3-fluoro-4-[1-(1-pyrrolidinyl)ethyl]phenoxy}acetamide

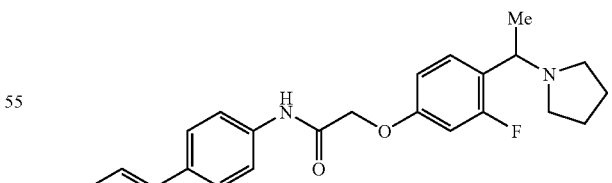

The title compound was obtained by a similar operation as in Reference Example 73 and using 1-(2-fluoro-4-hydroxyphenyl)ethanone.

¹H-NMR (DMSO-d$_6$) δ: 1.28 (3H, d, J=6.6 Hz), 1.65 (4H, m), 2.32 (2H, m), 2.43 (2H, m), 3.52 (1H, m), 4.73 (2H, s), 6.79-6.86 (2H, m), 7.38 (1H, m), 7.48 (2H, d, J=8.7 Hz), 7.63-7.69 (4H, m), 7.74 (2H, d, J=9.0 Hz), 10.20 (1H, s).
melting point: 154-156° C. (ethyl acetate-isopropyl ether)

REFERENCE EXAMPLE 75

N-(4'-chloro-1,1'-biphenyl-4-yl)-2-{3-methyl-4-[1-(1-pyrrolidinyl)ethyl]phenoxy}acetamide

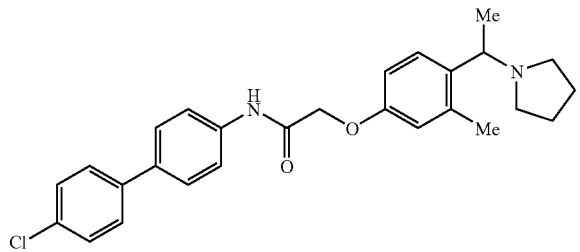

The title compound was obtained by a similar operation as in Reference Example 73 and using 1-(4-hydroxy-2-methylphenyl)ethanone.

$^1$H-NMR (DMSO-d$_6$) δ: 1.21 (3H, d, J=6.6 Hz), 1.66 (4H, m), 2.29 (5H, m), 2.42 (2H, m), 3.32 (1H, m), 4.66 (2H, s), 6.77-6.80 (2H, m), 7.32 (1H, d, J=8.4 Hz), 7.48 (2H, d, J=8.4 Hz), 7.63-7.69 (4H, m), 7.75 (2H, d, J=8.7 Hz), 10.15 (1H, s).
melting point: 130-132° C. (ethyl acetate-isopropyl ether)

REFERENCE EXAMPLE 76

2-bromo-5-(1-pyrrolidinylmethyl)pyridine

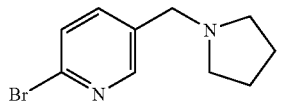

A solution of 2-bromo-5-(bromomethyl)pyridine (9.06 g, 36.1 mmol), pyrrolidine (3.62 ml, 43.3 mmol) and potassium carbonate (9.98 g, 72.2 mmol) in acetonitrile (45 ml) was stirred at room temperature for 6 hrs. Ethyl acetate was added to the reaction mixture, and the mixture was washed with saturated aqueous potassium carbonate solution and saturated, and dried over anhydrous sodium sulfate. The solvent was evaporated under reduced pressure, and the obtained residue was purified by NH-silica gel column chromatography (developing solvent; ethyl acetate) to give the title compound (7.31 g).

$^1$H-NMR (CDCl$_3$) δ: 1.79 (4H, m), 2.49 (4H, m), 3.58 (2H, s), 7.42 (1H, d, J=8.0 Hz), 7.56 (1H, dd, J=8.0, 2.2 Hz), 8.29 (1H, d, J=2.2 Hz).

REFERENCE EXAMPLE 77

1-(3-butynyl)-4-(4-chlorophenyl)piperidine

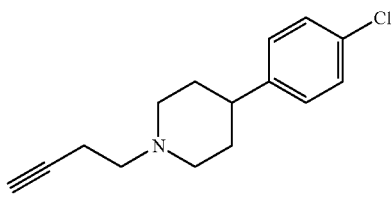

To a solution (50 ml) of 3-butyn-1-ol (700 mg, 10.0 mmol) and triethylamine (2.05 ml, 15 mmol) in tetrahydrofuran was added methanesulfonyl chloride (1.72 g, 15 mmol) at 0° C., and the mixture was stirred at room temperature for 1 hr. Ethyl acetate was added to the reaction mixture, and the mixrture was washed with saturated brine and dried over anhydrous sodium sulfate. The solvent was evaporated under reduced pressure. 4-(4-Chlorophenyl)piperidine hydrochloride (2.30 g, 10.0 mmol), potassium carbonate (1.38 g, 10.0 mmol) and acetonitrile (50 ml) were added to the obtained residue, and the mixture was stirred at 60° C. for 16 hrs. 2N Hydrochloric acid was added to the reaction mixture, and the mixture was washed with ethyl acetate. The aqueous layer was basified with 8N aqueous sodium hydroxide solution, and the mixture was extracted with ethyl acetate. The extract was washed with saturated brine and dried over anhydrous sodium sulfate. The solvent was evaporated under reduced pressure to give the title compound (1.31 g) as a solid.

$^1$H-NMR (CDCl$_3$) δ: 1.66-1.84 (4H, m), 1.97-2.19 (3H, m), 2.37-2.69 (5H, m), 3.01-3.06 (2H, m), 7.15 (2H, d, J=8.4 Hz), 7.25 (2H, d, J=8.4 Hz).

REFERENCE EXAMPLE 78

4-[4-(4-chlorophenyl)-1-piperidinyl]-1-(4-fluorophenyl)-4-oxo-1-butanone

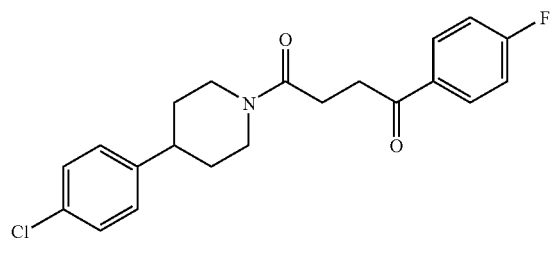

The title compound was obtained by a similar operation as in Example 2 and using 4-(4-chlorophenyl)piperidine and 4-(4-fluorophenyl)-4-oxobutanoic acid.

$^1$H-NMR (DMSO-d$_6$) δ: 1.37-1.42 (1H, m), 1.57-1.65 (1H, m), 1.73-1.84 (2H, m), 2.64 (1H, m), 2.72-2.84 (3H, m), 3.09-3.29 (3H, m), 4.05-4.09 (1H, m), 4.46-4.50 (1H, m), 7.26-7.38 (6H, m), 8.06 (2H, m).

REFERENCE EXAMPLE 79

4-(4-chlorophenyl)-1-(4-phenylbutanoyl)piperidine

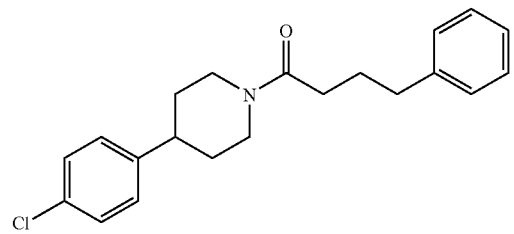

The title compound was obtained by a similar operation as in Example 2 and using 4-(4-chlorophenyl)piperidine and phenylbutanoic acid.

$^1$H-NMR (CDCl$_3$) δ: 1.49-1.59 (2H, m), 1.83-1.87 (2H, m), 1.95-2.02 (2H, m), 2.36 (2H, m), 2.55-2.74 (4H, m), 3.02-3.10 (1H, m), 3.85-3.89 (1H, m), 4.77-4.81 (1H, m), 7.10 (2H, d, J=8.4 Hz), 7.18-7.28 (7H, m).

REFERENCE EXAMPLE 80

1-(4-{4-[4-(4-chlorophenyl)-1-piperidinyl]-4-oxobutyl}phenyl)ethanone

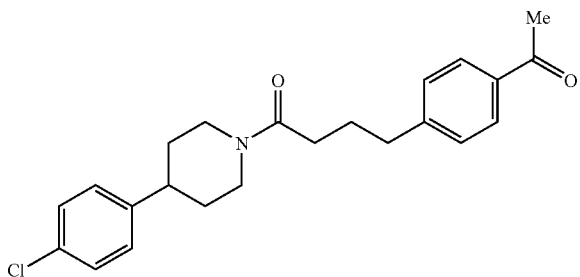

The title compound was obtained by a similar operation as in Reference Example 19 and using 4-(4-chlorophenyl)-1-(4-phenylbutanoyl)piperidine obtained in Reference Example 79.

$^1$H-NMR (DMSO-$d_6$) δ: 1.34-1.54 (2H, m), 1.73-1.88 (4H, m), 2.36 (2H, t, J=7.5 Hz), 2.55 (4H, m), 2.66-2.80 (3H, m), 3.02-3.10 (1H, m), 3.89-3.93 (1H, m), 4.52-4.56 (1H, m), 7.26 (2H, d, J=8.4 Hz), 7.32-7.37 (4H, m), 7.88 (2H, d, J=8.4 Hz).

REFERENCE EXAMPLE 81

1-(4-{4-[4-(4-chlorophenyl)-1-piperidinyl]-4-oxobutyl}phenyl)ethanol

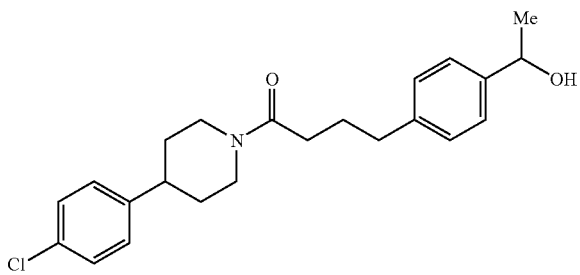

The title compound was obtained by a similar operation as in Reference Example 20 and using 1-(4-{4-[4-(4-chlorophenyl)-1-piperidinyl]-4-oxobutyl}phenyl)ethanone obtained in Reference Example 80.

$^1$H-NMR (CDCl$_3$) δ: 1.49 (3H, d, J=6.3 Hz), 1.59 (2H, m), 1.83-1.88 (2H, m), 1.99 (2H, m), 2.37 (2H, t, J=7.8 Hz), 2.56-2.74 (4H, m), 3.03-3.12 (1H, m), 3.87-3.91 (1H, m), 4.77-4.81 (1H, m), 4.87 (1H, m), 7.10 (2H, d, J=8.7 Hz), 7.18 (2H, d, J=8.1 Hz), 7.28 (4H, m).

REFERENCE EXAMPLE 82

1-{4-[4-(1-chloroethyl)phenyl]butanoyl}-4-(4-chlorophenyl)piperidine

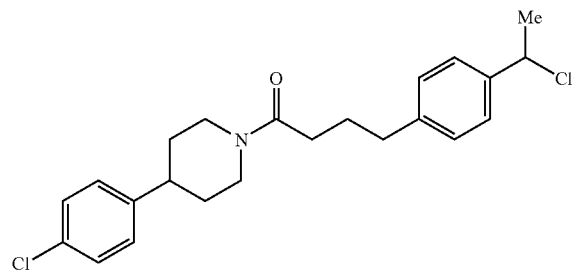

The title compound was obtained by a similar operation as in Reference Example 21 and using 1-(4-{4-[4-(4-chlorophenyl)-1-piperidinyl]-4-oxobutyl}phenyl)ethanol obtained in Reference Example 81.

$^1$H-NMR (CDCl$_3$) δ: 1.50-1.63 (2H, m), 1.83-1.88 (5H, m), 1.99 (2H, m), 2.37 (2H, t, J=7.5 Hz), 2.56-2.75 (4H, m), 3.03-3.11 (1H, m), 3.86-3.91 (1H, m), 4.77-4.81 (1H, m), 5.08 (1H, q, J=6.6 Hz), 7.10 (2H, d, J=8.1 Hz), 7.18 (2H, d, J=8.1 Hz), 7.27 (2H, d, J=8.1 Hz), 7.33 (2H, d, J=8.1 Hz).

REFERENCE EXAMPLE 83

N-(4-{4-[4-(4-chlorophenyl)-1-piperidinyl]butanoyl}benzyl)acetamide

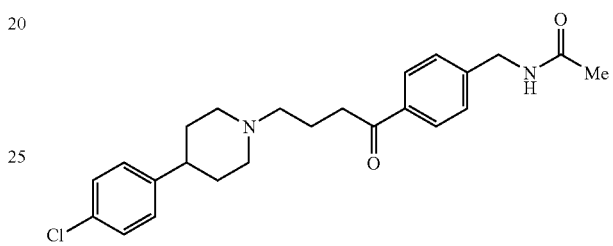

The title compound was obtained by a similar operation as in Example 10 and using N-[4-(4-chlorobutanoyl)benzyl]acetamide and 4-(4-chlorophenyl)piperidine.

$^1$H-NMR (CDCl$_3$) δ: 1.56-1.70 (2H, m), 1.75-1.78 (2H, m), 1.92-2.07 (7H, m), 2.43 (3H, m), 2.99 (4H, m), 4.49 (2H, d, J=6.3 Hz), 5.77 (1H, m), 7.10 (2H, d, J=8.7 Hz), 7.23 (2H, d, J=8.7 Hz), 7.36 (2H, d, J=8.1 Hz), 7.94 (2H, d, J=8.1 Hz).

REFERENCE EXAMPLE 84

5-bromo-2-(1-pyrrolidinylcarbonyl)pyridine

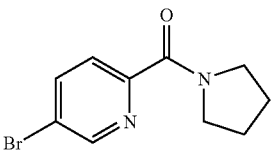

A solution of 2,5-dibromopyridine (5.00 g, 21.1 mmol), (triphenylphosphine)palladium(II) dichloride (0.44 g, 0.63 mmol), pyrrolidine (1.73 g, 24.27 mmol) and triethylamine (4.33 ml, 31.65 mmol) in toluene (50 ml) was stirred under carbon monoxide (5 atm) atmosphere in a stainless bottle at 70° C. for 6 hrs. The reaction solution was allowed to cool to room temperature, poured into saturated ammonium chloride solution (200 ml) and extracted with ethyl acetate (200 ml×2). The extract was washed with saturated brine and dried over anhydrous magnesium sulfate. The solvent was evaporated under reduced pressure. The residue was purified by silica gel column chromatography (developing solvent; hexane:ethyl acetate=4:1-1:1) to give a pale-yellow solid.

REFERENCE EXAMPLE 85

4-(4'-chloro-1,1'-biphenyl-4-yl)-N-methoxy-N-methylbutanamide

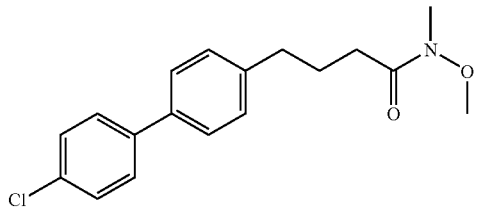

The title compound was obtained by a similar operation as in Example 2 and using 4-(4'-chloro-1,1'-biphenyl-4-yl)butyric acid and N,O-dimethylhydroxylamine hydrochloride.

$^1$H-NMR (CDCl$_3$) δ: 1.98-2.03 (2H, m), 2.47 (2H, t, J=7.2 Hz), 2.72 (2H, t, J=7.5 Hz), 3.18 (3H, s), 3.64 (3H, s), 7.27 (2H, d, J=8.7 Hz), 7.38 (2H, d, J=8.7 Hz), 7.45-7.51 (4H, m).

REFERENCE EXAMPLE 86

4-(4-acetylphenyl)-N-methoxy-N-methylbutanamide

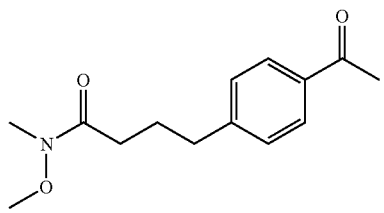

The title compound was obtained by a similar operation as in Example 2 and using 4-(4-acetylphenyl)butyric acid and N,O-dimethylhydroxylamine hydrochloride.

$^1$H-NMR (CDCl$_3$) δ: 1.99 (2H, m), 2.45 (2H, t, J=7.5 Hz), 2.59 (3H, s), 2.74 (2H, t, J=7.5 Hz), 3.18 (3H, s), 3.64 (3H, s) 7.30 (2H, d, J=8.2 Hz), 7.89 (2H, d, J=8.2 Hz).

REFERENCE EXAMPLE 87

4-[4-(1-hydroxyethyl)phenyl]-N-methoxy-N-methylbutanamide

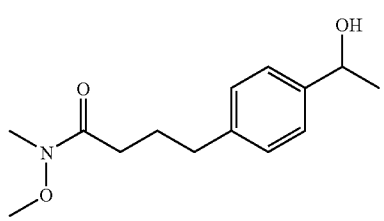

The title compound was obtained by a similar operation as in Reference Example 20 and using 4-(4-acetylphenyl)-N-methoxy-N-methylbutanamide obtained in Reference Example 86.

$^1$H-NMR (CDCl$_3$) δ: 1.49 (3H, d, J=6.3 Hz), 1.80 (1H, d, J=3.6 Hz), 1.96 (2H, m), 2.44 (2H, t, J=7.2 Hz), 2.67 (2H, t, J=7.2 Hz), 3.17 (3H, s), 3.63 (3H, s), 4.86-4.90 (1H, m), 7.19 (2H, d, J=7.8 Hz), 7.29 (2H, d, J=7.8 Hz).

REFERENCE EXAMPLE 88

4-[4-(1-chloroethyl)phenyl]-N-methoxy-N-methylbutanamide

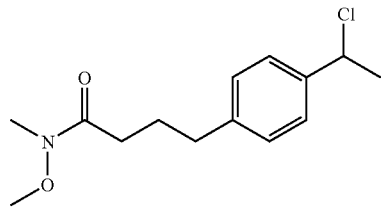

The title compound was obtained by a similar operation as in Reference Example 21 and using 4-[4-(1-hydroxyethyl)phenyl]-N-methoxy-N-methylbutanamide obtained in Reference Example 87.

$^1$H-NMR (CDCl$_3$) δ: 1.84 (3H, d, J=6.9 Hz), 1.97 (2H, m), 2.44 (2H, t, J=7.2 Hz), 3.17 (3H, s), 3.63 (3H, s), 5.09 (1H, q, J=8.1 Hz), 7.34 (2H, d, J=8.1 Hz).

REFERENCE EXAMPLE 89

N-methoxy-N-methyl-4-{4-[1-(1-pyrrolidinyl)ethyl]phenyl}butanamide

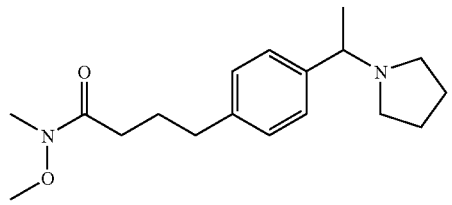

The title compound was obtained by a similar operation as in Example 10 and using 4-[4-(1-chloroethyl)phenyl]-N-methoxy-N-methylbutanamide obtained in Reference Example 88 and pyrrolidine.

$^1$H-NMR (CDCl$_3$) δ: 1.38 (3H, d, J=6.6 Hz), 1.73-1.77 (4H, m), 1.96 (2H, m), 2.33-2.38 (2H, m), 2.43 (2H, t, J=7.2 Hz), 2.51-2.55 (2H, m), 2.66 (2H, t, J=7.2 Hz), 3.15 (1H, q, J=6.6 Hz), 3.17 (3H, s), 3.62 (3H, s), 7.13 (2H, d, J=7.8 Hz), 7.25 (2H, d, J=7.8 Hz).

REFERENCE EXAMPLE 90

4-(4-chlorophenyl)-1-{4-[5-(1-pyrrolidinylmethyl)-2-pyridyl]-3-butynyl}piperidine

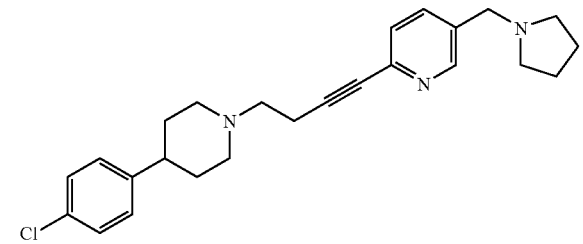

A solution of 2-Bromo-5-(1-pyrrolidinylmethyl)pyridine (243 mg, 1.01 mmol) obtained in Reference Example 76, 1-(3-butynyl)-4-(4-chlorophenyl)piperidine (500 mg, 2.02 mmol) obtained in Reference Example 77 and tetrakistriphenylphosphine palladium (58.3 mg, 50.5 μmol) in pyrrolidine (5 ml) was stirred at 80° C. for 2 hrs. The reaction mixture was concentrated under reduced pressure, and ethyl acetate was added to the residue. The mixture was washed with saturated aqueous potassium hydrogencarbonate solution and saturated brine, and dried over anhydrous sodium sulfate. The solvent was evaporated under reduced pressure, and the obtained residue was purified by NH-silica gel column chromatography (developing solvent; ethyl acetate), and powderized with hexane to give the title compound (278 mg).

$^1$H-NMR (CDCl$_3$) δ: 1.79 (8H, m), 2.11-2.24 (2H, m), 2.50 (5H, m), 2.64-2.76 (4H, m), 3.05-3.11 (2H, m), 3.60 (2H, s), 7.15 (2H, d, J=8.6 Hz), 7.26 (2H, d, J=8.6 Hz), 7.33 (1H, d, J=8.2 Hz), 7.62 (1H, dd, J=8.2, 2.2 Hz), 8.47 (1H, d, J=2.2 Hz). melting point: 86-88° C. (ethyl acetate-isopropyl ether) FABMS (pos) 408 [M+H]+

REFERENCE EXAMPLE 91

4-[4-(4-chlorophenyl)-1-piperidinyl]-1-[5-(1-pyrrolidinylmethyl)-2-pyridyl]-2-butanone trihydrochloride

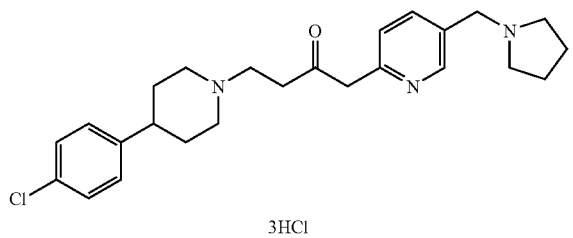

3HCl

To a solution of 4-(4-chlorophenyl)-1-{4-[5-(1-pyrrolidinylmethyl)-2-pyridyl]-3-butynyl}piperidine (200 mg, 0.490 mmol) obtained in Reference Example 90 in methanol (1 ml) was added a solution (5 ml) of HgO (35.3 mg, 0.163 mmol) in 40% aqueous sulfuric acid, and the mixture was stirred at 60° C. for 6 hrs. Ethyl acetate was added to the reaction mixture, and the mixture was washed with saturated aqueous potassium hydrogencarbonate solution and saturated brine, and dried over anhydrous sodium sulfate. The solvent was evaporated under reduced pressure, and the obtained residue was purified by alumina column chromatography (developing solvent; ethyl acetate). 4N Hydrogen chloride-ethyl acetate was added to the obtained oil, and the mixture was powderized with isopropyl ether to give the title compound (84.4 mg).

$^1$H-NMR (free base, CDCl$_3$) δ: 1.78 (8H, m), 1.98-2.10 (2H, m), 2.50 (5H, m), 2.66-2.79 (4H, m), 2.94-2.99 (2H, m), 3.61 (2H, s), 3.93 (2H, s), 7.10-7.26 (5H, m), 7.26 (2H, d, J=8.6 Hz), 7.68 (1H, m), 8.48 (1H, m). FABMS (pos) 426 [M+H]+

REFERENCE EXAMPLE 92

4-[4-(4-chlorophenyl)-1-piperidinyl]-4-oxo-1-[4-(1-pyrrolidinylmethyl)phenyl]-1-butanone

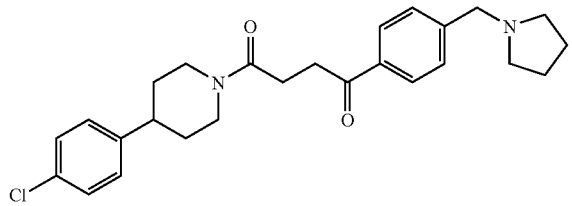

The title compound was obtained by similar operations as in Reference Example 32, Reference Example 28 and Example 2 and using methyl 4-[4-(bromomethyl)phenyl]-4-oxobutanoate.

$^1$H-NMR (DMSO-d$_6$) δ: 1.37-1.79 (8H, m), 2.43 (4H, m), 2.61-2.80 (4H, m), 3.07-3.23 (3H, m), 3.64 (2H, s), 4.08 (1H, m), 4.50 (1H, m), 7.32 (4H, m), 7.46 (2H, d, J=8.4 Hz), 7.94 (2H, d, J=8.4 Hz). melting point: 105-106° C. (ethyl acetate-isopropyl ether) FABMS (pos) 439 [M+H]+

REFERENCE EXAMPLE 93

4-[4-(4-chlorophenyl)-1-piperidinyl]-4-oxo-1-[4-(1-pyrrolidinylmethyl)phenyl]-1-butanol

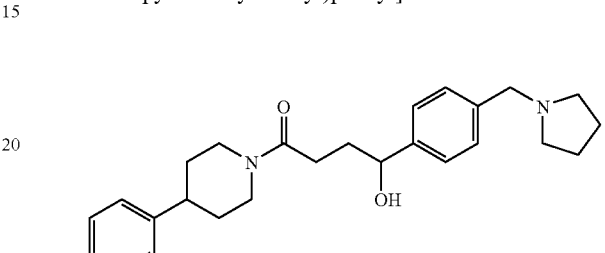

The title compound was obtained by a similar operation as in Reference Example 20 and using 4-[4-(4-chlorophenyl)-1-piperidinyl]-4-oxo-1-[4-(1-pyrrolidinylmethyl)phenyl]-1-butanone obtained in Reference Example 92.

$^1$H-NMR (DMSO-d$_6$) δ: 1.43 (2H, m), 1.67-1.86 (8H, m), 2.40 (6H, m), 2.55-2.82 (2H, m), 3.05 (1H, m), 3.54 (2H, s), 3.87 (1H, m), 4.57 (2H, m), 5.19 (1H, m), 7.25-7.37 (8H, m). melting point: 110-112° C. (ethyl acetate-isopropyl ether) FABMS (pos) 441 [M+H]+

REFERENCE EXAMPLE 94

4-(4-chlorophenyl)-1-{(E)-4-[4-(1-pyrrolidinylmethyl)phenyl]-3-butenoyl}piperidine

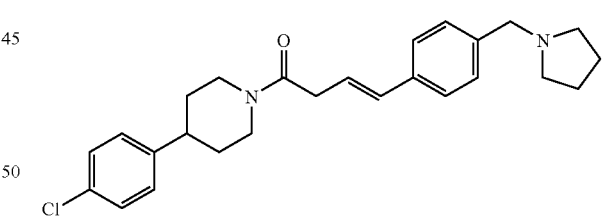

Using methyl 4-[4-(bromomethyl)phenyl]-4-oxobutanoate, a similar operation as in Reference Example 32 was performed. To a solution of the obtained oil (1.27 g, 4.61 mmol) in methanol (11 ml) was added sodium borohydride (174 mg, 4.61 mmol), and the mixture was stirred for 2 hrs. Ethyl acetate was added to the reaction mixture, and the mixture was washed with saturated aqueous potassium hydrogencarbonate solution and saturated brine, and dried over anhydrous sodium sulfate. The solvent was evaporated under reduced pressure to give an alcohol compound (1.17 g). Concentrated hydrochloric acid (20 ml) was added to the obtained alcohol compound, and the mixture was stirred at 100° C. for 16 hrs. The reaction mixture was concentrated, and toluene was added to the residue, and the mixture was concentrated. The title compound was obtained by a similar operation as in Example 2 and using the obtained carboxylic acid.

$^1$H-NMR (CDCl$_3$) δ: 1.59 (2H, m), 1.78 (4H, m), 1.88 (2H, m), 2.49 (4H, m), 2.61-2.76(2H, m), 3.16 (1H, m), 3.34 (2H, d, J=6.6 Hz), 3.59 (2H, s), 4.02 (1H, m), 4.80 (1H, m), 6.33 (1H, dt, J=6.6, 16.2 Hz), 6.48 (1H, d, J=16.2 Hz), 7.10 (2H, d, J=8.7 Hz), 7.28 (6H, m). melting point: 105-106° C. (ethyl acetate-isopropyl ether) FABMS (pos) 423 [M+H]+

REFERENCE EXAMPLE 95

4-[4-(4-chlorophenyl)-1-piperidinyl]-1-[4-(4-methyl-1-piperazinyl)phenyl]-4-oxo-1-butanone

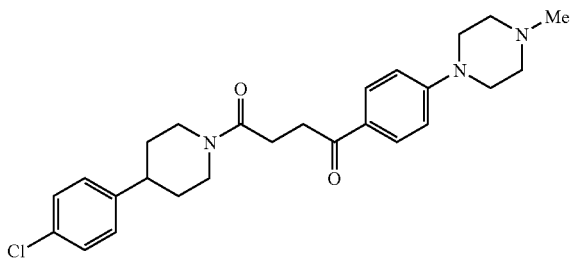

A solution (6 ml) of 4-[4-(4-chlorophenyl)-1-piperidinyl]-1-(4-fluorophenyl)-4-oxo-1-butanone (1.00 g, 2.67 mmol) obtained in Reference Example 78 and N-methylpiperazine (0.89 ml, 8.02 mmol) in dimethylsulfoxide was stirred at 100° C. for 16 hrs. Ethyl acetate was added to the reaction mixture, and the mixture was washed with aqueous saturated sodium carbonate solution and saturated brine, and dried over anhydrous sodium sulfate. The solvent was evaporated under reduced pressure, and the obtained residue was purified by alumina column chromatography (developing solvent; ethyl acetate), and powderized with isopropyl ether to give the title compound (1.06 g).

$^1$H-NMR (DMSO-d$_6$) δ: 1.42-1.78 (4H, m), 2.23 (3H, s), 2.44-2.51 (7H, m), 2.65-2.80 (3H, m), 3.13 (5H, m), 4.07 (1H, m), 4.47 (1H, m), 6.98 (2H, d, J=9.2 Hz), 7.31 (4H, m), 7.85 (2H, d, J=9.2 Hz). melting point: 152-153° C. (ethyl acetate-isopropyl ether) FABMS (pos) 454 [M+H]+

REFERENCE EXAMPLE 96

1-(4-{4-[4-(4-chlorophenyl)-1-piperidinyl]-4-oxobutyl}phenyl)-4-methylpiperazine

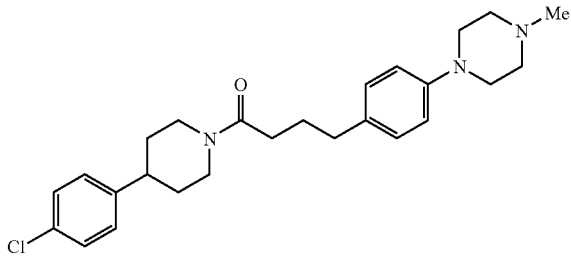

A solution (2 ml) of 4-[4-(4-chlorophenyl)-1-piperidinyl]-1-[4-(4-methyl-1-piperazinyl)phenyl]-4-oxo-1-butanone (500 mg, 1.10 mmol) obtained in Reference Example 95 and triethylsilane (0.53 ml) in trifluoroacetic acid was stirred at room temperature for 16 hrs. Ethyl acetate was added to the reaction mixture. The mixture was washed with 8N aqueous sodium hydroxide solution and saturated brine, and dried over anhydrous sodium sulfate. The solvent was evaporated under reduced pressure. The obtained residue was purified by NH-silica column chromatography (developing solvent; ethyl acetate:hexane=1:2), and powderized with isopropyl ether to give the title compound (129 mg).

$^1$H-NMR (DMSO-d$_6$) δ: 1.43 (2H, m), 1.75 (4H, m), 2.21 (3H, s), 2.31 (2H, m), 2.41-2.54 (7H, m), 2.76 (1H, m), 3.06 (5H, m), 3.90 (1H, m), 4.54 (1H, m), 6.83 (2H, d, J=8.8 Hz), 7.03 (2H, d, J=8.8 Hz), 7.30 (4H, m). melting point: 119-120° C. (ethyl acetate-isopropyl ether) FABMS (pos) 440 [M+H]+

REFERENCE EXAMPLE 97

4-(4-chlorophenyl)-1-(4-{4-[1-(1-pyrrolidinyl)ethyl]phenyl}butanoyl)piperidine hydrochloride

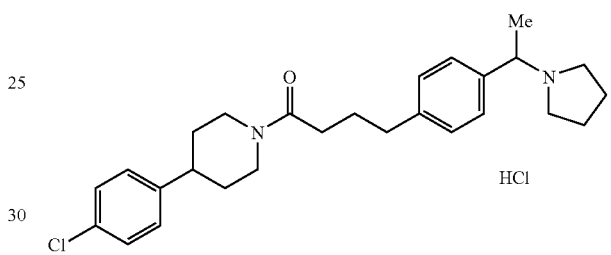

The title compound was obtained by a similar operation as in Example 10 and using 1-{4-[4-(1-chloroethyl)phenyl]butanoyl}-4-(4-chlorophenyl)piperidine obtained in Reference Example 82.

$^1$H-NMR (CDCl$_3$, free base) δ: 1.38 (3H, d, J=6.6 Hz), 1.49-1.63 (2H, m), 1.74 (4H, m), 1.82-1.86 (2H, m), 1.98 (2H, m), 2.35 (4H, m), 2.50-2.74 (6H, m), 3.02-3.10 (1H, m), 3.14 (1H, q, J=6.6 Hz), 3.84-3.89 (1H, m), 4.77-4.81 (1H, m), 7.10 (2H, d, J=8.4 Hz), 7.12 (2H, d, J=8.1 Hz), 7.22-7.28 (4H, m). FABMS (pos) 439 [M+H]+

REFERENCE EXAMPLE 98

1-[4-(aminomethyl)phenyl]-4-[4-(4-chlorophenyl)-1-piperidinyl]-1-butanone

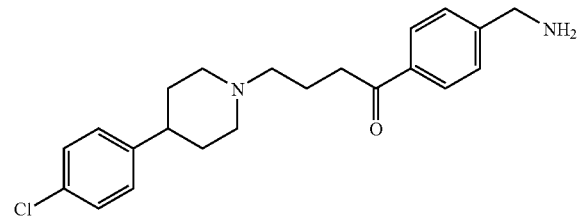

A solution of N-(4-{4-[4-(4-chlorophenyl)-1-piperidinyl]butanoyl}benzyl)acetamide (150 mg, 0.363 mmol) obtained in Reference Example 83 in concentrated hydrochloric acid (2 ml) was stirred at 100° C. for 16 hrs. The reaction mixture was basified with potassium carbonate and extracted with ethyl acetate. The extract was washed with saturated brine and dried over anhydrous sodium sulfate. The solvent was evaporated under reduced pressure, and powderized with hexane to give the title compound (104 mg).
¹H-NMR (CDCl₃) δ: 1.55-1.79 (6H, m), 1.95-2.08 (4H, m), 2.45 (3H, m), 3.00 (4H, m), 3.94 (2H, s), 7.11 (2H, d, J=8.7 Hz), 7.23 (2H, d, J=8.7 Hz), 7.41 (2H, d, J=8.1 Hz), 7.95 (2H, d, J=8.1 Hz). melting point: 94-96° C. (ethyl acetate-hexane)

REFERENCE EXAMPLE 99

4-[4-(4-chlorophenyl)-1-piperidinyl]-1-[4-(1-pyrrolidinylmethyl)phenyl]-1-butanone

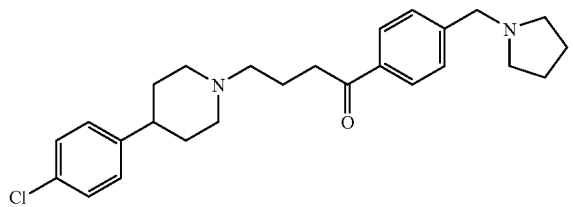

A solution of 1-[4-(aminomethyl)phenyl]-4-[4-(4-chlorophenyl)-1-piperidinyl]-1-butanone (50.0 mg, 0.135 mmol) obtained in Reference Example 98, 1,4-dibromobutane (16.1 μl, 0.135 mmol) and sodium carbonate (42.9 mg, 0.404 mmol) in dimethylformamide (1 ml) was stirred at 80° C. for 16 hrs. Ethyl acetate was added to the reaction mixture, and the mixture was washed with saturated aqueous potassium carbonate solution and saturated brine, and dried over anhydrous sodium sulfate. The solvent was evaporated under reduced pressure, and the obtained residue was purified by alumina column chromatography (developing solvent; ethyl acetate:hexane=1:3) to give the title compound (13.7 mg).
¹H-NMR (CDCl₃) δ: 1.60-1.81 (8H, m), 1.95-2.06 (4H, m), 2.41-2.50 (7H, m), 2.97-3.03 (4H, m), 3.66 (2H, s), 7.10 (2H, d, J=8.4 Hz), 7.24 (2H, d, J=8.4 Hz), 7.42 (2H, d, J=8.1 Hz), 7.93 (2H, d, J=8.1 Hz). melting point: 63-65° C. (ethyl acetate-hexane) FABMS (pos) 425 [M+H]+

REFERENCE EXAMPLE 100

4-(4-chlorophenyl)-1-{4-[2-fluoro-4-(1-pyrrolidinylmethyl)phenyl]-3-butynyl}piperidine

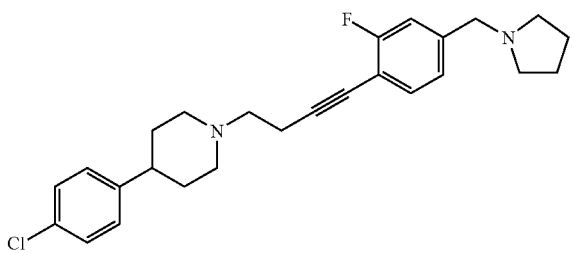

The title compound was obtained by similar operations as in Example 10 and Reference Example 90 and using 1-bromo-4-bromomethyl-2-fluorobenzene, pyrrolidine and 1-(3-butynyl)-4-(4-chlorophenyl)piperidine obtained in Reference Example 77.
¹H-NMR (CDCl₃) δ: 1.77-1.86 (8H, m), 2.09-2.25 (2H, m), 2.41-2.75 (9H, m), 3.04-3.06 (2H, m), 3.56 (2H, s), 7.01-7.32 (7H, m).

REFERENCE EXAMPLE 101

4-(4-chlorophenyl)-1-{4-[3-fluoro-4-(1-pyrrolidinylmethyl)phenyl]-3-butynyl}piperidine

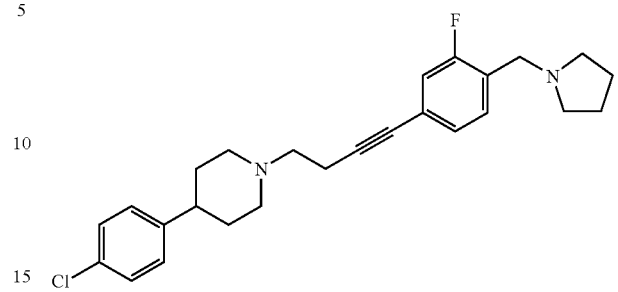

The title compound was obtained by similar operations as in Example 10 and Reference Example 90 and using 1-bromo-4-bromomethyl-3-fluorobenzene, pyrrolidine and 1-(3-butynyl)-4-(4-chlorophenyl) obtained in piperidine Reference Example 77.
¹H-NMR (CDCl₃) δ: 1.69-1.84(8H, m), 2.12-2.25 (2H, dt like), 2.43-2.75 (9H, m), 3.05-3.11 (2H, d like), 3.65 (2H, s), 7.03-7.17 (4H, m), 7.24-7.34 (3H, m). FABMS (pos) 425 [M+H]+

REFERENCE EXAMPLE 102

4-(4-chlorophenyl)-1-{4-[2-methyl-4-(1-pyrrolidinylmethyl)phenyl]-3-butynyl}piperidine

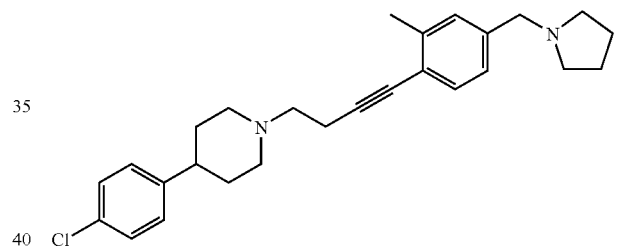

The title compound was obtained by a similar operation as in Reference Example 90 and using 1-(4-bromo-3-methylbenzyl)pyrrolidine and 1-(3-butynyl)-4-(4-chlorophenyl)piperidine obtained in Reference Example 77.
¹H-NMR (CDCl₃) δ: 1.73-1.92 (8H, m), 2.14-2.23 (2H, m), 2.34 and 2.40 (3H, s), 2.44-2.52 (5H, m), 2.60-2.75 (4H, m), 3.07-3.11 (2H, m), 3.55 and 3.57 (2H, s), 7.12-7.28 (7H, m).

REFERENCE EXAMPLE 103

4-(4-chlorophenyl)-1-{4-[3-methyl-4-(1-pyrrolidinylmethyl)phenyl]-3-butynyl}piperidine

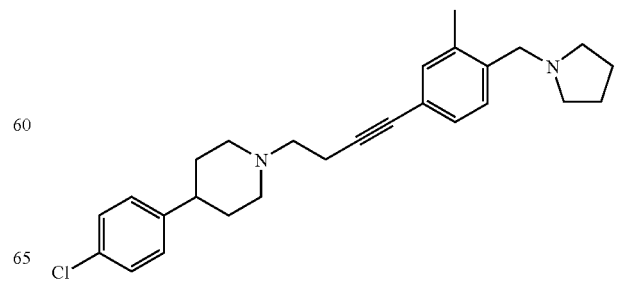

The title compound was obtained by a similar operation as in Reference Example 90 and using 1-(4-bromo-2-methylbenzyl)pyrrolidine and 1-(3-butynyl)-4-(4-chlorophenyl)piperidine obtained in Reference Example 77.
$^1$H-NMR (CDCl$_3$) δ: 1.75-1.81 (8H, m), 2.14-2.22 (2H, m) 2.31 and 2.35 (3H, s), 2.44-2.54 (5H, m), 2.59-2.64 (2H, m), 2.69-2.75 (2H, m), 3.06-3.10 (2H, m), 3.55 and 3.58 (2H, s), 7.12-7.29 (7H, m).

REFERENCE EXAMPLE 104

4-(4-chlorophenyl)-1-{4-[6-(1-pyrrolidinylmethyl)-3-pyridyl]-3-butynyl}piperidine

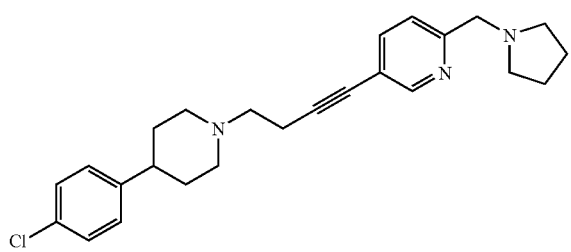

To a solution of 5-bromo-2-(1-pyrrolidinylcarbonyl)pyridine (500 mg, 2.00 mmol) obtained in Reference Example 84 in ether (20 ml) was added lithium aluminum hydride (150 mg, 4.00 mmol), and the mixture was stirred for 15 min. To a reaction solution were successively added ethyl acetate (5 ml) and water (5 ml), and the mixture was filtered through celite. The filtrate was partitioned between ethyl acetate (20 ml) and water (20 ml). The organic layer was washed with saturated brine and dried over anhydrous magnesium sulfate. The solvent was evaporated under reduced pressure. The title compound was obtained by a similar operation as in Reference Example 90 and using the obtained 5-bromo-2-(1-pyrrolidinylmethyl)pyridine and 1-(3-butynyl)-4-(4-chlorophenyl)piperidine obtained in Reference Example 77.
$^1$H-NMR (CDCl$_3$) δ: 1.71-1.83 (8H, m), 2.13-2.25 (2H, m), 2.44-2.77 (9H, m), 3.05-3.11 (2H, br m), 3.76 (2H, s), 7.15 (2H, d, J=8.4 Hz), 7.27-7.35 (3H, m), 7.64 (1H, dd, J=2.2 Hz, 8.2 Hz), 8.57 (1H, d, J=2.2 Hz). FABMS (pos) 408 [M+H]+

REFERENCE EXAMPLE 105

4-[4-(4-chlorophenyl)-1-piperidinyl]-1-[2-fluoro-4-(1-pyrrolidinylmethyl)phenyl]-1-butanone dihydrochloride

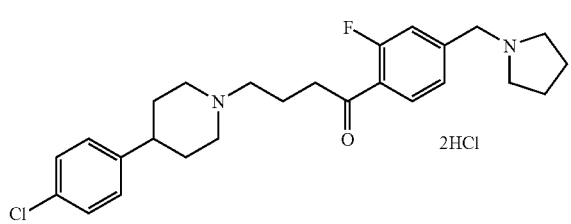

The title compound was obtained by a similar operation as in Reference Example 91 and using 4-(4-chlorophenyl)-1-{4-[2-fluoro-4-(1-pyrrolidinylmethyl)phenyl]-3-butynyl}piperidine obtained in Reference Example 100.

$^1$H-NMR (free base, CDCl$_3$) δ: 1.66-2.11 (1OH, m), 2.40-2.51 (9H, m), 2.95-3.06 (4H, m), 3.64 (2H, s), 7.08-7.28 (6H, m), 7.83 (1H, t, J=8.0 Hz). FABMS (pos) 443 [M+H]+

REFERENCE EXAMPLE 106

4-[4-(4-chlorophenyl)-1-piperidinyl]-1-[3-fluoro-4-(1-pyrrolidinylmethyl)phenyl]-1-butanone

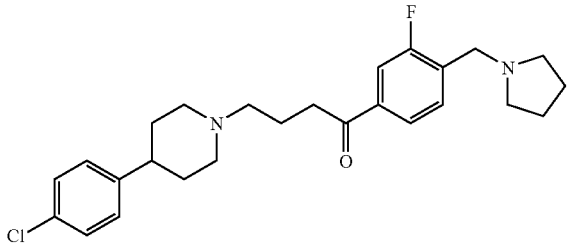

The title compound was obtained by a similar operation as in Reference Example 91 and using 4-(4-chlorophenyl)-1-{4-[3-fluoro-4-(1-pyrrolidinylmethyl)phenyl]-3-butynyl}piperidine obtained in Reference Example 101.
$^1$H-NMR (CDCl$_3$) δ: 1.54-1.82 (8H, m), 1.94-2.08 (2H, m), 2.39-2.60 (9H, m), 2.93-3.00 (4H, m), 3.73 (2H, s), 7.08-7.26 (5H, m), 7.48-7.76 (2H, m). FABMS (pos) 443 [M+H]+

REFERENCE EXAMPLE 107

4-[4-(4-chlorophenyl)-1-piperidinyl]-1-[2-methyl-4-(1-pyrrolidinylmethyl)phenyl]-1-butanone

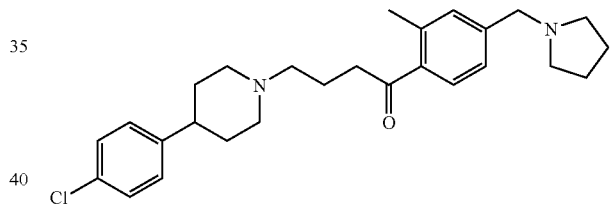

The title compound was obtained by a similar operation as in Reference Example 91 and using 4-(4-chlorophenyl)-1-{4-[2-methyl-4-(1-pyrrolidinylmethyl)phenyl]-3-butynyl}piperidine obtained in Reference Example 102.
$^1$H-NMR (CDCl$_3$) δ: 1.70-1.81 (8H, m), 1.90-2.04 (4H, m), 2.34 and 2.38 (3H, s), 2.34-2.50 (9H, m), 2.90-3.05 (2H, m), 3.57 and 3.61 (2H, s), 7.03-7.27 (6H, m), 7.63-7.67 (1H, m). FABMS (pos) 439 [M+H]+

REFERENCE EXAMPLE 108

4-[4-(4-chlorophenyl)-1-piperidinyl]-1-[3-methyl-4-(1-pyrrolidinylmethyl)phenyl]-1-butanone

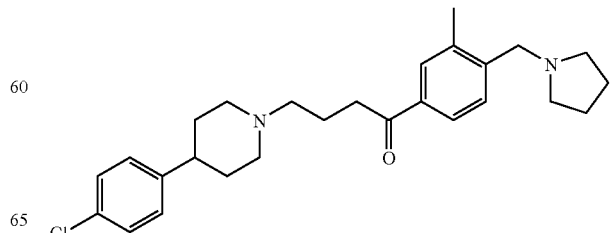

The title compound was obtained by a similar operation as in Reference Example 91 and using 4-(4-chlorophenyl)-1-{4-[3-methyl-4-(1-pyrrolidinylmethyl)phenyl]-3-butynyl}piperidine obtained in Reference Example 103.

¹H-NMR (CDCl₃) δ: 1.64-1.80 (8H, m), 1.93-2.09 (4H, m) 2.36 and 2.41 (3H, s), 2.36-2.55 (9H, m), 2.94-3.04 (2H, m), 3.59 and 3.62 (2H, s), 7.08-7.31 (6H, m), 7.75-7.78 (1H, m). FABMS (pos) 439 [M+H]+

REFERENCE EXAMPLE 109

4-[4-(4-chlorophenyl)-1-piperidinyl]-1-[6-(1-pyrrolidinylmethyl)-3-pyridyl]-1-butanone

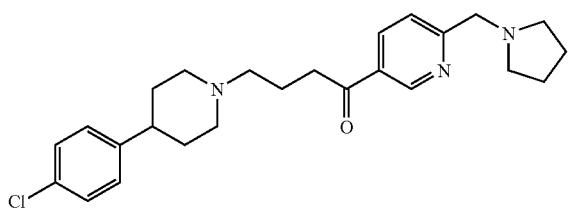

The title compound was obtained by a similar operation as in Reference Example 91 and using 4-(4-chlorophenyl)-1-{4-[6-(1-pyrrolidinylmethyl)-3-pyridyl]-3-butynyl}piperidine obtained in Reference Example 104.

¹H-NMR (CDCl₃) δ: 1.53-1.81 (8H, m), 1.97-2.08 (2H, m) 2.41-2.70 (9H, m), 2.97-3.03 (4H, m), 3.84 (2H, s), 7.09 (2H, d, J=8.4 Hz), 7.24 (2H, d overlapping with CDCl₃), 7.54 (1H, d, J=8.4 Hz), 8.23 (1H, dd, J=1.9 Hz, 8.4 Hz), 9.13 (1H, d, J=1.9 Hz) FABMS (pos) 426 [M+H]+

REFERENCE EXAMPLE 110

4-(4'-chloro-1,1'-biphenyl-4-yl)-1-[4-(1-pyrrolidinylmethyl)phenyl]-1-butanone

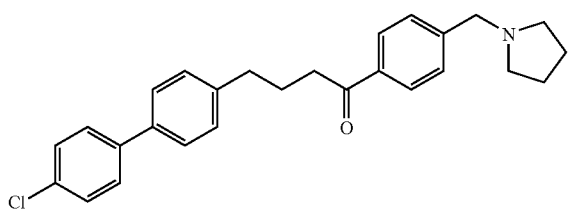

To a solution of 1-(4-bromobenzyl)pyrrolidine (240 mg, 1.00 mmol) in THF (7 ml) was added dropwise a solution (1.6 M, 0.63 ml) of n-butyllithium in hexane under a nitrogen atmosphere at −78° C. The obtained solution was stirred at −78° C. for 30 min., allowed to warm to −40° C., and a solution of 4-(4'-chloro-1,1'-biphenyl-4-yl)-N-methoxy-N-methylbutanamide (320 mg, 1.00 mol) obtained in Reference Example 85 in THF (3 ml) was added dropwise. The obtained solution was stirred at −40° C. for 30 min., and then at room temperature for 16 hrs. The reaction solution was poured into saturated ammonium chloride solution (40 ml) and extracted with ethyl acetate (40 ml×2). The extract was washed with saturated brine and dried over anhydrous magnesium sulfate. The solvent was evaporated under reduced pressure, and the residue was purified by alumina column chromatography (developing solvent; hexane:ethyl acetate=20:1), and the obtained colorless solid was disrupted in isopropyl ether to give the title compound.

¹H-NMR (CDCl₃) δ: 1.76-1.82 (4H, m), 2.04-2.18 (2H, m), 2.47-2.54 (4H, m), 2.76 (2H, t, J=7.4 Hz), 3.00 (2H, t, J=7.4 Hz), 3.65 (2H, s), 7.28 (2H, d, J=8.2 Hz), 7.36-7.53 (8H, m), 7.88 (2H, d, J=8.6 Hz). melting point: 114-115° C. (isopropyl ether) FABMS (pos) 418 [M+H]+

REFERENCE EXAMPLE 111

1-phenyl-4-{4-[1-(1-pyrrolidinyl)ethyl]phenyl}-1-butanone hydrochloride

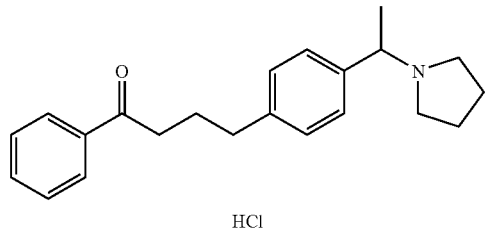

To a solution of phenylmagnesium bromide (2 mol/l THF solution, 1.6 ml) in toluene (7 ml) was added dropwise a solution of N-methoxy-N-methyl-4-{4-[1-(1-pyrrolidinyl)ethyl]phenyl}butanamide (200 mg, 0.66 mmol) obtained in Reference Example 89 in toluene (3 ml) under a nitrogen atmosphere under ice-cooling. After stirring at room temperature for 1 hr, the reaction solution was poured into water (40 ml), and extracted with ethyl acetate (40 ml×2). The extract was washed successively with 10% sodium hydrogencarbonate solution and saturated brine, and dried over anhydrous magnesium sulfate. The solvent was evaporated under reduced pressure, and the residue was purified by NH-silica gel column chromatography (developing solvent; hexane:ethyl acetate=10:1) to give a colorless oil. The oil was dissolved in ethyl acetate (10 ml), and 4N-hydrochloric acid (ethyl acetate solution; 0.2 ml) was added dropwise under ice-cooling. The mixture was stirred for 5 min., and the solvent was evaporated under reduced pressure. The residue was powderized with isopropyl ether and hexane, and washed with hexane to give the title compound.

¹H-NMR (free base, CDCl₃) δ: 1.39 (3H, d, J=6.6 Hz), 1.73-1.77 (4H, m), 2.03-2.12 (2H, m), 2.34-2.37 (2H, m), 2.53-2.59 (2H, m), 2.70 (2H, t, J=7.5 Hz), 2.98 (2H, t, J=7.5 Hz), 3.15 (1H, q, J=6.6 Hz), 7.14 (2H, d, J=8.1 Hz), 7.23-7.35 (3H, m), 7.40-7.44 (2H, m), 7.92 (2H, d like). melting point: 116-117° C. (hexane) FABMS (pos) 322 [M+H]+

REFERENCE EXAMPLE 112

1-[1,1'-biphenyl-4-yl]-4-{4-[1-(1-pyrrolidinyl)ethyl]phenyl}-1-butanone

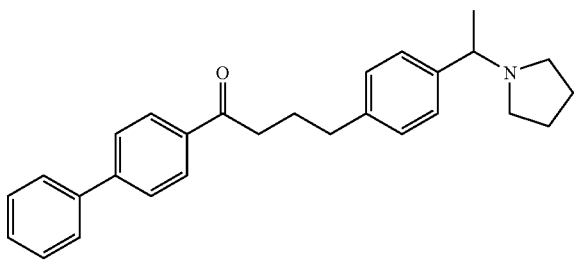

The title compound was obtained by a similar operation as in Reference Example 111 and using N-methoxy-N-methyl- 4-{4-[1-(1-pyrrolidinyl)ethyl]phenyl}butanamide obtained in Reference Example 89 and 4-biphenylmagnesium bromide.

¹H-NMR (CDCl₃) δ: 1.39 (3H, d, J=6.6 Hz), 1.71-1.80 (4H, m), 2.10 (2H, m), 2.34-2.39 (2H, m), 2.51-2.56 (2H, m), 2.72 (2H, t, J=7.5 Hz), 3.01 (2H, t, J=7.5 Hz), 3.16 (1H, q, J=6.6 Hz), 7.15 (2H, d, J=7.8 Hz), 7.24-7.27 (2H, m), 7.37-7.50 (3H, m), 7.60-7.68 (4H, m), 7.99 (2H, m). melting point: 70-72° C. (hexane) FABMS (pos) 398 [M+H]+

REFERENCE EXAMPLE 113

1-(4'-chloro-1,1'-biphenyl-4-yl)-4-{4-[1-(1-pyrrolidinyl)ethyl]phenyl}-1-butanone

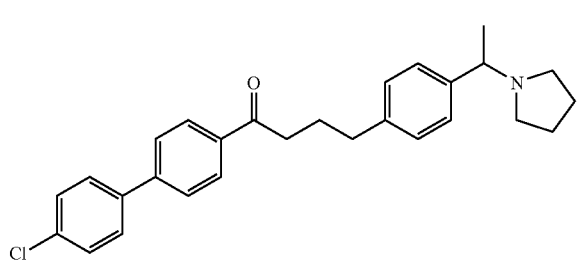

The title compound was obtained by a similar operation as in Reference Example 110 and using N-methoxy-N-methyl-4-{4-[1-(1-pyrrolidinyl)ethyl]phenyl}butanamide obtained in Reference Example 89 and 4-bromo-4'-chlorobiphenyl.

¹H-NMR (CDCl₃) δ: 1.39 (3H, d, J=6.6 Hz), 1.73-1.75 (4H, m), 2.09 (2H, m), 2.34-2.41 (2H, m), 2.51-2.61 (2H, m), 2.71 (2H, t; J=7.7 Hz), 3.00 (2H, t, J=7.7 Hz), 3.16 (1H, q, J=6.6 Hz), 7.15 (2H, d, J=7.9 Hz), 7.26 (2H, d, J=7.9 Hz), 7.43 (2H, d, J=8.4 Hz), 7.55 (2H, d, J=8.4 Hz), 7.62 (2H, d, J=8.2 Hz), 7.99 (2H, d, J=8.2 Hz). melting point: 81-82° C. (hexane) FABMS (pos) 432 [M+H]+

REFERENCE EXAMPLE 114

1-[1-(4-{3-[(4'-chloro-1,1'-biphenyl-4-yl)sulfonyl]propyl}phenyl)ethyl]pyrrolidine

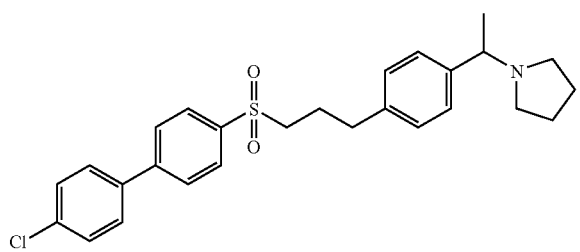

To a solution of 1-bromo-4-[(3-phenylpropyl)thio]benzene (5.00 g, 16.3 mmol) in chloroform (80 ml) was added mCPBA (10.2 g, 40.7 mmol), and the mixture was stirred at room temperature for 2 hrs. The solvent was evaporated, and the residue was dissolved in ethyl acetate, and the solution was washed with aqueous potassium carbonate solution and saturated brine, and dried over anhydrous sodium sulfate. The solvent was evaporated under reduced pressure, and the obtained residue was purified by alumina column chromatography (developing solvent; ethyl acetate:hexane=3:1), and powderized with hexane to give a sulfone derivative (4.81 g). The title compound was obtained by similar operations as in Reference Example 19-21, Example 10 and Example 6 and using this compound.

¹H-NMR (CDCl₃) δ: 1.37 (3H, d, J=6.6 Hz), 1.76 (4H, m), 2.07 (2H, m), 2.32 (2H, m), 2.51 (2H, m), 2.69 (2H, m), 3.13 (3H, m), 7.04 (2H, d, J=8.1 Hz), 7.23 (2H, d, J=8.1 Hz), 7.46 (2H, d, J=8.7 Hz), 7.55 (2H, d, J=8.7 Hz), 7.72 (2H, d, J=8.7 Hz), 7.92 (2H, d, J=8.7 Hz).

EXAMPLE 1

4-(4-chlorophenyl)-N-{2-[4-(1-pyrrolidinylmethyl)phenyl]ethyl}-1-piperidinecarboxamide

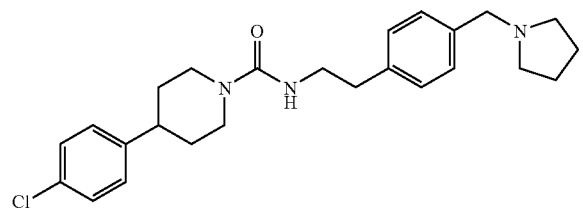

To a solution of 2-[4-(1-pyrrolidinylmethyl)phenyl]ethylamine (229 mg, 1.12 mmol) obtained in Reference Example 4 in dimethylacetamide (5.6 ml) was added carbonyldiimidazole (218 mg, 1.34 mmol) at 0° C., and the mixture was stirred for 1 hr. 4-(4-Chlorophenyl)piperidine hydrochloride (286 mg, 1.23 mmol) was added, and the mixture was stirred at room temperature for 5 hrs. Ethyl acetate was added to the reaction mixture, and the mixture was washed with saturated aqueous potassium carbonate solution and saturated brine, and dried over anhydrous sodium sulfate. The solvent was evaporated under reduced pressure, and the obtained residue was purified by alumina column chromatography (developing solvent; ethyl acetate:hexane=3:1), and powderized with hexane to give the title compound (151 mg).

¹H-NMR (DMSO-d₆) δ: 1.57 (2H, m), 1.77 (5H, m), 2.49 (4H, m), 2.63 (1H, m), 2.83 (4H, m), 3.50 (2H, m), 3.58 (2H, m), 3.99 (2H, m), 4.48 (1H, m), 7.13 (4H, m), 7.27 (4H, m). melting point: 116-117° C. (ethyl acetate-isopropyl ether) FABMS (pos) 426 [M+H]+

EXAMPLE 2

4'-chloro-N-{2-[4-(1-pyrrolidinylmethyl)phenyl]ethyl}[1,1'-biphenyl]-4-carboxamide

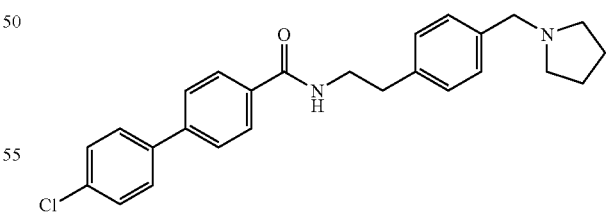

To a solution of 2-[4-(1-pyrrolidinylmethyl)phenyl]ethylamine (108 mg, 0.529 mmol) obtained in Reference Example 4, 4'-chloro[1,1'-biphenyl]-4-carboxylic acid (148 mg, 0.624 mmol) and 1-hydroxybenzotriazole (71.4 mg, 0.624 mmol) in dimethylformamide (1.5 ml) was added ethyldimethylaminopropylcarbodiimide hydrochloride (122 mg, 0.624 mmol) at 0° C., and the mixture was stirred at room temperature for 16 hrs. Ethyl acetate was added to the reaction mixture, and the mixture was washed with aqueous potassium carbonate solution and saturated brine, and dried over anhydrous sodium sulfate. The solvent was concentrated under reduced pressure, and the obtained residue was purified by NH-silica column chromatography (developing solvent; ethyl acetate), and powderized with isopropyl ether to give the title compound (112 mg).

$^1$H-NMR (DMSO-d$_6$) δ: 1.67 (4H, m), 2.39 (4H, m), 2.83 (2H, t, J=7.5 Hz), 3.47 (2H, m), 3.51 (2H, s), 7.20 (4H, m), 7.53 (2H, d, J=8.7 Hz), 7.76 (4H, m), 7.91 (2H, d, J=8.7 Hz), 8.62 (1H, t, J=5.7 Hz). melting point: 165-167° C. (ethyl acetate-isopropyl ether) FABMS (pos) 419 [M+H]$^+$

EXAMPLE 3

4-pentyl-N-{2-[4-(1-pyrrolidinylmethyl)phenyl]ethyl}benzamide

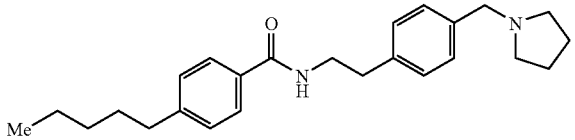

The title compound was obtained by a similar operation as in Example 2 and using 2-[4-(1-pyrrolidinylmethyl)phenyl]ethylamine obtained in Reference Example 4.

$^1$H-NMR (DMSO-d$_6$) δ: 0.86 (3H, t, J=6.9 Hz), 1.27 (4H, m), 1.57 (2H, m), 1.67 (4H, m), 2.41 (4H, m), 2.60 (2H, t, J=7.8 Hz), 2.81 (2H, t, J=7.8 Hz), 3.44 (2H, m), 3.52 (2H, s), 7.18 (4H, m), 7.25 (2H, d, J=8.4 Hz), 7.71 (2H, d, J=8.4 Hz), 8.44 (1H, m). melting point: 91-93° C. (ethyl acetate-isopropyl ether) FABMS (pos) 379 [M+H]$^+$

EXAMPLE 4

4-(2-oxopentyl)-N-{2-[4-(1-pyrrolidinylmethyl)phenyl]ethyl}benzamide

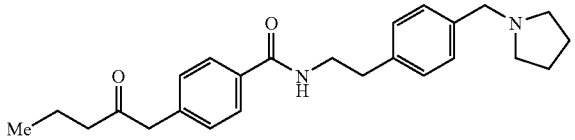

The title compound was obtained by a similar operation as in Example 2 and using 2-[4-(1-pyrrolidinylmethyl)phenyl]ethylamine obtained in Reference Example 4.

$^1$H-NMR (DMSO-d$_6$) δ: 0.82 (3H, t, J=7.4 Hz), 1.48 (2H, m), 1.67 (4H, m), 2.39 (4H, m), 2.44 (2H, m), 2.81 (2H, m), 3.48 (2H, m), 3.51 (2H, s), 3.81 (2H, s), 7.19 (4H, m), 7.24 (2H, d, J=8.2 Hz), 7.74 (2H, d, J=8.2 Hz), 8.50 (1H, m). melting point: 115-117° C. (ethyl acetate-isopropyl ether) FABMS (pos) 393 [M+H]$^+$

EXAMPLE 5

4-bromo-2-fluoro-N-{2-[4-(1-pyrrolidinylmethyl)phenyl]propyl}benzamide

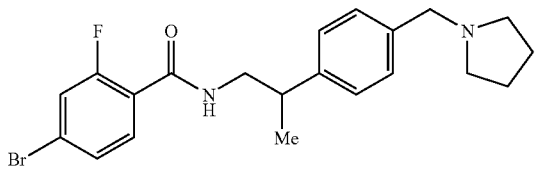

The title compound was obtained by similar operations as in Reference Example 4 and Example 2 and using tert-butyl 2-[4-(1-pyrrolidinylmethyl)phenyl]propylcarbamate obtained in Reference Example 13.

$^1$H-NMR (CDCl$_3$) δ: 1.33 (3H, d, J=7.2 Hz), 1.78 (4H, m), 2.51 (4H, m), 3.03 (1H, m), 3.46 (1H, m), 3.59 (2H, s), 3.79 (1H, m), 6.50 (1H, m), 7.16-7.30 (5H, m), 7.37 (1H, m), 7.92 (1H, m). melting point: 80-82° C. (ethyl acetate-isopropyl ether) FABMS (pos) 419 [M+H]$^+$

EXAMPLE 6

4'-chloro-3-fluoro-N-{2-[4-(1-pyrrolidinylmethyl)phenyl]propyl}[1,1'-biphenyl]-4-carboxamide

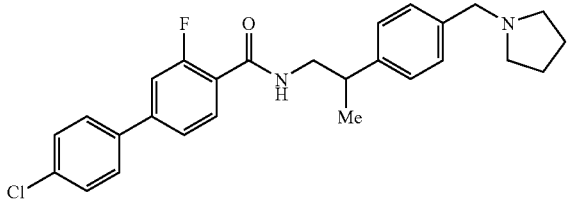

To a solution (7 ml) of 4-bromo-2-fluoro-N-{2-[4-(1-pyrrolidinylmethyl)phenyl]propyl}benzamide (300 mg, 0.715 mmol) obtained in Example 5, 4-chlorophenylboronic acid (224 mg, 1.43 mmol) and 2N aqueous sodium carbonate solution (0.715 ml) in tetrahydrofuran was added tetrakistriphenylphosphine palladium (24.8 mg, 21.5 mmol) under a nitrogen atmosphere. This was stirred at 90° C. for 16 hrs, and allowed to cool to room temperature. Ethyl acetate was added to the reaction mixture, and the mixture was washed with saturated brine and dried over anhydrous sodium sulfate. The solvent was evaporated under reduced pressure, and the obtained residue was purified by NH-silica gel column chromatography (developing solvent; ethyl acetate), and powderized with isopropyl ether to give the title compound (142 mg).

$^1$H-NMR (DMSO-d$_6$) δ: 1.24 (3H, d, J=7.0 Hz), 1.67 (4H, m), 2.41 (4H, m), 3.03 (1H, m), 3.40 (2H, m), 3.53 (2H, s), 7.22 (4H, m), 7.52-7.65 (5H, m), 7.77 (2H, d, J=8.6 Hz), 8.33 (1H, m). melting point: 119-121° C. (ethyl acetate-isopropyl ether) FABMS (pos) 451 [M+H]$^+$

EXAMPLE 7

4'-chloro-3-fluoro-N-{2-[4-(1-pyrrolidinylmethyl)phenyl]ethyl}[1,1'-biphenyl]-4-carboxamide

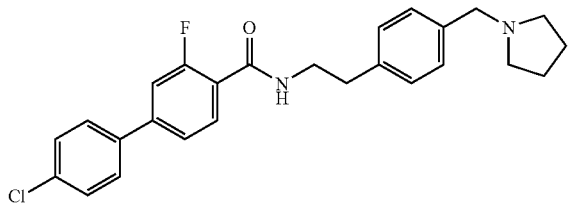

The title compound was obtained by similar operations as in Example 2 and Example 6 and using 2-[4-(1-pyrrolidinylmethyl)phenyl]ethylamine obtained in Reference Example 4.

$^1$H-NMR (DMSO-$d_6$) δ: 1.68 (4H, m), 2.42 (4H, m), 2.83 (2H, m), 3.48 (2H, m), 3.54 (2H, s), 7.21 (4H, m), 7.53-7.70 (5H, m), 7.79 (2H, d, J=8.4 Hz), 8.39 (1H, m). melting point: 128-131° C. (ethyl acetate-isopropyl ether) FABMS (pos) 437 [M+H]$^+$

EXAMPLE 8

4'-chloro-N-{2-[4-(1-pyrrolidinylmethyl)phenyl]propyl}[1,1'-biphenyl]-4-carboxamide

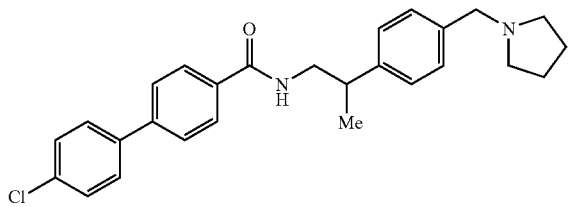

The title compound was obtained by similar operations as in Reference Example 4 and Example 2 and using tert-butyl 2-[4-(1-pyrrolidinylmethyl)phenyl]propylcarbamate obtained in Reference Example 13.

$^1$H-NMR (DMSO-$d_6$) δ: 1.23 (3H, d, J=6.9 Hz), 1.68 (4H, m), 2.43 (4H, m), 3.09 (1H, m), 3.33-3.44 (2H, m), 3.56 (2H, s), 7.22 (4H, m), 7.55 (2H, d, J=8.4 Hz), 7.75 (4H, m), 7.88 (2H, d, J=8.4 Hz), 8.55 (1H, m). melting point: 156-157° C. (ethyl acetate-isopropyl ether) FABMS (pos) 433 [M+H]$^+$

EXAMPLE 9

4-pentyl-N-{2-[4-(1-pyrrolidinylmethyl)phenyl]propyl}benzamide

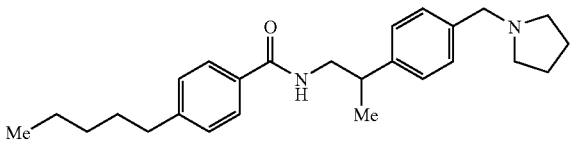

The title compound was obtained by similar operations as in Reference Example 4 and Example 2 and using tert-butyl 2-[4-(1-pyrrolidinylmethyl)phenyl]propylcarbamate obtained in Reference Example 13.

$^1$H-NMR (DMSO-$d_6$) δ: 1.85 (3H, t, J=6.8 Hz), 1.22 (3H, d, J=6.6 Hz), 1.28 (4H, m), 1.57 (2H, m), 1.67 (4H, m), 2.39 (4H, m), 2.59 (2H, t, J=7.4 Hz), 3.04 (1H, m), 3.37 (2H, m), 3.51 (2H, s), 7.20 (6H, m), 7.68 (2H, d, J=8.4 Hz), 8.38 (1H, m). melting point: 91-92° C. (ethyl acetate-isopropyl ether) FABMS (pos) 393 [M+H]$^+$

EXAMPLE 10

4-bromo-N-(2-{4-[1-(1-pyrrolidinyl)ethyl]phenyl}ethyl)benzamide

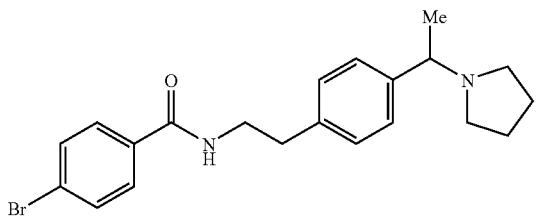

A solution of 4-bromo-N-{2-[4-(1-chloroethyl)phenyl]ethyl}benzamide (1.49 g, 4.06 mmol) obtained in Reference Example 21, pyrrolidine (1.02 ml, 12.2 mmol) and potassium carbonate (1.68 g, 12.2 mmol) in dimethylformamide (10 ml) was stirred at 80° C. for 16 hrs. Diethyl ether was added to the reaction mixture, and the mixture was washed with saturated brine and extracted with 1N hydrochloric acid. The extract was washed with diethyl ether, basified with potassium carbonate and extracted with ethyl acetate. The extract was washed with saturated brine and dried over anhydrous sodium sulfate. The solvent was concentrated under reduced pressure, and the obtained residue was purified by alumina column chromatography (developing solvent; ethyl acetate), and powderized with isopropyl ether-hexane (1:1) to give the title compound (1.00 g).

$^1$H-NMR (DMSO-$d_6$) δ: 1.26 (3H, d, J=6.6 Hz), 1.64 (4H, m), 2.25 (2H, m), 2.42 (2H, m), 2.81 (2H, m), 3.14 (1H, m), 3.46 (2H, m), 7.16 (2H, d, J=8.4 Hz), 7.22 (2H, d, J=8.4 Hz), 7.67 (2H, d, J=8.4 Hz), 7.76 (2H, d, J=8.4 Hz), 8.66 (1H, t, J=6.0 Hz). melting point: 124-126° C. (ethyl acetate-hexane) FABMS (pos) 401 [M+H]$^+$

EXAMPLE 11

4'-chloro-N-(2-{4-[1-(1-pyrrolidinyl)ethyl]phenyl}ethyl)[1,1'-biphenyl]-4-carboxamide

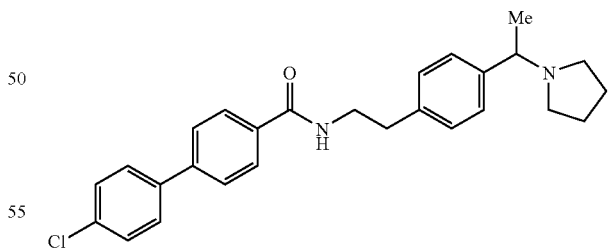

The title compound was obtained by a similar operation as in Example 6 and using 4-bromo-N-(2-{4-[1-(1-pyrrolidinyl)ethyl]phenyl}ethyl)benzamide obtained in Example 10.

$^1$H-NMR (DMSO-$d_6$) δ: 1.27 (3H, d, J=6.6 Hz), 1.64 (4H, m), 2.27 (2H, m), 2.44 (2H, m), 2.83 (2H, m), 3.15 (1H, m), 3.49 (2H, m), 7.20 (4H, m), 7.53 (2H, d, J=8.7 Hz), 7.75 (4H, m), 7.91 (2H, d, J=8.1 Hz), 8.62 (1H, t, J=5.4 Hz). melting point: 152-153° C. (ethyl acetate-isopropyl ether) FABMS (pos) 433 [M+H]$^+$

EXAMPLE 12

4'-methoxy-N-(2-{4-[1-(1-pyrrolidinyl)ethyl]phenyl}ethyl)[1,1'-biphenyl]-4-carboxamide

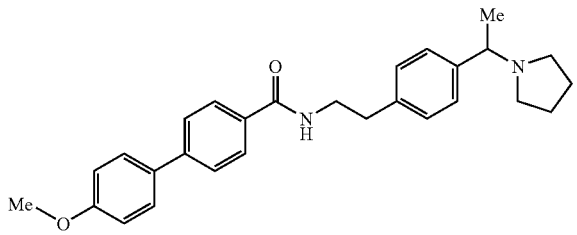

The title compound was obtained by a similar operation as in Example 6 and using 4-bromo-N-(2-{4-[1-(1-pyrrolidinyl)ethyl]phenyl}ethyl)benzamide obtained in Example 10.

$^1$H-NMR (DMSO-$d_6$) δ: 1.27 (3H, d, J=6.6 Hz), 1.64 (4H, m), 2.28 (2H, m), 2.43 (2H, m), 2.83 (2H, m), 3.17 (1H, m), 3.52 (2H, m), 3.81 (3H, s), 7.04 (2H, d, J=9.0 Hz), 7.24 (4H, m), 7.68 (4H, m), 7.88 (2H, d, J=8.4 Hz), 8.58 (1H, t, J=6.0 Hz). melting point: 163-165° C. (ethyl acetate-isopropyl ether) FABMS (pos) 429 [M+H]$^+$

EXAMPLE 13

4'-fluoro-N-(2-{4-[1-(1-pyrrolidinyl)ethyl]phenyl}ethyl)[1,1'-biphenyl]-4-carboxamide

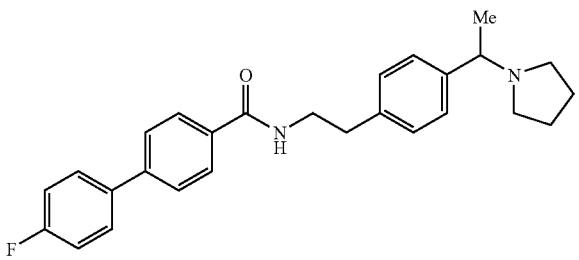

The title compound was obtained by a similar operation as in Example 6 and using 4-bromo-N-(2-{4-[1-(1-pyrrolidinyl)ethyl]phenyl}ethyl)benzamide obtained in Example 10.

$^1$H-NMR (DMSO-$d_6$) δ: 1.27 (3H, d, J=6.6 Hz), 1.64 (4H, m), 2.28 (2H, m), 2.42 (2H, m), 2.83 (2H, m), 3.16 (1H, m), 3.50 (2H, m), 7.15-7.36 (6H, m), 7.72-7.81 (4H, m), 7.92 (2H, d, J=8.4 Hz), 8.62 (1H, t, J=5.2 Hz). melting point: 141-143° C. (ethyl acetate-isopropyl ether) FABMS (pos) 417 [M+H]$^+$

EXAMPLE 14

4'-methyl-N-(2-{4-[1-(1-pyrrolidinyl)ethyl]phenyl}ethyl)[1,1'-biphenyl]-4-carboxamide

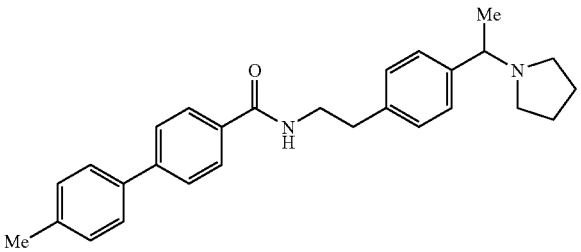

The title compound was obtained by a similar operation as in Example 6 and using 4-bromo-N-(2-{4-[1-(1-pyrrolidinyl)ethyl]phenyl}ethyl)benzamide obtained in Example 10.

$^1$H-NMR (DMSO-$d_6$) δ: 1.28 (3H, d, J=6.6 Hz), 1.65 (4H, m), 2.29 (2H, m), 2.35 (3H, s), 2.43 (2H, m), 2.83 (2H, m), 3.15 (1H, m), 3.50 (2H, m), 7.16-7.26 (4H, m), 7.29 (2H, d, J=8.0 Hz), 7.62 (2H, d, J=8.0 Hz), 7.72 (2H, d, J=8.4 Hz), 7.90 (2H, d, J=8.0 Hz), 8.60 (1H, m). melting point: 160-163° C. (ethyl acetate-isopropyl ether) FABMS (pos) 413 [M+H]$^+$

EXAMPLE 15

N-(2-{4-[1-(1-pyrrolidinyl)ethyl]phenyl}ethyl)-4'-(trifluoromethyl)[1,1'-biphenyl]-4-carboxamide

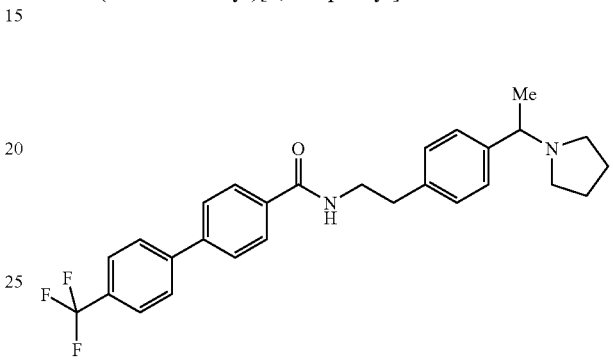

The title compound was obtained by a similar operation as in Example 6 and using 4-bromo-N-(2-{4-[1-(1-pyrrolidinyl)ethyl]phenyl}ethyl)benzamide obtained in Example 10.

$^1$H-NMR (DMSO-$d_6$) δ: 1.27 (3H, d, J=6.3 Hz), 1.64 (4H, m), 2.27 (2H, m), 2.44 (2H, m), 2.84 (2H, m), 3.15 (1H, m), 3.50 (2H, m), 7.17 (2H, d, J=8.1 Hz), 7.23 (2H, d, J=8.1 Hz), 7.84 (4H, m), 7.95 (4H, m), 8.66 (1H, t, J=5.7 Hz). melting point: 149-151° C. (ethyl acetate-isopropyl ether-hexane) FABMS (pos) 467 [M+H]$^+$

EXAMPLE 16

N-(2-{4-[1-(1-pyrrolidinyl)ethyl]phenyl}ethyl)-4'-(trifluoromethoxy)[1,1'-biphenyl]-4-carboxamide

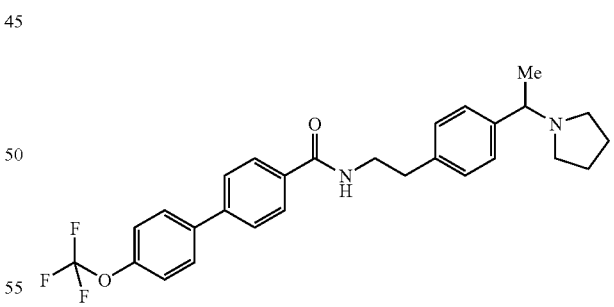

The title compound was obtained by a similar operation as in Example 6 and using 4-bromo-N-(2-{4-[1-(1-pyrrolidinyl)ethyl]phenyl}ethyl)benzamide obtained in Example 10.

$^1$H-NMR (DMSO-$d_6$) δ: 1.28 (3H, d, J=6.6 Hz), 1.65 (4H, m), 2.29 (2H, m), 2.43 (2H, m), 2.83 (2H, m), 3.17 (1H, m), 3.50 (2H, m), 7.18 (2H, d, J=8.4 Hz), 7.24 (2H, d, J=8.4 Hz), 7.48 (2H, d, J=8.4 Hz), 7.78 (2H, d, J=8.4 Hz), 7.86 (2H, d, J=8.4 Hz), 7.93 (2H, d, J=8.4 Hz), 8.65 (1H, t, J=5.4 Hz). melting point: 135-137° C. (ethyl acetate-isopropyl ether-hexane) FABMS (pos) 483 [M+H]$^+$

EXAMPLE 17

6-(4-methoxyphenyl)-N-{2-[4-(1-pyrrolidinylmethyl)phenyl]ethyl}nicotinamide

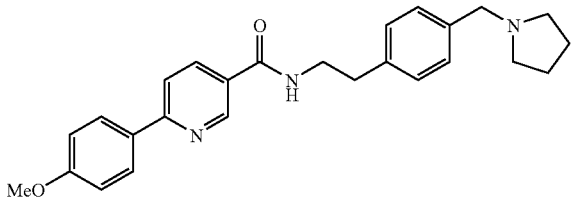

The title compound was obtained by a similar operation as in Example 2 and using 2-[4-(1-pyrrolidinylmethyl)phenyl]ethylamine obtained in Reference Example 4.

$^1$H-NMR (CDCl$_3$) δ: 1.79 (4H, m), 2.51 (4H, m), 2.94 (2H, t, J=6.8 Hz), 3.60 (2H, s), 3.75 (2H, q, J 6.6 Hz), 3.87 (3H, s), 6.14 (1H, t, J=5.9 Hz), 7.01 (2H, m), 7.19 (2H, d, J=8.1 Hz), 7.31 (2H, d, J=8.1 Hz), 7.72 (1H, d, J=8.4 Hz), 7.99 (2H, m), 8.07 (1H, dd, J=8.2, 2.4 Hz), 8.87 (1H, d, J=1.8 Hz). melting point: 177-178° C. (ethyl acetate-isopropyl ether)

EXAMPLE 18

4'-fluoro-N-{2-[4-(1-pyrrolidinylmethyl)phenyl]ethyl}[1,1'-biphenyl]-4-carboxamide

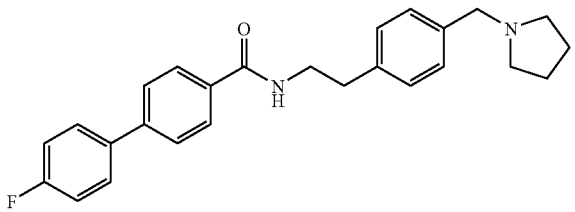

The title compound was obtained by a similar operation as in Example 2 and using 2-[4-(1-pyrrolidinylmethyl)phenyl]ethylamine obtained in Reference Example 4.

$^1$H-NMR (CDCl$_3$) δ: 1.79 (4H, m), 2.51 (4H, m), 2.93 (2H, t, j=6.8 Hz), 3.59 (2H, s), 3.73 (2H, q, J=6.7 Hz), 6.13 (1H, t, J=5.5 Hz), 7.13 (2H, m), 7.19 (2H, d, J=8.1 Hz), 7.29 (2H, m), 7.55 (4H, m), 7.74 (2H, d, J=8.6 Hz). melting point: 178-179° C. (ethyl acetate-isopropyl ether)

EXAMPLE 19

4-(benzyloxy)-N-{2-[4-(1-pyrrolidinylmethyl)phenyl]ethyl}benzamide

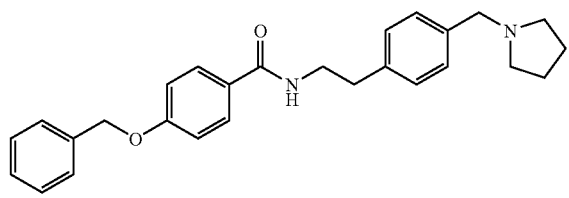

The title compound was obtained by a similar operation as in Example 2 and using 2-[4-(1-pyrrolidinylmethyl)phenyl]ethylamine obtained in Reference Example 4.

$^1$H-NMR (CDCl$_3$) δ: 1.79 (4H, m), 2.50 (4H, m), 2.90 (2H, t, J=6.8 Hz), 3.59 (2H, s), 3.69 (2H, q, J=6.7 Hz), 5.09 (2H, s), 6.00 (1H, t, J=5.6 Hz), 6.95 (2H, m), 7.17 (2H, d, J=8.1 Hz), 7.28 (2H, m), 7.37 (5H, m), 7.63 (2H, d, J=9.4 Hz). melting point: 131° C. (ethyl acetate-isopropyl ether)

EXAMPLE 20

2-fluoro-4-(3-methylbutoxy)-N-{2-[4-(1-pyrrolidinylmethyl)phenyl]ethyl}benzamide

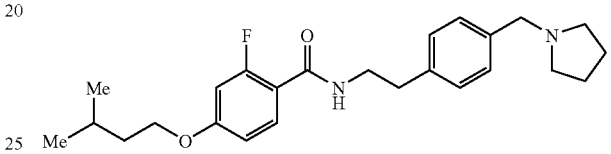

The title compound was obtained by a similar operation as in Example 2 and using 2-[4-(1-pyrrolidinylmethyl)phenyl]ethylamine obtained in Reference Example 4.

$^1$H-NMR (CDCl$_3$) δ: 0.96 (6H, d, J=6.6 Hz), 1.68 (2H, m), 1.79 (5H, m), 2.50 (4H, m), 2.90 (2H, t, J=6.8 Hz), 3.59 (2H, s), 3.71 (2H, m), 4.00 (2H, t, J=6.6 Hz), 6.55 (1H, dd, J=14.2, 2.2 Hz), 6.66 (1H, m), 6.75 (1H, dd, J=8.8, 2.4 Hz), 7.17 (2H, d, J=8.1 Hz), 7.27 (2H, d, J=8.1 Hz), 8.02 (1H, t, J=9.2 Hz). melting point: 86-87° C. (ethyl acetate-isopropyl ether)

EXAMPLE 21

3,4'-difluoro-N-{2-[4-(1-pyrrolidinylmethyl)phenyl]ethyl}[1,1'-biphenyl]-4-carboxamide

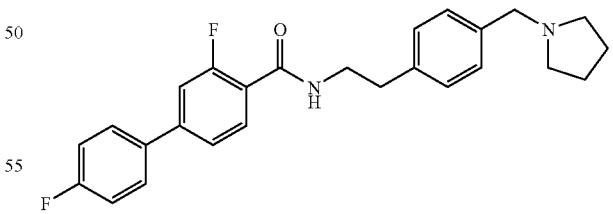

The title compound was obtained by similar operations as in Example 2 and Example 6 and using 2-[4-(1-pyrrolidinylmethyl)phenyl]ethylamine obtained in Reference Example 4.

$^1$H-NMR (CDCl$_3$) δ: 1.78 (4H, m), 2.50 (4H, m), 2.94 (2H, t, J=7.0 Hz), 3.60 (2H, s), 3.75 (2H, m), 6.79 (1H, m), 7.20 (8H, m), 7.43 (1H, dd, J=8.1, 1.8 Hz), 7.55 (2H, m). melting point: 139-140° C. (ethyl acetate-isopropyl ether)

EXAMPLE 22

4-butoxy-N-{2-[4-(1-pyrrolidinylmethyl)phenyl]ethyl}benzamide

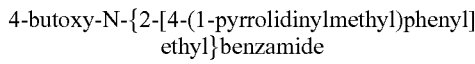

The title compound was obtained by a similar operation as in Example 2 and using 2-[4-(1-pyrrolidinylmethyl)phenyl]ethylamine obtained in Reference Example 4.

$^1$H-NMR (CDCl$_3$) δ: 0.98 (3H, t, J=7.3 Hz), 1.49 (2H, m), 1.78 (6H, m), 2.50 (4H, m), 2.90 (2H, t, J=6.7 Hz), 3.59 (2H, s), 3.69 (2H, m), 3.99 (2H, t, J=6.5 Hz), 6.02 (1H, t, J=5.8 Hz), 6.88 (2H, m), 7.18 (2H, d, J=8.3 Hz), 7.29 (2H, m), 7.63 (2H, m). melting point: 114° C. (ethyl acetate-isopropyl ether)

EXAMPLE 23

3'-isobutyrylamino-N-{2-[4-(1-pyrrolidinylmethyl)phenyl]ethyl}[1,1'-biphenyl]-4-carboxamide

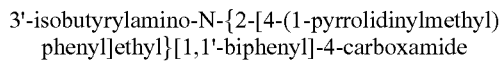

The title compound was obtained by similar operations as in Example 2 and Example 6 and using 2-[4-(1-pyrrolidinylmethyl)phenyl]ethylamine obtained in Reference Example 4.

$^1$H-NMR (CDCl$_3$) δ: 1.28 (6H, d, J=6.9 Hz), 1.78 (4H, m), 2.53 (5H, m), 2.94 (2H, t, J=6.7 Hz), 3.60 (2H, s), 3.73 (2H, q, J=6.6 Hz), 6.16 (1H, t, J=5.6 Hz), 7.20 (2H, d, J=8.3 Hz), 7.30 (3H, m), 7.34 (1H, t, J=1.5 Hz), 7.40 (1H, t, J=7.7 Hz), 7.49 (1H, m), 7.62 (2H, m), 7.73 (2H, m), 7.89 (1H, s). melting point: 185-186° C. (ethyl acetate-isopropyl ether)

EXAMPLE 24

4-(2-oxo-2-phenylethyl)-N-{2-[4-(1-pyrrolidinylmethyl)phenyl]ethyl}benzamide

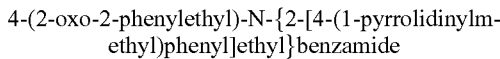

The title compound was obtained by a similar operation as in Example 2 and using 2-[4-(1-pyrrolidinylmethyl)phenyl]ethylamine obtained in Reference Example 4.

$^1$H-NMR (CDCl$_3$) δ: 1.78 (4H, m), 2.51 (4H, m), 2.91 (2H, t, J=6.9 Hz), 3.60 (2H, s), 3.70 (2H, m), 4.32 (2H, s), 6.08 (1H, t, J=5.9 Hz), 7.18 (2H, d, J=8.0 Hz), 7.29 (4H, m), 7.46 (2H, m), 7.58 (1H, m), 7.65 (2H, d, J=8.5 Hz), 8.00 (2H, m). melting point: 148° C. (ethyl acetate-isopropyl ether)

EXAMPLE 25

N-{2-[4-(1-pyrrolidinylmethyl)phenyl]ethyl}-4'-(trifluoromethyl)[1,1'-biphenyl]-4-carboxamide

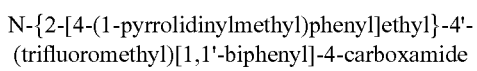

The title compound was obtained by similar operations as in Example 2 and Example 6 and using 2-[4-(1-pyrrolidinylmethyl)phenyl]ethylamine obtained in Reference Example 4.

$^1$H-NMR (CDCl$_3$) δ: 1.78 (4H, m), 2.51 (4H, m), 2.94 (2H, t, J=6.8 Hz), 3.60 (2H, s), 3.74 (2H, m), 6.13 (1H, t, J=5.0 Hz), 7.19 (2H, d, J=8.1 Hz), 7.30 (2H, m), 7.62 (2H, m), 7.70 (4H, m), 7.77 (2H, d, J=8.6 Hz). melting point: 185-186° C. (ethyl acetate-isopropyl ether)

EXAMPLE 26

N-(2-{4-[(dimethylamino)methyl]phenyl}ethyl)-4'-methoxy[1,1'-biphenyl]-4-carboxamide

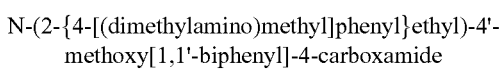

The title compound was obtained by a similar operation as in Example 2 and using N-[4-(2-aminoethyl)benzyl]-N,N-dimethylamine trifluoroacetate obtained in Reference Example 5.

$^1$H-NMR (CDCl$_3$) δ: 2.24 (6H, s), 2.94 (2H, t, J=6.8 Hz), 3.40 (2H, s), 3.73 (2H, q, J=6.8 Hz), 3.85 (3H, s), 6.13 (1H, t, J=6.1 Hz), 6.98 (2H, m), 7.20 (2H, d, J=8.3 Hz), 7.26 (2H, m), 7.55 (4H, m), 7.72 (2H, d, J=8.5 Hz). melting point: 197° C. (ethyl acetate-isopropyl ether)

EXAMPLE 27

4'-chloro-N-{2-[4-(1-piperidinylmethyl)phenyl]ethyl}[1,1'-biphenyl]-4-carboxamide

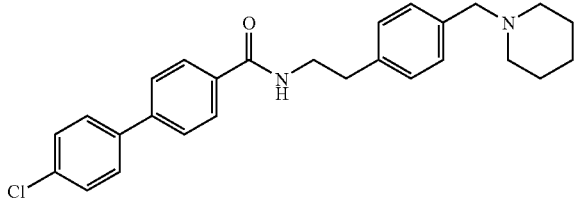

The title compound was obtained by a similar operation as in Example 2 and using 2-[4-(1-piperidinylmethyl)phenyl]ethylamine dihydrochloride obtained in Reference Example 6.

$^1$H-NMR (CDCl$_3$) δ: 1.43 (2H, m), 1.56 (4H, m), 2.37 (4H, m), 2.94 (2H, t, J=6.8 Hz), 3.45 (2H, s), 3.74 (2H, m), 6.15 (1H, t, J=5.7 Hz), 7.19 (2H, m), 7.28 (2H, m), 7.42 (2H, m), 7.53 (2H, m), 7.58 (2H, m), 7.76 (2H, d, J=8.4 Hz). melting point: 176° C. (ethyl acetate-isopropyl ether)

EXAMPLE 28

4'-chloro-N-(2-{4-[(4-methylpiperazin-1-yl)methyl]phenyl}ethyl)[1,1'-biphenyl]-4-carboxamide

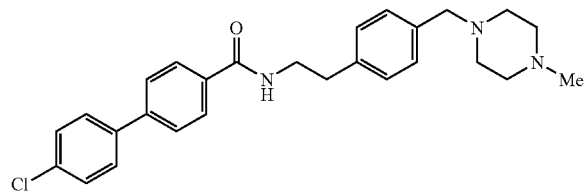

The title compound was obtained by a similar operation as in Example 2 and using 2-{4-[(4-methylpiperazin-1-yl)methyl]phenyl}ethylamine trihydrochloride obtained in Reference Example 7.

$^1$H-NMR (CDCl$_3$) δ: 2.28 (3H, s), 2.46 (8H, m), 2.94 (2H, t, J=7.0 Hz), 3.50 (2H, s), 3.73 (2H, m), 6.16 (1H, t, J=5.9 Hz), 7.19 (2H, d, J=8.1 Hz), 7.29 (2H, m), 7.50 (6H, m), 7.76 (2H, m). melting point: 177° C. (ethyl acetate-isopropyl ether)

EXAMPLE 29

4'-fluoro-N-{2-[4-(1-piperidinylmethyl)phenyl]ethyl}[1,1'-biphenyl]-4-carboxamide

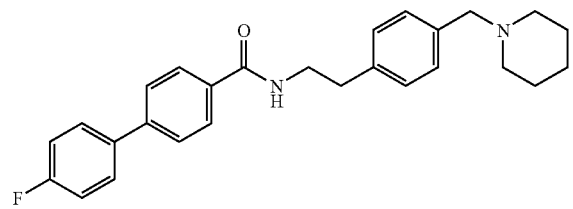

The title compound was obtained by a similar operation as in Example 2 and using 2-[4-(1-piperidinylmethyl)phenyl]ethylamine dihydrochloride obtained in Reference Example 6.

$^1$H-NMR (CDCl$_3$) δ: 1.43 (2H, m), 1.57 (4H, m), 2.37 (4H, m), 2.94 (2H, t, J=6.9 Hz), 3.45 (2H, s), 3.74 (2H, m), 6.15 (1H, t, J=5.6 Hz), 7.15 (4H, m), 7.29 (2H, m), 7.56 (4H, m), 7.75 (2H, m). melting point: 175° C. (ethyl acetate-isopropyl ether)

EXAMPLE 30

4'-fluoro-N-(2-{4-[(4-methylpiperazin-1-yl)methyl]phenyl}ethyl)[1,1'-biphenyl]-4-carboxamide

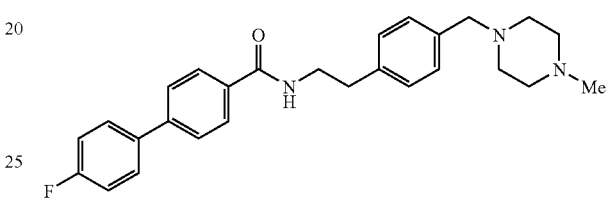

The title compound was obtained by a similar operation as in Example 2 and using 2-{4-[(4-methylpiperazin-1-yl)methyl]phenyl}ethylamine trihydrochloride obtained in Reference Example 7.

$^1$H-NMR (CDCl$_3$) δ: 2.28 (3H, s), 2.47 (8H, m), 2.94 (2H, t, J=6.9 Hz), 3.50 (2H, s), 3.74 (2H, m), 6.14 (1H, t, J=5.6 Hz), 7.14 (2H, m) 7.20 (2H, d, J=8.3 Hz), 7.29 (2H, m), 7.56 (4H, m), 7.76 (2H, d, J=8.5 Hz). melting point: 170° C. (ethyl acetate-isopropyl ether)

EXAMPLE 31

N-(2-{4-[1-(1-pyrrolidinyl)ethyl]phenyl}ethyl)[1,1'-biphenyl]-4-carboxamide

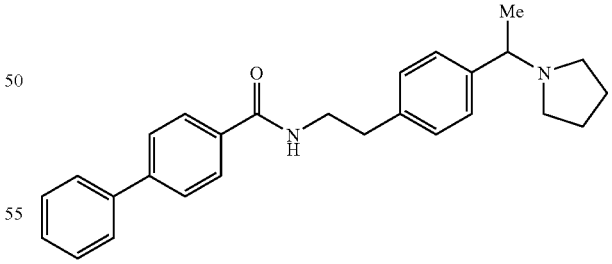

The title compound was obtained by a similar operation as in Example 6 and using 4-bromo-N-(2-{4-[1-(1-pyrrolidinyl)ethyl]phenyl}ethyl)benzamide obtained in Example 10.

$^1$H-NMR (DMSO-d$_6$) δ: 1.28 (3H, d, J=6.6 Hz), 1.65 (4H, m), 2.28 (2H, m), 2.45 (2H, m), 2.84 (2H, m), 3.16 (1H, m), 3.50 (2H, m), 7.18 (2H, d, J=8.4 Hz), 7.24 (2H, d, J=8.4 Hz), 7.41 (1H, m), 7.50 (2H, m), 7.73 (2H, d, J=8.4 Hz), 7.76 (2H, d, J=8.4 Hz), 7.92 (2H, d, J=8.4 Hz), 8.64 (1H, t, J=5.7 Hz).

EXAMPLE 32

4-bromo-N-(2-{4-[1-(1-pyrrolidinyl)propyl]phenyl}ethyl)benzamide

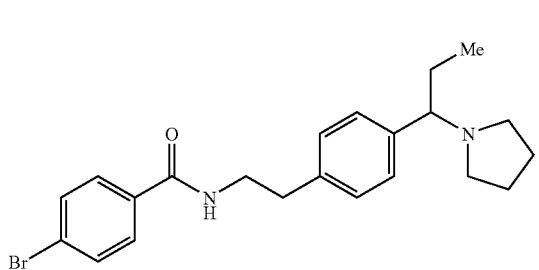

The title compound was obtained by similar operations as in Reference Example 19-21 and Example 10 and using 4-bromo-N-(2-phenylethyl)benzamide.

$^1$H-NMR (DMSO-d$_6$) δ: 0.59 (3H, t, J=7.5 Hz), 1.63 (5H, m), 1.85 (1H, m), 2.27 (2H, m), 2.49 (2H, m), 2.79 (2H, m), 2.99 (1H, m), 3.47 (2H, m), 7.17 (4H, m), 7.66 (2H, d, J=8.7 Hz), 7.75 (2H, d, J=8.7 Hz), 8.65 (1H, m). melting point: 90-92° C. (ethyl acetate-isopropyl ether-hexane) FABMS (pos) 415 [M+H]$^+$

EXAMPLE 33

4'-chloro-N-(2-{4-[1-(1-pyrrolidinyl)propyl]phenyl}ethyl)[1,1'-biphenyl]-4-carboxamide

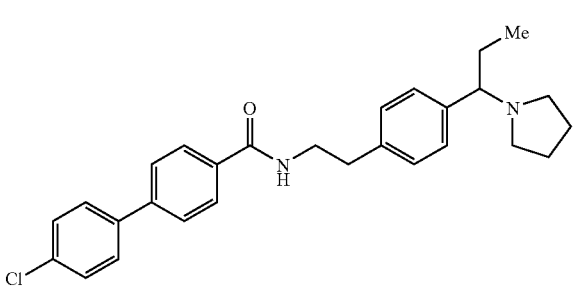

The title compound was obtained by a similar operation as in Example 6 and using 4-bromo-N-(2-{4-[1-(1-pyrrolidinyl)propyl]phenyl}ethyl)benzamide obtained in Example 32.

$^1$H-NMR (DMSO-d$_6$) δ: 0.60 (3H, t, J=7.5 Hz), 1.63 (5H, m), 1.85 (1H, m), 2.27 (2H, m), 2.43 (2H, m), 2.84 (2H, m), 2.98 (1H, m), 3.50 (2H, m), 7.16 (2H, d, J=8.4 Hz), 7.33 (2H, d, J=7.6 Hz), 7.55 (2H, d, J=8.4 Hz), 7.77 (4H, m), 7.92 (2H, d, J=8.4 Hz), 8.62 (1H, m). melting point: 151-153° C. (ethyl acetate-isopropyl ether) FABMS (pos) 447 [M+H]$^+$ melting point: 136-138° C. (ethyl acetate-isopropyl ether-hexane) FABMS (pos) 399 [M+H]$^+$

EXAMPLE 34

4'-chloro-N-[2-(4-{1-[(2R,6S)-2,6-dimethyl-1-piperidinyl]ethyl}phenyl)ethyl][1,1'-biphenyl]-4-carboxamide

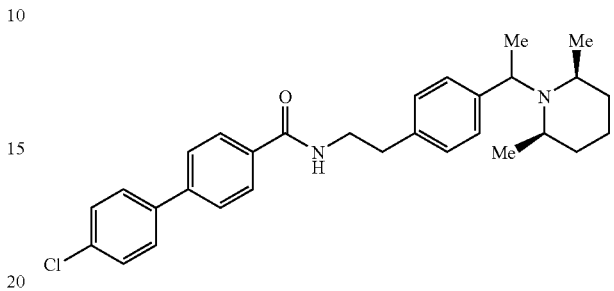

The title compound was obtained by similar operations as in Example 10 and Example 6 and using 4-bromo-N-{2-[4-(1-chloroethyl)phenyl]ethyl}benzamide obtained in Reference Example 21.

$^1$H-NMR (DMSO-d$_6$) δ: 0.69 (3H, d, J=6.6 Hz), 1.08 (3H, d, J=6.6 Hz), 1.27 (3H, d, J=6.6 Hz), 1.44-1.61 (6H, m), 2.57 (1H, m), 2.82 (2H, m), 3.02 (1H, m), 3.50 (2H, m), 4.02 (1H, m), 7.17 (2H, d, J=8.4 Hz), 7.33 (2H, d, J=7.6 Hz), 7.55 (2H, d, J=8.4 Hz), 7.77 (4H, m), 7.92 (2H, d, J=8.4 Hz), 8.62 (1H, m). melting point: 137-139° C. (ethyl acetate-isopropyl ether-hexane)

EXAMPLE 35

4'-chloro-N-[2-(4-{1-[3-(methylsulfonyl)-1-pyrrolidinyl]ethyl}phenyl)ethyl][1,1'-biphenyl]-4-carboxamide

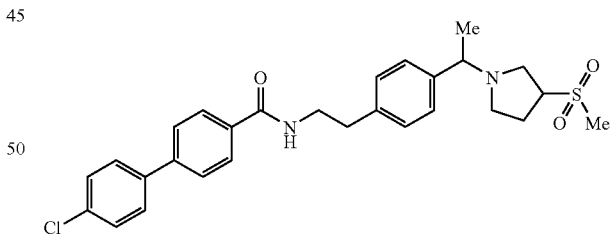

The title compound was obtained by similar operations as in Example 10 and Example 6 and using 4-bromo-N-{2-[4-(1-chloroethyl)phenyl]ethyl}benzamide obtained in Reference Example 21.

$^1$H-NMR (DMSO-d$_6$) δ: 1.29 (3H, d, J=6.6 Hz), 2.07 (2H, m), 2.37 (1H, m), 2.62-2.87 (5H, m), 2.89, 2.90 (3H, s×2), 3.26 (1H, m), 3.51 (2H, m), 3.70 (1H, m), 7.21 (4H, m), 7.53 (2H, d, J=8.7 Hz), 7.76 (4H, m), 7.91 (2H, d, J=8.1 Hz), 8.63 (1H, t, J=5.4 Hz). Elemental analysis for $C_{28}H_{31}ClN_2O_3S$ Calculated: C, 65.80; H, 6.11; N, 5.48. Found: C, 65.66; H, 6.13; N, 5.39. FABMS (pos) 511 [M+H]$^+$

EXAMPLE 36

4'-chloro-N-(2-{4-[2-methyl-1-(1-pyrrolidinyl)propyl]phenyl}ethyl)[1,1'-biphenyl]-4-carboxamide

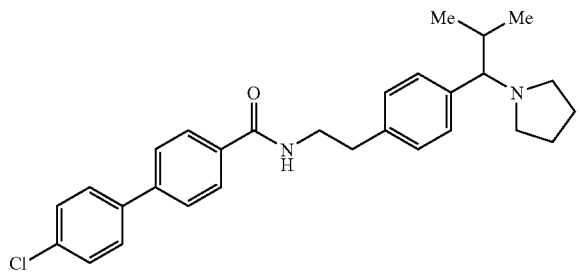

The title compound was obtained by similar operations as in Reference Example 19-21, Example 10 and Example 6 and using 4-bromo-N-(2-phenylethyl)benzamide.

$^1$H-NMR (DMSO-$d_6$) δ: 0.71 (6H, m), 1.62 (4H, m), 2.15 (1H, m), 2.30-2.35 (4H, m), 2.84 (2H, m), 2.98 (1H, m), 3.50 (2H, m), 7.15 (4H, m), 7.55 (2H, d, J=9.0 Hz), 7.77 (4H, m), 7.91 (2H, d, J=8.7 Hz), 8.65 (1H, t, J=5.7 Hz). melting point: 143-145° C. (ethyl acetate-isopropyl ether-hexane) FABMS (pos) 461 [M+H]$^+$

EXAMPLE 37

4'-chloro-N-(2-{4-[1-(4-thiomorpholinyl)ethyl]phenyl}ethyl)[1,1'-biphenyl]-4-carboxamide

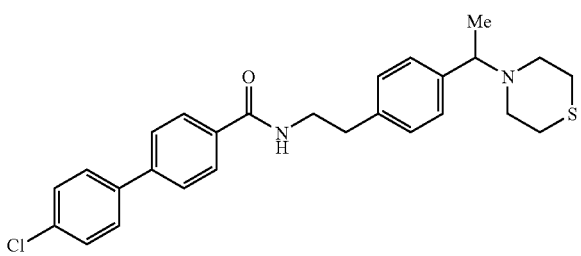

The title compound was obtained by similar operations as in Example 10 and Example 6 and using 4-bromo-N-{2-[4-(1-chloroethyl)phenyl]ethyl}benzamide obtained in Reference Example 21.

$^1$H-NMR (DMSO-$d_6$) δ: 1.28 (3H, d, J=6.9 Hz), 2.56 (4H, m), 2.59 (4H, m), 2.84 (2H, m), 3.49 (2H, m), 3.57 (1H, m), 7.20 (4H, m), 7.54 (2H, d, J=8.4 Hz), 7.74 (4H, m), 7.91 (2H, d, J=8.7 Hz), 8.63 (1H, t, J=5.7 Hz). melting point: 168-169° C. (ethyl acetate-isopropyl ether-hexane) FABMS (pos) 465 [M+H]$^+$

EXAMPLE 38

4-pentyl-N-(2-{4-[1-(1-pyrrolidinyl)ethyl]phenyl}ethyl)benzamide

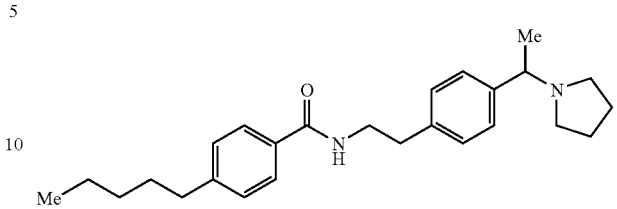

The title compound was obtained by a similar operation as in Example 2 and using 2-{4-[1-(1-pyrrolidinyl)ethyl]phenyl}ethylamine obtained in Reference Example 14.

$^1$H-NMR (CDCl$_3$) δ: 0.88 (3H, t, J=6.3 Hz), 1.31 (4H, m), 1.40 (3H, d, J=6.6 Hz), 1.61 (2H, t, J=8.1 Hz), 1.76 (4H, m), 2.38 (2H, m), 2.55 (2H, m), 2.63 (2H, t, J=7.1 Hz), 2.91 (2H, t, J=6.9 Hz), 3.18 (1H, q, J=6.6 Hz), 3.70 (2H, q, J=6.9 Hz), 6.09 (1H, m), 7.18 (4H, m), 7.28 (2H, m), 7.59 (2H, d, J=8.1 Hz). melting point: 76-77° C. (ethyl acetate-hexane) ESIMS (pos) 393 [M+H]$^+$

EXAMPLE 39

4-butoxy-N-(2-{4-[1-(1-pyrrolidinyl)ethyl]phenyl}ethyl)benzamide

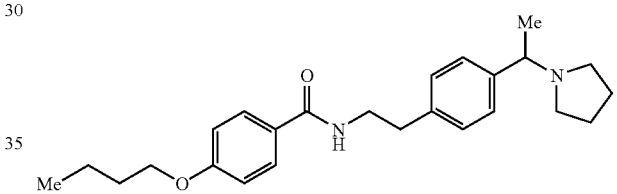

The title compound was obtained by a similar operation as in Example 2 and using 2-{4-[1-(1-pyrrolidinyl)ethyl]phenyl}ethylamine obtained in Reference Example 14.

$^1$H-NMR (CDCl$_3$) δ: 0.98 (3H, t, J=7.2 Hz), 1.40 (3H, d, J=6.6 Hz), 1.48 (2H, m), 1.73 (6H, m), 2.36 (2H, m), 2.57 (2H, m), 2.90 (2H, t, J=6.6 Hz), 3.18 (1H, q, J=6.3 Hz), 3.71 (2H, q, J=7.2 Hz), 3.99 (2H, t, J=6.6 Hz), 6.04 (1H, m), 6.87 (2H, d, J=8.7 Hz), 7.17 (2H, d, J=7.8 Hz), 7.29 (2H, d, J=8.1 Hz), 7.63 (2H, d, J=8.7 Hz). melting point: 99-100° C. (ethyl acetate-hexane)

EXAMPLE 40

4-cyclopropylmethoxy-N-(2-{4-[1-(1-pyrrolidinyl)ethyl]phenyl}ethyl)benzamide

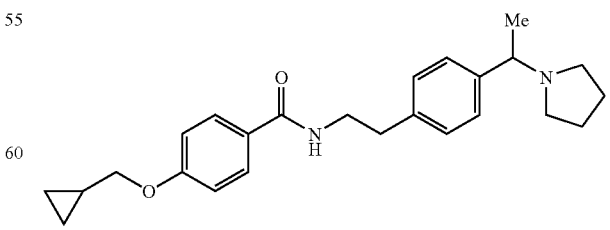

The title compound was obtained by a similar operation as in Example 2 and using 2-{4-[1-(1-pyrrolidinyl)ethyl]phenyl}ethylamine obtained in Reference Example 14.

¹H-NMR (CDCl₃) δ: 0.35 (2H, m), 0.64 (2H, m), 1.28 (1H, m), 1.40 (3H, d, J=6.6 Hz), 1.76 (4H, m), 2.39 (2H, m), 2.54 (2H, m), 2.90 (2H, t, J=6.6 Hz), 3.18 (1H, q, J=6.6 Hz), 3.69 (2H, q, J=6.6 Hz), 3.83 (2H, d, J=7.0 Hz), 6.04 (1H, m), 6.88 (2H, d, J=8.8 Hz), 7.17 (2H, d, J=7.8 Hz), 7.29 (2H, d, J=8.6 Hz), 7.63 (2H, d, J=8.8 Hz). melting point: 122-123° C. (ethyl acetate-hexane)

EXAMPLE 41

4-benzyloxy-N-(2-{4-[1-(1-pyrrolidinyl)ethyl]phenyl}ethyl)benzamide

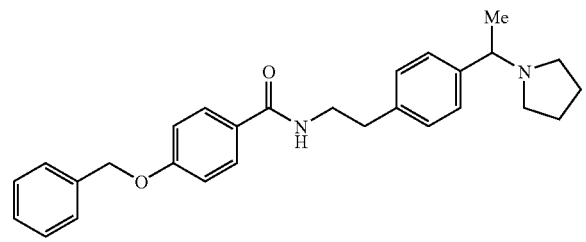

The title compound was obtained by a similar operation as in Example 2 and using 2-{4-[1-(1-pyrrolidinyl)ethyl]phenyl}ethylamine obtained in Reference Example 14.

¹H-NMR (CDCl₃) δ: 1.39 (3H, d, J=6.6 Hz), 1.76 (4H, m), 2.36 (2H, m), 2.54 (2H, m), 2.90 (2H, t, J=7.0 Hz), 3.16 (1H, q, J=6.2 Hz), 3.69 (2H, q, J=6.2 Hz), 5.10 (2H, s), 6.03 (1H, m), 6.96 (2H, d, J=8.8 Hz), 7.16 (2H, d, J=8.0 Hz), 7.26-7.41 (7H, m), 7.64 (2H, d, J=8.8 Hz). melting point: 132-133° C. (ethyl acetate-hexane)

EXAMPLE 42

4-(2-oxo-2-phenylethyl)-N-(2-{4-[1-(1-pyrrolidinyl)ethyl]phenyl}ethyl)benzamide

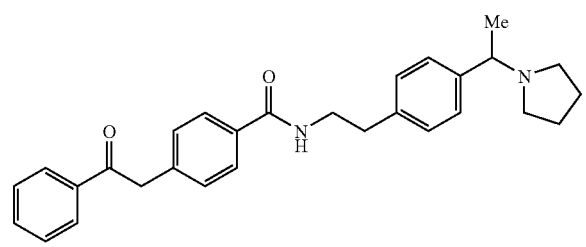

The title compound was obtained by a similar operation as in Example 2 and using 2-{4-[1-(1-pyrrolidinyl)ethyl]phenyl}ethylamine obtained in Reference Example 14.

¹H-NMR (CDCl₃) δ: 1.53 (3H, d, J=7.0 Hz), 1.84 (4H, m), 2.60 (2H, m), 2.79 (2H, m), 2.92 (2H, t, J=7.0 Hz), 3.46 (1H, q, J=7.0 Hz), 3.69 (2H, q, J=7.0 Hz), 4.32 (2H, s), 6.30 (1H, m), 7.18-7.68 (11H, m), 8.00 (2H, d, J=8.8 Hz). melting point: 123-124° C. (ethyl acetate-hexane)

EXAMPLE 43

2-fluoro-4-(3-methyl-2-oxobutyl)-N-(2-{4-[1-(1-pyrrolidinyl)ethyl]phenyl}ethyl)benzamide

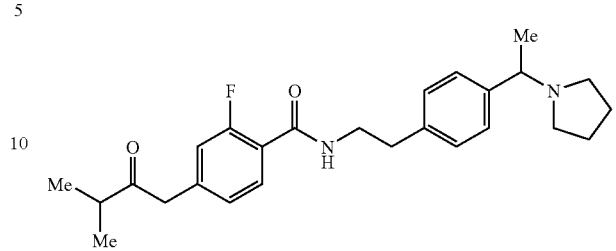

The title compound was obtained by a similar operation as in Example 2 and using 2-{4-[1-(1-pyrrolidinyl)ethyl]phenyl}ethylamine obtained in Reference Example 14.

¹H-NMR (CDCl₃) δ: 1.12 (6H, d, J=6.9 Hz), 1.39 (3H, d, J=6.6 Hz), 1.76 (4H, m), 2.36 (2H, m), 2.52 (2H, m), 2.71 (1H, m), 2.90 (2H, t, J=7.2 Hz), 3.17 (1H, q, J=6.6 Hz), 3.71 (2H, q, J=6.6 Hz), 3.77 (2H, s), 6.72 (1H, m), 6.93 (1H, d, J=12.9 Hz), 7.05 (1H, d, J=8.1 Hz), 7.16 (2H, d, J=8.1 Hz), 7.26 (2H, d, J=8.1 Hz), 8.02 (1H, t, J=8.1 Hz). melting point: 97-98° C. (ethyl acetate-hexane)

EXAMPLE 44

N-(2-{4-[1-(2-methyl-1-pyrrolidinyl)ethyl]phenyl}ethyl)-4-pentylbenzamide

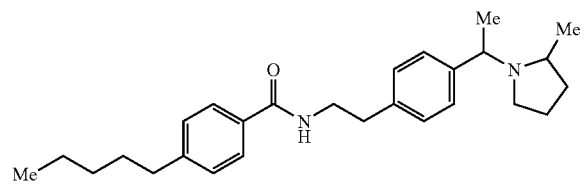

The title compound was obtained by a similar operation as in Example 2 and using 2-{4-[1-(2-methyl-1-pyrrolidinyl)ethyl]phenyl}ethylamine obtained in Reference Example 16.

¹H-NMR (CDCl₃) δ: 0.85, 1.10 (3H, d×2, J=6.6 Hz), 0.89 (3H, m), 1.25 (6H, m), 1.37, 1.47 (3H, d×2, J=6.6 Hz), 1.39-1.52 (2H, m), 1.62-1.87 (4H, m), 2.38-2.59 (2H, m), 2.77 (1H, m), 2.90 (2H, m), 3.70 (2H, m), 3.85 (1H, m), 6.12 (1H, m), 7.13-7.38 (6H, m), 7.62 (2H, m). FABMS (pos) 407 [M+H]⁺

EXAMPLE 45

4-butoxy-N-(2-{4-[1-(2-methyl-1-pyrrolidinyl)ethyl]phenyl}ethyl)benzamide

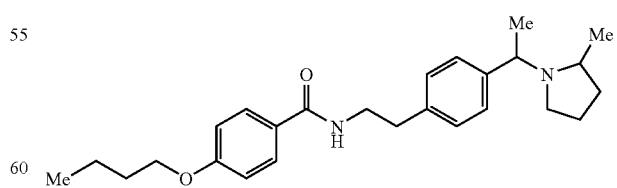

The title compound was obtained by a similar operation as in Example 2 and using 2-{4-[1-(2-methyl-1-pyrrolidinyl)ethyl]phenyl}ethylamine obtained in Reference Example 16.

¹H-NMR (CDCl₃) δ: 0.85, 1.10 (3H, d×2, J=6.6 Hz), 0.97 (3H, t, J=7.4 Hz), 1.37, 1.47 (3H, d×2, J=6.6 Hz), 1.39-1.52

(2H, m), 1.62-1.87 (6H, m), 2.38-2.59 (2H, m), 2.77 (1H, m), 2.90 (2H, m), 3.70 (2H, m), 3.85 (1H, m), 3.96 (2H, t, J=6.6 Hz), 6.14 (1H, m), 6.86 (2H, m), 7.10-7.34 (4H, m), 7.64 (2H, m). FABMS (pos) 409 [M+H]$^+$

EXAMPLE 46

4-(4-methyl-2-oxopentyl)-N-(2-{4-[1-(2-methyl-1-pyrrolidinyl)ethyl]phenyl}ethyl)benzamide

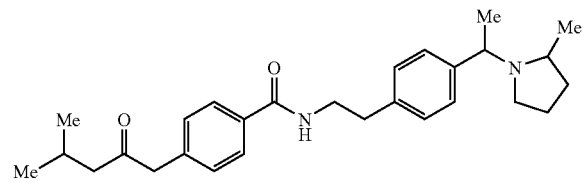

The title compound was obtained by a similar operation as in Example 2 and using 2-{4-[1-(2-methyl-1-pyrrolidinyl)ethyl]phenyl}ethylamine obtained in Reference Example 16.

$^1$H-NMR (CDCl$_3$) δ: 0.84, 1.09 (3H, d×2, J=6.6 Hz), 0.88 (7H, m), 1.37, 1.45 (3H, d×2, J=6.6 Hz), 1.59-2.16 (4H, m), 2.31-2.58 (4H, m), 2.74 (1H, m), 2.88 (2H, m), 3.74 (4H, m), 3.86 (1H, m), 6.29 (1H, m), 7.14-7.43 (6H, m), 7.65 (2H, m). FABMS (pos) 435 [M+H]$^+$

EXAMPLE 47

4-benzyloxy-N-(2-{4-[1-(2-methyl-1-pyrrolidinyl)ethyl]phenyl}ethyl)benzamide

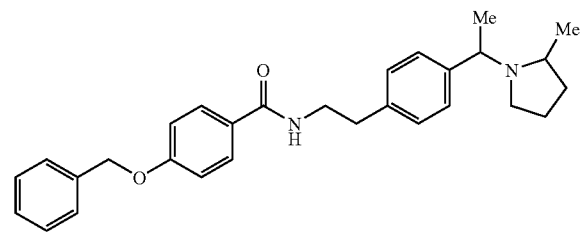

The title compound was obtained by a similar operation as in Example 2 and using 2-{4-[1-(2-methyl-1-pyrrolidinyl)ethyl]phenyl}ethylamine obtained in Reference Example 16.

$^1$H-NMR (CDCl$_3$) δ: 0.85, 1.09 (3H, d×2, J=6.6 Hz), 1.33, 1.45 (3H, d×2, J=6.6 Hz), 1.62-1.87 (4H, m), 2.36-2.54 (2H, m), 2.74 (1H, m), 2.89 (2H, m), 3.68 (2H, m), 3.85 (1H, m), 5.08 (2H, s), 6.14 (1H, m), 6.95 (2H, m), 7.18-7.43 (9H, m), 7.67 (2H, m). FABMS (pos) 443 [M+H]$^+$

EXAMPLE 48

N-(2-{4-[1-(2-methyl-1-pyrrolidinyl)ethyl]phenyl}ethyl)-4-(2-oxo-2-phenylethyl)benzamide

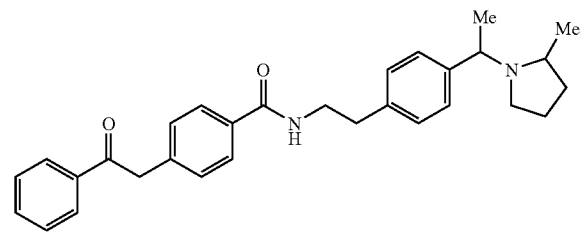

The title compound was obtained by a similar operation as in Example 2 and using 2-{4-[1-(2-methyl-1-pyrrolidinyl)ethyl]phenyl}ethylamine obtained in Reference Example 16.

$^1$H-NMR (CDCl$_3$) δ: 0.83, 1.09 (3H, d×2, J=6.3 Hz), 1.35, 1.44 (3H, d×2, J=6.6 Hz), 1.53-1.90 (4H, m), 2.35-2.56 (2H, m), 2.74 (1H, m), 2.90 (2H, m), 3.70 (2H, m), 3.79 (1H, m), 4.31 (2H, s), 6.31 (1H, m), 7.13-7.68 (11H, m), 8.00 (2H, m). FABMS (pos) 455 [M+H]$^+$

EXAMPLE 49

4-cyclopropylmethoxy-N-(2-{4-[1-(2-methyl-1-pyrrolidinyl)ethyl]phenyl}ethyl)benzamide

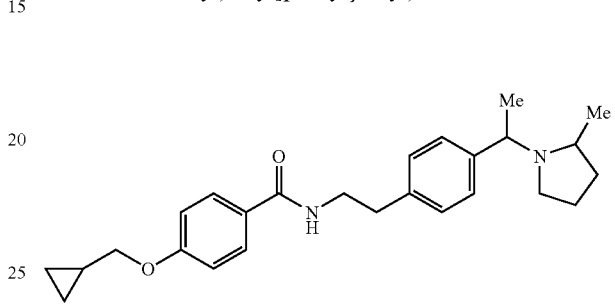

The title compound was obtained by a similar operation as in Example 2 and using 2-{4-[1-(2-methyl-1-pyrrolidinyl)ethyl]phenyl}ethylamine obtained in Reference Example 16.

$^1$H-NMR (CDCl$_3$) δ: 0.34 (2H, m), 0.64 (2H, m), 0.84, 1.08 (3H, d×2, J=6.6 Hz), 1.25 (1H, m), 1.35, 1.42 (3H, d×2, J=6.6 Hz), 1.53-1.94 (4H, m), 2.33-2.55 (2H, m), 2.73 (1H, m), 2.89 (2H, m.), 3.68 (3H, m), 3.82 (2H, d, J=6.3 Hz), 6.27 (1H, m), 6.85 (2H, m), 7.17 (3H, m), 7.28 (1H, m), 7.65 (2H, m). FABMS (pos) 407 [M+H]$^+$

EXAMPLE 50

4'-chloro-N-(2-{4-[1-(2-methyl-1-pyrrolidinyl)ethyl]phenyl}ethyl)[1,1'-biphenyl]-4-carboxamide

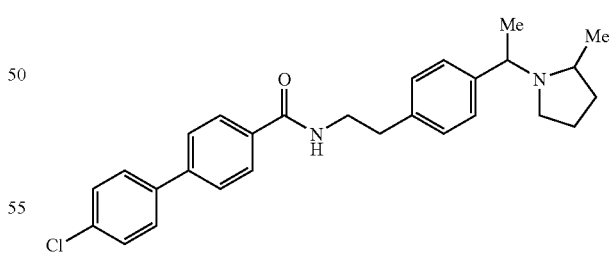

The title compound was obtained by a similar operation as in Example 2 and using 2-{4-[1-(2-methyl-1-pyrrolidinyl)ethyl]phenyl}ethylamine obtained in Reference Example 16.

$^1$H-NMR (CDCl$_3$) δ: 0.85, 1.10 (3H, d×2, J=6.6 Hz), 1.35, 1.46 (3H, d×2, J=6.6 Hz), 1.55-1.92 (4H, m), 2.35-2.56 (2H, m), 2.76 (1H, m), 2.90 (2H, m), 3.73 (2H, m), 3.85 (1H, q, J=6.9 Hz), 6.37 (1H, m), 7.18 (2H, m), 7.47-7.55 (8H, m), 7.76 (2H, m). FABMS (pos) 447 [M+H]$^+$

EXAMPLE 51

4'-fluoro-N-(2-{4-[1-(2-methyl-1-pyrrolidinyl)ethyl]phenyl}ethyl)[1,1'-biphenyl]-4-carboxamide

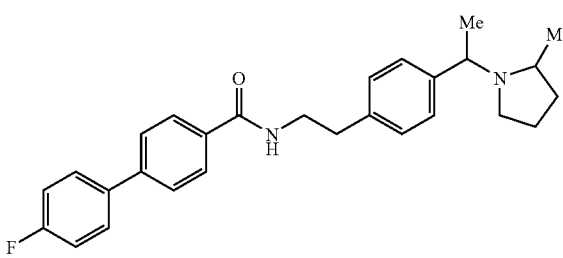

The title compound was obtained by a similar operation as in Example 2 and using 2-{4-[1-(2-methyl-1-pyrrolidinyl)ethyl]phenyl}ethylamine obtained in Reference Example 16.

$^1$H-NMR (CDCl$_3$) δ: 0.87, 1.11 (3H, d×2, J=6.6 Hz), 1.39, 1.47 (3H, d×2, J=6.6 Hz), 1.58-1.90 (4H, m), 2.45-2.58 (2H, m), 2.83 (1H, m), 2.92 (2H, m), 3.74 (2H, m), 3.90 (1H, q, J=6.9 Hz), 6.23 (1H, m), 7.10-7.45 (6H, m), 7.59 (4H, m), 7.76 (2H, m). FABMS (pos) 431 [M+H]$^+$

EXAMPLE 52

N-(2-{4-[1-(2-methyl-1-pyrrolidinyl)ethyl]phenyl}ethyl)-4'-(trifluoromethyl)[1,1'-biphenyl]-4-carboxamide

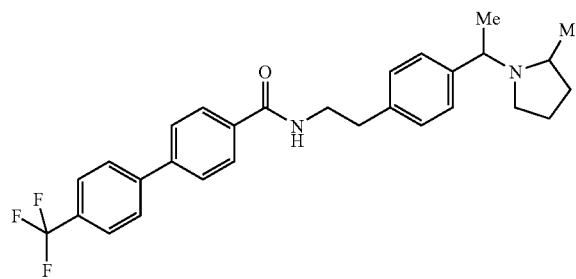

The title compound was obtained by similar operations as in Example 2 and Example 6 and using 2-{4-[1-(2-methyl-1-pyrrolidinyl)ethyl]phenyl}ethylamine obtained in Reference Example 16.

$^1$H-NMR (CDCl$_3$) δ: 0.86, 1.10 (3H, d×2, J=6.6 Hz), 1.35, 1.45 (3H, d×2, J=6.6 Hz), 1.54-2.00 (4H, m), 2.36-2.57 (2H, m), 2.73 (1H, m), 2.93 (2H, m), 3.74 (2H, m), 3.90 (1H, q, J=6.9 Hz), 6.44 (1H, m), 7.20-7.79 (10H, m), 7.76 (2H, m). FABMS (pos) 481 [M+H]$^+$

EXAMPLE 53

4'-methoxy-N-(2-{4-[1-(2-methyl-1-pyrrolidinyl)ethyl]phenyl}ethyl)[1,1'-biphenyl]-4-carboxamide

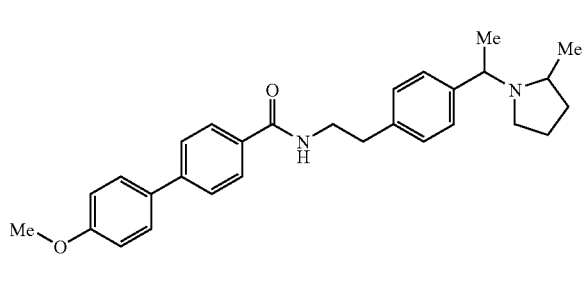

The title compound was obtained by a similar operation as in Example 2 and using 2-{4-[1-(2-methyl-1-pyrrolidinyl)ethyl]phenyl}ethylamine obtained in Reference Example 16.

$^1$H-NMR (CDCl$_3$) δ: 0.86, 1.10 (3H, d×2, J=6.6 Hz), 1.35, 1.46 (3H, d×2, J=6.6 Hz), 1.56-2.04 (4H, m), 2.41-2.53 (2H, m), 2.75 (1H, m), 2.92 (2H, m), 3.75 (3H, m), 3.85 (3H, s), 6.31 (1H, m), 6.76 (2H, m), 6.96 (2H, m), 7.20 (2H, m), 7.40-7.54 (4H, m), 7.73 (2H, m). FABMS (pos) 443 [M+H]$^+$

EXAMPLE 54

N-(2-{4-[1-(2-methyl-1-pyrrolidinyl)ethyl]phenyl}ethyl)-4'-(trifluoromethoxy)[1,1'-biphenyl]-4-carboxamide

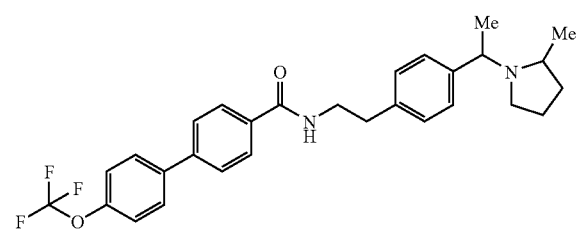

The title compound was obtained by similar operations as in Example 2 and Example 6 and using 2-{4-[1-(2-methyl-1-pyrrolidinyl)ethyl]phenyl}ethylamine obtained in Reference Example 16.

$^1$H-NMR (CDCl$_3$) δ: 0.85, 1.10 (3H, d×2, J=6.6 Hz), 1.36, 1.44 (3H, d×2, J=6.6 Hz), 1.59-2.07 (4H, m), 2.37-2.54 (2H, m), 2.77 (1H, m), 2.93 (2H, m), 3.75 (2H, m), 3.84 (1H, q, J=6.9 Hz), 6.15 (1H, m), 7.15-7.32 (6H, m), 7.59 (4H, m), 7.76 (2H, m). FABMS (pos) 497 [M+H]$^+$

EXAMPLE 55

4'-chloro-N-(2-{4-[1-(1-piperidinyl)ethyl]phenyl}ethyl)[1,1'-biphenyl]-4-carboxamide

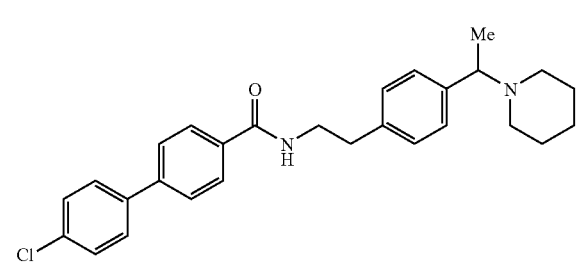

The title compound was obtained by a similar operation as in Example 2 and using 2-{4-[1-(1-piperidinyl)ethyl]phenyl}ethylamine obtained in Reference Example 15.

$^1$H-NMR (CDCl$_3$) δ: 1.36 (3H, d, J=6.6 Hz), 1.38 (2H, m), 1.55 (4H, m), 2.36 (4H, m), 2.94 (2H, t, J=6.6 Hz), 3.39 (1H, q, J=6.6 Hz), 3.73 (2H, q, J=6.6 Hz), 6.16 (1H, m), 7.17-7.27 (4H, m), 7.41 (2H, d, J=8.0 Hz), 7.51 (2H, d, J=8.4 Hz), 7.57 (2H, d, J=8.0 Hz), 7.75 (2H, d, J=7.8 Hz). melting point: 152-153° C. (ethyl acetate-hexane)

EXAMPLE 56

4'-fluoro-N-(2-{4-[1-(1-piperidinyl)ethyl]phenyl}ethyl)[1,1'-biphenyl]-4-carboxamide

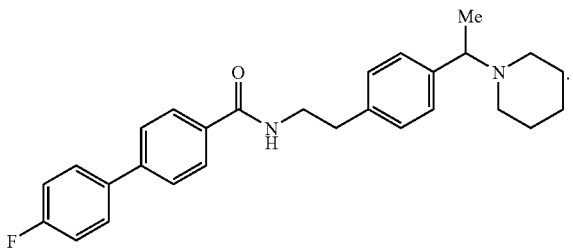

The title compound was obtained by a similar operation as in Example 2 and using 2-{4-[1-(1-piperidinyl)ethyl]phenyl}ethylamine obtained in Reference Example 15.

$^1$H-NMR (CDCl$_3$) δ: 1.36 (3H, d, J=6.6 Hz), 1.38 (2H, m), 1.54 (4H, m), 2.35 (4H, m), 2.93 (2H, t, J=6.6 Hz), 3.39 (1H, q, J=7.2 Hz), 3.73 (2H, q, J=6.0 Hz), 6.15 (1H, m), 7.10-7.27 (6H, m), 7.55 (4H, m), 7.75 (2H, d, J=8.0 Hz). melting point: 133-134° C. (ethyl acetate-hexane)

EXAMPLE 57

4'-methoxy-N-(2-{4-[1-(1-piperidinyl)ethyl]phenyl}ethyl)[1,1'-biphenyl]-4-carboxamide

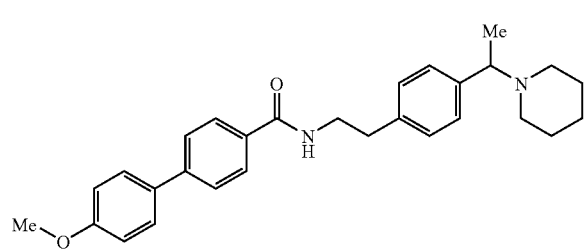

The title compound was obtained by a similar operation as in Example 2 and using 2-{4-[1-(1-piperidinyl)ethyl]phenyl}ethylamine obtained in Reference Example 15.

$^1$H-NMR (CDCl$_3$) δ: 1.36 (3H, d, J=6.9 Hz), 1.38 (2H, m), 1.55 (4H, m), 2.35 (4H, m), 2.93 (2H, t, J=6.6 Hz), 3.39 (1H, q, J=6.6 Hz), 3.74 (2H, q, J=6.3 Hz), 3.85 (3H, s), 6.14 (1H, m), 6.97 (2H, d, J=8.7 Hz), 7.17-7.27 (4H, m), 7.52-7.59 (4H, m), 7.72 (2H, d, J=8.1 Hz). melting point: 156-157° C. (ethyl acetate-hexane)

EXAMPLE 58

4'-methyl-N-(2-{4-[1-(1-piperidinyl)ethyl]phenyl}ethyl)[1,1'-biphenyl]-4-carboxamide

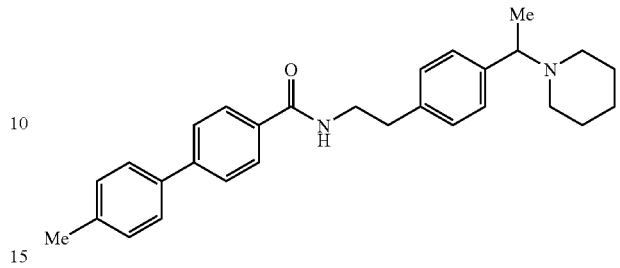

The title compound was obtained by a similar operation as in Example 2 and using 2-{4-[1-(1-piperidinyl)ethyl]phenyl}ethylamine obtained in Reference Example 15.

$^1$H-NMR (CDCl$_3$) δ: 1.36 (3H, d, J=6.9 Hz), 1.38 (2H, m), 1.53 (4H, m), 2.34 (4H, m), 2.41 (3H, s), 2.93 (2H, t, J=6.9 Hz), 3.37 (1H, q, J=6.6 Hz), 3.73 (2H, q, J=6.6 Hz), 6.15 (1H, m), 7.17 (2H, d, J=8.1 Hz), 7.25 (4H, m), 7.49 (2H, d, J=8.4 Hz), 7.60 (2H, d, J=8.4 Hz), 7.72 (2H, d, J=8.4 Hz). melting point: 172-173° C. (ethyl acetate-hexane)

EXAMPLE 59

N-(2-{4-[1-(1-piperidinyl)ethyl]phenyl}ethyl)[1,1'-biphenyl]-4-carboxamide

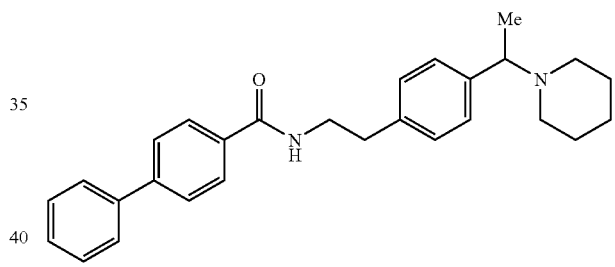

The title compound was obtained by a similar operation as in Example 2 and using 2-{4-[1-(1-piperidinyl)ethyl]phenyl}ethylamine obtained in Reference Example 15.

$^1$H-NMR (CDCl$_3$) δ: 1.36 (3H, d, J=6.6 Hz), 1.38 (2H, m), 1.54 (4H, m), 2.34 (4H, m), 2.94 (2H, t, J=6.8 Hz), 3.39 (1H, q, J=6.6 Hz), 3.73 (2H, q, J=6.6 Hz), 6.16 (1H, m), 7.17-7.37 (4H, m), 7.37-7.47 (3H, m), 7.60 (4H, m), 7.74 (2H, d, J=8.4 Hz). melting point: 136-137° C. (ethyl acetate-hexane)

EXAMPLE 60

N-(2-{4-[1-(1-piperidinyl)ethyl]phenyl}ethyl)-4'-(trifluoromethoxy)[1,1'-biphenyl]-4-carboxamide

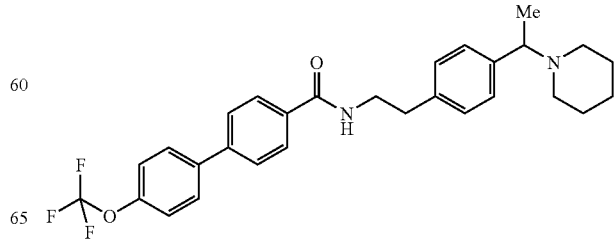

The title compound was obtained by similar operations as in Example 2 and Example 6 and using 2-{4-[1-(1-piperidinyl)ethyl]phenyl}ethylamine obtained in Reference Example 15.

$^1$H-NMR (CDCl$_3$) δ: 1.36 (3H, d, J=6.6 Hz), 1.38 (2H, m), 1.55 (4H, m), 2.35 (4H, m), 2.94 (2H, t, J=6.9 Hz), 3.39 (1H, q, J=6.6 Hz), 3.74 (2H, q, J=6.6 Hz), 6.17 (1H, m), 7.17 (2H, d, J=8.1 Hz), 7.27 (4H, m), 7.59 (4H, m), 7.75 (2H, d, J=8.1 Hz). melting point: 138-139° C. (ethyl acetate-hexane)

EXAMPLE 61

N-(2-{4-[1-(1-piperidinyl)ethyl]phenyl}ethyl)-4'-(trifluoromethyl)[1,1'-biphenyl]-4-carboxamide

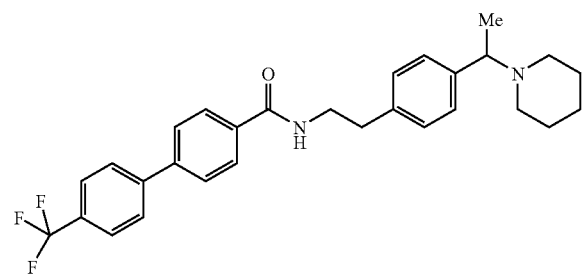

The title compound was obtained by similar operations as in Example 2 and Example 6 and using 2-{4-[1-(1-piperidinyl)ethyl]phenyl}ethylamine obtained in Reference Example 15.

$^1$H-NMR (CDCl$_3$) δ: 1.36 (3H, d, J=6.6 Hz), 1.38 (2H, m), 1.57 (4H, m), 2.35 (4H, m), 2.94 (2H, t, J=6.9 Hz), 3.40 (1H, q, J=6.6 Hz), 3.74 (2H, q, J=6.6 Hz), 6.16 (1H, m), 7.18 (2H, d, J=8.4 Hz), 7.20 (2H, m), 7.61-7.73 (6H, m), 7.75 (2H, d, J=8.4 Hz). melting point: 150-152° C. (ethyl acetate-hexane)

EXAMPLE 62

4-benzyloxy-N-(2-{4-[1-(1-piperidinyl)ethyl]phenyl}ethyl)benzamide

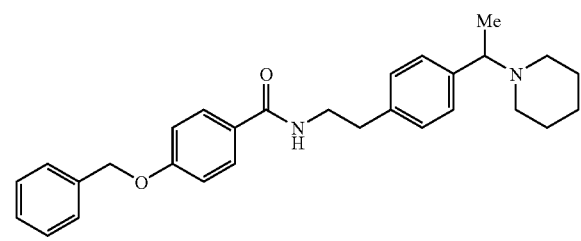

The title compound was obtained by a similar operation as in Example 2 and using 2-{4-[1-(1-piperidinyl)ethyl]phenyl}ethylamine obtained in Reference Example 15.

$^1$H-NMR (CDCl$_3$) δ: 1.36 (3H, d, J=6.8 Hz), 1.38 (2H, m), 1.53 (4H, m), 2.34 (4H, m), 2.90 (2H, t, J=6.8 Hz), 3.38 (1H, q, J=6.8 Hz), 3.69 (2H, q, J=6.2 Hz), 5.09 (2H, s), 6.02 (1H, m), 6.95 (2H, d, J=8.4 Hz), 7.15-7.40 (9H, m), 7.62 (2H, d, J=8.6 Hz). melting point: 124-125° C. (ethyl acetate-hexane)

EXAMPLE 63

4-cyclopropylmethoxy-N-(2-{4-[1-(1-piperidinyl)ethyl]phenyl}ethyl)benzamide

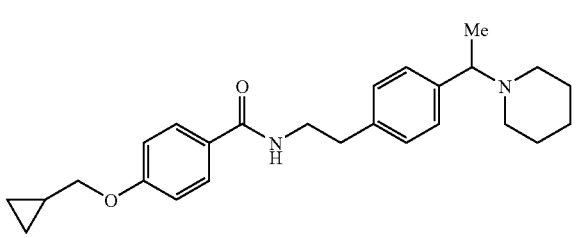

The title compound was obtained by a similar operation as in Example 2 and using 2-{4-[1-(1-piperidinyl)ethyl]phenyl}ethylamine obtained in Reference Example 15.

$^1$H-NMR (CDCl$_3$) δ: 0.34 (2H, m), 0.65 (2H, m), 1.25 (1H, m), 1.35 (3H, d, J=6.8 Hz), 1.38 (2H, m), 1.53 (4H, m), 2.34 (4H, m), 2.90 (2H, t, J=6.8 Hz), 3.38 (1H, q, J=6.6 Hz), 3.68 (2H, q, J=6.6 Hz), 3.82 (2H, d, J=6.8 Hz), 6.03 (1H, m), 6.87 (2H, d, J=9.0 Hz), 7.16 (2H, d, J=7.8 Hz), 7.23 (2H, d, J=7.8 Hz), 7.62 (2H, d, J=8.8 Hz). melting point: 141-142° C. (ethyl acetate-hexane)

EXAMPLE 64

4-(2-cyclopropylethoxy)-N-(2-{4-[1-(1-piperidinyl)ethyl]phenyl}ethyl)benzamide

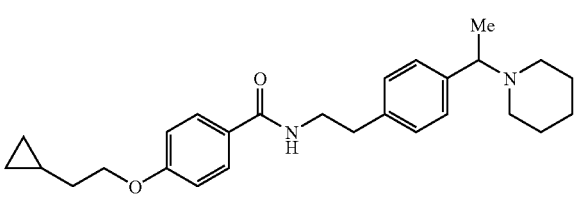

The title compound was obtained by a similar operation as in Example 2 and using 2-{4-[1-(1-piperidinyl)ethyl]phenyl}ethylamine obtained in Reference Example 15.

$^1$H-NMR (CDCl$_3$) δ: 0.11 (2H, m), 0.48 (2H, m), 0.85 (1H, m), 1.35 (3H, d, J=6.6 Hz), 1.38 (2H, m), 1.55 (4H, m), 1.75 (2H, q, J=6.6 Hz), 2.36 (4H, m), 2.90 (2H, t, J=6.8 Hz), 3.40 (1H, q, J=6.8 Hz), 3.68 (2H, q, J=6.6 Hz), 4.05 (2H, d, J=6.6 Hz), 6.04 (1H, m), 6.88 (2H, d, J=8.8 Hz), 7.16 (2H, d, J=7.2 Hz), 7.23 (2H, d, J=7.2 Hz), 7.63 (2H, d, J=8.8 Hz). melting point: 125-126° C. (ethyl acetate-hexane)

EXAMPLE 65

4-isobutoxy-N-(2-{4-[1-(1-piperidinyl)ethyl]phenyl}ethyl)benzamide

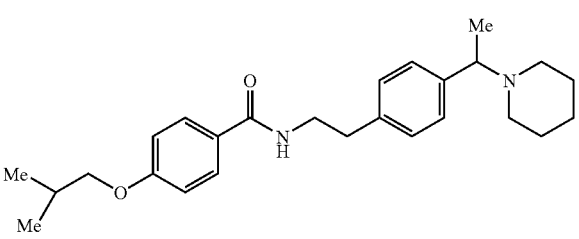

The title compound was obtained by a similar operation as in Example 2 and using 2-{4-[1-(1-piperidinyl)ethyl]phenyl}ethylamine obtained in Reference Example 15.

¹H-NMR (CDCl₃) δ: 1.02 (6H, d, J=6.6 Hz), 1.36 (3H, d, J=6.8 Hz), 1.38 (2H, m), 1.55 (4H, m), 2.09 (1H, m), 2.34 (4H, m), 2.90 (2H, t, J=7.2 Hz), 3.39 (1H, q, J=6.8 Hz), 3.68 (2H, q, J=6.6 Hz), 3.73 (2H, d, J=6.6 Hz), 6.03 (1H, m), 6.88 (2H, d, J=8.8 Hz), 7.15 (2H, d, J=7.8 Hz), 7.23 (2H, d, J=7.8 Hz), 7.62 (2H, d, J=8.8 Hz). melting point: 93-94° C. (ethyl acetate-hexane)

EXAMPLE 66

4-isopentyloxy-N-(2-{4-[1-(1-piperidinyl)ethyl]phenyl}ethyl)benzamide

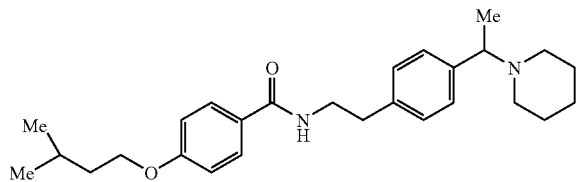

The title compound was obtained by a similar operation as in Example 2 and using 2-{4-[1-(1-piperidinyl)ethyl]phenyl}ethylamine obtained in Reference Example 15.

¹H-NMR (CDCl₃) δ: 0.95 (6H, d, J=6.6 Hz), 1.35 (3H, d, J=6.8 Hz), 1.38 (2H, m), 1.53 (4H, m), 1.71 (2H, m), 1.83 (1H, m), 2.34 (4H, m), 2.90 (2H, t, J=6.8 Hz), 3.38 (1H, q, J=6.6 Hz), 3.69 (2H, q, J=6.6 Hz), 4.00 (2H, t, J=6.6 Hz), 6.03 (1H, m), 6.86 (2H, d, J=8.6 Hz), 7.16 (2H, d, J=7.8 Hz), 7.31 (2H, d, J=7.8 Hz), 7.62 (2H, d, J=8.6 Hz). melting point: 91-92° C. (ethyl acetate-hexane)

EXAMPLE 67

N-(2-{4-[1-(1-azepanyl)ethyl]phenyl}ethyl)-4'-chloro[1,1'-biphenyl]-4-carboxamide

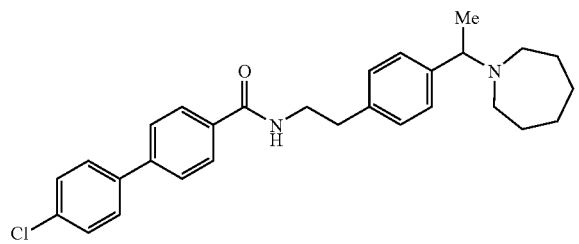

The title compound was obtained by a similar operation as in Example 2 and using 2-{4-[1-(1-azepanyl)ethyl]phenyl}ethylamine obtained in Reference Example 17.

¹H-NMR (CDCl₃) δ: 1.34 (3H, d, J=6.6 Hz), 1.57 (8H, m), 2.62 (4H, m), 2.93 (2H, t, J=6.9 Hz), 3.75 (3H, m), 6.15 (1H, m), 7.17 (2H, d, J=7.8 Hz), 7.32 (2H, d, J=8.1 Hz), 7.41 (2H, d, J=8.1 Hz), 7.52 (2H, d, J=8.1 Hz), 7.56 (2H, d, J=8.1 Hz), 7.74 (2H, d, J=8.1 Hz). melting point: 147-148° C. (ethyl acetate-hexane)

EXAMPLE 68

N-(2-{4-[1-(1-azepanyl)ethyl]phenyl}ethyl)-4'-fluoro[1,1'-biphenyl]-4-carboxamide

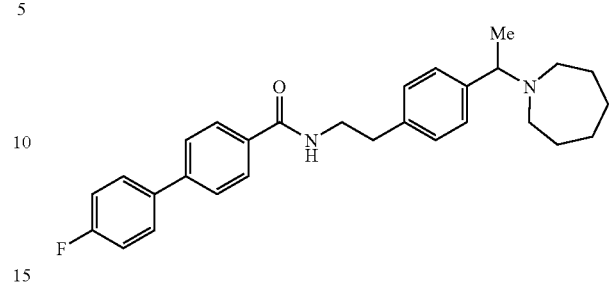

The title compound was obtained by a similar operation as in Example 2 and using 2-{4-[1-(1-azepanyl)ethyl]phenyl}ethylamine obtained in Reference Example 17.

¹H-NMR (CDCl₃) δ: 1.34 (3H, d, J=6.6 Hz), 1.57 (8H, m), 2.61 (4H, m), 2.93 (2H, t, J=6.6 Hz), 3.75 (3H, m), 6.15 (1H, m), 7.10-7.25 (4H, m), 7.32 (2H, d, J=8.1 Hz), 7.54 (4H, m), 7.74 (2H, d, J=8.4 Hz). melting point: 128-129° C. (ethyl acetate-hexane)

EXAMPLE 69

N-(2-{4-[1-(1-azepanyl)ethyl]phenyl}ethyl)-4'-methoxy[1,1'-biphenyl]-4-carboxamide

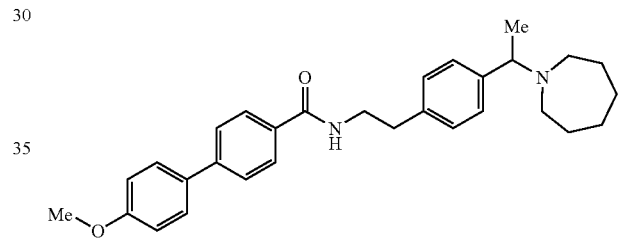

The title compound was obtained by a similar operation as in Example 2 and using 2-{4-[1-(1-azepanyl)ethyl]phenyl}ethylamine obtained in Reference Example 17.

¹H-NMR (CDCl₃) δ: 1.35 (3H, d, J=6.6 Hz), 1.58 (8H, m), 2.62 (4H, m), 2.93 (2H, t, J=7.0 Hz), 3.72 (3H, m), 3.86 (3H, s), 6.14 (1H, m), 6.99 (2H, d, J=8.8 Hz), 7.16-7.35 (4H, m), 7.56 (4H, m), 7.73 (2H, d, J=8.0 Hz). melting point: 136-137° C. (ethyl acetate-hexane)

EXAMPLE 70

N-(2-{4-[1-(1-azepanyl)ethyl]phenyl}ethyl)-4'-methyl[1,1'-biphenyl]-4-carboxamide

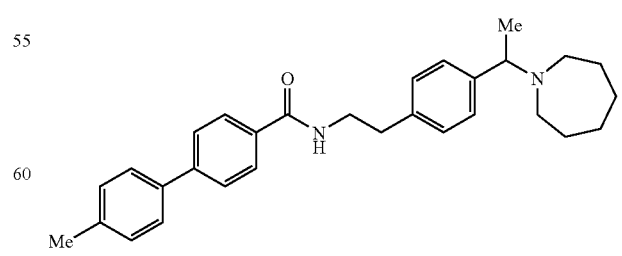

The title compound was obtained by a similar operation as in Example 2 and using 2-{4-[1-(1-azepanyl)ethyl]phenyl}ethylamine obtained in Reference Example 17.

$^1$H-NMR (CDCl$_3$) δ: 1.35 (3H, d, J=6.6 Hz), 1.57 (8H, m), 2.40 (3H, s), 2.61 (4H, m), 2.93 (2H, t, J=6.6 Hz), 3.74 (3H, m), 6.14 (1H, m), 7.16-7.35 (6H, m), 7.49 (2H, d, J=8.2 Hz), 7.60 (2H, d, J=8.6 Hz), 7.73 (2H, d, J=8.0 Hz). melting point: 146-148° C. (ethyl acetate-hexane)

EXAMPLE 71

N-(2-{4-[1-(1-azepanyl)ethyl]phenyl}ethyl)[1,1'-biphenyl]-4-carboxamide

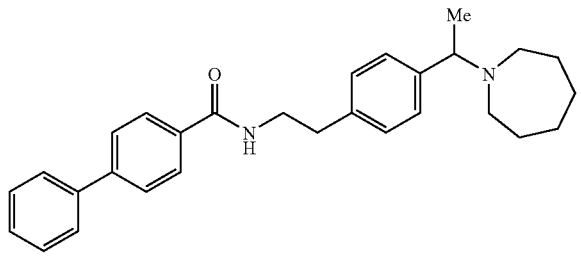

The title compound was obtained by a similar operation as in Example 2, and using 2-{4-[1-(1-azepanyl)ethyl]phenyl}ethylamine obtained in Reference Example 17.

$^1$H-NMR (CDCl$_3$) δ: 1.34 (3H, d, J=6.6 Hz), 1.57 (8H, m), 2.62 (4H, m), 2.94 (2H, t, J=6.6 Hz), 3.75 (3H, m), 6.18 (1H, m), 7.18-7.48 (7H, m), 7.61 (4H, m), 7.76 (2H, d, J=8.4 Hz). melting point: 104-105° C. (ethyl acetate-hexane)

EXAMPLE 72

N-(2-{4-[1-(1-azepanyl)ethyl]phenyl}ethyl)-4'-(trifluoromethoxy)[1,1'-biphenyl]-4-carboxamide

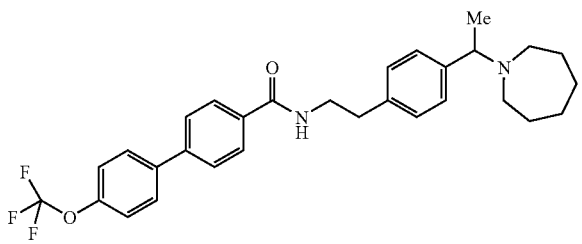

The title compound was obtained by similar operations as in Example 2 and Example 6 and using 2-{4-[1-(1-azepanyl)ethyl]phenyl}ethylamine obtained in Reference Example 17.

$^1$H-NMR (CDCl$_3$) δ: 1.35 (3H, d, J=6.6 Hz), 1.57 (8H, m), 2.62 (4H, m), 2.93 (2H, t, J=6.6 Hz), 3.75 (3H, m), 6.16 (1H, m), 7.16-7.33 (6H, m), 7.78 (4H, m), 7.74 (2H, d, J=8.1 Hz). melting point: 97-99° C. (ethyl acetate-hexane)

EXAMPLE 73

N-(2-{4-[1-(1-azepanyl)ethyl]phenyl}ethyl)-4'-(trifluoromethyl)[1,1'-biphenyl]-4-carboxamide

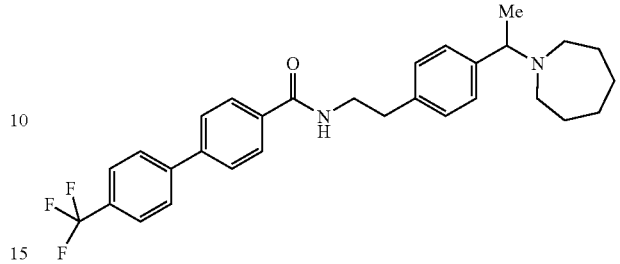

The title compound was obtained by similar operations as in Example 2 and Example 6 and using 2-{4-[1-(1-azepanyl)ethyl]phenyl}ethylamine obtained in Reference Example 17.

$^1$H-NMR (CDCl$_3$) δ: 1.35 (3H, d, J=6.9 Hz), 1.57 (8H, m), 2.62 (4H, m), 2.94 (2H, t, J=6.6 Hz), 3.75 (3H, m), 6.19 (1H, m), 7.17 (2H, d, J=8.1 Hz), 7.32 (2H, d, J=8.1 Hz), 7.66 (6H, m), 7.77 (2H, d, J=8.1 Hz). melting point: 107-109° C. (ethyl acetate-hexane)

EXAMPLE 74

N-(2-{4-[1-(1-azepanyl)ethyl]phenyl}ethyl)-4-(benzyloxy)benzamide

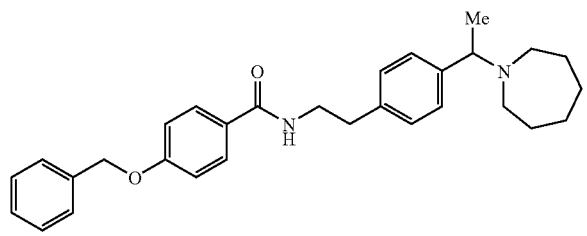

The title compound was obtained by a similar operation as in Example 2 and using 2-{4-[1-(1-azepanyl)ethyl]phenyl}ethylamine obtained in Reference Example 17.

$^1$H-NMR (CDCl$_3$) δ: 1.34 (3H, d, J=6.4 Hz), 1.57 (8H, m), 2.61 (4H, m), 2.90 (2H, t, J=6.6 Hz), 3.73 (3H, m), 5.10 (2H, s), 6.02 (1H, m), 6.90 (2H, d, J=8.1 Hz), 7.14-7.40 (9H, m), 7.64 (2H, d, J=8.1 Hz). melting point: 121-122° C. (ethyl acetate-hexane)

EXAMPLE 75

N-(2-{4-[1-(1-azepanyl)ethyl]phenyl}ethyl)-4-(cyclopropylmethoxy)benzamide

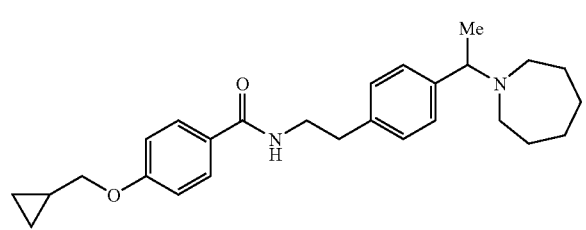

The title compound was obtained by a similar operation as in Example 2 and using 2-{4-[1-(1-azepanyl)ethyl]phenyl}ethylamine obtained in Reference Example 17.

$^1$H-NMR (CDCl$_3$) δ: 0.37 (2H, m), 0.65 (2H, m), 1.27 (1H, m), 1.34 (3H, d, J=6.4 Hz), 1.57 (8H, m), 2.61 (4H, m), 2.90 (2H, t, J=7.0 Hz), 3.68 (3H, m), 3.82 (2H, d, J=7.0 Hz), 6.02 (1H, m), 6.88 (2H, d, J=8.8 Hz), 7.16 (2H, d, J=8.0 Hz), 7.31 (2H, d, J=8.0 Hz), 7.63 (2H, d, J=8.8 Hz). melting point: 95-96° C. (ethyl acetate-hexane)

EXAMPLE 76

N-(2-{4-[1-(1-azepanyl)ethyl]phenyl}ethyl)-4-(2-cyclopropylethoxy)benzamide

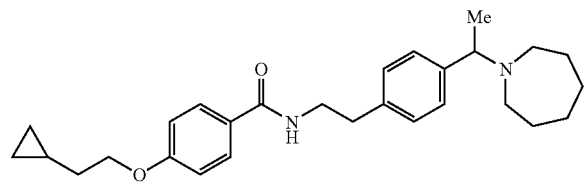

The title compound was obtained by a similar operation as in Example 2 and using 2-{4-[1-(1-azepanyl)ethyl]phenyl}ethylamine obtained in Reference Example 17.

$^1$H-NMR (CDCl$_3$) δ: 0.11 (2H, m), 0.49 (2H, m), 0.84 (1H, m), 1.34 (3H, d, J=6.9 Hz), 1.57 (8H, m), 1.68 (2H, q, J=6.6 Hz), 2.61 (4H, m), 2.90 (2H, t, J=6.9 Hz), 3.75 (3H, m), 4.05 (2H, t, J=6.9 Hz), 6.01 (1H, m), 6.88 (2H, d, J=8.7 Hz), 7.16 (2H, d, J=8.1 Hz), 7.31 (2H, d, J=7.8 Hz), 7.62 (2H, d, J=8.7 Hz). melting point: 87-88° C. (ethyl acetate-hexane)

EXAMPLE 77

N-(2-{4-[1-(1-azepanyl)ethyl]phenyl}ethyl)-4-(isobutoxy)benzamide

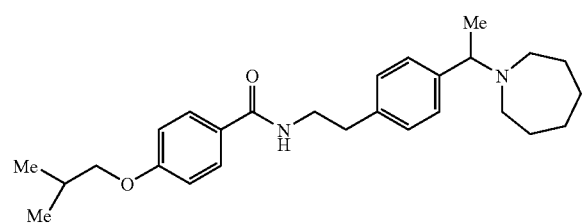

The title compound was obtained by a similar operation as in Example 2 and using 2-{4-[1-(1-azepanyl)ethyl]phenyl}ethylamine obtained in Reference Example 17.

$^1$H-NMR (CDCl$_3$) δ: 1.02 (6H, d, J=6.6 Hz), 1.33 (3H, d, J=6.8 Hz), 1.58 (8H, m), 2.08 (1H, m), 2.61 (4H, m), 2.90 (2H, t, J=6.9 Hz), 3.72 (5H, m), 6.13 (1H, m), 6.88 (2H, d, J=8.7 Hz), 7.16 (2H, d, J=8.1 Hz), 7.30 (2H, d, J=7.8 Hz), 7.64 (2H, d, J=8.7 Hz). melting point: 76-77° C. (ethyl acetate-hexane)

EXAMPLE 78

N-(2-{4-[1-(1-azepanyl)ethyl]phenyl}ethyl)-4-(isopentyloxy)benzamide

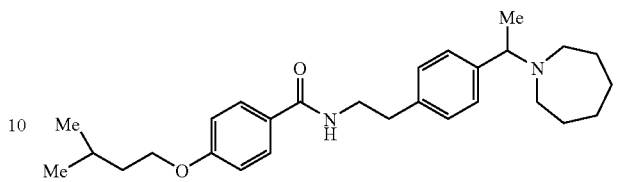

The title compound was obtained by a similar operation as in Example 2 and using 2-{4-[1-(1-azepanyl)ethyl]phenyl}ethylamine obtained in Reference Example 17.

$^1$H-NMR (CDCl$_3$) δ: 0.96 (6H, d, J=6.6 Hz), 1.35 (3H, d, J=6.9 Hz), 1.57 (8H, m), 1.69 (2H, q, J=6.6 Hz), 1.83 (1H, m), 2.61 (4H, m), 2.90 (2H, t, J=6.3 Hz), 3.70 (3H, m), 4.00 (2H, t, J=6.6 Hz), 6.03 (1H, m), 6.87 (2H, d, J=8.7 Hz), 7.15 (2H, d, J=7.8 Hz), 7.31 (2H, d, J=7.8 Hz), 7.62 (2H, d, J=8.7 Hz). melting point: 78-79° C. (ethyl acetate-hexane)

EXAMPLE 79

4'-methoxy-N-(2-{4-[1-(4-methyl-1-piperazinyl)ethyl]phenyl}ethyl)[1,1'-biphenyl]-4-carboxamide

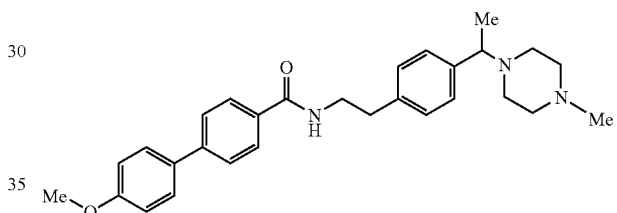

The title compound was obtained by a similar operation as in Example 2 and using 2-{4-[1-(4-methyl-1-piperazinyl)ethyl]phenyl}ethylamine obtained in Reference Example 18.

$^1$H-NMR (CDCl$_3$) δ: 1.36 (3H, d, J=6.9 Hz), 2.25 (3H, s), 2.42 (8H, m), 2.92 (2H, t, J=6.9 Hz), 3.35 (1H, q, J=6.9 Hz), 3.72 (2H, q, J=6.6 Hz), 3.85 (3H, s), 6.15 (1H, m), 6.97 (2H, d, J=9.0 Hz), 7.22 (2H, d, J=8.1 Hz), 7.26 (2H, d, J=8.4 Hz), 7.53 (2H, d, J=8.4 Hz), 7.57 (2H, d, J=8.4 Hz), 7.73 (2H, d, J=8.4 Hz). melting point: 152-154° C. (ethyl acetate-hexane)

EXAMPLE 80

4'-methyl-N-(2-{4-[1-(4-methyl-1-piperazinyl)ethyl]phenyl}ethyl)[1,1'-biphenyl]-4-carboxamide

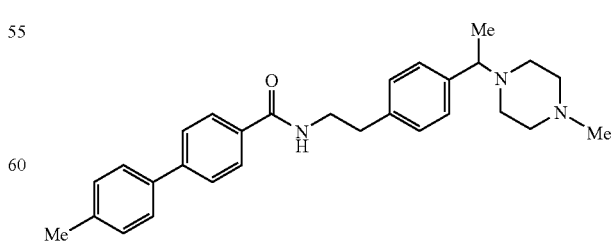

The title compound was obtained by a similar operation as in Example 2 and using 2-{4-[1-(4-methyl-1-piperazinyl)ethyl]phenyl}ethylamine obtained in Reference Example 18.

¹H-NMR (CDCl₃) δ: 1.36 (3H, d, J=6.6 Hz), 2.26 (3H, s), 2.40 (3H, s), 2.42 (8H, m), 2.93 (2H, t, J=6.6 Hz), 3.35 (1H, q, J=6.9 Hz), 3.72 (2H, q, J=6.9 Hz), 6.15 (1H, m), 7.18 (2H, d, J=8.1 Hz), 7.25 (4H, m), 7.49 (2H, d, J=8.1 Hz), 7.60 (2H, d, J=8.1 Hz), 7.73 (2H, d, J=8.1 Hz). melting point: 165-167° C. (ethyl acetate-hexane)

EXAMPLE 81

4-benzyloxy-N-(2-{4-[1-(4-methyl-1-piperazinyl)ethyl]phenyl}ethyl)benzamide

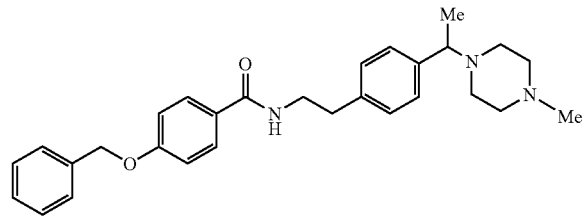

The title compound was obtained by a similar operation as in Example 2 and using 2-{4-[1-(4-methyl-1-piperazinyl)ethyl]phenyl}ethylamine obtained in Reference Example 18.

¹H-NMR (CDCl₃) δ: 1.35 (3H, d, J=6.6 Hz), 2.56 (3H, s), 2.42 (8H, m), 2.89 (2H, t, J=7.2 Hz), 3.34 (1H, q, J=6.6 Hz), 3.68 (2H, q, J=6.3 Hz), 5.09 (2H, s), 6.05 (1H, m), 6.96 (2H, d, J=8.7 Hz), 7.16 (2H, d, J=8.1 Hz), 7.24 (2H, d, J=7.8 Hz), 7.39 (5H, m), 7.65 (2H, d, J=8.4 Hz). melting point: 129-130° C. (ethyl acetate-hexane)

EXAMPLE 82

4-cyclopropylmethoxy-N-(2-{4-[1-(4-methyl-1-piperazinyl)ethyl]phenyl}ethyl)benzamide

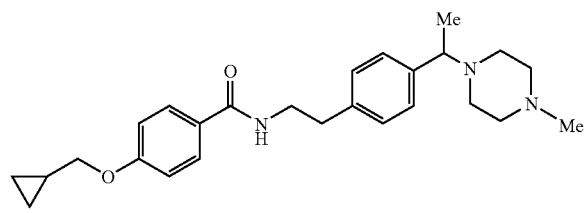

The title compound was obtained by a similar operation as in Example 2 and using 2-{4-[1-(4-methyl-1-piperazinyl)ethyl]phenyl}ethylamine obtained in Reference Example 18.

¹H-NMR (CDCl₃) δ: 0.34 (2H, m), 0.63 (2H, m), 1.26 (1H, m), 1.35 (3H, d, J=6.6 Hz), 2.26 (3H, s), 2.42. (8H, m), 2.92 (2H, t, J=6.9 Hz), 3.33 (1H, q, J=6.6 Hz), 3.68 (2H, q, J=6.6 Hz), 3.82 (2H, d, J=6.9 Hz), 6.02 (1H, m), 6.88 (2H, d, J=8.7 Hz), 7.16 (2H, d, J=8.1 Hz), 7.24 (2H, d, J=8.1 Hz), 7.63 (2H, d, J=8.4 Hz). melting point: 117-119° C. (ethyl acetate-hexane)

EXAMPLE 83

4-(2-cyclopropylethoxy)-N-(2-{4-[1-(4-methyl-1-piperazinyl)ethyl]phenyl}ethyl)benzamide

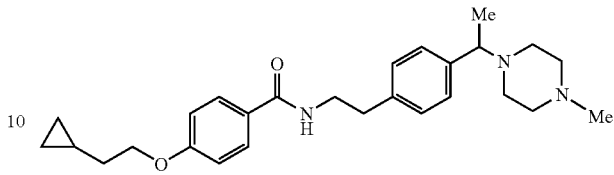

The title compound was obtained by a similar operation as in Example 2 and using 2-{4-[1-(4-methyl-1-piperazinyl)ethyl]phenyl}ethylamine obtained in Reference Example 18.

¹H-NMR (CDCl₃) δ: 0.11 (2H, m), 0.49 (2H, m), 0.85 (1H, m), 1.35 (3H, d, J=6.6 Hz), 1.68 (2H, q, J=6.6 Hz), 2.26 (3H, s), 2.42 (8H, m), 2.90 (2H, t, J=6.6 Hz), 3.34 (1H, q, J=6.6 Hz), 3.68 (2H, q, J=6.6 Hz), 4.06 (2H, t, J=6.9 Hz), 6.04 (1H, m), 6.88 (2H, d, J=8.7 Hz), 7.16 (2H, d, J=8.1 Hz), 7.25 (2H, d, J=8.1 Hz), 7.65 (2H, d, J=8.4 Hz). melting point: 102-103° C. (ethyl acetate-hexane)

EXAMPLE 84

4-isobutoxy-N-(2-{4-[1-(4-methyl-1-piperazinyl)ethyl]phenyl}ethyl)benzamide

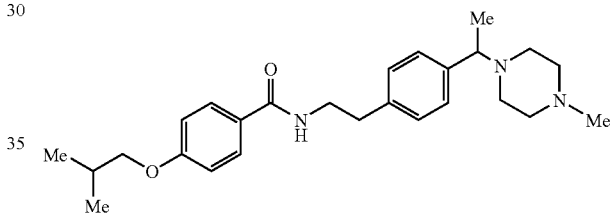

The title compound was obtained by a similar operation as in Example 2 and using 2-{4-[1-(4-methyl-1-piperazinyl)ethyl]phenyl}ethylamine obtained in Reference Example 18.

¹H-NMR (CDCl₃) δ: 1.02 (6H, d, J=6.6 Hz), 1.35 (3H, d, J=6.9 Hz), 2.08 (1H, m), 2.26 (3H, s), 2.42 (8H, m), 2.90 (2H, t, J=6.6 Hz), 3.34 (1H, q, J=6.6 Hz), 3.68 (2H, q, J=6.6 Hz), 3.73 (2H, d, J=6.6 Hz), 6.04 (1H, m), 6.87 (2H, d, J=8.4 Hz), 7.15 (2H, d, J=8.1 Hz), 7.25 (2H, d, J=7.8 Hz), 7.64 (2H, d, J=8.4 Hz). melting point: 92-93° C. (ethyl acetate-hexane)

EXAMPLE 85

4-isopentyloxy-N-(2-{4-[1-(4-methyl-1-piperazinyl)ethyl]phenyl}ethyl)benzamide

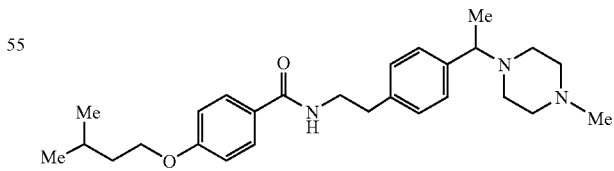

The title compound was obtained by a similar operation as in Example 2 and using 2-{4-[1-(4-methyl-1-piperazinyl)ethyl]phenyl}ethylamine obtained in Reference Example 18.

¹H-NMR (CDCl₃) δ: 0.96 (6H, d, J=6.6 Hz), 1.35 (3H, d, J=6.6 Hz), 1.68 (2H, q, J=6.6 Hz), 1.83 (1H, m), 2.26 (3H, s), 2.42 (8H, m), 2.90 (2H, t, J=6.9 Hz), 3.35 (1H, q, J=6.6 Hz), 3.69 (2H, q, J=6.6 Hz), 4.01 (2H, t, J=6.6 Hz), 6.04 (1H, m), 6.88 (2H, d, J=8.4 Hz), 7.15 (2H, d, J=7.8 Hz), 7.26 (2H, d, J=7.8 Hz), 7.62 (2H, d, J=8.4 Hz). melting point: 91-92° C. (ethyl acetate-hexane)

EXAMPLE 86

4-bromo-N-(2-{4-[1-(4-methyl-1-piperazinyl)ethyl]phenyl}ethyl)benzamide

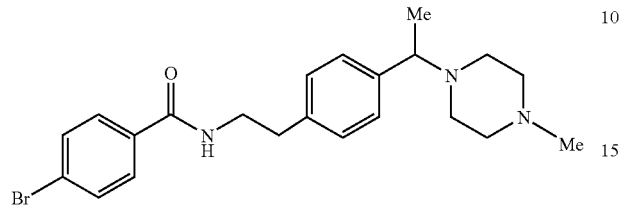

The title compound was obtained by a similar operation as in Example 2 and using 2-{4-[1-(4-methyl-1-piperazinyl)ethyl]phenyl}ethylamine obtained in Reference Example 18.

$^1$H-NMR (CDCl$_3$) δ: 1.36 (3H, d, J=6.6 Hz), 2.12-2.64 (11H, m), 2.91 (2H, t, J=7.0 Hz), 3.36 (1H, q, J=6.6 Hz), 3.70 (2H, q, J=6.6 Hz), 6.11 (1H, br), 7.10-7.30 (4H, m), 7.55 (4H, s-like). melting point: 110-112° C. (ethyl acetate-isopropyl ether)

EXAMPLE 87

4'-chloro-N-(2-{4-[1-(4-methyl-1-piperazinyl)ethyl]phenyl}ethyl)[1,1'-biphenyl]-4-carboxamide

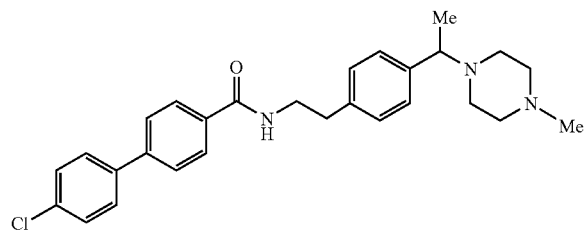

The title compound was obtained by a similar operation as in Example 2 and using 2-{4-[1-(4-methyl-1-piperazinyl)ethyl]phenyl}ethylamine obtained in Reference Example 18.

$^1$H-NMR (CDCl$_3$) δ: 1.36 (3H, d, J=6.6 Hz), 2.20-2.66 (11H, m), 2.93 (2H, t, J=6.8 Hz), 3.36 (1H, q, J=6.6 Hz), 3.73 (2H, q, J=6.6 Hz), 6.15 (1H, br), 7.18 (2H, d, J=8.1 Hz), 7.26 (2H, d, J=8.1 Hz), 7.42 (2H, d, J=8.8 Hz), 7.52 (2H, d, J=8.8 Hz), 7.58 (2H, d, J=8.5 Hz), 7.75 (2H, d, J=8.5 Hz). melting point: 151-152° C. (ethyl acetate-isopropyl ether)

EXAMPLE 88

4'-fluoro-N-(2-{4-[1-(4-methyl-1-piperazinyl)ethyl]phenyl}ethyl)[1,1'-biphenyl]-4-carboxamide

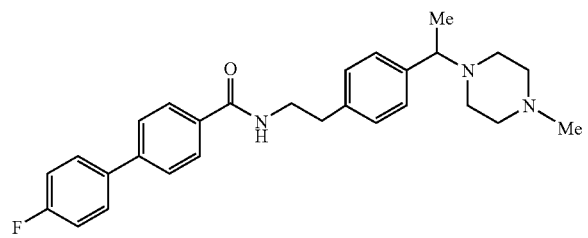

The title compound was obtained by a similar operation as in Example 2 and using 2-{4-[1-(4-methyl-1-piperazinyl)ethyl]phenyl}ethylamine obtained in Reference Example 18.

$^1$H-NMR (CDCl$_3$) δ: 1.36 (3H, d, J=7.0 Hz), 2.17-2.63 (11H, m), 2.93 (2H, t, J=7.0 Hz), 3.36 (1H, q, J=7.0 Hz), 3.73 (2H, q, J=6.4 Hz), 6.16 (1H, br), 7.08-7.32 (6H, m), 7.48-7.64 (4H, m), 7.76 (2H, d, J=8.4 Hz). melting point: 134-135° C. (ethyl acetate-isopropyl ether)

EXAMPLE 89

N-(2-{4-[1-(4-methyl-1-piperazinyl)ethyl]phenyl}ethyl)-4'-(trifluoromethoxy)[1,1'-biphenyl]-4-carboxamide

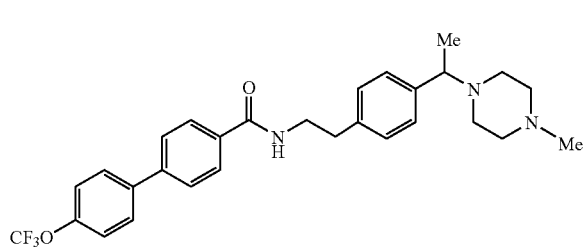

The title compound was obtained by similar operations as in Example 2 and Example 6 and using 2-{4-[1-(4-methyl-1-piperazinyl)ethyl]phenyl}ethylamine obtained in Reference Example 18.

$^1$H-NMR (CDCl$_3$) δ: 1.36 (3H, d, J=6.6 Hz), 2.15-2.65 (11H, m), 2.94 (2H, t, J=6.8 Hz), 3.37 (1H, q, J=6.6 Hz), 3.74 (2H, q, J=6.5 Hz), 6.17 (1H, br), 7.13-7.36 (6H, m), 7.54-7.68 (4H, m), 7.78 (2H, d, J=8.4 Hz). melting point: 140-143° C. (ethyl acetate-isopropyl ether)

EXAMPLE 90

4'-chloro-3-fluoro-N-(2-{4-[(4-methyl-1-piperazinyl)methyl]phenyl}ethyl)[1,1'-biphenyl]-4-carboxamide

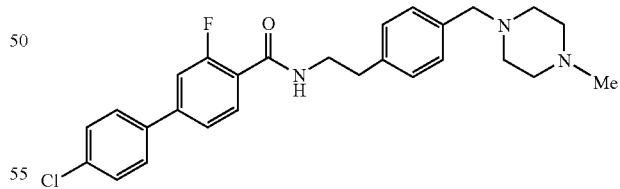

The title compound was obtained by similar operations as in Example 2 and Example 6 and using 2-{4-[(4-methyl-1-piperazinyl)methyl]phenyl}ethylamine trihydrochloride obtained in Reference Example 7.

$^1$H-NMR (CDCl$_3$) δ: 2.28 (3H, s), 2.46 (8H, m), 2.93 (2H, t, J=7.1 Hz), 3.49 (2H, s), 3.74 (2H, m), 6.75 (1H, m), 7.19 (2H, d, J=8.1 Hz), 7.27 (3H, m), 7.43 (3H, m), 7.51 (2H, m), 8.15 (1H, t, J=8.3 Hz). melting point: 116-117° C. (ethyl acetate-isopropyl ether)

EXAMPLE 91

4'-fluoro-N-(2-{4-[(2-methyl-1-pyrrolidinyl)methyl]phenyl}ethyl)[1,1'-biphenyl]-4-carboxamide

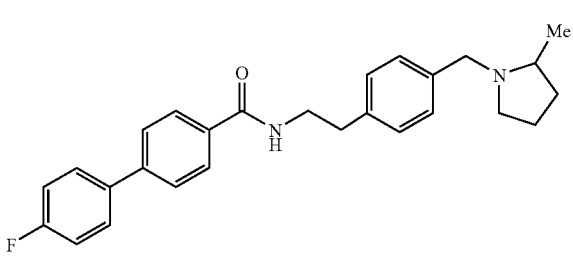

The title compound was obtained by a similar operation as in Example 2 and using 2-{4-[(2-methyl-1-pyrrolidinyl)methyl]phenyl}ethylamine dihydrochloride obtained in Reference Example 11.

$^1$H-NMR (CDCl$_3$) δ: 1.17 (3H, d, J=6.1 Hz), 1.46 (1H, m), 1.67 (2H, m), 1.94 (1H, m), 2.10 (1H, q, J=9.0 Hz), 2.38 (1H, m), 2.88 (1H, d, J=2.7 Hz), 2.93 (2H, t, J=6.7 Hz), 3.12 (1H, d, J=12.7 Hz), 3.73 (2H, m), 3.99 (1H, d, J=12.9 Hz), 6.12 (1H, m), 7.13 (2H, m), 7.18 (2H, d, J=8.3 Hz), 7.28 (2H, m), 7.55 (4H, m), 7.74 (2H, d, J=8.6 Hz). melting point: 172-173° C. (ethyl acetate-isopropyl ether)

EXAMPLE 92

4'-chloro-N-(2-{4-[(2-methyl-1-pyrrolidinyl)methyl]phenyl}ethyl)[1,1'-biphenyl]-4-carboxamide

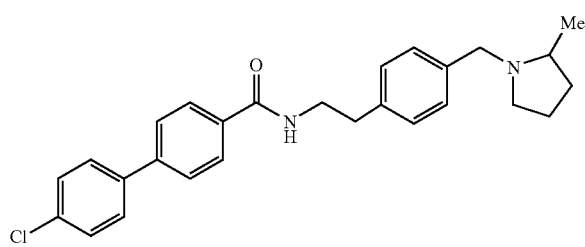

The title compound was obtained by a similar operation as in Example 2 and using 2-{4-[(2-methyl-1-pyrrolidinyl)methyl]phenyl}ethylamine dihydrochloride obtained in Reference Example 11.

$^1$H-NMR (CDCl$_3$) δ: 1.17 (3H, d, J=5.9 Hz), 1.45 (1H, m), 1.67 (2H, m), 1.94 (1H, m), 2.10 (1H, q, J=8.8 Hz), 2.38 (1H, m), 2.88 (1H, m), 2.93 (2H, t, J=6.8 Hz), 3.11 (1H, d, J=12.9 Hz), 3.73 (2H, m), 3.99 (1H, d, J=12.7 Hz), 6.13 (1H, t, J=5.5 Hz), 7.18 (2H, d, J=8.1 Hz), 7.28 (2H, m), 7.41 (2H, d, J=8.9 Hz), 7.51 (2H, d, J=8.9 Hz), 7.57 (2H, d, J=8.6 Hz), 7.74 (2H, d, J=8.5 Hz). melting point: 176-177° C. (ethyl acetate-isopropyl ether)

EXAMPLE 93

4'-chloro-3-fluoro-N-{2-[4-(1-piperidinylmethyl)phenyl]ethyl}[1,1'-biphenyl]-4-carboxamide

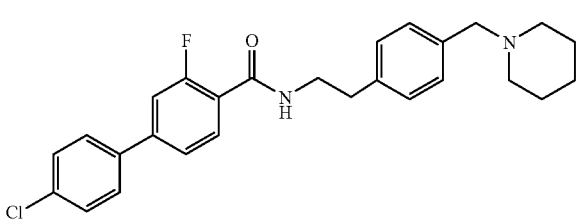

The title compound was obtained by similar operations as in Example 2 and Example 6 and using 2-[4-(1-piperidinylmethyl)phenyl]ethylamine dihydrochloride obtained in Reference Example 6.

$^1$H-NMR (CDCl$_3$) δ: 1.43 (2H, m), 1.57 (4H, m), 2.36 (4H, m), 2.94 (2H, t, J=7.0 Hz), 3.45 (2H, s), 3.75 (2H, m), 6.79 (1H, m), 7.20 (2H, d, J=8.3 Hz), 7.26 (3H, m), 7.44 (3H, m), 7.52 (2H, m), 8.16 (1H, t, J=8.3 Hz). melting point: 134° C. (ethyl acetate-isopropyl ether)

EXAMPLE 94

4-(4-methyl-2-oxopentyl)-N-{2-[4-(1-pyrrolidinylmethyl)phenyl]ethyl}benzamide

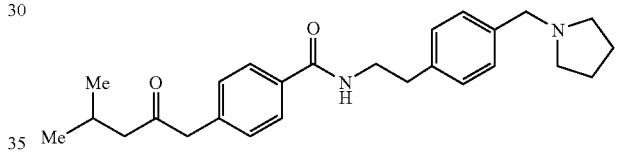

The title compound was obtained by a similar operation as in Example 2 and using 2-[4-(1-pyrrolidinylmethyl)phenyl]ethylamine obtained in Reference Example 4.

$^1$H-NMR (CDCl$_3$) δ: 0.88 (6H, d, J=6.8 Hz), 1.79 (4H, m), 2.14 (1H, m) 2.33 (2H, d, J=6.7 Hz), 2.52 (4H, m), 2.91 (2H, t, J=7.0 Hz), 3.60 (2H, s), 3.71 (4H, m), 6.08 (1H, t, J=5.8 Hz), 7.18 (2H, d, J=7.9 Hz), 7.23 (2H, d, J=8.3 Hz), 7.29 (2H, m), 7.64 (2H, d, J=8.3 Hz). melting point: 137-138° C. (ethyl acetate-isopropyl ether)

EXAMPLE 95

2-fluoro-4-(3-methyl-2-oxobutyl)-N-{2-[4-(1-pyrrolidinylmethyl)phenyl]ethyl}benzamide

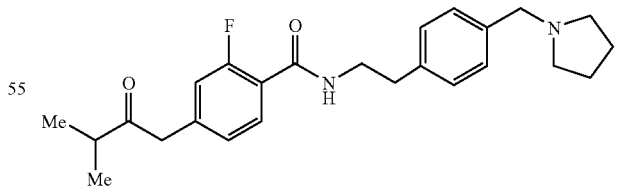

The title compound was obtained by a similar operation as in Example 2 and using 2-[4-(1-pyrrolidinylmethyl)phenyl]ethylamine obtained in Reference Example 4.

$^1$H-NMR (CDCl$_3$) δ: 1.13 (6H, d, J=6.8 Hz), 1.79 (4H, m), 2.50 (4H, m), 2.71 (1H, m), 2.91 (2H, t, J=7.1 Hz), 3.59 (2H, s), 3.72 (2H, m), 3.77 (2H, s), 6.72 (1H, m), 6.95 (1H, dd, J=12.8, 1.5 Hz), 7.06 (1H, dd, J=8.1, 1.7 Hz), 7.18 (2H, d,

J=8.3 Hz), 7.28 (2H, m), 8.03 (1H, t, J=8.1 Hz). melting point: 98-99° C. (ethyl acetate-isopropyl ether)

EXAMPLE 96

4-cyclopropylmethoxy-N-{2-[4-(1-pyrrolidinylmethyl)phenyl]ethyl}benzamide

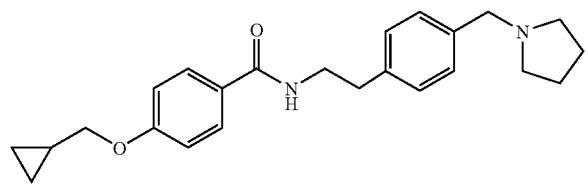

The title compound was obtained by a similar operation as in Example 2 and using 2-[4-(1-pyrrolidinylmethyl)phenyl]ethylamine obtained in Reference Example 4.

¹H-NMR (CDCl₃) δ: 0.36 (2H, m), 0.66 (2H, m), 1.27 (1H, m), 1.78 (4H, m), 2.50 (4H, m), 2.90 (2H, t, J=6.8 Hz), 3.59 (2H, s), 3.69 (2H, m), 3.82 (2H, d, J=6.8 Hz), 6.01 (1H, t, J=5.6 Hz), 6.88 (2H, d, J=9.4 Hz), 7.17 (2H, d, J=8.1 Hz), 7.28 (2H, m), 7.62 (2H, m). melting point: 136-137° C. (ethyl acetate-isopropyl ether)

EXAMPLE 97

4'-methoxy-N-{2-[4-(1-pyrrolidinylmethyl)phenyl]ethyl}[1,1'-biphenyl]-4-carboxamide

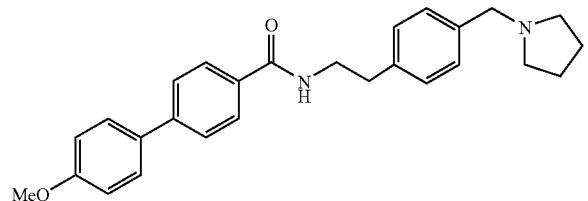

The title compound was obtained by a similar operation as in Example 2 and using 2-[4-(1-pyrrolidinylmethyl)phenyl]ethylamine obtained in Reference Example 4.

¹H-NMR (CDCl₃) δ: 1.78 (4H, m), 2.51 (4H, m), 2.93 (2H, t, J=6.8 Hz), 3.60 (2H, s), 3.73 (2H, m), 3.85 (3H, s), 6.13 (1H, t, J=6.1 Hz), 6.98 (2H, d, J=9.4 Hz), 7.19 (2H, d, J=8.1 Hz), 7.29 (2H, m), 7.55 (4H, m), 7.72 (2H, d, J=8.6 Hz). melting point: 184-185° C. (ethyl acetate-isopropyl ether)

EXAMPLE 98

3-fluoro-N-{2-[4-(1-pyrrolidinylmethyl)phenyl]ethyl}-4'-(trifluoromethyl)[1,1'-biphenyl]-4-carboxamide

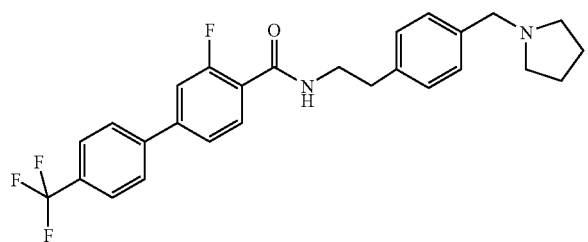

The title compound was obtained by similar operations as in Example 2 and Example 6 and using 2-[4-(1-pyrrolidinylmethyl)phenyl]ethylamine obtained in Reference Example 4.

¹H-NMR (CDCl₃) δ: 1.78 (4H, m), 2.50 (4H, m), 2.94 (2H, t, J=7.0 Hz), 3.59 (2H, s), 3.76 (2H, m), 6.78 (1H, m), 7.20 (2H, d, J=8.1 Hz), 7.30 (3H, m), 7.48 (1H, dd, J=8.2, 1.8 Hz), 7.70 (4H, m), 8.18 (1H, t, J=8.2 Hz). melting point: 139° C. (ethyl acetate-isopropyl ether)

EXAMPLE 99

3-fluoro-N-{2-[4-(1-pyrrolidinylmethyl)phenyl]ethyl}-4'-(trifluoromethoxy)[1,1'-biphenyl]-4-carboxamide

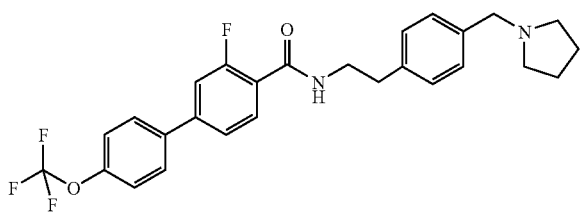

The title compound was obtained by similar operations as in Example 2 and Example 6 and using 2-[4-(1-pyrrolidinylmethyl)phenyl]ethylamine obtained in Reference Example 4.

¹H-NMR (CDCl₃) δ: 1.78 (⁴H, m), 2.50 (4H, m), 2.94 (2H, t, J=7.0 Hz), 3.59 (2H, s), 3.75 (2H, m), 6.78 (1H, m), 7.19 (2H, d, J=8.3 Hz), 7.28 (5H, m), 7.44 (1H, dd, J=8.3, 1.7 Hz), 7.59 (2H, m), 8.16 (1H, t, J=8.2 Hz). melting point: 131-132° C. (ethyl acetate-isopropyl ether)

EXAMPLE 100

3-fluoro-4'-methoxy-N-{2-[4-(1-pyrrolidinylmethyl)phenyl]ethyl}[1,1'-biphenyl]-4-carboxamide

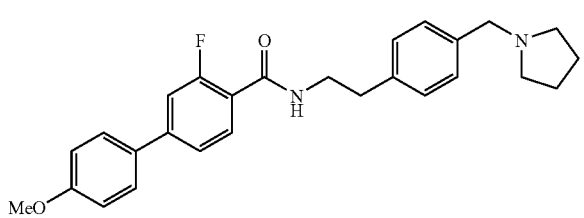

The title compound was obtained by similar operations as in Example 2 and Example 6 and using 2-[4-(1-pyrrolidinylmethyl)phenyl]ethylamine obtained in Reference Example 4.

¹H-NMR (CDCl₃) δ: 1.78 (4H, m), 2.51 (4H, m), 2.93 (2H, t, J=7.0 Hz), 3.60 (2H, s), 3.75 (2H, m), 3.86 (3H, s), 6.79 (1H, m), 6.99 (2H, m), 7.25 (5H, m), 7.44 (1H, dd, J=8.3, 1.7 Hz), 7.54 (2H, m), 8.13 (1H, t, J=8.3 Hz). melting point: 149° C. (ethyl acetate-isopropyl ether)

EXAMPLE 101

3-fluoro-4'-methyl-N-{2-[4-(1-pyrrolidinylmethyl)phenyl]ethyl}[1,1'-biphenyl]-4-carboxamide

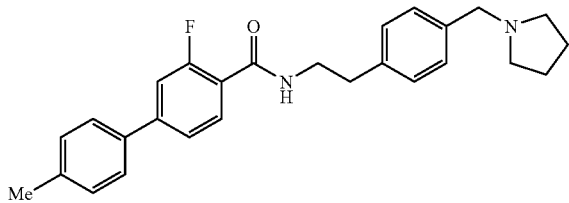

The title compound was obtained by similar operations as in Example 2 and Example 6 and using 2-[4-(1-pyrrolidinylmethyl)phenyl]ethylamine obtained in Reference Example 4.

$^1$H-NMR (CDCl$_3$) δ: 1.78 (4H, m), 2.40 (3H, s), 2.50 (4H, m), 2.93 (2H, t, J=7.0 Hz), 3.59 (2H, s), 3.74 (2H, m), 6.78 (1H, m), 7.19 (2H, d, J=8.1 Hz), 7.28 (5H, m), 7.47 (3H, m), 8.12 (1H, t, J=8.3 Hz). melting point: 147-148° C. (ethyl acetate-isopropyl ether)

EXAMPLE 102

3-fluoro-N-{2-[4-(1-pyrrolidinylmethyl)phenyl]ethyl}[1,1'-biphenyl]-4-carboxamide

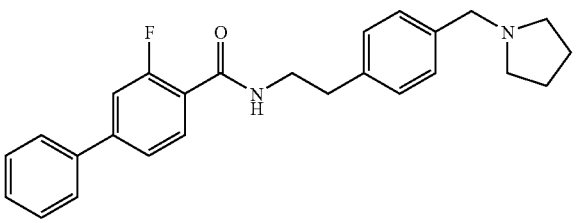

The title compound was obtained by similar operations as in Example 2 and Example 6 and using 2-[4-(1-pyrrolidinylmethyl)phenyl]ethylamine obtained in Reference Example 4.

$^1$H-NMR (CDCl$_3$) δ: 1.79 (4H, m), 2.50 (4H, m), 2.94 (2H, t, J=7.0 Hz), 3.59 (2H, s), 3.76 (2H, m), 6.79 (1H, m), 7.20 (2H, d, J=8.1 Hz), 7.29 (3H, m), 7.44 (4H, m), 7.58 (2H, m), 8.15 (1H, t, J=8.3 Hz). melting point: 134-135° C. (ethyl acetate-isopropyl ether)

EXAMPLE 103

N-{2-[4-(1-pyrrolidinylmethyl)phenyl]ethyl}-4'-(trifluoromethoxy)[1,1'-biphenyl]-4-carboxamide

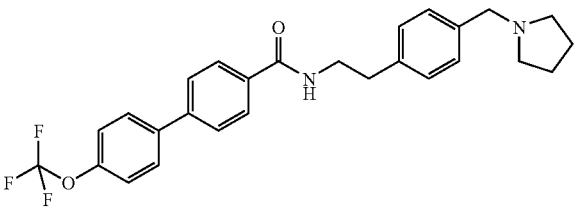

The title compound was obtained by similar operations as in Example 2 and Example 6 and using 2-[4-(1-pyrrolidinylmethyl)phenyl]ethylamine obtained in Reference Example 4.

$^1$H-NMR (CDCl$_3$) δ: 1.78 (4H, m), 2.51 (4H, m), 2.94 (2H, t, J=6.8 Hz), 3.60 (2H, s), 3.74 (2H, m), 6.13 (1H, t, J=6.2 Hz), 7.19 (2H, d, J=8.1 Hz), 7.28 (4H, m), 7.59 (4H, m), 7.75 (2H, d, J=8.6 Hz). melting point: 181-183° C. (ethyl acetate-isopropyl ether)

EXAMPLE 104

4'-methyl-N-{2-[4-(1-pyrrolidinylmethyl)phenyl]ethyl}[1,1'-biphenyl]-4-carboxamide

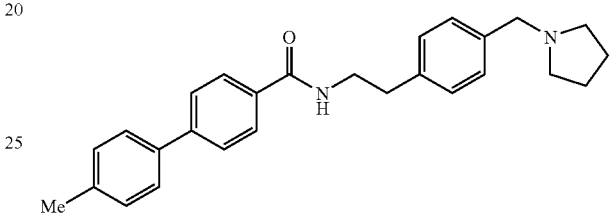

The title compound was obtained by a similar operation as in Example 2 and using 2-[4-(1-pyrrolidinylmethyl)phenyl]ethylamine obtained in Reference Example 4.

$^1$H-NMR (CDCl$_3$) δ: 1.79 (4H, m), 2.40 (3H, s), 2.51 (4H, m), 2.94 (2H, t, J=6.8 Hz), 3.60 (2H, s), 3.74 (2H, m), 6.13 (1H, t, J=5.8 Hz), 7.20 (2H, d, J=7.9 Hz), 7.27 (2H, d, J=7.9 Hz), 7.30 (2H, m), 7.51 (2H, m), 7.61 (2H, m), 7.74 (2H, m). melting point: 176-178° C. (ethyl acetate-isopropyl ether)

EXAMPLE 105

N-{2-[4-(1-pyrrolidinylmethyl)phenyl]ethyl}[1,1'-biphenyl]-4-carboxamide

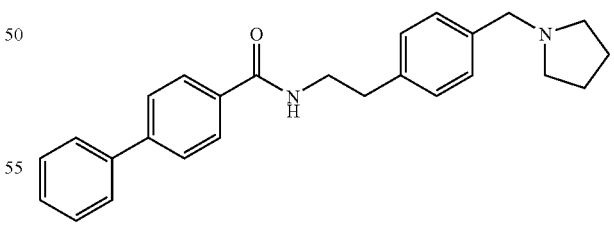

The title compound was obtained by a similar operation as in Example 2 and using 2-[4-(1-pyrrolidinylmethyl)phenyl]ethylamine obtained in Reference Example 4.

$^1$H-NMR (CDCl$_3$) δ: 1.78 (4H, m), 2.51 (4H, m), 2.94 (2H, t, J=6.9 Hz), 3.60 (2H, s), 3.74 (2H, m), 6.15 (1H, t, J=5.5 Hz), 7.20 (2H, d, J=7.9 Hz), 7.30 (2H, m), 7.42 (3H, m), 7.61 (4H, m), 7.76 (2H, m). melting point: 169-171° C. (ethyl acetate-isopropyl ether)

EXAMPLE 106

4-cyclopropylmethoxy-N-(2-{4-[(2-methyl-1-pyrrolidinyl)methyl]phenyl}ethyl)benzamide

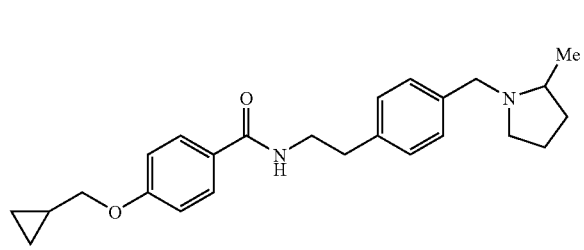

The title compound was obtained by a similar operation as in Example 2 and using 2-{4-[(2-methyl-1-pyrrolidinyl)methyl]phenyl}ethylamine dihydrochloride obtained in Reference Example 11.

$^1$H-NMR (CDCl$_3$) δ: 0.35 (2H, m), 0.66 (2H, m), 1.17 (3H, d, J=6.1 Hz), 1.27 (1H, m), 1.45 (1H, m), 1.68 (2H, m), 1.94 (1H, m), 2.09 (1H, m), 2.38 (1H, m), 2.90 (3H, m), 3.11 (1H, d, J=12.9 Hz), 3.68 (2H, m), 3.82 (2H, d, J=6.8 Hz), 3.99 (1H, d, J=12.7 Hz), 6.00 (1H, t, J=5.4 Hz), 6.87 (2H, d, J=9.4 Hz), 7.16 (2H, d, J=8.1 Hz), 7.27 (2H, m), 7.62 (2H, d, J=9.4 Hz). melting point: 116-118° C. (ethyl acetate-isopropyl ether)

EXAMPLE 107

4-benzyloxy-N-(2-{4-[(2-methyl-1-pyrrolidinyl)methyl]phenyl}ethyl)benzamide

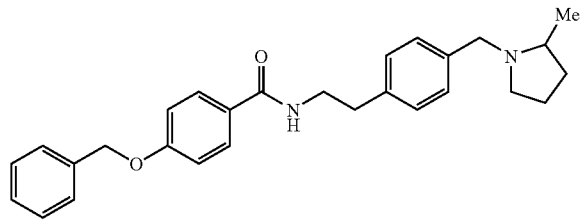

The title compound was obtained by a similar operation as in Example 2 and using 2-{4-[(2-methyl-1-pyrrolidinyl)methyl]phenyl}ethylamine dihydrochloride obtained in Reference Example 11.

$^1$H-NMR (CDCl$_3$) δ: 1.17 (3H, d, J=6.1 Hz), 1.46 (1H, m), 1.66 (2H, m), 1.94 (1H, m), 2.09 (1H, m), 2.38 (1H, m), 2.90 (3H, m), 3.11 (1H, d, J=12.7 Hz), 3.69 (2H, m), 3.99 (1H, d, J=12.9 Hz), 5.09 (2H, s), 6.00 (1H, t, J=6.1 Hz), 6.96 (2H, d, J=9.4 Hz), 7.16 (2H, d, J=8.1 Hz), 7.27 (2H, m), 7.37 (5H, m), 7.63 (2H, m). melting point: 129-131° C. (ethyl acetate-isopropyl ether)

EXAMPLE 108

2-fluoro-4-(3-methylbutoxy)-N-(2-{4-[(2-methyl-1-pyrrolidinyl)methyl]phenyl}ethyl)benzamide

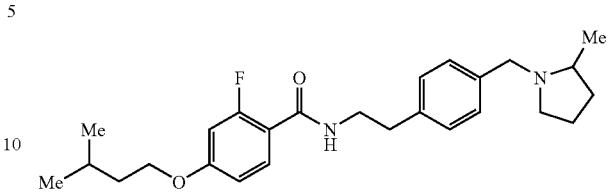

The title compound was obtained by a similar operation as in Example 2 and using 2-{4-[(2-methyl-1-pyrrolidinyl)methyl]phenyl}ethylamine dihydrochloride obtained in Reference Example 11.

$^1$H-NMR (CDCl$_3$) δ: 0.96 (6H, d, J=6.6 Hz), 1.16 (3H, d, J=6.0 Hz), 1.45 (1H, m), 1.65 (2H, m), 1.68 (2H, m), 1.81 (1H, m), 1.94 (1H, m), 2.09 (1H, m), 2.37 (1H, m), 2.89 (3H, m), 3.12 (1H, d, J=12.8 Hz), 3.71 (2H, m), 4.00 (3H, m), 6.56 (1H, dd, J=14.3, 2.5 Hz), 6.68 (1H, m), 6.76 (1H, dd, J=8.9, 2.5 Hz), 7.18 (2H, d, J=8.1 Hz), 7.27 (2H, m), 8.03 (1H, t, J=9.1 Hz). melting point: 70-74° C. (ethyl acetate-isopropyl ether)

EXAMPLE 109

4'-chloro-N-[2-(4-{[(2R,6S)-2,6-dimethyl-1-piperidinyl]methyl}phenyl)ethyl][1,1'-biphenyl]-4-carboxamide

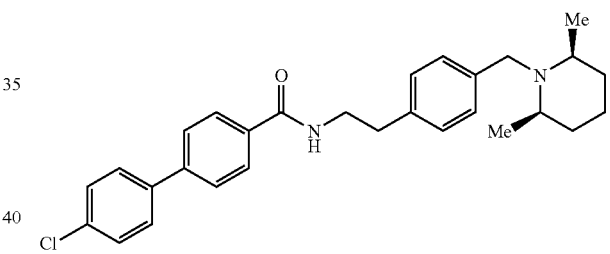

The title compound was obtained by a similar operation as in Example 2 and using 2-(4-{[(2R,6S)-2,6-dimethyl-1-piperidinyl]methyl}phenyl)ethylamine dihydrochloride obtained in Reference Example 8.

$^1$H-NMR (CDCl$_3$) δ: 1.08 (6H, d, J=6.2 Hz), 1.44 (6H, m), 2.49 (2H, m), 2.93 (2H, t, J=6.8 Hz), 3.74 (4H, m) 6.13 (1H, m), 7.17 (2H, d, J=8.1 Hz), 7.35 (2H, m), 7.43 (2H, m), 7.55 (4H, m), 7.75 (2H, d, J=8.5 Hz). melting point: 157-158° C. (ethyl acetate-isopropyl ether)

EXAMPLE 110

4-(2-cyclopropylethoxy)-N-{2-[4-(1-pyrrolidinylmethyl)phenyl]ethyl}benzamide

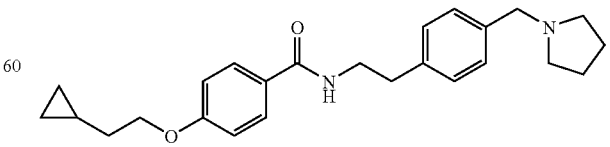

The title compound was obtained by a similar operation as in Example 2 and using 2-[4-(1-pyrrolidinylmethyl)phenyl]ethylamine obtained in Reference Example 4.

¹H-NMR (CDCl₃) δ: 0.12 (2H, m), 0.49 (2H, m), 0.84 (1H, m), 1.68 (2H, q, J=6.7 Hz), 1.78 (4H, m), 2.50 (4H, m), 2.90 (2H, t, J=6.8 Hz), 3.59 (2H, s), 3.69 (2H, m), 4.05 (2H, t, J=6.7 Hz), 6.03 (1H, t, J=5.9 Hz), 6.88 (2H, d, J=9.3 Hz), 7.17 (2H, d, J=8.1 Hz), 7.28 (2H, m), 7.63 (2H, d, J=9.4 Hz). melting point: 129° C. (ethyl acetate-isopropyl ether)

EXAMPLE 111

4-isobutoxy-N-{2-[4-(1-pyrrolidinylmethyl)phenyl]ethyl}benzamide

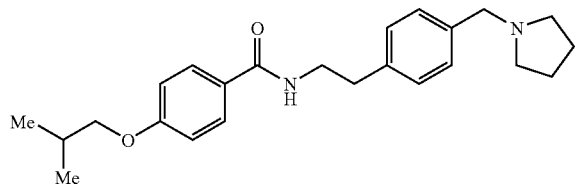

The title compound was obtained by a similar operation as in Example 2 and using 2-[4-(1-pyrrolidinylmethyl)phenyl]ethylamine obtained in Reference Example 4.

¹H-NMR (CDCl₃) δ: 1.02 (6H, d, J=6.6 Hz), 1.78 (4H, m), 2.09 (1H, m), 2.50 (4H, m), 2.90 (2H, t, J=6.8 Hz), 3.59 (2H, s), 3.69 (2H, m), 3.74 (2H, d, J=6.6 Hz), 6.01 (1H, t, J=5.8 Hz), 6.87 (2H, d, J=9.3 Hz), 7.17 (2H, d, J=8.1 Hz), 7.28 (2H, m), 7.62 (2H, m). melting point: 120° C. (ethyl acetate-isopropyl ether)

EXAMPLE 112

4-(3-methylbutoxy)-N-{2-[4-(1-pyrrolidinylmethyl)phenyl]ethyl}benzamide

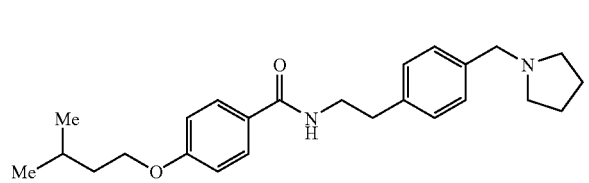

The title compound was obtained by a similar operation as in Example 2 and using 2-[4-(1-pyrrolidinylmethyl)phenyl]ethylamine obtained in Reference Example 4.

¹H-NMR (CDCl₃) δ: 0.96 (6H, d, J=6.6 Hz), 1.68 (2H, q, J=6.9 Hz), 1.81 (5H, m), 2.50 (4H, m), 2.90 (2H, t, J=6.8 Hz), 3.59 (2H, s), 3.69 (2H, m), 4.01 (2H, m), 6.00 (1H, t, J=5.5 Hz), 6.87 (2H, m), 7.17 (2H, d, J=8.1 Hz), 7.28 (2H, m), 7.62 (2H, m). melting point: 106° C. (ethyl acetate-isopropyl ether)

EXAMPLE 113

4-(2-cyclopropylethoxy)-N-{2-[4-(1-piperidinylmethyl)phenyl]ethyl}benzamide

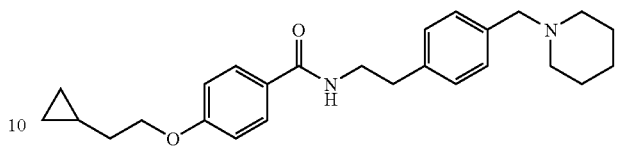

The title compound was obtained by a similar operation as in Example 2 and using 2-[4-(1-piperidinylmethyl)phenyl]ethylamine dihydrochloride obtained in Reference Example 6.

¹H-NMR (CDCl₃) δ: 0.12 (2H, m), 0.49 (2H, m), 0.84 (1H, m), 1.43 (2H, m), 1.57 (4H, m), 1.68 (2H, q, J=6.8 Hz), 2.36 (4H, m), 2.90 (2H, t, J=6.8 Hz), 3.44 (2H, s), 3.69 (2H, m), 4.05 (2H, m), 6.01 (1H, t, J=5.6 Hz), 6.88 (2H, m), 7.16 (2H, d, J=7.8 Hz), 7.26 (2H, m), 7.63 (2H, m). melting point: 143° C. (ethyl acetate-isopropyl ether)

EXAMPLE 114

4-isobutoxy-N-{2-[4-(1-piperidinylmethyl)phenyl]ethyl}benzamide

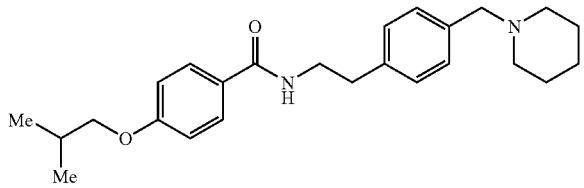

The title compound was obtained by a similar operation as in Example 2 and using 2-[4-(1-piperidinylmethyl)phenyl]ethylamine dihydrochloride obtained in Reference Example 6.

¹H-NMR (CDCl₃) δ: 1.02 (6H, d, J=6.6 Hz), 1.43 (2H, m), 1.57 (4H, m), 2.09 (1H, m), 2.36 (4H, m), 2.90 (2H, t, J=6.8 Hz), 3.44 (2H, s), 3.69 (2H, m), 3.74 (2H, d, J=6.6 Hz), 6.00 (1H, t, J=5.9 Hz), 6.87 (2H, d, J=9.3 Hz), 7.16 (2H, d, J=8.1 Hz), 7.26 (2H, m), 7.62 (2H, m). melting point: 139° C. (ethyl acetate-isopropyl ether)

EXAMPLE 115

4-(3-methylbutoxy)-N-{2-[4-(1-piperidinylmethyl)phenyl]ethyl}benzamide

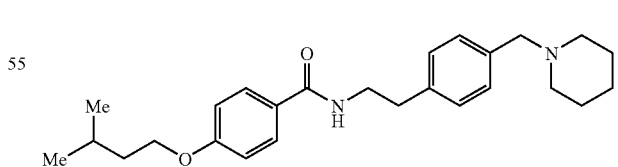

The title compound was obtained by a similar operation as in Example 2 and using 2-[4-(1-piperidinylmethyl)phenyl]ethylamine dihydrochloride obtained in Reference Example 6.

¹H-NMR (CDCl₃) δ: 0.96 (6H, d, J=6.6 Hz), 1.44 (2H, m), 1.57 (4H, m), 1.68 (2H, q, J=6.7 Hz), 1.83 (1H, m), 2.36 (4H, m), 2.90 (2H, t, J=6.8 Hz), 3.44 (2H, s), 3.69 (2H, m), 4.01

(2H, m), 6.00 (1H, t, J=5.8 Hz), 6.87 (2H, d, J=9.3 Hz), 7.16 (2H, d, J=8.1 Hz), 7.26 (2H, m), 7.62 (2H, d, J=9.3 Hz). melting point: 135° C. (ethyl acetate-isopropyl ether)

EXAMPLE 116

4-benzyloxy-N-{2-[4-(1-piperidinylmethyl)phenyl]ethyl}benzamide

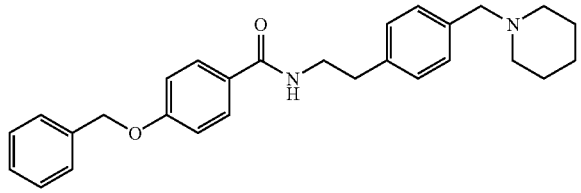

The title compound was obtained by a similar operation as in Example 2 and using 2-[4-(1-piperidinylmethyl)phenyl]ethylamine dihydrochloride obtained in Reference Example 6.

$^1$H-NMR (CDCl$_3$) δ: 1.43 (2H, m), 1.57 (4H, m), 2.36 (4H, m), 2.90 (2H, t, J=6.8 Hz), 3.44 (2H, s), 3.69 (2H, m), 5.09 (2H, s), 6.00 (1H, m), 6.96 (2H, d, J=9.3 Hz), 7.16 (2H, d, J=8.3 Hz), 7.26 (2H, m), 7.36 (5H, m), 7.63 (2H, d, J=9.4 Hz). melting point: 137-138° C. (ethyl acetate-isopropyl ether)

EXAMPLE 117

4-(cyclopropylmethoxy)-N-{2-[4-(1-piperidinylmethyl)phenyl]ethyl}benzamide

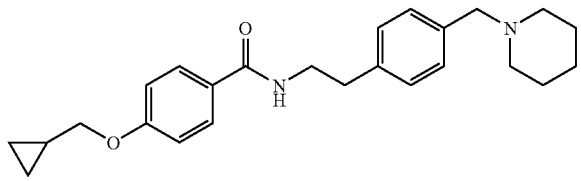

The title compound was obtained by a similar operation as in Example 2 and using 2-[4-(1-piperidinylmethyl)phenyl]ethylamine dihydrochloride obtained in Reference Example 6.

$^1$H-NMR (CDCl$_3$) δ: 0.36 (2H, m), 0.66 (2H, m), 1.27 (1H, m), 1.43 (2H, m), 1.57 (4H, m), 2.37 (4H, m), 2.90 (2H, t, J=6.7 Hz), 3.44 (2H, s), 3.69 (2H, m), 3.82 (2H, d, J=6.8 Hz), 6.00 (1H, t, J=6.0 Hz), 6.88 (2H, d, J=9.3 Hz), 7.16 (2H, d, J=8.1 Hz), 7.26 (2H, m), 7.62 (2H, d, J=9.3 Hz). melting point: 154° C. (ethyl acetate-isopropyl ether)

EXAMPLE 118

4-(2-cyclopropylethoxy)-N-(2-{4-[(2-methyl-1-pyrrolidinyl)methyl]phenyl}ethyl)benzamide

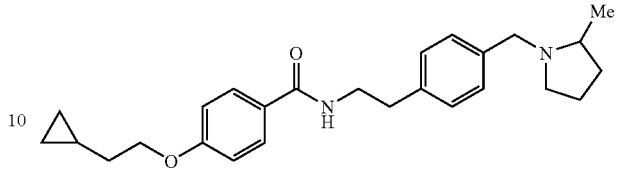

The title compound was obtained by a similar operation as in Example 2 and using 2-{4-[(2-methyl-1-pyrrolidinyl)methyl]phenyl}ethylamine dihydrochloride obtained in Reference Example 11.

$^1$H-NMR (CDCl$_3$) δ: 0.12 (2H, m), 0.49 (2H, m), 0.85 (1H, m), 1.17 (3H, d, J=6.1 Hz), 1.45 (1H, m), 1.66 (4H, m), 1.94 (1H, m), 2.09 (1H, q, J=9.0 Hz), 2.38 (1H, m), 2.90 (3H, m), 3.11 (1H, d, J=12.9 Hz), 3.69 (2H, m), 3.99 (1H, d, J=12.7 Hz), 4.06 (2H, m), 5.99 (1H, m), 6.88 (2H, m), 7.17 (2H, d, J=7.8 Hz), 7.27 (2H, m), 7.62 (2H, m). melting point: 115-116° C. (ethyl acetate-isopropyl ether)

EXAMPLE 119

4-isobutoxy-N-(2-{4-[(2-methyl-1-pyrrolidinyl)methyl]phenyl}ethyl)benzamide

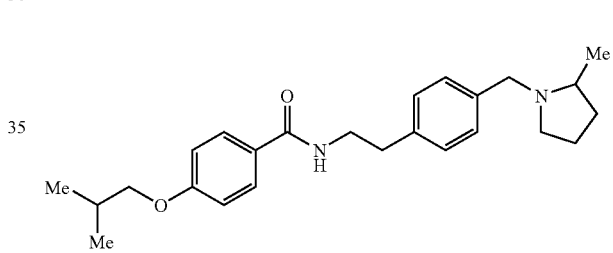

The title compound was obtained by a similar operation as in Example 2 and using 2-{4-[(2-methyl-1-pyrrolidinyl)methyl]phenyl}ethylamine dihydrochloride obtained in Reference Example 11.

$^1$H-NMR (CDCl$_3$) δ: 1.02 (6H, d, J=6.6 Hz), 1.16 (3H, d, J=5.9 Hz), 1.46 (1H, m), 1.66 (2H, m), 1.94 (1H, m), 2.09 (2H, m), 2.38 (1H, m), 2.90 (3H, m), 3.11 (1H, d, J=12.9 Hz), 3.69 (2H, m), 3.74 (2H, d, J=6.6 Hz), 3.99 (1H, d, J=12.7 Hz), 5.99 (1H, t, J=5.0 Hz), 6.87 (2H, d, J=9.3 Hz), 7.16 (2H, d, J=8.3 Hz), 7.27 (2H, m), 7.62 (2H, m). melting point: 105° C. (ethyl acetate-isopropyl ether)

EXAMPLE 120

4-(3-methylbutoxy)-N-(2-{4-[(2-methyl-1-pyrrolidinyl)methyl]phenyl}ethyl)benzamide

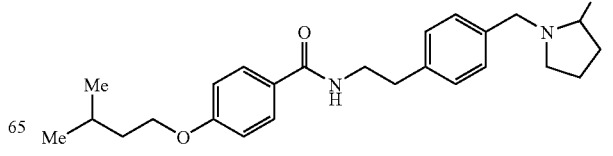

The title compound was obtained by a similar operation as in Example 2 and using 2-{4-[(2-methyl-1-pyrrolidinyl)methyl]phenyl}ethylamine dihydrochloride obtained in Reference Example 11.

$^1$H-NMR (CDCl$_3$) δ: 0.96 (6H, d, J=6.6 Hz), 1.17 (3H, d, J=6.0 Hz), 1.45 (1H, m), 1.69 (4H, m), 1.83 (1H, m), 1.94 (1H, m), 2.10 (1H, q, J=9.0 Hz), 2.37 (1H, m), 2.90 (3H, m), 3.12 (1H, d, J=12.6 Hz), 3.70 (2H, m), 4.00 (3H, m), 6.00 (1H, t, J=5.6 Hz), 6.88 (2H, m), 7.17 (2H, d, J=8.1 Hz), 7.28 (2H, m), 7.63 (2H, m). melting point: 91-93° C. (ethyl acetate-isopropyl ether)

EXAMPLE 121

4-benzyloxy-N-(2-{4-[(4-methyl-1-piperazinyl)methyl]phenyl}ethyl)benzamide

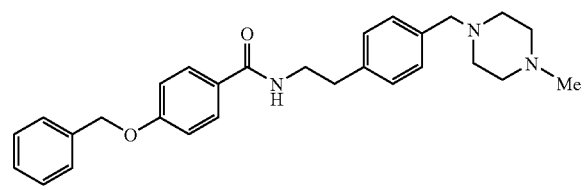

The title compound was obtained by a similar operation as in Example 2 and using 2-{4-[(4-methyl-1-piperazinyl)methyl]phenyl}ethylamine trihydrochloride obtained in Reference Example 7.

$^1$H-NMR (CDCl$_3$) δ: 2.28 (3H, s), 2.46 (8H, m), 2.90 (2H, t, J=6.8 Hz), 3.49 (2H, s), 3.69 (2H, m), 5.10 (2H, s), 6.02 (1H, t, J=5.6 Hz), 6.97 (2H, d, J=9.3 Hz), 7.18 (2H, d, J=7.9 Hz), 7.27 (2H, m), 7.38 (5H, m), 7.65 (2H, m). melting point: 143-144° C. (ethyl acetate-isopropyl ether)

EXAMPLE 122

4-cyclopropylmethoxy-N-(2-{4-[(4-methyl-1-piperazinyl)methyl]phenyl}ethyl)benzamide

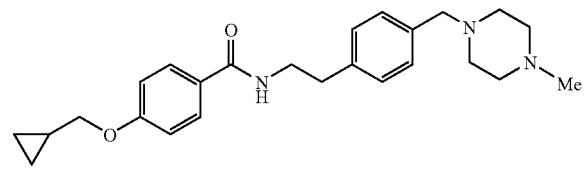

The title compound was obtained by a similar operation as in Example 2 and using 2-{4-[(4-methyl-1-piperazinyl)methyl]phenyl}ethylamine trihydrochloride obtained in Reference Example 7.

$^1$H-NMR (CDCl$_3$) δ: 0.36 (2H, m), 0.66 (2H, m), 1.28 (1H, m), 2.28 (3H, s), 2.46 (8H, m), 2.90 (2H, t, J=6.8 Hz), 3.49 (2H, s), 3.69 (2H, m), 3.83 (2H, d, J=6.7 Hz), 6.02 (1H, t, J=5.5 Hz), 6.89 (2H, m), 7.18 (2H, d, J=7.9 Hz), 7.27 (2H, m), 7.64 (2H, d, J=9.4 Hz). melting point: 162° C. (ethyl acetate-isopropyl ether)

EXAMPLE 123

4-(2-cyclopropylethoxy)-N-(2-{4-[(4-methyl-1-piperazinyl)methyl]phenyl}ethyl)benzamide

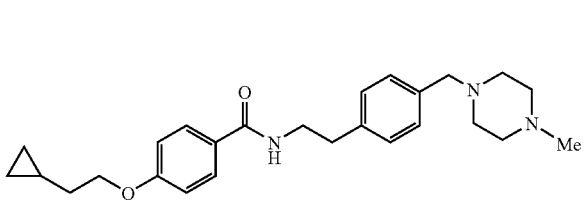

The title compound was obtained by a similar operation as in Example 2 and using 2-{4-[(4-methyl-1-piperazinyl)methyl]phenyl}ethylamine trihydrochloride obtained in Reference Example 7.

$^1$H-NMR (CDCl$_3$) δ: 0.12 (2H, m), 0.49 (2H, m), 0.84 (1H, m), 1.69 (2H, q, J=6.8 Hz), 2.29 (3H, s), 2.46 (8H, m), 2.91 (2H, t, J=6.8 Hz), 3.50 (2H, s), 3.69 (2H, m), 4.06 (2H, t, J=6.8 Hz), 6.03 (1H, t, J=5.6 Hz), 6.90 (2H, d, J=9.3 Hz), 7.18 (2H, d, J=7.9 Hz), 7.28 (2H, m), 7.64 (2H, m). melting point: 132-133° C. (ethyl acetate-isopropyl ether)

EXAMPLE 124

4-isobutoxy-N-(2-{4-[(4-methyl-1-piperazinyl)methyl]phenyl}ethyl)benzamide

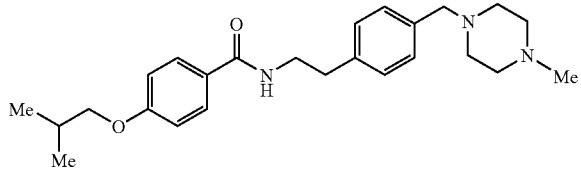

The title compound was obtained by a similar operation as in Example 2 and using 2-{4-[(4-methyl-1-piperazinyl)methyl]phenyl}ethylamine trihydrochloride obtained in Reference Example 7.

$^1$H-NMR (CDCl$_3$) δ: 1.03 (6H, d, J=6.8 Hz), 2.09 (1H, m), 2.28 (3H, s), 2.47 (8H, m), 2.91 (2H, t, J=7.0 Hz), 3.49 (2H, s), 3.69 (2H, m), 3.74 (2H, d, J=6.4 Hz), 6.03 (1H, t, J=5.5 Hz), 6.88 (2H, d, J=9.3 Hz), 7.18 (2H, d, J=7.9 Hz), 7.28 (2H, m), 7.64 (2H, m). melting point: 130° C. (ethyl acetate-isopropyl ether)

EXAMPLE 125

4-(3-methylbutoxy)-N-(2-{4-[(4-methyl-1-piperazinyl)methyl]phenyl}ethyl)benzamide

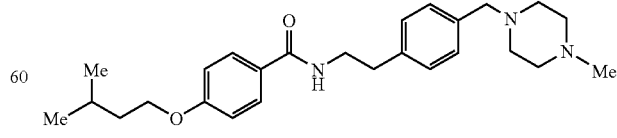

The title compound was obtained by a similar operation as in Example 2 and using 2-{4-[(4-methyl-1-piperazinyl)methyl]phenyl}ethylamine trihydrochloride obtained in Reference Example 7.

¹H-NMR (CDCl₃) δ: 0.96 (6H, d, J=6.4 Hz), 1.68 (2H, q, J=6.7 Hz), 1.83 (1H, m), 2.28 (3H, s), 2.46 (8H, m), 2.90 (2H, t, J=7.0 Hz), 3.49 (2H, s), 3.69 (2H, m), 4.01 (2H, m), 6.02 (1H, t, J=5.5 Hz), 6.88 (2H, m), 7.18 (2H, d, J=7.9 Hz), 7.28 (2H, m), 7.64 (2H, m). melting point: 117° C. (ethyl acetate-isopropyl ether)

EXAMPLE 126

N-{2-[4-(1-azepanylmethyl)phenyl]ethyl}-4-(benzyloxy)benzamide

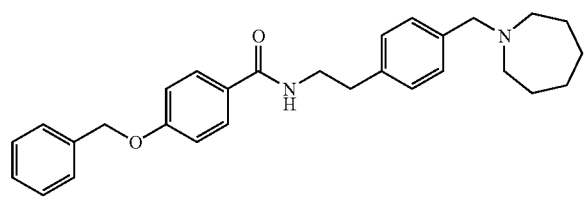

The title compound was obtained by a similar operation as in Example 2 and using 2-[4-(1-azepanylmethyl)phenyl]ethylamine dihydrochloride obtained in Reference Example 9.

¹H-NMR (CDCl₃) δ: 1.62 (8H, m), 2.62 (4H, m), 2.90 (2H, t, J=6.9 Hz), 3.62 (2H, s), 3.70 (2H, m), 5.10 (2H, s), 6.01 (1H, t, J=5.5 Hz), 6.97 (2H, m), 7.17 (2H, d, J=8.1 Hz), 7.30 (2H, d, J=8.1 Hz), 7.38 (5H, m), 7.64 (2H, m). melting point: 116-120° C. (ethyl acetate-isopropyl ether)

EXAMPLE 127

N-{2-[4-(1-azepanylmethyl)phenyl]ethyl}-4-(cyclopropylmethoxy)benzamide

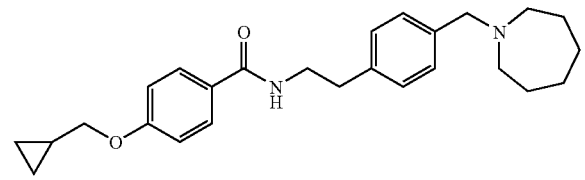

The title compound was obtained by a similar operation as in Example 2 and using 2-[4-(1-azepanylmethyl)phenyl]ethylamine dihydrochloride obtained in Reference Example 9.

¹H-NMR (CDCl₃) δ: 0.35 (2H, m), 0.66 (2H, m), 1.27 (1H, m), 1.62 (8H, m), 2.62 (4H, m), 2.90 (2H, t, J=6.9 Hz), 3.62 (2H, s), 3.69 (2H, m), 3.83 (2H, m), 6.01 (1H, t, J=6.0 Hz), 6.89 (2H, m), 7.17 (2H, d, J=7.9 Hz), 7.30 (2H, m), 7.63 (2H, m). melting point: 122-123° C. (ethyl acetate-isopropyl ether)

EXAMPLE 128

N-{2-[4-(1-azepanylmethyl)phenyl]ethyl}-4-(2-cyclopropylethoxy)benzamide

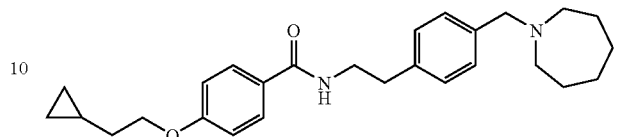

The title compound was obtained by a similar operation as in Example 2 and using 2-[4-(1-azepanylmethyl)phenyl]ethylamine dihydrochloride obtained in Reference Example 9.

¹H-NMR (CDCl₃) δ: 0.12 (2H, m), 0.49 (2H, m), 0.84 (1H, m), 1.62 (8H, m), 1.69 (2H, q, J=6.8 Hz), 2.63 (4H, m), 2.91 (2H, t, J=6.8 Hz), 3.62 (2H, s), 3.70 (2H, m), 4.06 (2H, t, J=6.8 Hz), 6.03 (1H, t, J=5.4 Hz), 6.89 (2H, m), 7.17 (2H, d, J=8.1 Hz), 7.30 (2H, m), 7.63 (2H, m). melting point: 112° C. (ethyl acetate-isopropyl ether)

EXAMPLE 129

N-{2-[4-(1-azepanylmethyl)phenyl]ethyl}-4-(isobutoxy)benzamide

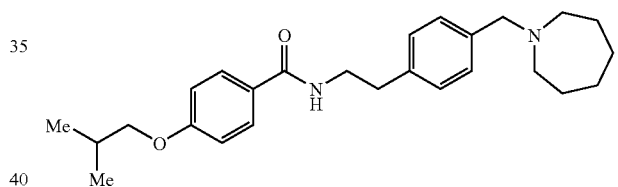

The title compound was obtained by a similar operation as in Example 2 and using 2-[4-(1-azepanylmethyl)phenyl]ethylamine dihydrochloride obtained in Reference Example 9.

¹H-NMR (CDCl₃) δ: 1.02 (6H, d, J=6.8 Hz), 1.62 (8H, m), 2.09 (1H, m), 2.63 (4H, m), 2.90 (2H, t, J=6.9 Hz), 3.62 (2H, s), 3.70 (2H, m), 3.74 (2H, d, J=6.6 Hz), 6.01 (1H, t, J=5.5 Hz), 6.88 (2H, m), 7.17 (2H, d, J=7.9 Hz), 7.30 (2H, m), 7.63 (2H, m). melting point: 104-106° C. (ethyl acetate-isopropyl ether)

EXAMPLE 130

N-{2-[4-(1-azepanylmethyl)phenyl]ethyl}-4-(3-methylbutoxy)benzamide

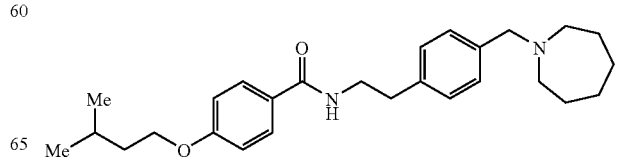

The title compound was obtained by a similar operation as in Example 2 and using 2-[4-(1-azepanylmethyl)phenyl]ethylamine dihydrochloride obtained in Reference Example 9.

$^1$H-NMR (CDCl$_3$) δ: 0.96 (6H, d, J=6.6 Hz), 1.62 (8H, m), 1.68 (2H, m), 1.83 (1H, m), 2.63 (4H, m), 2.90 (2H, t, J=6.9 Hz), 3.62 (2H, m), 3.69 (2H, m), 4.01 (2H, t, J=7.0 Hz), 6.03 (1H, t, J=5.6 Hz), 6.88 (2H, m), 7.17 (2H, d, J=8.1 Hz), 7.30 (2H, m), 7.63 (2H, m). melting point: 107-108° C. (ethyl acetate-isopropyl ether)

EXAMPLE 131

4-benzyloxy-N-[2-(4-{[(2R,6S)-2,6-dimethyl-1-piperidinyl]methyl}phenyl)ethyl]benzamide

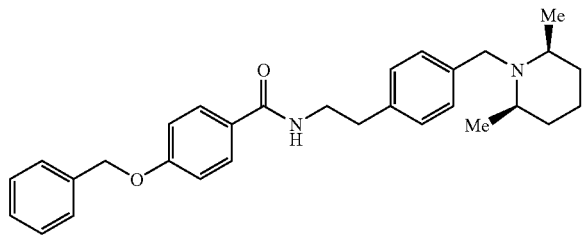

The title compound was obtained by a similar operation as in Example 2 and using 2-(4-{[(2R,6S)-2,6-dimethyl-1-piperidinyl]methyl}phenyl)ethylamine dihydrochloride obtained in Reference Example 8.

$^1$H-NMR (CDCl$_3$) δ: 1.08 (6H, d, J=6.2 Hz), 1.49 (6H, m), 2.48 (2H, m), 2.90 (2H, t, J=6.9 Hz), 3.70 (2H, q, J=6.7 Hz), 3.80 (2H, s), 5.10 (2H, s), 6.00 (1H, t, J=5.0 Hz), 6.96 (2H, d, J=8.7 Hz), 7.15 (2H, d, J=8.1 Hz), 7.37 (7H, m), 7.64 (2H, d, J=8.7 Hz). melting point: 124° C. (ethyl acetate-isopropyl ether)

EXAMPLE 132

4-cyclopropylmethoxy-N-[2-(4-{[(2R,6S)-2,6-dimethyl-1-piperidinyl]methyl}phenyl)ethyl]benzamide

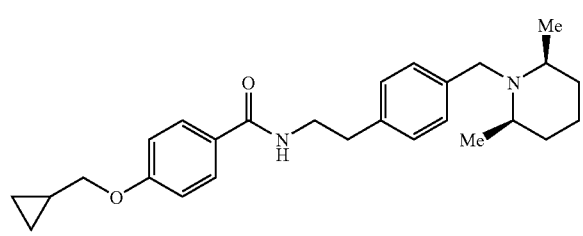

The title compound was obtained by a similar operation as in Example 2 and using 2-(4-{[(2R,6S)-2,6-dimethyl-1-piperidinyl]methyl}phenyl)ethylamine dihydrochloride obtained in Reference Example 8.

$^1$H-NMR (CDCl$_3$) δ: 0.36 (2H, m), 0.66 (2H, m), 1.08 (6H, d, J=6.2 Hz), 1.28 (4H, m), 1.60 (3H, m), 2.49 (2H, m), 2.90 (2H, t, J=6.8 Hz), 3.69 (2H, m), 3.79 (2H, s), 3.83 (2H, m), 6.01 (1H, t, J=4.52 Hz), 6.88 (2H, d, J=8.85 Hz), 7.15 (2H, d, J=8.1 Hz), 7.33 (2H, d, J=7.9 Hz), 7.63 (2H, d, J=8.85 Hz). melting point: 141-142° C. (ethyl acetate-isopropyl ether)

EXAMPLE 133

4-(2-cyclopropylethoxy)-N-[2-(4-{[(2R,6S)-2,6-dimethyl-1-piperidinyl]methyl}phenyl)ethyl]benzamide

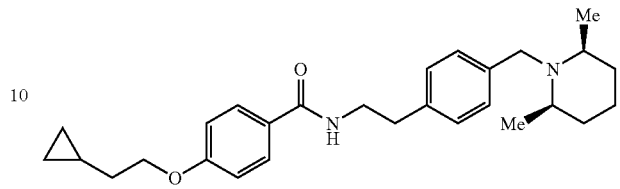

The title compound was obtained by a similar operation as in Example 2 and using 2-(4-{[(2R,6S)-2,6-dimethyl-1-piperidinyl]methyl}phenyl)ethylamine dihydrochloride obtained in Reference Example 8.

$^1$H-NMR (CDCl$_3$) δ: 0.12 (2H, m), 0.49 (2H, m), 0.85 (1H, m), 1.08 (6H, d, J=6.2 Hz), 1.31 (3H, m), 1.58 (3H, m), 1.69 (2H, q, J=6.8 Hz), 2.48 (2H, m), 2.90 (2H, t, J=6.9 Hz), 3.70 (2H, m), 3.80 (2H, s), 4.06 (2H, t, J=6.8 Hz), 6.02 (1H, t, J=5.3 Hz), 6.89 (2H, m), 7.16 (2H, d, J=8.1 Hz), 7.34 (2H, d, J=8.3 Hz), 7.63 (2H, m). melting point: 99-102° C. (ethyl acetate-isopropyl ether)

EXAMPLE 134

N-[2-(4-{[(2R,6S)-2,6-dimethyl-1-piperidinyl]methyl}phenyl)ethyl]-4-(isopentyloxy)benzamide

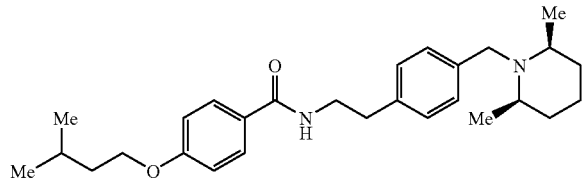

The title compound was obtained by a similar operation as in Example 2 and using 2-(4-{[(2R,6S)-2,6-dimethyl-1-piperidinyl]methyl}phenyl)ethylamine dihydrochloride obtained in Reference Example 8.

$^1$H-NMR (CDCl$_3$) δ: 0.96 (6H, d, J=6.6 Hz), 1.08 (6H, d, J=6.2 Hz), 1.29 (3H, m), 1.58 (3H, m), 1.68 (2H, q, J=6.7 Hz), 1.82 (1H, m), 2.49 (2H, m), 2.90 (2H, t, J=6.9 Hz), 3.69 (2H, m), 3.80 (2H, s), 4.01 (2H, t, J=6.7 Hz), 6.02 (1H, t, J=5.4 Hz), 6.88 (2H, m), 7.15 (2H, d, J=8.1 Hz), 7.34 (2H, d, J=8.1 Hz), 7.63 (2H, m). melting point: 108° C. (ethyl acetate-isopropyl ether)

EXAMPLE 135

4'-chloro-N-(2-{4-[2-(diethylamino)ethoxy]phenyl}ethyl)[1,1'-biphenyl]-4-carboxamide

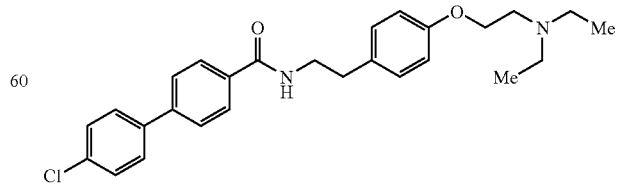

To a solution of 4'-chloro-N-[2-(4-methoxyphenyl)ethyl][1,1'-biphenyl]-4-carboxamide (700 mg, 1.91 mmol)

obtained in Reference Example 22 in dichloromethane (10 ml) was added dropwise 1.0 mol/l solution (4.21 ml, 4.21 mmol) of boron tribromide in dichloroethane at 0° C., and the mixture was stirred at room temperature for 15 hrs. Water was added to the reaction mixture, and the mixture was extracted with ethyl acetate, and the extract was dried over anhydrous sodium sulfate. The solvent was concentrated under reduced pressure to give a demethylated compound (620 mg). A solution of 4'-chloro-N-[2-(4-hydroxyphenyl)ethyl][1,1'-biphenyl]-4-carboxamide (620 mg), N-(2-chloroethyl)-N,N-diethylamine hydrochloride (364 mg, 2.11 mmol) and potassium carbonate (876 mg, 6.34 mmol) in dimethylformamide (10 ml) was stirred at room temperature for 6 hrs and at 100° C. for 4 days. Ethyl acetate was added to the reaction mixture, and the mixture was washed with 1N aqueous sodium hydroxide solution and brine, and dried over anhydrous sodium sulfate. The solvent was concentrated under reduced pressure, and the obtained residue was purified by NH-silica column chromatography (developing solvent; chloroform:ethyl acetate:hexane=1:1:2), and powderized with isopropyl ether to give the title compound (318 mg).

$^1$H-NMR (CDCl$_3$) δ: 1.07 (6H, t, J=7.2 Hz), 2.64 (4H, q, J=7.2 Hz), 2.88 (4H, m), 3.71 (2H, m), 4.04 (2H, t, J=6.5 Hz), 6.12 (1H, t, J=6.1 Hz), 6.88 (2H, d, J=9.1 Hz), 7.15 (2H, m), 7.43 (2H, d, J=8.8 Hz), 7.53 (2H, d, J=8.9Hz), 7.59 (2H, d, J=8.6 Hz), 7.76 (2H, d, J=8.5 Hz). melting point: 178-179° C. (ethyl acetate-isopropyl ether)

EXAMPLE 136

4-bromo-N-{2-[4-(1-methyl-2-pyrrolidinyl)phenyl]ethyl}benzamide

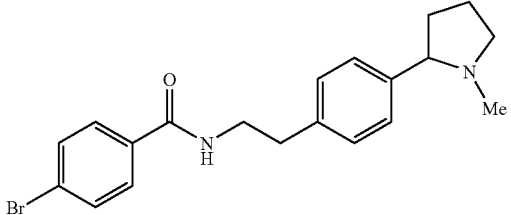

A solution of 4-bromo-N-{2-[4-(cyclopropylcarbonyl)phenyl]ethyl}benzamide (3.00 g, 8.06 mmol) obtained in Reference Example 24 and magnesium chloride (76.7 mg, 0.806 mmol) in methylformamide (2.83 ml, 48.4 mmol) was stirred at 200° C. for 1 day. Aqueous potassium carbonate solution was added to the reaction mixture. The mixture was extracted with ethyl acetate, and the extract was washed with saturated brine and dried over anhydrous sodium sulfate. The solvent was concentrated under reduced pressure, and the obtained residue was purified by NH-silica gel column chromatography (developing solvent; ethyl acetate), and powderized with isopropyl ether to give the title compound (1.86 g).

$^1$H-NMR (DMSO-d$_6$) δ: 1.57 (1H, m), 1.78 (2H, m), 2.04 (3H, s), 2.08-2.24 (2H, m), 2.81 (2H, m), 2.98 (1H, m), 3.12 (1H, m), 3.45 (2H, m), 7.16 (2H, d, J=8.4 Hz), 7.22 (2H, d, J=8.4 Hz), 7.66 (2H, d, J=8.7 Hz), 7.76 (2H, d, J=8.7 Hz), 8.65 (1H, t, J=5.7 Hz). melting point: 133-134° C. (ethyl acetate-isopropyl ether)

EXAMPLE 137

4'-chloro-N-{2-[4-(1-methyl-2-pyrrolidinyl)phenyl]ethyl}[1,1'-biphenyl]-4-carboxamide

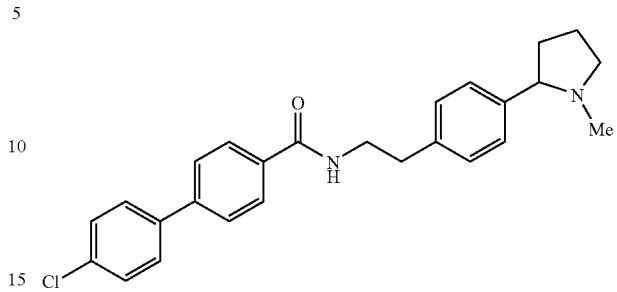

The title compound was obtained by a similar operation as in Example 6 and using 4-bromo-N-{2-[4-(1-methyl-2-pyrrolidinyl)phenyl]ethyl}benzamide obtained in Example 136.

$^1$H-NMR (DMSO-d$_6$) δ: 1.57 (1H, m), 1.78 (2H, m), 2.04 (3H, s), 2.09-2.24 (2H, m), 2.84 (2H, m), 2.99 (1H, m), 3.13 (1H, m), 3.49 (2H, m), 7.23 (4H, m), 7.55 (2H, d, J=8.7 Hz), 7.77 (4H, m), 7.93 (2H, d, J=8.4 Hz), 8.68 (1H, t, J=5.4 Hz). melting point: 169-171° C. (ethyl acetate-isopropyl ether) FABMS (pos) 419 [M+H]$^+$

EXAMPLE 138

4-cyclopropylmethoxy-N-{2-[4-(1-methyl-2-pyrrolidinyl)phenyl]ethyl}benzamide

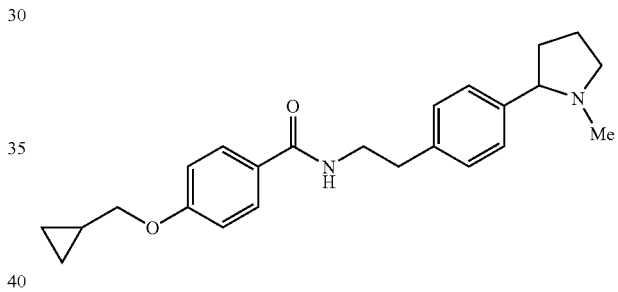

The title compound was obtained by a similar operation as in Example 2 and using 2-[4-(1-methyl-2-pyrrolidinyl)phenyl]ethylamine obtained in Reference Example 25.

$^1$H-NMR (DMSO-d$_6$) δ: 0.33 (2H, m), 0.57 (2H, m), 1.23 (1H, m), 1.57 (1H, m), 1.69-1.85 (2H, m), 2.04 (3H, s), 2.08-2.24 (2H, m), 2.80 (2H, m), 2.99 (1H, m), 3.13 (1H, m), 3.44 (2H, m), 3.86 (2H, d, J=6.9 Hz), 6.97 (2H, d, J=8.7 Hz), 7.17 (2H, d, J=8.4 Hz), 7.24 (2H, d, J=8.4 Hz), 7.79 (2H, d, J=8.7 Hz), 8.43 (1H, t, J=5.4 Hz). melting point: 143-145° C. (ethyl acetate-isopropyl ether) FABMS (pos) 379 [M+H]$^+$

EXAMPLE 139

4'-methoxy-N-{2-[4-(1-methyl-2-pyrrolidinyl)phenyl]ethyl}[1,1'-biphenyl]-4-carboxamide

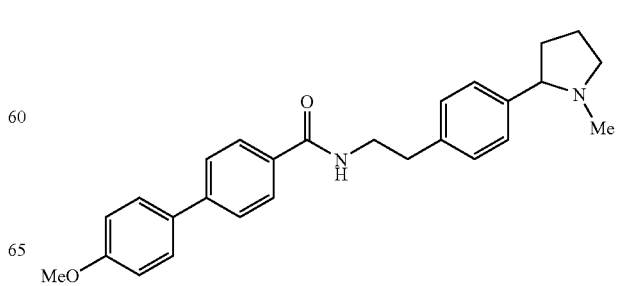

The title compound was obtained by a similar operation as in Example 6 and using 4-bromo-N-{2-[4-(1-methyl-2-pyrrolidinyl)phenyl]ethyl}benzamide obtained in Example 136.

¹H-NMR (DMSO-d₆) δ: 1.55 (1H, m), 1.76 (2H, m), 2.05 (3H, s), 2.09-2.22 (2H, m), 2.84 (2H, m), 3.00 (1H, m), 3.13 (1H, m), 3.49 (2H, m), 3.81 (3H, s), 7.05 (2H, d, J=8.7 Hz), 7.18-7.27 (4H, m), 7.67-7.73 (4H, m), 7.89 (2H, d, J=8.4 Hz), 8.61 (1H, t, J=5.7 Hz). melting point: 165-167° C. (ethyl acetate-isopropyl ether) FABMS (pos) 415 [M+H]⁺

EXAMPLE 140

4-cyclopropylmethoxy-2-fluoro-N-{2-[4-(1-pyrrolidinylmethyl)phenyl]ethyl}benzamide

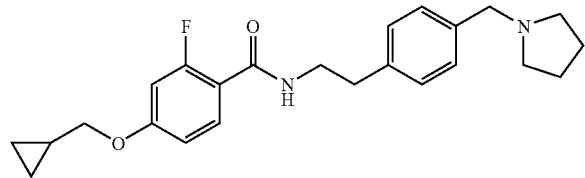

The title compound was obtained by a similar operation as in Example 2 and using 2-[4-(1-pyrrolidinylmethyl)phenyl]ethylamine obtained in Reference Example 4.

¹H-NMR (DMSO-d₆) δ: 0.31 (2H, m), 0.55 (2H, m), 1.20 (1H, m), 1.64 (4H, m), 2.38 (4H, m), 2.77 (2H, m), 3.42 (2H, m), 3.50 (2H, s), 3.85 (2H, d, J=7.2 Hz), 6.78-6.86 (2H, m), 7.15 (2H, d, J=8.4 Hz), 7.20 (2H, d, J=8.4 Hz), 7.55 (1H, t, J=9.0 Hz), 8.07 (1H, m). melting point: 90-92° C. (ethyl acetate-isopropyl ether) FABMS (pos) 397 [M+H]⁺

EXAMPLE 141

4-(2-cyclopropylethoxy)-2-fluoro-N-{2-[4-(1-pyrrolidinylmethyl)phenyl]ethyl}benzamide

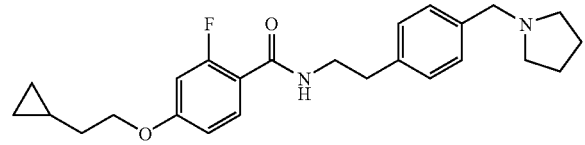

The title compound was obtained by a similar operation as in Example 2 and using 2-[4-(1-pyrrolidinylmethyl)phenyl]ethylamine obtained in Reference Example 4.

¹H-NMR (DMSO-d₆) δ: 0.12 (2H, m), 0.42 (2H, m), 0.80 (1H, m), 1.60 (2H, m), 1.65 (4H, m), 2.39 (4H, m), 2.78 (2H, m), 3.42 (2H, m), 3.51 (2H, s), 4.06 (2H, d, J=6.6 Hz), 6.80-6.88 (2H, m), 7.16 (2H, d, J=8.4 Hz), 7.21 (2H, d, J=8.4 Hz), 7.56 (1H, t, J=9.0 Hz), 8.08 (1H, m). melting point: 66-68° C. (ethyl acetate-isopropyl ether) FABMS (pos) 411 [M+H]⁺

EXAMPLE 142

4'-chloro-N-(2-{4-[(2-methyl-4,5-dihydro-1H-imidazol-1-yl)methyl]phenyl}ethyl)[1,1'-biphenyl]-4-carboxamide

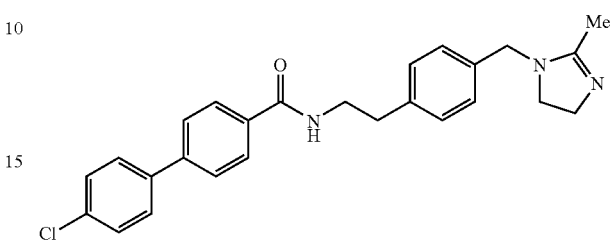

tert-Butyl (2-{4-[(2-methyl-4,5-dihydro-1H-imidazol-1-yl)methyl]phenyl}ethyl)carbamate was obtained by a similar operation as in Reference Example 3 and using methyl 4-{2-[(tert-butoxycarbonyl)amino]ethyl}benzoate obtained in Reference Example 2. (2-{4-[(2-Methyl-4,5-dihydro-1H-imidazol-1-yl)methyl]phenyl}ethyl)amine hydrochloride was obtained by a similar operation as in Reference Example 4 and using this compound. The title compound was obtained by a similar operation as in Example 2 and using this compound.

¹H-NMR (CDCl₃) δ: 2.08 (3H, s), 2.96 (2H, t, J=7.1 Hz), 3.28 (2H, t, J=9.9 Hz), 3.68-3.77 (4H, m), 4.31 (2H, s), 6.30 (1H, m), 7.19 (2H, d, J=8.4 Hz), 7.25 (2H, d, J=8.4 Hz), 7.43 (2H, d, J=8.4 Hz), 7.53 (2H, d, J=8.4 Hz), 7.60 (2H, d, J=8.4 Hz), 7.79 (2H, d, J=8.4 Hz), 8.02 (1H, s). melting point: 170-172° C. (isopropyl ether)

EXAMPLE 143

4-(3-methylbutoxy)-N-(2-{4-[(2-methyl-1-pyrrolidinyl)methyl]phenyl}ethyl)benzamide

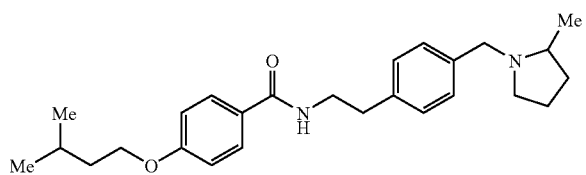

The title compound was obtained by a similar operation as in Example 2 and using 2-{4-[(2-methyl-1-pyrrolidinyl)methyl]phenyl}ethylamine dihydrochloride obtained in Reference Example 11.

¹H-NMR (CDCl₃) δ: 0.96 (6H, d, J=6.6 Hz), 1.17 (3H, d, J=6.1 Hz), 1.38-1.53 (2H, m), 1.60-1.68 (1H, m), 1.64-1.72 (2H, m), 1.78-1.98 (2H, m), 2.09 (1H, q, J=9.0 Hz), 2.33-2.41 (1H, m), 2.86-2.94 (3H, m), 3.11 (1H, d, J=12.7 Hz), 3.65-3.73 (2H, m), 3.96-4.04 (3H, m), 5.99 (1H, s), 6.84-6.90 (2H, m), 7.14-7.19 (2H, m), 7.25-7.30 2H, m), 7.59-7.65 (2H, m). melting point: 91-93° C. (ethyl acetate-isopropyl ether)

EXAMPLE 144

4-cyclopropylmethoxy-2-fluoro-N-(2-{4-[1-(1-piperidinyl)ethyl]phenyl}ethyl)benzamide

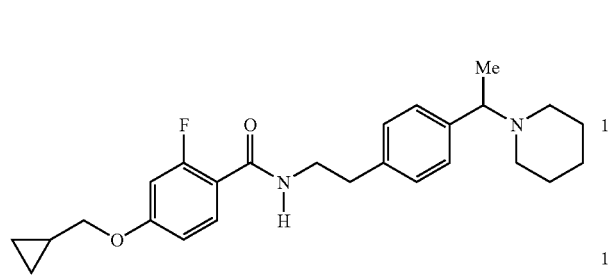

To a solution of 4-(cyclopropylmethoxy)-2-fluorobenzoic acid (242 mg, 1.15 mmol) and dimethylformamide (1 drop) in tetrahydrofuran (3 ml) was added dropwise oxalyl dichloride (113 μl, 1.30 mmol) at 0° C., and the mixture was stirred at room temperature for 30 min. The reaction mixture was concentrated under reduced pressure and the obtained residue was dissolved in tetrahydrofuran (3 ml). The solution was added dropwise to a solution of 2-{4-[1-(1-piperidinyl)ethyl]phenyl}ethylamine (310 mg, 1.02 mmol) obtained in Reference Example 15 and triethylamine (558 μl, 4.00 mmol) in tetrahydrofuran (2 ml) at 0° C., and the mixture was stirred at room temperature for 3 hrs. Water was added to the reaction mixture. The mixture was extracted with ethyl acetate, and the extract was washed with saturated brine, and dried over anhydrous sodium sulfate. The solvent was concentrated under reduced pressure, and the obtained residue was purified by NH-silica gel column chromatography (developing solvent; ethyl acetate) to give the title compound (200 mg).

$^1$H-NMR (CDCl$_3$) δ: 0.36 (2H, m), 0.66 (2H, m), 1.24 (1H, m), 1.34 (2H, m), 1.36 (3H, d, J=6.6 Hz), 1.55 (4H, m), 2.35 (4H, m), 2.90 (2H, t, J=6.0 Hz), 3.39 (1H, q, J=6.9 Hz), 3.71 (2H, q, J=6.9 Hz), 3.82 (2H, d, J=6.9 Hz), 6.53 (1H, d, J=14.4 Hz), 6.54 (1H, m),), 6.76 (1H, d, J=8.7 Hz), 7.16 (2H, d, J=8.1 Hz), 7.24 (2H, d, J=8.1 Hz), 8.03 (1H, t, J=9.3 Hz).

EXAMPLE 145

4-(2-cyclopropylethoxy)-2-fluoro-N-(2-{4-[1-(1-piperidinyl)ethyl]phenyl}ethyl)benzamide

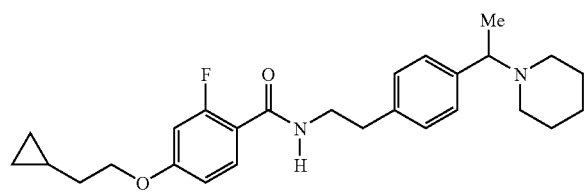

The title compound was obtained by a similar operation as in Example 144 and using 2-{4-[1-(1-piperidinyl)ethyl]phenyl}ethylamine obtained in Reference Example 15.

$^1$H-NMR (CDCl$_3$) δ: 0.02 (2H, m), 0.38 (2H, m), 0.72 (1H, m), 1.24 (2H, m), 1.26 (3H, d, J=6.6 Hz), 1.44 (4H, m), 1.56 (2H, q, J=6.6 Hz), 2.23 (4H, m), 2.79 (2H, t, J=7.2 Hz), 3.27 (1H, q, J=6.6 Hz), 3.59 (2H, q, J=6.3 Hz), 3.82 (2H, d, J=6.6 Hz), 6.42 (1H, d, J=14.4 Hz), 6.48 (1H, m), 6.64 (1H, d, J=8.7 Hz), 7.05 (2H, d, J=8.1 Hz), 7.12 (2H, d, J=8.1 Hz), 7.91 (1H, t, J=9.3 Hz).

EXAMPLE 146

4-cyclopropylmethoxy-N-methyl-N-(2-{4-[1-(1-pyrrolidinyl)ethyl]phenyl}ethyl)benzamide

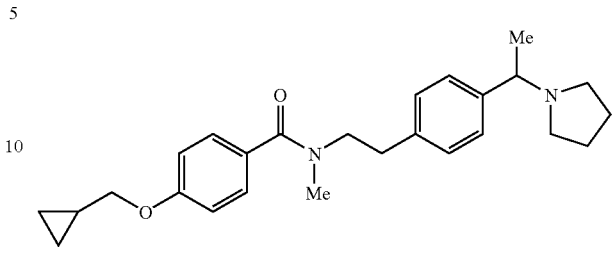

The title compound was obtained by a similar operation as in Example 144 and using N-methyl-2-{4-[1-(1-pyrrolidinyl)ethyl]phenyl}ethylamine obtained in Reference Example 26.

$^1$H-NMR (CDCl$_3$) δ: 0.36 (2H, m), 0.63 (2H, m), 1.22 (1H, m), 1.42 (3H, d, J=6.6 Hz), 1.78 (4H, m), 2.45 (2H, m), 2.45 (2H, m), 2.57 (2H, m), 2.86 (3H, m), 2.95 (1H, m), 3.19 (1H, m), 3.44 (1H, m), 3.78 (4H, m), 6.81-6.89 (2H, m), 6.94 (1H, m), 7.12 (1H, m), 7.15 (2H, m), 7.33 (2H, m).

EXAMPLE 147

N-methyl-N-(2-{4-[1-(1-pyrrolidinyl)ethyl]phenyl}ethyl)[1,1'-biphenyl]-4-carboxamide

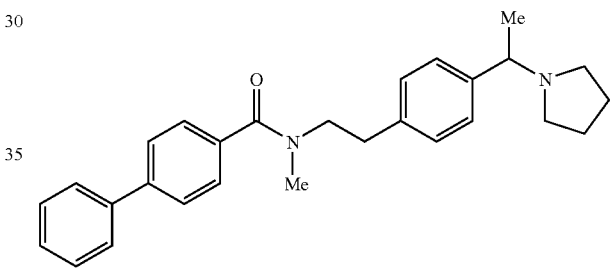

The title compound was obtained by a similar operation as in Example 144 and using N-methyl-2-{4-[1-(1-pyrrolidinyl)ethyl]phenyl}ethylamine obtained in Reference Example 26.

$^1$H-NMR (CDCl$_3$) δ: 1.41 (3H, d, J=6.1 Hz), 1.75 (4H, m), 2.37 (2H, m), 2.55 (2H, m), 2.86 (3H, m), 2.98 (1H, m), 3.15 (2H, m), 3.52 (1H, m), 3.79 (1H, m), 6.93 (1H, m), 7.13 (1H, m), 7.24-7.62 (11H, m).

EXAMPLE 148

4-(2-cyclopropylethoxy)-N-(2-{4-[1-(1-pyrrolidinyl)ethyl]phenyl}ethyl)benzamide

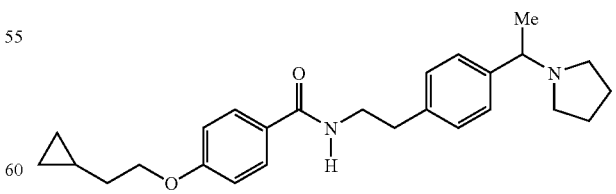

The title compound was obtained by a similar operation as in Example 144 and using 2-{4-[1-(1-pyrrolidinyl)ethyl]phenyl}ethylamine obtained in Reference Example 14.

$^1$H-NMR (CDCl$_3$) δ: 0.96 (2H, m), 0.48 (2H, m), 0.84 (1H, m), 1.41 (3H, d, J=6.6 Hz), 1.64 (2H, m), 1.76 (4H, m), 2.35

(2H, m), 2.54 (2H, m), 2.90 (2H, t, J=6.9 Hz), 3.16 (1H, q, J=6.3 Hz), 3.69 (2H, q, J=6.6 Hz), 4.05 (2H, t, J=6.6 Hz), 6.02 (1H, m), 6.87 (2H, d, J=9.0 Hz), 7.16 (2H, d, J=8.1 Hz), 7.27 (2H, d, J=9.0 Hz), 7.63 (2H, d, J=9.0 Hz). melting point: 102-103° C. (ethyl acetate-isopropyl ether)

EXAMPLE 149

4-(3-methylbutoxy)-N-(2-{4-[1-(1-pyrrolidinyl)ethyl]phenyl}ethyl)benzamide

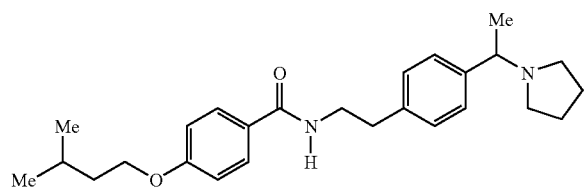

The title compound was obtained by a similar operation as in Example 144 and using 2-{4-[1-(1-pyrrolidinyl)ethyl]phenyl}ethylamine obtained in Reference Example 14.

$^1$H-NMR (CDCl$_3$) δ: 0.96 (6H, d, J=6.2 Hz), 1.39 (3H, d, J=6.2 Hz), 7.76 (6H, m), 2.37 (2H, m), 2.54 (2H, m), 2.90 (2H, t, J=6.6 Hz), 3.16 (1H, q, J=6.3 Hz), 3.68 (2H, q, J=6.0 Hz), 4.01 (2H, t, J=6.6 Hz), 6.02 (1H, m), 6.87 (2H, d, J=8.4 Hz), 7.16 (2H, d, J=8.1 Hz), 7.27 (2H, d, J=9.0 Hz), 7.62 (2H, d, J=8.6 Hz). melting point: 103-104° C. (ethyl acetate-isopropyl ether)

FORMULATION EXAMPLE 1

| | | |
|---|---|---|
| (1) | compound obtained in Example 8 | 50 mg |
| (2) | lactose | 34 mg |
| (3) | cornstarch | 10.6 mg |
| (4) | cornstarch (paste) | 5 mg |
| (5) | magnesium stearate | 0.4 mg |
| (6) | carboxymethyl cellulose calcium | 20 mg |
| | total | 120 mg |

According to conventional methods, the above-mentioned (1)-(6) were mixed and punched by a tableting machine to give tablets.

EXPERIMENTAL EXAMPLE 1

Determination of Antagonistic Activity of Test Compound Using GTP γ S Binding Assay Using human SLC-1 expression CHO cell clone 57 and rat SLC-1 expression CHO cell clone 44 described in WO01/82925, SLC-1 expression CHO cell membrane fractions were prepared by the following method. In phosphate buffered saline (pH 7.4) supplemented with 5 mM EDTA (ethylenediaminetetraacetic acid) were suspended human and rat SLC-1 expression CHO cells (1×10$^8$) and centrifuged. Homogenate buffer (10 ml, 10 mM NaHCO$_3$, 5 mM EDTA, pH 7.5) was added to the pellets of the cells and, using Polytron Homogeniser, the mixture was homogenated. The supernatant obtained after centrifugation at 400×g for 15 min was further centrifuged at 100,000×g for 1 hr to give precipitate of the membrane fraction. The precipitate was suspended in 2 ml of an assay buffer [50 mM Tris-HCl (pH 7.5), 1 mM EDTA, 0.1% BSA (bovine serum albumin), 10 mM MgCl$_2$, 100 mM NaCl, 1 μM GDP (guanosine 5'-diphosphate), 0.25 mM PMSF (phenylmethylsulfonylfluoride), 1 mg/ml pepstatin, 20 mg/ml leupeptin, 10 mg/ml phosphoramidon] and centrifuged at 100,000×g for 1 hr. The membrane fraction recovered as precipitate was suspended again in 20 ml of an assay buffer, and after dispensing, preserved at −80° C. and used upon thawing each time when in use.

The antagonistic activity of the test compound was determined as follows. The SLC-1 expression CHO cell membrane fraction (171 μl) diluted with an assay buffer was dispensed to a polypropylene 96 well plate and 3×10$^{-10}$ M MCH (2 μl) diluted with DMSO solution, test compound solution (2 μl) diluted to various concentrations and [$^{35}$S]-Guanosine5'-(γ-thio)triphosphate (25 μl, Daiichi Pure Chemicals Co., Ltd.) were respectively added (cell membrane final concentration: 20 μg/ml, [$^{35}$S]-Guanosine 5'-(γ-thio)triphosphate final concentration: 0.33 nM). The reaction mixture was reacted at 25° C. for 1 hr with stirring, suction filtered with a glass filter (GF-C) and washed 3 times with a wash solution (300 μl, 50 mM Tris-HCl buffer, pH 7.5). Liquid scintillator (50 ml) was added to the glass filter and the residual radioactivity was determined by a liquid scintillation counter.

Binding inhibition (%)=(radioactivity upon addition of test compound and MCH−radioactivity upon addition of DMSO solution)/(radioactivity upon addition of MCH−radioactivity upon addition of DMSO solution)×100

From the binding inhibition (%), IC$_{50}$ of the test compound was calculated. The results are shown in the following.

| Compound No. | Inhibitory activity (IC$_{50}$: nM) |
|---|---|
| Example 67 | 3 |

INDUSTRIAL APPLICABILITY

The compound of the present invention has a superior MCH receptor antagonistic action and is useful as an agent for the prophylaxis or treatment of obesity and the like.

The invention claimed is:

1. A compound represented by the formula:

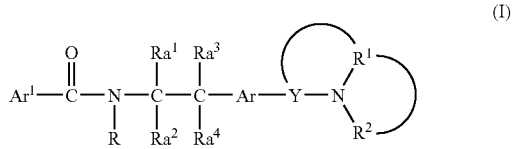

wherein
Ar$^1$ is
a phenyl having a C$_{3-6}$ cycloalkyl-C$_{1-6}$ alkoxy, wherein the phenyl is optionally having a halogen atom
R is
(i) a hydrogen atom;
(ii) an optionally halogenated C$_{1-6}$ alkyl;
(iii) a phenyl; or
(iv) a pyridyl,
each of (iii) and (iv) optionally having 1 to 5 substituents selected from the following Group C:
(a) a halogen atom,
(b) a C$_{1-3}$ alkylenedioxy,
(c) a nitro, (d) a cyano,
(e) an optionally halogenated $C_{1-10}$ alkyl,
(f) an optionally halogenated $C_{3-6}$ cycloalkyl,
(g) an optionally halogenated $C_{1-10}$ alkoxy,
(h) an optionally halogenated $C_{1-10}$ alkylthio,
(i) a hydroxy,
(j) an amino,
(k) a mono- or di-$C_{1-10}$ alkylamino,
(l) a formyl,
(m) a carboxy,
(n) a carbamoyl,
(o) a thiocarbamoyl,
(p) an optionally halogenated $C_{1-6}$ alkyl-carbonyl,
(q) a $C_{1-6}$ alkoxy-carbonyl,
(r) a mono- or di-$C_{1-6}$ alkyl-carbamoyl,
(s) an optionally halogenated $C_{1-6}$ alkylsulfonyl,
(t) a formylamino,
(u) an optionally halogenated $C_{1-6}$ alkyl-carboxamido,
(v) a $C_{1-6}$ alkoxy-carboxamido,
(w) a $C_{1-6}$ alkylsulfonylamino,
(x) a $C_{1-6}$ alkyl-carbonyloxy,
(y) a $C_{1-6}$ alkoxy-carbonyloxy,
(z) a mono- or di-$C_{1-6}$ alkyl-carbamoyloxy,
(aa-1) phenyl,
(aa-2) a 5- or 6-membered aromatic heterocyclic group,
(aa-3) a 9- to 14-membered fused bi- or tri-cyclic aromatic hydrocarbon group, and
(aa-4) a 9- to 14-membered fused bi- or tri-cyclic aromatic heterocyclic group,
each of (aa-1)-(aa-4) optionally having 1 to 5 substituents selected from the following Group B:
a halogen atom
a $C_{1-3}$ alkylenedioxy,
a nitro,
a cyano,
an optionally halogenated $C_{1-10}$ alkyl,
a hydroxy-$C_{1-10}$ alkyl,
an optionally halogenated $C_{3-6}$ cycloalkyl,
an optionally halogenated $C_{1-10}$ alkoxy,
an optionally halogenated $C_{1-10}$ alkylthio,
a hydroxy,
an amino,
a mono- or di-$C_{1-10}$ alkylamino,
an amino-$C_{1-10}$ alkyl,
a mono- or di-$C_{1-10}$ alkylamino-$C_{1-6}$ alkyl,
a formyl,
a carboxy,
a carbamoyl,
a thiocarbamoyl,
an optionally halogenated $C_{1-6}$ alkyl-carbonyl,
a $C_{1-6}$ alkoxy-carbonyl,
a 5- or 6-membered heterocyclylcarbonyl,
a mono- or di-$C_{1-6}$ alkyl-carbamoyl,
a 5- or 6-membered heterocyclylcarbamoyl,
a carbamoyl-$C_{1-6}$ alkyl,
a mono- or di-$C_{1-6}$ alkyl-carbamoyl-$C_{1-6}$ alkyl,
a 5- or 6-membered heterocyclylcarbonyl-$C_{1-6}$ alkyl,
a 5- or 6-membered heterocyclylcarbamoyl-$C_{1-6}$ alkyl,
an optionally halogenated $C_{1-6}$ alkylsulfonyl,
a formylamino,
an optionally halogenated $C_{1-6}$ alkyl-carboxamido,
a $C_{1-6}$ alkoxy-carboxamido,
a $C_{1-6}$ alkylsulfonylamino,
a $C_{1-6}$ alkyl-carbonyloxy,
a $C_{1-6}$ alkoxy-carbonyloxy,
a mono- or di-$C_{1-6}$ alkyl-carbamoyloxy,
a mono- or di-$C_{1-6}$ alkyl-carbamoyl-$C_{1-6}$ alkoxy and
a 5- or 6-membered non-aromatic heterocyclic group;
$Ra^1$, $Ra^2$, $Ra^3$ and $Ra^4$ are the same or different and each is
(i) a hydrogen atom,
(ii) an optionally halogenated $C_{1-6}$ alkyl,
(iii) a phenyl,
(vi) a halogen atom,
(v) a pyridyl,
(vi) a cyano,
(vii) an optionally halogenated $C_{1-6}$ alkoxy,
(viii) an optionally halogenated $C_{1-6}$ alkylthio,
(ix) an amino,
(x) a mono- or di-$C_{1-6}$ alkylamino,
(xi) a formyl,
(xii) an optionally halogenated $C_{1-6}$ alkyl-carbonyl, or
(xiii) an optionally halogenated $C_{1-6}$ alkylsulfonyl,
each of (iii) and (v) optionally having 1 to 5 substituents selected from the above-mentioned Group C;
Ar is
(i) benzene, or
(ii) a 5- or 6-membered aromatic heterocycle, each of (i) and (ii) optionally having 1 to 4 substituents selected from the above-mentioned Group B;
Y is an optionally halogenated alkylene group; and
$R^1$ and $R^2$ are
(1) the same or different and each is a hydrogen atom or a $C_{1-6}$ alkyl,
(2) $R^1$ and $R^2$ form a nitrogen-containing heterocycle together with the adjacent nitrogen atom, optionally having 1 to 5 substituent(s) selected from the following Group D:
(a) the above-mentioned Group B,
(b) a $C_{7-19}$ aralkyl,
(c-1) phenyl,
(c-2) a 5- or 6-membered aromatic heterocyclic group,
(c-3) a 9- to 14-membered fused bi- or tri-cyclic aromatic hydrocarbon group, and
(c-4) a 9- to 14-membered fused bi- or tri-cyclic aromatic heterocyclic group, each of (b) and (c-1)-(c-4) optionally having 1 to 5 substituents selected from the above-mentioned Group B, or
(3) $R^1$ and Y form a nitrogen-containing heterocycle together with the adjacent nitrogen atom, optionally having 1 to 5 substituent(s) selected from the above-mentioned Group D, and $R^2$ is a hydrogen atom or a $C_{1-6}$ alkyl;
or a salt thereof.

2. The compound of claim 1, wherein $R^1$ and $R^2$ are the same or different and each is a hydrogen atom or a $C_{1-6}$ alkyl, or $R^1$ and $R^2$ form a nitrogen-containing heterocycle optionally having substituent(s) together with the adjacent nitrogen atom.

3. The compound of claim 1, wherein R is a hydrogen atom.

4. The compound of claim 1, wherein $Ra^1$, $Ra^2$, $Ra^3$ and $Ra^4$ are each a hydrogen atom.

5. The compound of claim 1, wherein Ar is a benzene ring.

6. The compound of claim 1, wherein Y is a $C_{1-6}$ alkylene group.

7. The compound of claim 1, wherein $R^1$ and $R^2$ form a nitrogen-containing heterocycle optionally having substituent(s) together with the adjacent nitrogen atom.

8. The compound of claim 7, wherein the nitrogen-containing heterocycle is a piperidine, a pyrrolidine, a hexamethylenimine, a morpholine or a thiomorpholine.

9. The compound of claim 1, which is
4-(cyclopropylmethoxy)-N-(2-{4-[1-(1-pyrrolidinyl) ethyl]phenyl}ethyl)benzamide;

N-{2-[4-(1-azepanylmethyl)phenyl]ethyl}-4-(cyclopropylmethoxy)benzamide;

N-{2-[4-(1-azepanylmethyl)phenyl]ethyl}-4-(2-cyclopropylmethoxy)benzamide; or 4-(2-cyclopropylethoxy)-N-(2-{4-[1-(1-pyrrolidinyl)ethyl]phenyl}ethyl)benzamide.

10. A pharmaceutical agent which comprises the compound of claim 1 or a salt thereof or a prodrug thereof.

11. The pharmaceutical agent of claim 10, which is a melanin-concentrating hormone antagonist.

12. The pharmaceutical agent of claim 10, which is an agent for the treatment of a disease caused by a melanin-concentrating hormone.

13. The pharmaceutical agent of claim 10, which is an agent for the treatment of obesity.

14. The pharmaceutical agent of claim 10, which is a feeding deterrent.

15. The pharmaceutical agent of claim 10, which is an agent for the treatment of depression.

16. The pharmaceutical agent of claim 10, which is an agent for the treatment of anxiety.

17. A method for antagonizing a melanin-concentrating hormone receptor in a mammal, which comprises administering an effective amount of the compound of claim 1 or a salt thereof or a prodrug thereof to said mammal.

18. A method for treating obesity in a mammal, which comprises administering an effective amount of the compound of claim 1 or a salt thereof or a prodrug thereof to said mammal.

19. A method for suppressing food intake by a mammal, which comprises administering an effective amount of the compound of claim 1 or a salt thereof or a prodrug thereof to said mammal.

20. A method for treating depression in a mammal, which comprises administering an effective amount of the compound of claim 1 or a salt thereof or a prodrug thereof to said mammal.

21. A method for treating anxiety in a mammal, which comprises administering an effective amount of the compound of claim 1 or a salt thereof or a prodrug thereof to said mammal.

* * * * *